US007001771B1

(12) United States Patent
Morell et al.

(10) Patent No.: US 7,001,771 B1
(45) Date of Patent: Feb. 21, 2006

(54) GENES ENCODING WHEAT STARCH SYNTHASES AND USES THEREOF

(75) Inventors: Matthew Morell, Aranda (AU); Zhongyi Li, Kaleen (AU); Sadequr Rahman, Melba (AU); Rudolph Appels, Aranda (AU)

(73) Assignees: Commonwealth Scientific and Industrial Research Organisation, Campbell (AU); Biogemma SAS, Paris (FR); Goodman Fielder PTY Limited, Sydney (AU)

( * ) Notice: Subject to any disclaimer, the term of this patent is extended or adjusted under 35 U.S.C. 154(b) by 0 days.

(21) Appl. No.: 10/018,418

(22) PCT Filed: Apr. 28, 2000

(86) PCT No.: PCT/AU00/00385

§ 371 (c)(1),
(2), (4) Date: May 9, 2002

(87) PCT Pub. No.: WO00/66745

PCT Pub. Date: Nov. 9, 2000

(30) Foreign Application Priority Data

Apr. 29, 1999 (AU) .................................... PQ0052

(51) Int. Cl.
*C12N 15/29* (2006.01)
*C12N 15/82* (2006.01)
*C12N 15/90* (2006.01)
*A01H 5/00* (2006.01)

(52) U.S. Cl. .................. 435/468; 435/320.1; 536/23.6; 800/284; 800/285; 800/286

(58) Field of Classification Search ............. 435/320.1, 435/410, 419, 468; 536/23.6, 24.33; 800/260, 800/278, 285, 284, 286
See application file for complete search history.

(56) References Cited

U.S. PATENT DOCUMENTS 6,307,125 B1 * 10/2001 Block et al. ................ 800/284
6,734,339 B1 5/2004 Block et al. ................ 800/284

FOREIGN PATENT DOCUMENTS

WO WO 97/45545 12/1997

OTHER PUBLICATIONS

Holmes, S., Henderson's Dictionary of Biological Terms, 9th Ed., Van Nostrand Reinhold Co., New York, 1979, p. 218.*

Mazzolini et al., Plant Mol. Biol., 1992, vol. 20, pp. 715-731.*

Kull et al., J. Genet. Breed. 1995, vol. 49, pp. 69-76.*

Puchta, Plant Mol. Biol., 2002, vol. 48, pp. 173-182.*

Terada et al., Nature Biotech., 2002, vol. 20, pp. 1030-1034.*

Thomas et al., Plant J., 2001, vol. 25, pp. 417-425.*

Abel, G.J.W. et al., Cloning and functional analysis of a cDNA encoding a novel 139 kDa starch synthase from potato (*Solanum tuberosum* L.), (1996) *Plant J.* 10(6):981-991.

Ainsworth, C. et al., "Expression, organisation and structure of the genes encoding the waxy protein (granule-bound starch synthase) in wheat," (1993) *Plant Mol. Biol.* 22:67-82.

Baba, T. et al., "Identification, cDNA cloning, and gene expression of soluble starch synthase in rice (*Oryza sativa* L.) immature seeds," (1993) *Plant Physiol.* 103:565-573.

Craig, J. et al., "Mutations in the gene encoding starch synthase II profoundly alter amylopectin structure in pea embryos," (Mar. 1998) *Plant Cell* 10:413-426.

Denyer, K. et al., "Identification of multiple isoforms of soluble and granule-bound starch synthase in developing wheat endosperm," (1995) *Planta* 196:256-265.

Dry, I. et al., "Characterization of cDNAs encoding two isoforms of granule-bound starch synthase which show differential expression in developing storage organs of pea and potato," (1992) *Plant J.* 2(2):193-202.

Edwards, A. et al., "Biochemical and molecular characterization of a novel starch synthase from potato tubers," (1995) *Plant J.* 8(2):283-294.

Gao, M. et al., "Characterization of dull1, a maize gene coding for a novel starch synthase," (Mar. 1998) *Plant Cell* 10:399-412.

Harn, C. et al., "Isolation and characterization of the zSSIIa and zSSIIb starch synthase cDNA clones from maize endosperm," (Jul. 1998) *Plant Mol. Biol.* 37:639-649.

Klösgen, R.B. et al., "Molecular analysis of the waxy locus of *Zea mays*," (1986) *Mol. Gen. Genet.* 203:237-244.

Knight, M.E. et al., "Molecular cloning of starch synthase I from maize (W64) endosperm and expression in *Escherichia coli*," (Jun. 1998) *Plant J.* 14(5):613-622.

Li, Z. et al., "Cloning and characterization of a gene encoding wheat starch synthase I," (1999) *Theor. Appl. Genet.* 98:1208-1216.

(Continued)

*Primary Examiner*—Ashwin Mehta
(74) *Attorney, Agent, or Firm*—John P. White, Esq.; Cooper & Dunham LLP

(57) ABSTRACT

The present invention provides isolated nucleic acid molecules encoding wheat starch syntheses, and probes and primers derived therefrom, which are useful in the modificaiton of plant starch content and/or composition, and for screening plant lines to determine the presence of natural and/or induced mutations in starch synthase genes which affect starch content and/or composition. More particularly the isolated nucleic acid molecules of the present invention further provide for the screening-assisted breeding of plants having desirable starch content and/or composition, in addition to providing for the direct genetic manipulation of plant starch content and/or composition.

15 Claims, 50 Drawing Sheets

OTHER PUBLICATIONS

Li, Z. et al., "The localization and expression of the class II starch synthases of wheat," (Aug. 1999) *Plant Physiology* 120:1147-1155.

Okagaki, R.J., "Nucleotide sequence of a long cDNA from the rice waxy gene," (1992) *Plant Molecular Biology* 19: 513-516.

Rahman, S. et al., "A complex arrangement of genes at a starch branching enzyme I locus in the D-genome donor of wheat," (1997) *Genome* 40:465-474.

Rahman, S. et al., "The major proteins of wheat endosperm starch granules," (1995) *Aust. J. Plant Physiol.* 22:793-803.

Rahman, S. et al., "Characterisation of a gene encoding wheat endosperm starch branching enzyme-I," (1999) *Theor. Appl. Genet.* 98:156-163.

Takaoka, M. et al., "Structural characterization of high molecular weight starch granule-bound proteins in wheat (*Triticum aestivum* L.)," (1997) *J. Agric. Food Chem.* 45: 2929-2934.

van der Leij, F.R. et al., "Sequence of the structural gene for granule-bound starch synthase of potato (*Solanum tuberosum* L.) and evidence for a single point deletion in the amf allele," (1991) *Mol. Gen. Genet.* 228:240-248.

Abel et al., GenBank Accession #Y10416 (Jan. 1997) *S. tuberosum* mRNA for soluble starch synthase.

Block et al., GenBank Accession #U48227 (Jun. 1996) *Triticum aestivum* soluble starch synthase mRNA, partial cds.

Walter et al., GenBank Accession #AAB17085 (Oct. 1996) Starch synthase.

Walter et al., GenBank Accession #U66377 (Oct. 1996) *Triticum aestivum* starch synthase mRNA, partial cds.

Gao et al. GenBank Accession #AAC14014 (Apr. 1998) Starch synthase DULL1 [*Zea mays*].

Gao et al. GenBank Accession #AAC14015 (Apr. 1998) Starch synthase DULL1 [*Zea mays*].

D'Holst et al., GenBank Accession #AAC17969 (Nov. 2001) Granule-bound starch synthase I precursor [*Chlamydomonas reinhardtii*].

Bhullar et al., GenBank Accession #CAB40374 (Apr. 1999) Starch synthase isoform SS III [*Vigna unguiculata*].

Gao et al., GenBank Accession #CAB86618 (Apr. 2002) Starch synthase IIa-1 [*Triticum aestivum*].

Gao et al., GenBank Accession #AJ269502 (Apr. 2002) *Triticum aestivum* mRNA for starch synthase IIa-1 (wSs2a-1 gene).

Rahman et al., GenBank Accession #AF076680 (May 1999) *Aegilops tauschii* starch branching enzyme-I (SBE-I) gene, complete cds.

* cited by examiner

| |
|---|
| FIGURE 2A |
| FIGURE 2B |
| FIGURE 2C |
| FIGURE 2D |
| FIGURE 2E |
| FIGURE 2F |
| FIGURE 2G |
| FIGURE 2H |
| FIGURE 2I |
| FIGURE 2J |
| FIGURE 2K |
| FIGURE 2L |
| FIGURE 2M |
| FIGURE 2N |
| FIGURE 2O |

FIGURE 2

```
        1                                                    50
wSSIIB  ATTTCCTCGG CCTGACCCCG TGCGTTTACC CCACACAGAG CACACTCCAG
wSSIID  ~~~~~~~~~~ ~~~~~~~~~~ ~~~~~~~~~~ ~~~~~~~~~~ ~~~~~~~~~~
wSSIIA  ~~~~~~~~~~ ~~~~~~~~~~ ~~~~~~~~~~ ~~~~~~~~~~ ~~~~~~~~~~

        51                                                  100
wSSIIB  TCCAGTCCAG CCCACTGCCG CGCTACTCCC CACTCCCACT GCCACCACCT
wSSIID  ~~~~~~~~~~ ~~~~~~~~~~ ~~~~~~~~~~ ~~~~~~~~~~ ~~~~~~~~~~
wSSIIA  ~~~~~~~~~~ ~~~~~~~~~~ ~~~~~~~~~~ ~~~~~~~GCT GCCACCACCT

        101                                                 150
wSSIIB  CCGCcTGCGC CGCGCTCTGG GCGGACCAAC CCGCGCATCG TATCACGATC
wSSIID  ~~~~~~~~~~ ~~~~~~~~~~ ~~~~~~~~~~ ~~~~~~~~~~ ~~~~~~~~~~
wSSIIA  CCGCCTGCGC CGCGCTCTGG GCGGAGGACC AACCCGCGCA TCGTACCATC

        151                                                 200
wSSIIB  ACCCACCCCG ATCCCGGCCG CCGCCATGTC GTCGGCGGTC GCGTCCGCCG
wSSIID  ~~~~~~~~~~ ~~~~~~~~~~ ~~~~~~~~~~ ~~~~~~~~~~ ~~~~~~~~~~
wSSIIA  GCCCGCCCCG ATCCCGGCCG CCGCCATGTC GTCGGCGGTC GCGTCCGCCG
```

FIGURE 2A

```
        201                                                  250
wSSIIB  CGTCCTTCCT CGCGCTCGCG TCCGCCTCCC CCGGGAGATC ACGGAGGAGG
wSSIID  ~~~~~~~~~~ ~~~~~~~~~~ ~~~~~~~~~~ ~~~~~~~~~~ ~~~~~~~~~~
wSSIIA  CGTCCTTCCT CGCGCTCGCC TCCGCCTCCC CCGGGAGATC ACGCAGGCGG

        251                                                  300
wSSIIB  ACGAGGGTGA GCGCGTCGCC ACCCCACACC GGGGCTGGCA GGTTGCACTG
wSSIID  ~~~~~~~~~~ ~~~~~~~~~~ ~~~~~~~~~~ ~~~~~~~~~~ ~~~~~~~~~~
wSSIIA  GCGAGGGTGA GCGCGCCGCC ACCCCACGCC GGGGCCGGCA GGCTGCACTG

        301                                                  350
wSSIIB  GCCGCCGTCG CCGCCGCAGC GCACGGCTCG CGACGGAGCG GTGGCCGCGC
wSSIID  ~~~~~~~~~~ ~~~~~~~~~~ ~~~~~~~~~~ ~~~~~~~~~~ ~~~~~~~~~~
wSSIIA  GCCGCCGTGG CCGCCGCAGC GCACGGCTCG CGACGGAGGT GTGGCCGCGC

        351                                                  400
wSSIIB  GCGCCGCCGG GAAGAAGGAC GCGGGGAT.. .CGACGACGC CGCGCCCGCG
wSSIID  ~~~~~~~~~~ ~~~~~~~~~~ ~~~~~~~~~~ ~~~~~~~~~~ ~~~~~~~~~~
wSSIIA  GCGCCGCCGG GAAGAAGGAC GCGAGGGTCG ACGACGACGC CGCGTCCGCG
```

FIGURE 2B

```
        401                                                450
wSSIIB  AGGCAGCCCC GCGCACTCCG CGGTGGCGCC GCCACCAAGG TTGCGGAGCG
wSSIID  ~~~~~~~~~~ ~~~~~~~~~~ ~~~~~~~~~~ ~~~~~~~~~~ ~~~~~~~~~~
wSSIIA  AGGCAGCCCC GCGCACGCCG CGGTGGCGCC GcCACCAAGG TCGCGGAGCG

        451                                                500
wSSIIB  GAGGGATCCC GTCAAGACGC TCGATCGCGA CGCCGCGGAA GGTGGCGCGC
wSSIID  ~~~~~~~~~~ ~~~~~~~~~~ ~~~~~~~~~~ ~~~~~~~~~~ ~~~~~~~~~~
wSSIIA  GAGGGATCCC GTCAAGACGC TCGATCGCGA CGCCGCGGAA GGTGGCGCGC

        501                                                550
wSSIIB  CGTCCCCGCC GGCACCGAGG CAGGAGGACG CCCGTCTGCC GAGCATGAAC
wSSIID  ~~~~~~~~~~ ~~~~~~~~~~ ~~~~~~~~~~ ~~~~~~~~~~ ~~~~~~~~~~
wSSIIA  CGGCACCGCC GGCACCGAGG CAGGACGCCG CCCGTCCaCC GAGTATGAAC

        551                                                600
wSSIIB  GGCATGCCGG TGAACGGTGA AAACAAATCT ACCGGCGGCG GCGGCGCGAC
wSSIID  ~~~~~~~~~~ ~~~~~~~~~~ ~~~~~~~~~~ ~~~~~~~~~~ ~~~~~~~~~~
wSSIIA  GGCACGCCGG TGAACGGTGA GAACAAATCT ACCGGCGGCG GCGGCGCGAC
```

FIGURE 2C

```
        601                                                650
wSSIIB  TAAAGACAGC GGGCTGCCCG CACCCGCACG CGCGCCCCAG CCGTCGAGCC
wSSIID  ~~~~~~~~~~ ~~~~~~~~~~ ~~~~~~~~~~ ~~~~~~~~~~ ~~~~~~~~~~
wSSIIA  cAAAGACAGC GGGCTgcCCG CACCCGcACG CGCGCCCCAT cCGTCGAcCC

        651                                                700
wSSIIB  AGAACAGAGT ACCGGTGAAT GGTGAAAACA AAGCTAACGT CGCCTCGCCG
wSSIID  ~~~~~~~~~~ ~~~~~~~~~~ ~~~~~~~~~~ ~~~~~~~~~~ ~~~~~~~~~~
wSSIIA  AgAACAgAGT ACCAGTGAAC GGTGAAAACA AAGCTAACGT CGCCTCGCCG

        701                                                750
wSSIIB  CCGACGAGCA TAGCCGAGGT CGCGGCTCCG GATCCCGCAG CTACCATTTC
wSSIID  ~~~~~~~~~~ ~~~~~~~~~~ ~~~~~~~~~~ ~~~~~~~~~~ ~~~~~~~~~~
wSSIIA  CCGACGAGCA TAGCCGAGGT CGTGGCTCCG GATTCCGCAG CTACCATTTC

        751                                                800
wSSIIB  CATCAGTGAC AAGGCGCCAG AGTCCGTTGT CCCAGCCGAG AAGGcgccgc
wSSIID  ~~~~~~~~~~ ~~~~~~~~~~ ~~~~~~~~~~ ~CCAGCTGAG AAGACGCCGC
wSSIIA  CATCAGTGAC AAGGCGCCGG AGTCCGTTGT CCCAGCCGAG AAGCCGCCGC
```

FIGURE 2D

```
        801                                                850
wSSIIB  CGtCgtcCgg CtcAAATtTc gtgCcCtCgg cttctGctCc cggGtctGAC
wSSIID  CGTCGTCCGG CTCAAATTTC GAGTCCTCGG CCTCTGCTCC CGGGTCTGAC
wSSIIA  CGTCGTCCGG CTCAAATTTC GTGgTCTCGG CTTCTGCTCC CAGGCTGGAC

        851                                                900
wSSIIB  actgtCaGCG acGtGGaact TgaActGAAg aAGGGtgCgg tCattgTcaA
wSSIID  ACTGTCAGCG ACGTGGAACA AGAACTGAAG AAGGGTGCGG TCGTTGTCGA
wSSIIA  ATTGACAGCG ATGTTGAACC TGAACTGAAG AAGGGTGCGG TCATCGTCGA

        901                                                950
wSSIIB  aGAAgcTcCa aaCcCaAaGG CTCTTTCGCC GCCCGCAGCA CCCGCTGTAC
wSSIID  AGAAGCTCCA AAGCCAAAGG CTCTTTCGCC GCCtGCAGCc CCCGCTGTAC
wSSIIA  AGAAGCTCCA AACCCAAAGG CTCTTTCGCC GCCTGCAGCC CCCGCTGTAC

        951                                                1000
wSSIIB  AACAAGACCT TTGGGACTTC AAGAAATACA TTGGTTTCGA GGAGCCCGTG
wSSIID  AAgAAGACCT TTGGGAtTTC AAGAAATACA TTGGTTTCGA GGAGCCCGTG
wSSIIA  AAGAAGACCT TTGGGACTTC AAGAAATACA TTGGCTTCGA GGAGCCCGTG
```

FIGURE 2E

```
          1001                                                  1050
wSSIIB    GAGGCCAAGG ATGATGGCCG GGCTGTTGCA GATGATGCGG GCTCCTTCGA
wSSIID    GAGGCCAAGG ATGATGGCCG GGCTGTcGCA GATGATGCGG GCTCCTTtGA
wSSIIA    GAGGCCAAGG ATGATGGCTG GGCTGTTGCA GATGATGCGG GCTCCTTTGA

          1051                                                  1100
wSSIIB    ACACCACCAG AATCACGATT CCGGGCCTTT GGCAGGGGAG AACGTCATGA
wSSIID    ACACCACCAG AATCACGAcT CCGGaCCTTT GGCAGGGGAG AAtGTCATGA
wSSIIA    ACATCACCAG AACCATGATT CCGGACCTTT GGCAGGGGAG AACGTCATGA

          1101                                                  1150
wSSIIB    ACGTGGTCGT CGTGGCTGCT GAATGTTCTC CCTGGTGCAA AACAGGTGGT
wSSIID    ACGTGGTCGT CGTGGCTGCT GAgTGTTCTC CCTGGTGCAA AACAGGTGGT
wSSIIA    ACGTGGTCGT CGTGGCTGCT GAATGTTCTC CCTGGTGCAA AACAGGTGGT

          1151                                                  1200
wSSIIB    CTTGGAGATG TTGCCGGTGC TTTGCCCAAG GCTTTGGCGA AGAGAGGACA
wSSIID    CTgGGAGATG TTGCgGGTGC TcTGCCCAAG GCTTTGGCaA AGAGAGGACA
wSSIIA    CTTGGAGATG TTGCCGGTGC TTTGCCCAAG GCTTTGGCGA AGAGAGGACA
```

FIGURE 2F

```
         1201                                                  1250
wSSIIB   TCGTGTTATG GTTGTGGTAC CAAGGTATGG GGACTATGAG GAAGCCTACG
wSSIID   TCGTGTTATG GTTGTGGTAC CAAGGTATGG GGACTATGAa GAACCTACGg
wSSIIA   TCGTGTTATG GTTGTGGTAC CAAGGTATGG GGACTATGAG GAAGCCTACG

         1251                                                  1300
wSSIIB   ATGTCGGAGT CCGAAAATAC TACAAGGCTG CTGGACAGGA TATGGAAGTG
wSSIID   ATGTCGGAGT CCGAAAATAC TACAAGGCTG CTGGACAGGA TATGGAAGTG
wSSIIA   ATGTCGGAGT CCGAAAATAC TACAAGGCTG CTGGACAGGA TATGGAAGTG

         1301                                                  1350
wSSIIB   AATTATTTCC ATGCTTATAT CGATGGAGTT GATTTTGTGT TCATTGACGC
wSSIID   AATTATTTCC ATGCTTaTAT CGATGGAGTT GATTTTGTGT TCATTGACGC
wSSIIA   AATTATTTCC ATGCTTATAT CGATGGAGTT GATTTTGTGT TCATTGACGC

         1351                                                  1400
wSSIIB   TCCTCTCTTC CGACACCGCC AGGAAGACAT TTATGGGGGC AGCAGACAGG
wSSIID   TCCTCTCTTC CGACACCGAG AGGAAGACAT TTATGGGGGC AGCAGACAGG
wSSIIA   TCCTCTCTTC CGACACCGCC AGGAAGACAT TTATGGGGGC AGCAGACAGG
```

FIGURE 2G

```
        1401                                                1450
wSSIIB  AAATTATGAA GCGCATGATT TTGTTCTGCA AGGCCGCTGT CGAGGTTCCA
wSSIID  AAATTATGAA GCGCATGATT TTGTTCTGCA AGGCCGCTGT TGAGGTTCCA
wSSIIA  AAATTATGAA GCGCATGATT TTGTTCTGCA AGGCCGCTGT CGAGGTTCCT

        1451                                                1500
wSSIIB  TGGCACGTTC CATGCGGCGG TGTCCCTTAT GGGGATGGAA ATCTGGTGTT
wSSIID  TGGCACGTTC CATGCGGCGG TGTCCCTTAT GGGGATGGAA ATCTGGTGTT
wSSIIA  TGGCACGTTC CATGCGGCGG TGTCCCTTAT GGGGATGGAA ATCTGGTGTT

        1501                                                1550
wSSIIB  TATTGCAAAT GATTGGCACA CGGCACTCCT GCCTGTCTAT CTGAAAGCAT
wSSIID  TATTGCAAAT GATTGGCACA CGGCACTCCT GCCTGTCTAT CTGAAAGCAT
wSSIIA  TATTGCAAAT GATTGGCACA CGGCACTCCT GCCTGTCTAT CTGAAAGCAT

        1551                                                1600
wSSIIB  ATTACAGGGA CCATGGTTTG ATGCAGTACA CTCGGTCCAT TATGGTGATA
wSSIID  ATTACAGGGA CCATGGTTTG ATGCAGTACA CTCGGTCCAT TATGGTGATA
wSSIIA  ATTACAGGGA CCATGGTTTG ATGCAGTACA CTCGGTCCAT TATGGTGATA
```

FIGURE 2H

```
        1601                                                1650
wSSIIB  CATAACATCG CTCACCAGGG CCGTGGCCCA GTAGATGAGT TCCCGTTCAC
wSSIID  CATAACATCG CTCACCAGGG CCGTGGCCCT GTAGATGAAT TCCCGTTCAC
wSSIIA  CATAACATCG CGCACCAGGG CCGTGGCCCA GTAGATGAAT TCCCGTTCAC

        1651                                                1700
wSSIIB  CGAGTTGCCT GAGCACTACC TGGAACACTT CAGACTGTAC GACCCCGTGG
wSSIID  CGAGTTGCCT GAGCACTACC TGGAACACTT CAGACTGTAC GACCCCGTGG
wSSIIA  CGAGTTGCCT GAGCACTACC TGGAACACTT CAGACTGTAC GACCCCGTGG

        1701                                                1750
wSSIIB  GTGGTGAACA CGCCAACTAC TTCGCCGCCG GCCTGAAGAT GGCGGACCAG
wSSIID  GTGGTGAACA CGCCAACTAC TTCGCCGCCG GCCTGAAGAT GGCGGACCAG
wSSIIA  GTGGTGAGCA CGCCAACTAC TTCGCCGCCG GCCTgAAGAT GgCGGACCAG

        1751                                                1800
wSSIIB  GTTGTCGTCG TGAGCCCGGG GTACCTGTGG GAGCTGAAGA CGGTGGAGGG
wSSIID  GTTGTCGTGG TGAGCCCCGG GTACCTGTGG GAGCTGAAGA CGGTGGAGGG
wSSIIA  GTTGTCGTGG TGAGCCCCGG GTACCTGTGG gAGCTCAAGA CGGTGGAgGG
```

FIGURE 2I

```
        1801                                                1850
wSSIIB  CGGCTGGGGG CTTCACGACA TCATACGGCA GAACGACTGG AAGACCCGCG
wSSIID  CGGCTGGGGG CTTCACGACA TCATACGGCA GAACGACTGG AAGACCCGCG
wSSIIA  CGGCTGGGGG CTTCACGACA TCATACGGCA GAACGACTGG AAGACCCGCG

        1851                                                1900
wSSIIB  GCATCGTGAA CGGCATCGAC AACATGGAGT GGAACCCCGA GGTGGACGTC
wSSIID  GCATCGTCAA CGGCATCGAC AACATGGAGT GGAACCCCGA GGTGGACGCC
wSSIIA  GCATCGTCAA CGGCATCGAC AACATGGAGT GGAACCCCGA GGTGGACGTC

        1901                                                1950
wSSIIB  CACCTCAAGT CGGACGGCTA CACCAACTTC TCCCTGGGGA CGCTGGACTC
wSSIID  CACCTCAAGT CGGACGGCTA CACCAACTTC TCCCTGAGGA CGCTGGACTC
wSSIIA  CACCTCAAGT CGGACGGCTA CACCAACTTC TCCCTGGGGA CGCTGGACTC

        1951                                                2000
wSSIIB  CGGCAAGCGG CAGTGCAAGG AGGCCCTGCA GCGGGAGCTG GGCCTGCAGG
wSSIID  CGGCAAGCGG CAGTGCAAGG AGGCCCTGCA GCGCGAGCTG GGCCTGCAGG
wSSIIA  CGGCAAGCGG CAGTGCAAGG AGGCCCTGCA GCGCGAGCTG GGCCTGCAGG
```

FIGURE 2J

```
        2001                                                2050
wSSIIB  TCCGCGGCGA CGTGCCGCTG CTCGGCTTCA TCGGGCGCCT GGACGGGCAG
wSSIID  TCCGCGCCGA CGTGCCGCTG CTCGGCTTCA TCGGCCGCCT GGACGGGCAG
wSSIIA  TCCGCGCCGA CGTGCCGCTG CTCGGCTTCA TCGGCCGCCT GGACGGGCAG

        2051                                                2100
wSSIIB  AAGGGCGTGG AGATCATCGC GGACGCGATG CCCTGGATCG TGAGCCAGGA
wSSIID  AAGGGCGTGG AGATCATCGC GGACGCCATG CCCTGGATCG TGAGCCAGGA
wSSIIA  AAGGGCGTGG AGATCATCGC GGACGCCATG CCCTGGaTCG TGAGCCAGgA

        2101                                                2150
wSSIIB  CGTGCAGCTG GTCATGCTGG GCACCGGGCG CCACGACCTG GAGGGCATGC
wSSIID  CGTGCAGCTG GTGATGCTGG GCACCGGGCG CCACGACCTG GAGAGCATGC
wSSIIA  CGTGCAGCTG GTCATGCTGG GCACCGGCCG CCACGACcTG gAGAGCATGc

        2151                                                2200
wSSIIB  TGCGGCACTT CGAGCGGGAG CACCACGACA AGGTGCGCGG GTGGGTGGGG
wSSIID  TGCAGCACTT CGAGCGGGAG CACCACGACA AGGTGCGCGG GTGGGTGGGG
wSSIIA  TgCGGCACTT CGAGCGGGAG CACCACGACA AGGTGCGCGG gTGGGTGGGG
```

FIGURE 2K

```
    2201                                                    2250
wSSIIB  TTCTCCGTGC GGCTGGCGCA CCGGATCACG GCCGGCGCCG ACGCGCTCCT
wSSIID  TTCTCCGTGC GCCTGGCGCA CCGGATCACG GCGGGGGCGG ACGCGCTCCT
wSSIIA  TTCTCCGTgc GccTGGCGCA CCGGATCACG GCGGGCGCCG ACGCGCTCcT

        2251                                                2300
wSSIIB  CATGCCCTCC CGGTTCGAGC CGTGCGGACT GAACCAGCTC TACGCCATGG
wSSIID  CATGCCCTCC CGGTTCGTGC CGTGCGGGCT GAACCAGCTC TACGCCATGG
wSSIIA  CATGCCCTCC CGGTTCGAgC CGTGCGGGTT GAACCAGCTt TACGCCATGG

        2301                                                2350
wSSIIB  CCTACGGCAC CGTCCCCGTC GTGCATGCCG TCGGTGGCCT GAGGGACACC
wSSIID  CCTACGGCAC CGTCCCCGTC GTGCACGCCG TCGGCGGCCT CAGGGACACC
wSSIIA  CCTACGGCAC CGTCCCCGTC GTGCACGCCG TCGGCGGGGT GAGGGACACC

        2351                                                2400
wSSIIB  GTGCCGCCGT TCGACCCCTT CAACCACTCC GGGCTCGGGT GGACGTTCGA
wSSIID  GTGCCGCCGT TCGACCCCTT CAACCACTCC GGGCTCGGGT GGACGTTCGA
wSSIIA  GTGCCGCCGT TCGACCCCTT CAACCACTCC GGcCTCGGGT GGACGTTCGA
```

FIGURE 2L

```
         2401                                                2450
wSSIIB   CCGCGCAGAG GCGCAGAAGC TGATCGAGGC GCTCGGGCAC TGCCTCCGCA
wSSIID   CCGCGCCGAG GCGCACAAGC TGATCGAGGC GCTCGGGCAC TGCCTCCGCA
wSSIIA   CCGCGCcGAG GCGCAcAAGC TGATCGAGGC GCTCGGGCAC TGCCTCCGCA

         2451                                                2500
wSSIIB   CCTACCGGGA CTACAAGGAG AGCTGGAGGG GGCTCCAGGA GCGCGGCATG
wSSIID   CCTACCGAGA CTTCAAGGAG AGCTGGAGGG CCCTCCAGGA GCGCGGCATG
wSSIIA   CCTACCGGGA CTACAAGGAG AGCTGGAGGG GcCTCCAGGA GCGCGGCATG

         2501                                                2550
wSSIIB   TCGCAGGACT TCAGCTGGGA GCATGCCGCC AAGCTCTACG AGGACGTCCT
wSSIID   TCGCAGGACT TCAGCTGGGA GCACGCCGCC AAGCTCTACG AGGACGTCCT
wSSIIA   TCGCAGGACT TCAGCTGGGA GCATGCCGCC AAGCTCTACG AGGACGTCCT

         2551                                                2600
wSSIIB   CGTCAAGGCC AAGTACCAGT GGTGAACGCT AGCTGCTAGC CGGTCCAGCC
wSSIID   CGTCAAGGCC AAGTACCAGT GGTGAACGCT AGCTGCTAGC CGCTCCAGCC
wSSIIA   CcTCAAGGCC AAGTACCAGT GGTGAACGCT AGCTGCTAGC CGcTCCAGCC
```

FIGURE 2M

```
          2601                                                  2650
wSSIIB    CCGCATGCG. ...TGCATGA CAGGATGGAA TTGCGCATTG CGCACGCAGG
wSSIID    CCGCATGCG. ...TGCATGA CAGGATGGAA CT..GCATTG CGCACGCAGG
wSSIIA    CCGCATGCGT GCATGcatgA gAGGgTGGAA cTGCGCATTG CGCcCGCAGG

          2651                                                  2700
wSSIIB    AAGGTGCCAT .......... .GGAGCGCCG GCATCCGCGA AGTACAGTGA
wSSIID    AAAGTGCCAT .......... .GGAGCGCCG GCATCCGCGA AGTACAGTGA
wSSIIA    AAcGTGCCAT ccttctcgat gGGAGCGCCG GCATCCGCGA gGTgCAGTGA

          2701                                                  2750
wSSIIB    CAT..GAGGT GTGTGTGGTT GAGACGCTGA TTC......C GATCTGGTCC
wSSIID    CAT..GAGGT GTGTGTGGTT GAGACGCTGA TTC......C AATCCGGCCC
wSSIIA    CATGAGagGT GTGTGTGGTT GAGACGCTGA TTCCGATCTc gatctGGTCC

          2751                                                  2800
wSSIIB    GTAGCAGAGT AGAGCGGAGG TAGGGAAGCG CTCCTTGTTA CAGGTATATG
wSSIID    GTAGCAGAGT AGAGCGGAGG TATATGGGAA TCTTAACTTG GTATTGTAAT
wSSIIA    GTAGCAGAGT AGAGCGGAcG TAGGGAAGCG CTCCTTGTTg CAGGTATATG
```

FIGURE 2N

```
         2801                                               2850
wSSIIB   GGAATGTTGT TAACTTGGTA TTGTAATTTG TTATGTTGTG TGCATTATTA
wSSIID   TTGTTATGTT GTGTGCATTA TTACAATGTT GTTACTTATT CTTGTTAAGT
wSSIIA   GGAATGTTGT cAACTTGGTA TTGTAgTTTG cTATGTTGTa TGCgTTATTA

         2851                                               2900
wSSIIB   CAGAGGGCAA CGATCTGCGC CGGCGCACCG GCCCAACTGT TGGGCCGGTC
wSSIID   CGGAGGCCAA GGGCGAAAGC TAGCTCACAT GTCTGATGGA TGCAAAAAAA
wSSIIA   caatgttgtt acttattctt gtTAAAAAAA AAAAAAAAAA AAAA~~~~~~

         2901                                               2950
wSSIIB   GCACAGCAGC CGTTGGATCC GACCGCCTGG GCCGTTGGAT CCCACCGAAA
wSSIID   AAAAAAAAAA AAA~~~~~~~ ~~~~~~~~~~ ~~~~~~~~~~ ~~~~~~~~~~
wSSIIA   ~~~~~~~~~~ ~~~~~~~~~~ ~~~~~~~~~~ ~~~~~~~~~~ ~~~~~~~~~~

         2951       2965
wSSIIB   AAAAAAAAAA AAAAA
wSSIID   ~~~~~~~~~~ ~~~~~
wSSIIA   ~~~~~~~~~~ ~~~~~
```

FIGURE 2O

```
WSSIIA   1 MSSAVASAAS ---FLALASA SP-GRSRRRA RVSAPPPHAG AGRL----HW PPWPP-QRTA  51
WSSIIB   1 ********** ---******* **-******T ****S***T* ****----** **S**-****  51
WSSIID     ---------- ---------- ---------- ---------- ---------- ----------
ZSSIIA   1 ****AV*SS* STF******* **G**--*** **GSS*F*T* *-S*SFAFWA **S**RAPRD  57
ZSSIIB   1 *PG*-I*SS* SAFL*PV**S **---R***G S*G*ALRSY* YSGAELRL** ARRG*P*DG*  56
PEASSII  1 *MLSLG*D*T VLP*H*KNLK FTPKL*TLNG --DLAFSKGL GVGRLNCGSV ---------R  49
POTSSII 10 PVNFIFCDFY VMENSI*LHS GNQFHPNLPL ---LALRPKK LSLIHGSSRE ---------Q  57

                     ⇓ Transit peptide cleavage site
WSSIIA.  52 RDGGVAARAA GKKDARVDDD AASARQPRAR RGGAATKVAE RRDPVKTLDR DAAEGGAPAP 111
WSSIIB   52 ***A****** *****GI-** **P******L ********** ********** ********S* 110
WSSIID      ---------- ---------- ---------- ---------- ---------- ----------
ZSSIIA   58 AALVR*EAE* *G***PPERS GDA**L**** *----NA*SK ****------ ----------  97
ZSSIIB   57 -ASVR**A*P AGG------- ---------- ---------- ---------- ----------  68
PEASSII  50 LNHKQHV**V **SFGADENG DG*EDDVVNA TIEKSK**LA LQRELIQQIA ERKKLVSSID 109
POTSSII  58 MWRNQRVK*T *ENSGEAA-S *DESNDALQV TIEKSK**LA MQQDLLQQIA ERRKVVSSIK 116
```

FIGURE 3A

```
WSSIIA  112 PAPRQDAARP PSMNGTPVNG ENKSTGGGGA TKDSGLPAPA RAPHPSTQNR VPVNGENKAN 171
WSSIIB  111 *****ED**L *****M**** ********** ********** ***Q**S*** ********** 170
WSSIID      ---------- ---------- ---------- ---------- ---------- ----------
ZSSIIA   98 ---------- ---------- -----LQPVG RYG*ATGNT* *TGAA*C**A ALADV*I*SI 132
ZSSIIB   69 ---------- ---------- ---------- -ESEEAAKSS SSSQAGAVQG STAKAVDS*S  97
PEASSII 110 SDSIPGLEGN GVSYESSEKS LSR------- ---------- ------DS*P QKGSSSSGSA 146
POTSSII 117 S----SL*NA KGTYDGGSGS LSDVDIPDVD KDYNVTVPST A*TGITDVDK NTPPAISHDF 172

WSSIIA  172 VASPPTSIAE VVAPDSAATI SISDKAPESV VPAEKPPPSS GSNFVVSASA PRLDIDSDVE 231
WSSIIB  171 ********** *A***P**** ********** *****A**** *****P**** *GS*TV**** 230
WSSIID  203 ---------- ---------- ---------- -****T**** ****ES**** *GS*TV**** 231
ZSSIIA  134 **A*****VK FP**GYRMIL PSG*I***T* L**P**--LH E*PA*DGD*N --GIAPPT** 188
ZSSIIB   99 PPN*L**APK QSQSAAMQNG TSGGSSASTA A*VSG*KADH P*AP*TKREI DASAVKPEPA 158
PEASSII 147 *ETKR--WHC FQQ-----LC RSKETETWA* SSVGINQGFD EIEKKND*VK ASSKLHFNEQ 199
POTSSII 173 *E*KREIKRD LADERAPPLS RS*IT*SSQI SSTVSSK--R TL*VPPETPK SSQETLL**N 230
```

FIGURE 3B

```
                                                                   wSSIIp1 Region
WSSIIA   232 PELKKGAVIV EEAPNPKALS PPAAPAVQED LWDFKKYIGF EEPVEAKDDG WAVADDAGSF 291
WSSIIB   231 L********* K********* ********Q* ********** ********** R********* 290
WSSIID   232 Q*******V* ****K***** ********** ********** ********** R********* 291
ZSSIIA   189 *--------- ---------- -----L***A T********* D**D*****S RVG******* 224
ZSSIIB   159 GDDARPVESI ---------- ---------- ---------*I A***D**A*- A*P*T**AAS 188
PEASSII  200 IKN*LYERPD TKDIS--SSI R--------- ------TSSL KFENFEGANE PSSKEV*NEA 242
POTSSII  231 SRKSLVD*PG KKIQSYMPSL R--------- ----*ESSAS HVEQRNENLE GSS*EANEET 277

                                              Region 1              Region 2
WSSIIA.  292 EHHQNHD--S GPLAGENVMN VVVVAAECSP WCKTGGLGDV AGALPKALAK RGHRVMVVVP 349
WSSIIB   291 *******--* ********** ********** ********** ********** ********** 348
WSSIID   292 *******--* ********** ********** ********** ********** ********** 349
ZSSIIA   225 **YGDN*--* ********** *I******** ********** V********R ********** 282
ZSSIIB   189 APYDRE*NEP *****P**** *****S**A* F********* V********R ********I* 248
PEASSII  243 *NFESGGEKP P****T**** IIL*S***A* *S******** **S******R ******I*A* 302
POTSSII  278 *DPV*I*EKP P****T**** IIL**S**A* *S******** *********R ********A* 337
```

FIGURE 3C

```
                                                Sgp-1 Peptide 3
WSSIIA   350 RYGDYEEAYD VGVRKYYKAA GQDMEVNYFH AYIDGVDFVF IDAPLFRHRQ EDIYGGSRQE 409
WSSIIB   349 ********** ********** ********** ********** ********** ********** 408
WSSIID   350 *******PT* ********** ********** ********** *********E ********** 409
ZSSIIA   283 *****V**F* **I******* ***L****** *F******** ********** D********* 342
ZSSIIB   249 ***E*A**R* L***RR**V* ***S**T*** S********* VE**P****H NN****E*LD 308
PEASSII  303 H**N*A**H* I****R**V* ******T*** T******I** **S*I**NLE SN****N*LD 362
POTSSII  338 **DN*P*PQ* S****I**VD ***VD*T**Q *LLMDC**** *HSHM***IG NN****N*VD 397

                                                           Region 3
WSSIIA   410 IMKRMILFCK AAVEVPWHVP CGGVPYGDGN LVFIANDWHT ALLPVYLKAY YRDHGLMQYT 469
WSSIIB   409 ********** ********** ********** ********** ********** ********** 468
WSSIID   410 ********** ********** ********** ********** ********** ********** 469
ZSSIIA   343 ********** V********* ****C***** ********** ********** ********** 402
ZSSIIB   309 *L******** *******YA* ***TV***** ********** ********** ***N*****A 368
PEASSII  363 *LR**V**** ********** ***IC***** ********** ********** *******N** 422
POTSSII  398 *L***V**** **I******* ****C***** ********** ****A***** ***N*I*N** 457
```

FIGURE 3D

```
WSSIIA  470 RSIMVIHNIA HQGRGPVDEF PFTELPEHYL EHFRLYDPVG GEHANYFAAG LKMADQVVVV 529
WSSIIB  469 ********** ********** ********** ********** ********** ********** 528
WSSIID  470 ********** ********** ********** ********** ********** ********** 529
ZSSIIA  404 **VL****** ********** *YMD****** Q**E****** *****I**** *****R**T* 462
ZSSIIB  369 **VL****** ********D* VNFD*****I D**K***NI* *D*S*V**** **T**R**T* 428
PEASSII 423 **VL****** *******ED* NTVD*SGN** DL*KM***** ***F*I**** **T**RI*T* 482
POTSSII 458 **VL****** ******LED* SYVD**P**M DP*K****** ***F*I**** **T**R**T* 517

                                      Region 4
WSSIIA  530 SPGYLWELKT VEGGWGLHDI IRQNDWKTRG IVNGIDNMEW NPEVDVHLK- SDGYTNFSLG 588
WSSIIB  529 ********** ********** ********** ********** *********- ********** 587
WSSIID  530 ********** ********** ********** ********** *****A***- *********R 588
ZSSIIA  463 *R******** ********** **S****IN* ******HQ** **K*****R- ******Y**E 521
ZSSIIB  429 *N**M***** S********* *N*****LQ* ******MS** **A*****H- **D***YTFE 487
PEASSII 483 *H**A***** S*******N* *NES***F** ****V*TKD* **QF*AY*T- ******YN*K 541
POTSSII 518 *H**S***** SQ******Q* *NE****LQ* ******TK** ***L****PR ****M*Y**D 577
```

FIGURE 3E

```
                                       Region 5                                    Region 5a
WSSIIA  589 TLDSGKRQCK EALQRELGLQ VRADVPLLGF IGRLDGQKGV EIIADAMPWI VSQDVQLVML 648
WSSIIB  588 ********** ********** **G******* ********** ********** ********** 647
WSSIID  588 ********** ********** ********** ********** ********** ********** 648
ZSSIIA  522 ***A****** A********E **D******* ********** D**G****** AG******** 581
ZSSIIB  488 ***T****** A****Q**** **D****I** *****H**** D*****IH** AG******** 547
PEASSII 542 **QT****** A********P **E***IIS* *****H**** DL**E*I**M M*H******* 601
POTSSII 578 **QT**P*** A***K****P **D****I** *****P**** DL**E*V**M MG******** 637

                                                 Region 6
WSSIIA  649 GTGRHDLESM LRHFEREHHD KVRGWVGFSV RLAHRITAGA DALLMPSRFE PCGLNQLYAM 708
WSSIIB  648 ********G* ********** ********** ********** ********** ********** 707
WSSIID  649 ********** *Q******** ********** ********** *********V ********** 708
ZSSIIA  582 ****A***R* *Q*L****PN ********** PM******** *V*V****** ********** 641
ZSSIIB  548 ****A***D* **R**S**S* ***A****** P********* *I******** ********** 607
PEASSII 602 ****A***Q* *KE**AQ*C* *I*S****** KM*******S *I******** ********** 661
POTSSII 638 ****R***Q* **Q**CQ*N* *I******** KTS******* *I******** **A******* 697
```

FIGURE 3F

```
                                 Region 7
WSSIIA  709 AYGTVPVVHA VGGVRDTVPP FDPFNHSGLG WTFDRAEAHK LIEALGHCLR TYRDYKESWR 768
WSSIIB  708 ********** ***L****** ********** ********Q* ********** ********** 767
WSSIID  709 ********** ***L****** ********** ********** ********** ****F***** 768
ZSSIIA  642 ********** ***L****A* ****GDA*** ********N* *****R***D ***K*G***K 701
ZSSIIB  608 ********** ***L****A* *****DT*** ********NR M*D**S***T ***N****** 667
PEASSII 662 S********G ***L****Q* *N**DE**V* ********N* *MA**WN**L **K***K**E 721
POTSSII 698 K***I***** ***L****Q* ***LMSQDW* GPS*****SQ **PRIRN**L ***E**K**E 757

WSSIIA  769 GLQERGMSQD FSWEHAAKLY EDVLLKAKYQ W 799
WSSIIB  768 ********** ********** ****V***** * 798
WSSIID  769 ********** ********** ****V***** * 799
ZSSIIA  702 S**A****** L**D***E** ****V***** * 732
ZSSIIB  668 ACRA***AE* L**D***V** ****V***** * 698
PEASSII 722 *I******** L**DN**QQ* *E**VA**** * 752
POTSSII 759 *I*T*C*T** L**DN**QN* *E**IA**** * 788
```

FIGURE 3G

```
        1                                                      50
wSSIII  MEMSLWPRSP LCPRSRQPLV VVRP..AGRG GLTQPFLMNG RFTRSRTLRC
mSSIII  MEMVLRSQSP LCLRS.GPVL IFRPTVAGGG GGTQSLLRTT RFARRRVIRC
pSSIII  ~~~~~~~~~~ ~~~~~~~~~~ ~~~~~~~~~~ ~~~~~~~~~~ ~~~~~~~~~~

        51                                                    100
wSSIII  MVASSDPPNR KSRRMVPPQV KVISSRGYTT RLIVEPSNEN TEHNNRD...
mSSIII  VVASPGCPNR KS.RTASPNV KVAAYSNYAP RLLVESSSKK SEHHDSSRHR
pSSIII  ~~~~~~~~~~ ~~~~~~~~~~ ~~~~~~~~~~ ~~~~~~~~~~ ~~~~~~~~~~

        101                                                   150
wSSIII  EETLDTYNAL LSTETAEWTD NREAE..... ..TAKADSSQ NALSSSIIGE
mSSIII  EETIDTYNGL SGSDAAELTS NRDVEIEVDL QHISEEELPG KVSINASLGE
pSSIII  ~~~~~~~~~~ ~~~~~~~~~~ ~~~~~~~~~~ ~~~~~~~~~~ ~~~~~~~~~~

        151                                                   200
wSSIII  VDVAD..... EDILAADLTV YSLSSVMKKE VDAADKARVK EDAFELDLPA
mSSIII  METVDEAEVE EDKFEVDTSG IVLRNVAVRE VDPKDEHNAK .DVFVVDSSG
pSSIII  ~~~~~~~~~~ ~~~~~~~~~~ ~~~~~~~~~~ ~~~~~~~~~~ ~~~~~~~~~~
```

FIGURE 7A

```
        201                                                  250
wSSIII  TTLRSVIVDV MDHNGTVQET LRSVIVDVMD .HNGTVQE.. TLRSVIVDVM
mSSIII  TAPDNAAVEE VVDEAEVEED MVDVDILGLD LNNATIEEID LMEEALLENF
pSSIII  ~~~~~~~~~~ ~~~~~~~~~~ ~~~~~~~~~~ ~~~~~~~~~~ ~~~~~~~~~~

        251                                                  300
wSSIII  D.DAADKARV EEDVFELDLS GNISSSAT.. .......... ......TVEL
mSSIII  DVDSPGNASS GRTYGGVDEL GELPSTSVDC IAINGKRRSL KPKPLPIVRF
pSSIII  ~~~~~~~~~~ ~~~~~~~~~~ ~~~~~~~~~~ ~~~~~~~~~~ ~~~~~~~~~~

        301                                                  350
wSSIII  DAVDEVGPVQ DKFEATSSGN VSNSATVREV DASDE...AG NDQGIFRADL
mSSIII  QEQEQIVLSI VDEEGLIASS CEEGQPVVDY DKQEENSTAF DEQKQLTDDF
pSSIII  ~~~~~~~~~~ ~~~~~~~~~~ ~~~~~~~~~~ ~~~~~~~~~~ ~~~~~~~~~~

        351                                                  400
wSSIII  SGNVFSSSTT VEVG..AVDE AGSIKDRFET DSSGNVSTSA PMWDAIDETV
mSSIII  PEEGISIVHF PEPNNDIVGS SKFLEQKQEL DGSYKQDRST TGLHEQDQSV
pSSIII  ~~~~~~~~~~ ~~~~~~~~~~ ~~~~~~~~~~ ~~~~~~~~~~ ~~~~~~~~~~
```

FIGURE 7B

```
        401                                                   450
wSSIII  ADQDTFEADL SGNASSCATY REVDDVVDET RSEEETFAMD LFASESGHEK
mSSIII  VSSHGQDKSI VG.VPQQIQY NDQSIAGSHR QDQSIAGAPE QIQSVAGYIK
pSSIII  ~~~~~~~~~~ ~~~~~~~~~~ ~~~~~~~~~~ ~~~~~~~~~~ ~~~~~MDVPF

        451                                                   500
wSSIII  HMAVDYVGEA TDEEETYQQQ YPVPSSFSMW DKAIAKTGVS LNPELRLVRV
mSSIII  PNQ.SIVGSC KQHELIIPEP KKIESIISYN EIDQSIVGSH KQDKSVVSVP
pSSIII  PLHRSLSCTS VSNAITHLKI KPILGFVSHG TTSLSVQSSS WRKDGMVTGV

        501                                                   550
wSSIII  EEQGKVNFSD KKDLSIDDLP GQNQSIIGSY KQDKSIADVA GPTQSIFGSS
mSSIII  EQIQSIVSHS KPNQSTVDSY RQAESIIGVP EKVQSITSYD KLDQSIVGSL
pSSIII  SFSICANFSG RRRRKVSTPR SQGSSPKGFV PRKPSGMSTQ RKVQKSNGDK

        551                                                   600
wSSIII  KQHRSIVAFP KQNQSIVSVT EQKQSIVGFR SQDLSAVSL. .........P
mSSIII  KQDEPIISVP EKIQSIVHYT KPNQSIVGLP KQQQSIVHIV EPKQSIDGFP
pSSIII  ESKSTSTSKE SEISNQKTVE ARVETSDDDT KGVVRDHKFL EDEDEINGST
```

FIGURE 7C

```
          601                                                      650
wSSIII    KQ.NVPIVGT SREGQTKQVP VVDRQDALYV NGLEAKEGDH TSEKTDEDAL
mSSIII    KQ.DLSIVGI SNEFQTKQLA TVGTHDGLLM KGVEAKE... TSQKTEGDTL
pSSIII    KSISMSPVRV SSQFVESEET GGDDKDAVKL N..KSKRSEE SGFIIDSVIR

          651                                                      700
wSSIII    HVKFNVDNVL RKHQADRTQA VEKKTWKKVD EEHLYMTEHQ KRAA..EGQM
mSSIII    QATFNVDNLS QKQEGLTKEA DEITIIEKIN DEDLVMIEEQ KSIAMNEEQT
pSSIII    EQSGSQGETN ASSKGSHAVG TKLYEILQVD VEPQQLKEN. .NAGNVEYKG

          701                                                      750
wSSIII    VVNEDELSIT EIGMGRGD.K IQHVLSEEEL SWSEDEVQLI EDDGQYEVDE
mSSIII    IVTEEDIPMA KVEIGIDKAK FLHLLSEEES SWDENEVGII EADEQYEVDE
pSSIII    PVASKLLEIT KA......SD VEHTESNEID DLDTN..SFF KSDLIEEDEP

          751                                                      800
wSSIII    TSVSVNVEQD IQGSPQDVVD PQALKVMLQE LAEKNYSMRN KLFVFPEVVK
mSSIII    TSMS..TEQD IQESPNDDLD PQALWSMLQE LAEKNYSLGN KLFTYPDVLK
pSSIII    LAAGTVETGD SSLNLRLEME ANLRRQAIER LAEENLLQGI RLFCFPEVVK
```

FIGURE 7D

```
        801                                                  850
wSSIII  ADSVIDLYLN RDLTALANEP DVVIKGAFNG WKWRLFTERL HKSDLGGVWW
mSSIII  ADSTIDLYFN RDLSAVANEP DVLIKGAFNG WKWRFFTEKL HKSELAGDWW
pSSIII  PDEDVEIFLN RGLSTLKNES DVLIMGAFNE WRYRSFTTRL TETHLNGDWW

        851                                                  900
wSSIII  SCKLYIPKEA YRLDFVFFNG RTVYENNGNN DFCIGIEGTM NEDLFEDFLV
mSSIII  CCKLYIPKQA YRMDFVFFNG HTVYENNNNN DFVIQIESTM DENLFEDFLA
pSSIII  SCKIHVPKEA YRADFVFFNG QDVYDNNDGN DFSITVKGGM QIIDFENFLL

        901                                                  950
wSSIII  KEKQRELEKL AMEEAERRTQ TEEQRRRKEA RAADEAVRAQ AKAEIEIKKK
mSSIII  EEKQRELENL ANEEAERRRQ TDEQRRMEEE RAADKADRVQ AKVEVETKKN
pSSIII  EEKWREQEKL AKEQAERERL AEEQRRIEAE KAEIEADRAQ AKEEAAKKKK

        951                                                 1000
wSSIII  KLQSMLSLAR TCVDNLWYIE ASTDTRGDTI RLYYNRNSRP LAHSTEIWMH
mSSIII  KLCNVLGLAR APVDNLWYIE PITTGQEATV RLYYNINSRP LVHSTEIWMH
pSSIII  VLRELMVKAT KTRDITWYIE PSEFKCEDKV RLYYNKSSGP LSHAKDLWIH
```

FIGURE 7E

```
        1001                                                1050
wSSIII  GGYNNWTDGL SIVESFVKCN DKDGDWWYAD VIPPEKALVL DWVFADGPAG
mSSIII  GGYNNWIDGL SFAERLVHHH DKDCDWWFAD VVVPERTYVL DWVFADGPPG
pSSIII  GGYNNWKDGL SIVKKLVKSE RIDGDWWYTE VVIPDQALFL DWVFADGPPK

        1051                                                1100
wSSIII  NARNYDNNAR QDFHAILPNN NVTEEGFWAQ EEQNIYTRLL QERREKEETM
mSSIII  SARNYDNNGG HDFHATLP.N NMTEEEYWME EEQRIYTRLQ QERREREEAI
pSSIII  HAIAYDNNHR QDFHAIVP.N HIPEELYWVE EEHQIFKTLQ EERRLREAAM

        1101                                                1150
wSSIII  KRKAERSANI KAEMKAKTMR RFLLSQKHIV YTEPLEIRAG TTVDVLYNPS
mSSIII  KRKAERNAKM KAEMKEKTMR MFLVSQKHIV YTEPLEIHAG TTIDVLYNPS
pSSIII  RAKVEKTALL KTETKERTMK SFLLSQKHVV YTEPLDIQAG SSVTVYYNPA

        1151                                                1200
wSSIII  NTVLNGKSEG WFRCSFNLWM HSSGALPPQK MVKSGDGPLL KATVDVPPDA
mSSIII  NTVLTGKPEV WFRCSFNRWM YPGGVLPPQK MVQAENGSHL KATVYVPRDA
pSSIII  NTVLNGKPEI WFRCSFNRWT HRLGPLPPQK MSPAENGTHV RATVKVPLDA
```

FIGURE 7F

```
         1201                                                  1250
wSSIII   YMMDFVFSEW EEDGIYDNRN GMDYHIPVSD SIETENYMRI IHIAVEMAPV
mSSIII   YMMDFVFSES EEGGIYDNRN GLDYHIPVFG SIAKEPPMHI VHIAVEMAPI
pSSIII   YMMDFVFSER EDGGIFDNKS GMDYHIPVFG GVAKEPPMHI VHIAVEMAPI

         1251                                                  1300
wSSIII   AKVGGLGDVV TSLSRAIQDL GHTVEVILPK YDCLNQSSVK DLHLYQSFSW
mSSIII   AKVGGLGDVV TSLSRAVQDL GHNVEVILPK YGCLNLSNVK NLQIHQSFSW
pSSIII   AKVGGLGDVV TSLSRAVQDL NHNVDIILPK YDCLKMNNVK DFRFHKNYFW

         1301                                                  1350
wSSIII   GGTEIKVWVG RVEDLTVYFL EPQNGMFGVG CVYG.RNDDR RFGFFCHSAL
mSSIII   GGSEINVWRG LVEGLCVYFL EPQNGMFGVG YVYG.RDDDR RFGFFCRSAL
pSSIII   GGTEIKVWFG KVEGLSVYFL EPQNGLFSKG CVYGCSNDGE RFGFFCHAAL

         1351                                                  1400
wSSIII   EFILQNEFSP HIIHCHDWSS APVAWLYKEH YSQSRMASTR VVFTIHNLEF
mSSIII   EFLLQSGSSP NIIHCHDWSS APVAWLHKEN YAKSSLANAR VVFTIHNLEF
pSSIII   EFLLQGGFSP DIIHCHDWSS APVAWLFKEQ YTHYGLSKSR IVFTIHNLEF
```

FIGURE 7G

```
          1401                                                  1450
wSSIII    GAHYIGKAMT YCDKATTVSP TYSRDVAGHG AIAPHREKFY GILNGIDPDI
mSSIII    GAHHIGKAMR YCDKATTVSN TYSKEVSGHG AIVPHLGKFY GILNGIDPDI
pSSIII    GADLIGRAMT NADKATTVSP TYSQEVSGNP VIAPHLHKFH GIVNGIDPDI

          1451                                                  1500
wSSIII    WDPYTDNFIP VPYTCENVVE GKRAAKRALQ QKFGLQQTDV PIVGIITRLT
mSSIII    WDPYNDNFIP VHYTCENVVE GKRAAKRALQ QKFGLQQIDV PVVGIVTRLT
pSSIII    WDPLNDKFIP IPYTSENVVE GKTAAKEALQ RKLGLKQADL PLVGIITRLT

          1501                                                  1550
wSSIII    AQKGIHLIKH AIHRTLESNG HVVLLGSAPD HRIQGDFCRL ADALHGVYHG
mSSIII    AQKGIHLIKH AIHRTLERNG QVVLLGSAPD SRIQADFVNL ANTLHGVNHG
pSSIII    HQKGIHLIKH AIWRTLERNG QVVLLGSAPD PRVQNNFVNL ANQLHSKYND

          1551                                                  1600
wSSIII    RVKLVLTYDE PLSHLIYAGS DFIIVPSIFE PCGLTQLVAM RYGSIPIVRK
mSSIII    QVRLSLTYDE PLSHLIYAGS DFILVPSIFE PCGLTQLVAM RYGTIPIVRK
pSSIII    RARLCLTYDE PLSHLIYAGA DFILVPSIFE PCGLTQLTAM RYGSIPVVRK
```

FIGURE 7H

```
        1601                                               1650
wSSIII  TGGLHDTVFD VDNDKDRARS LGLEPNGFSF DGADSNGVDY ALNRAIGAWF
mSSIII  TGGLFDTVFD VDNDKERARD RGLEPNGFSF DGADSNGVDY ALNRAISAWF
pSSIII  TGGLYDTVFD VDHDKERAQQ CGLEPNGFSF DGADAGGVDY ALNRALSAWY

        1651                                   1689
wSSIII  DARDWFHSLC KRVMEQDWSW NRPALDYIEL YHAARKF*~
mSSIII  DARSWFHSLC KRVMEQDWSW NRPALDYIEL YRSASKL~~
pSSIII  DGRDWFNSLC KQVMEQDWSW NRPALDYLEL YHAARKLE*
```

FIGURE 7I

```
                          Region 1                    Regior. 2
                  10         20         30         40         50
wGBSS    81  FVGAEMAPWS KTGGLGDLLG GLPPAMAANG HRVMVISPRY DQYKDAWDT-
wSS1    144  -*TG*A**YA *S*****VC* S**I*L**R* *****VM*** LNGSSDKNYA
wSS2    314  --A**CS**C *******VA* A**K*L*KR* *****VV*** GD*EE*Y*V-
wSS3   1187  -IAV****VA *V*****VVT S*SR*IQDL* *T*E**L*K* *CLNQSSVK-

                 100        110        120        130        140
wGBSS   171  LEKVRGKTKE KIYGPDAGTD YEDNQQRFSL LCQAALEVPR ILNLDNNPYF
wSS1    234  -HRPGSLYGD ------NFGA FG***F*YT* **Y**C*A*L **E*GGYI*G
wSS2    404  RHRQEDIYGG ---------S RQEIMK*MI* F*K**V***W HVPCGGV**G
wSS3   1277  **PQN*MFGV ------GCVY GRNDDR**GF F*HS***--F **QNEFS*H-

                 190        200        210        220        230
wGBSS   261  FCIHNISYQG RFSFDDFAQL NLPD-----R FKSSFDFIDG YDKPVEGRKI
wSS1    324  LV***LAH** LEPASTYPD* G**PEWYGAL EWVFPEWARR HALDKGEAVN
wSS2    494  MV****AH** *GPV*E*PFT E**------- -EHYLEHFRL **PVGGEHAN
wSS3   1367  *T***L-EF* AHYIGKAMTY CDK------- ---------- ---------
```

FIGURE 9A

```
     60         70         80         90
-----SVVSE IKVVDKYERV RYFHCYKRGV DRVFVDHPCF  170
KALYTGKHIK *PCFGGSHE* TF**E*RDN* *W******SY  233
-----G*RKY Y*AAGQDME* N***A*ID** *F**I*A*L*  403
---------- -DLHLYQSFS WGGTEI*VW* G**EDLTVY* 1276

           Region 3
    150        160        170        180
SGPYGEDVVF VCNDWHTGLL ACYLKSNYQS NGIYRAAKVA  260
QN-----CM* *V****AS*V PVL*AAK*RP Y*V**DSRST  323
D*----NL** IA*****A** PV***AY*RD H*LMQYTRSI  493
--------II H*H**SSAPV *WLY*EH*SQ -SRMASTR*V 1366

    240        250        260        270
NWMKAGILQA DKVLTVSPYY AEELISGEAR GCELDNIMRL  350
FLKG*VVTAD RI*TVSQG*S W*VTTAEGGQ *LNELLSS*K  413
YFAAGLKMAD QV*VVSPG*L W*LKTVEGGW *LHDIIRQND  583
---------- --------AT TVSPTYSRDV AGHGAIAPHR 1456
```

FIGURE 9B

```
                      Region 4
                   280        290         300         310         320
wGBSS    351  TGITTIVNGM DVSEWDPTKD KFLAVNYDIT TALEGKALNK EALEGKALNK
wSS1     414  SVLNG****I *IND*N**T* *C*PHH*SV- ---------- DD*S***KC*
wSS2     584  WKTRG****I *NM**N*EV* VH*KSDGYTN ------FSLG TLDS**RQC*
wSS3    1457  EKFYG*L**I *PDI***YT* N*IP*P*TCE ----NVVEG* **AKRALQQ*

                     Region 5a
                   370        380         390         400         410
wGBSS    441  LKEEDVQIVL LGTGKKKFER LLKSIEEKFP SKVRAVVRFN ------APLA
wSS1     504  *MR****F*M **S*DPI**G WMR*T*SSYK D*F*GW*G*S ------V*VS
wSS2     674  V-SQ***L*M ****RHDL*S M*RHF*REHH D***GW*G*S ------VR**
wSS3    1547  TL*SNG*V** **SAPDHRIQ GDFCRLADAL HG*YHGRVKL -VLTYDE**S
```

FIGURE 9C

```
                  Region 5
  330         340          350          360
EALQAEVGLP VDRKVPLVAF IGRLEEQKGP DVMIASIPEI   440
AE**K*L*** *RED***IG* ****DY***I *LIKMA***-   503
****R*L**Q *RAD***LG* ****DG***V EIIADAM*W*   673
FG**QT---- ---D**I*GI *T**TA***I -HL*KHAIHR  1546

 Region 6                              Region 7
  420         430          440         450
HQMMAGADVL AVTSRFEPCG LIQLQGMRYG TPCACASTGG   530
*RIT**C*I* LMP******* *N**YA*Q** *VPVVHG***   593
*RIT****A* LMP******* *N**YA*A** *VPVVHAV**   763
*LIY**S*FI I*P*I***** *T**VA**** SIPIVRK***  1636
```

FIGURE 9D

```
             Region 7 (Continued)
               460        470        480        490        500

wGBSS  531 LVDTIVEGKT GFHMGRLSYD CNVVEPADVK KVVTTLKRAV KVVGTPAYHE
wSS1   594 *R**-**TFN ---------- --PFGAKGEE GTGWAFSPLT VDKMLW*LRT
wSS2   764 VR**-*PPFD ---------- --PFNHSGLG ---W*FD**E AHKLIE*LGH
wSS3  1637 ****-*FDVD NDKDRAR*LG LEPNGFSFDG ADSNGVDY*L NRAIGAWFDA

550            560        570        580        590        600
wGBSS  621 APLAMENVAA P*........ .......... .......... ..........
wSS1   684 FVDQPYVM.. .......... .......... .......... ..........
wSS2   854 KYQW...... .......... .......... .......... ..........
wSS3  1727 .......... .......... .......... .......... ..........
```

FIGURE 9E

```
    510        520        530        540
MVKNCMIQDL SWKGPAKNWE DVLLELGVEG SEPGIVGEEI  620
AMSTFREHKP **E*LM*RGM TKDHTWDHAA EQYEQIF*WA  683
CLRTYRDYKE **R*LQERGM SQDFSWEHAA KLYED*LLKA  853
RDWFHSLCKK VMEQDWSWNR PA*DYIELYH AARKF*....  1726

    610        620        630
.......... .......... .......... ..........  710
.......... .......... .......... ..........  773
.......... .......... .......... ..........  943
.......... .......... .......... ..........  1816
```

GENES ENCODING WHEAT STARCH SYNTHASES AND USES THEREOF

CROSS REFERENCE TO RELATED APPLICATIONS

This application was filed under 35 U.S.C. 371, based on PCT/AU00/00385, which application was filed Apr. 28, 2000 and claims priority from Australian Patent Application No. PQ0052/99 filed Apr. 29, 1999.

FIELD OF THE INVENTION

The present invention relates generally to isolated nucleic acid molecules encoding wheat starch synthase enzymes and more particularly, to isolated nucleic acid molecules that encode wheat SSII and SSIII enzyme activities. The isolated nucleic acid molecules provide the means for modifying starch content and composition in plants, for example the ratio of amylose:amylopectin in the starch granule of the endosperm during the grain-filling phase of endosperm development. The isolated nucleic acid molecules of the present invention also provide the means for screening plant lines to determine the presence of natural and/or induced mutations in starch synthase genes which affect starch content and/or composition. The isolated nucleic acid molecules of the present invention further provide for the screening-assisted breeding of plants having desirable starch content and/or composition, in addition to providing for the direct genetic manipulation of plant starch content and/or composition.

GENERAL

Bibliographic details of the publications numerically referred to in this specification are collected at the end of the description. Reference herein to any published document is not to be taken as an indication or admission that any such published document is part of the common general knowledge or background information of a skilled worker in the relevant field.

This specification contains nucleotide and amino acid sequence information (SEQ ID NOS:) prepared using the programme PatentIn Version 2.0, presented herein at the end of the specification. Each nucleotide or amino acid sequence is identified in the sequence listing by the numeric indicator <210>followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212>and <213>, respectively. Nucleotide and amino acid sequences (SEQ ID NOs:) referred to in the specification are defined by the information provided in numeric indicator field <400> followed by the sequence identifier (eg. SEQ ID NO: 1 is <400>1, etc).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

The designations for naturally-occurring amino acid residues referred to herein are set forth in Table I. The designations for a non-limiting set of non-naturally-occurring amino acids is listed in Table 2.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of steps or elements or integers.

TABLE 1

| Amino Acid | Three-letter Code | One-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Aspartate/glutamate | Baa | B |
| Asparagine/glutamine | | |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |

TABLE 2-continued

| Non-conventional amino acid | Code |
| --- | --- |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Nepro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only. Functionally-equivalent products, compositions and methods are clearly within the scope of the invention, as described herein.

BACKGROUND TO THE INVENTION

The biosynthesis of the starch granule is a complex process which involves the action of an array of isoforms of enzymes involved in the starch biosynthesis. Following the formation of glucose-1-phosphate, the enzyme activities required for the synthesis of granular starch include ADP glucose pyrophosphorylase (EC 2.7.7.27), starch synthases (EC 2.4.1.21), branching enzymes (EC 2.4.1.18) and debranching enzymes (EC 3.2.1.41 and EC 3.2.1.68) (Mouille et al., 1996). Plants contain isozymes of each of these activities, and the definition of these isoforms and their roles has been conducted through investigation of the properties of the suite of soluble enzymes found in the stroma of the plastid, analysis of the proteins entrapped within the matrix of the starch granule, and mutational studies to identify genes and define linkages between individual genes and their specific roles.

Starch synthases extend regions of α-1, 4 glucan through the transfer of the glucosyl moiety of ADPglucose to the non-reducing end of a pre-existing α-1, 4 glucan. In addition to GBSS, 3 other classes of starch synthase have been identified in plants, SSI (wheat, Li et al., 1999 and GenBank Accession No. U48227; rice, Baba et al., 1993; potato, Genbank Accession No. Y10416, SSII (pea, Dry et al. 1992; potato, Edwards et al., 1995; maize, Harn et al., 1998 and GenBank Accession No. U66377) and SSIII (potato, Abel et al., 1996; maize, Gao et al., 1998). In the cereals, the most comprehensively studied species is maize, where in addition to GBSS, cDNAs encoding SSI, and SSIIb have been isolated, and both cDNA and genomic clones for dull1 have been characterised (Knight et al., 1998; Harn et al., 1998; Goa et al., 1998). In maize, the product of the du1 gene is known as maize SSII, however this gene is the homologue of potato SSIII.

The proteins within the matrix of the wheat starch granule have been extensively studied (Denyer et al., 1995; Rahman et al., 1995; Takaoka et al., 1997; Yamamori and Endo, 1996) and 60, 75, 85, 100, 104 and 105 kDa protein bands can be visualised following SDS-PAGE. The predominant 60 kDa protein is exclusively granule-bound and is analogous to the "waxy" granule bound starch synthase (GBSS) gene in maize (Rahman et al., 1995). The combination of three null alleles for this enzyme from each of the wheat genomes (Nakamura et al., 1995) results in the amylose-free "waxy" phenotype found in other species The 75 kDa starch synthase I (wSSI) is found in both the granule and the soluble fraction of wheat endosperm (Denyer et al., 1995; Li et al., 1999) and has been assigned to chromosomes 7A, 7B and 7D (Yamamori and Endo, 1996; Li et al., 1999). The 85 kDa band contains a class II branching enzyme and an unidentified polypeptide (Rahman et al., 1995). The 100, 104 and 105 kDa proteins of the wheat starch granule (designated Sgp-B1, Sgp-D1 and Sgp-A1 by Yamamori and Endo, 1996) have been shown to be encoded by a homeologous set of genes on the short arm of chromosome 7B, 7A and 7D respectively (Yamamori and Endo, 1996; Takaoka et al., 1997). Denyer et al. (1995) concluded on the basis of enzyme activity assays that these proteins were also starch synthases. These genes are referred to hereinafter as the "wheat SSII genes".

While GBSS has been established to be essential for amylose synthesis, the remaining starch synthases are thought to be primarily responsible for the elongation of amylopectin chains, although this does not preclude them from also having non-essential roles in amylose biosynthesis. Differences in kinetic properties between isoforms, and the analysis of mutants lacking various isoforms, suggests that each isoenzyme contributes to the extension of specific subsets of the available non-reducing ends.

SUMMARY OF THE INVENTION

The production of plants that produce improved starches that are modified for particular end-use applications, such as, for example, starches having high or low amylose:amylopectin ratios, requires the availability of genes encoding the various starch synthase isoforms. Because of species-specific codon usages, and variations in the kinetic parameters of the starch synthase isoforms between species, the production of modified starches may require the use of genes derived from particular species.

Furthermore, the screening-assisted breeding of plants having desirable starch content and/or composition requires specific gene sequences to be provided that can be used to distinguish between different homeologous genes encoding the various isoforms of wheat starch synthases, such as, for example, to identify and distinguish between naturally-occurring variant gene sequences. It is a particular object of the present invention to provide gene sequences to facilitate the screening-assisted selection of wheat plants having starch traits which are associated with the presence and/or expression of one or more wheat SSI and/or SSIII genes.

Accordingly, the present invention provides isolated nucleotide sequences encoding the wheat SSII (i.e. wSSII) and wheat SSIII (i.e. wSSIII) isoenzymes, and DNA markers derived therefrom. The present invention further facilitates the production of transformed plants carrying these nucleotide sequences.

More particularly, the present invention provides isolated nucleic acid molecules encoding the 100, 104 and 105 kDa SSII (Sgp-1) polypeptides of the wheat starch granule matrix, as determined using the SDS/PAGE system of Rahman et al. (1995), which polypeptides are equivalent to the 100, 108 and 115 kDa polypeptides described by Yamamori and Endo (1996).

The present invention further provides isolated nucleic acid molecules encoding the soluble dull1-type wheat starch synthase III polypeptide. Analysis of the polypeptides encoded by these nucleic acid molecules reveals several consensus amino acid sequence motifs that are highly conserved in wheat starch synthase isoenzymes, in addition to isoenzyme-specific sequences, which sequences possess utility in isolating related starch synthase-encoding sequences and in assaying plants for their expression of one or more starch synthase isoenzymes.

Accordingly, one aspect of the present invention provides an isolated nucleic acid molecule which comprises a sequence of nucleotides which encodes, or is complementary to a nucleic acid molecule which encodes a wheat starch synthase polypeptide, protein or enzyme molecule or a functional subunit thereof selected from the following:

(i) a wheat starch synthase II (wSSII) polypeptide, protein or enzyme or functional subunit thereof which comprises an amino acid sequence which is at least about 85% identical overall to an amino acid sequence set forth in any one of SEQ ID NOS: 2, 4, or 6;

(ii) a wheat starch synthase III (wSSIII) polypeptide, protein or enzyme or functional subunit thereof which comprises an amino acid sequence which is at least about 85% identical overall to an amino acid sequence set forth in any one of SEQ ID NOS: 8 or 10;

(iii) a wheat starch synthase polypeptide, protein or enzyme or functional subunit thereof which comprises a conserved amino acid sequence having at least 25% identity to an amino acid sequence selected from the group consisting of:

(a) KVGGLGDVVTS (SEQ ID NO: 39);
(b) GHTVEVILPKY (SEQ ID NO: 40);
(c) HDWSSAPVAWLYKEHY (SEQ ID NO: 41);
(d) GILNGIDPDIWDPYTD (SEQ ID NO: 42);
(e) DVPIVGIITRLTAQKG (SEQ ID NO: 43);
(f) NGQWLLGSA (SEQ ID NO: 44);
(g) AGSDFIIVPSIFEPCGLTQLVAMRYGS (SEQ ID NO: 45); and
(h) TGGLVDTV (SEQ ID NO: 46);

wherein said wheat starch synthase polypeptide further comprises an amino acid sequence having at least about 85% identity overall to an amino acid sequence set forth in any one of SEQ ID NOS: 2, 4, 6, 8 or 10; and (iv) a wheat starch synthase polypeptide, protein or enzyme or functional subunit thereof which comprises a conserved amino acid sequence having at least 25% identity to an amino acid sequence selected from the group consisting of:

(a) KTGGLGDVAGA (SEQ ID NO: 47);
(b) GHRVMVVVPRY (SEQ ID NO: 48);
(c) NDWHTALLPVYLKAYY (SEQ ID NO: 49);
(d) GIVNGIDNMEWNPEVD (SEQ ID NO: 50);
(e) DVPLLGFIGRLDGQKG (SEQ ID NO: 51);
(f) DVQLVMLGTG (SEQ ID NO: 52);
(g) AGADALLMPSRF(E/V)PCGLNQLYAMAYGT (SEQ ID NO: 53); and
(h) VGG(V/L)RDTV (SEQ ID NO: 54);

wherein said wheat starch synthase polypeptide further comprises an amino acid sequence having at least about 85% identity overall to an amino acid sequence set forth in any one of SEQ ID NOS: 2, 4, 6, 8 or 10.

In a preferred embodiment, the isolated nucleic acid molecule encodes a starch synthase polypeptide, protein or enzyme having at least about 90% amino acid sequence identity to any one of SEQ ID NOS: 2, 4, 6, 8 or 10, more preferably having at least about 95% or about 97% or about 99% identity to any one of said amino acid sequences.

In an alternative embodiment, the isolated nucleic acid molecule of the present invention encodes a wheat starch synthase polypeptide which comprises one or more amino acid sequences selected from the group consisting of:

(A) GHTVEVILPKY (SEQ ID NO:40);
(B) HDWSSAPVAWLYKEHY (SEQ ID NO:41);
(C) DVPIVGIITRLTAQKG (SEQ ID NO:43);
(D) NGQVVLLGSA (SEQ ID NO:44);
(E) AGSDFIIVPSIFEPCGLTQLVAMRYGS (SEQ ID NO:45);
(F) TGGLVDTV (SEQ ID NO:46);
(G) GIVNGIDNMEWNPEVD (SEQ ID NO:50); and
(H) AGADALLMPSRF(E/V)PCGLNQLYAMAYGT (SEQ ID NO:53).

In an alternative embodiment, the present invention provides an isolated nucleic acid molecule which encodes a wheat starch synthase polypeptide, protein or enzyme molecule or a functional subunit thereof, wherein said nucleic acid molecule comprises a nucleotide sequence having at least about 85% nucleotide sequence identity to any one of SEQ ID NOS: 1, 3, 5, 7, 9, 11–16, 37 or 38 or a complementary nucleotide sequence thereto.

In a preferred embodiment, the isolated nucleic acid molecule comprises the nucleotide sequence set forth in any one of SEQ ID NOS: 1, 3, 5, 7, 9, 11–16, 37 or 38, or is at least about 90% identical, more preferably at least about 95% or 97% or 99% identical to all or a protein-encoding part thereof.

In an alternative embodiment, the present invention provides an isolated nucleic acid molecule which encodes a wheat starch synthase polypeptide, protein or enzyme molecule or a functional subunit thereof, wherein said nucleic acid molecule comprises a nucleotide sequence that is capable of hybridising under at least moderate stringency hybridisation conditions to at least about 30 contiguous nucleotides derived from any one of SEQ ID NOS: 1, 3, 5, 7, 9, 11–16, 37 or 38, or a complementary nucleotide sequence thereto.

A second aspect of the present invention provides a method of isolating a nucleic acid molecule that encodes a starch synthase polypeptide, protein or enzyme described supra, said method comprising:

(i) hybridising a probe or primer comprising at least about 15 contiguous nucleotides in length derived from any one of SEQ ID NOS: 1, 3, 5, 7, 9, 11–16, 37 or 38, or a complementary nucleotide sequence thereto to single-stranded or double-stranded mRNA, cDNA or genomic DNA; and (ii) detecting the hybridised mRNA, cDNA or genomic DNA using a detecting means.

Preferably, the detecting means is a reporter molecule covalently attached to the probe or primer molecule or alternatively, a polymerase chain reaction format. Accordingly, the present invention clearly extends to the use of the nucleic acid molecules provided herein to isolate related starch synthase-encoding sequences using standard hybridisation and/or polymerase chain reaction techniques.

A third aspect of the invention provides an isolated probe or primer comprising at least about 15 contiguous nucleotides in length derived from any one of SEQ ID NOS: 1, 3, 5, 7, 9, 11–16, 37 or 38, or a complementary nucleotide sequence thereto.

Preferably, the probe or primer comprises a nucleotide sequence set forth in any one of SEQ ID NOS: 25 to 34.

A fourth aspect of the present invention is directed to an isolated or recombinant starch synthase polypeptide, protein or enzyme, preferably substantially free of conspecific or non-specific proteins, which comprises an amino acid sequence selected from the following:

(i) a wheat starch synthase II (WSSII) polypeptide, protein or enzyme or functional subunit thereof which comprises an amino acid sequence which is at least about 85% identical overall to an amino acid sequence set forth in any one of SEQ ID NOS: 2, 4, or 6;

(ii) a wheat starch synthase III (WSSIII) polypeptide, protein or enzyme or functional subunit thereof which comprises an amino acid sequence which is at least about 85% identical overall to an amino acid sequence set forth in any one of SEQ ID NOS: 8 or 10;

(iii) a wheat starch synthase polypeptide, protein or enzyme or functional subunit thereof which comprises a conserved amino acid sequence having at least 25% identity to an amino acid sequence selected from the group consisting of:

(A) KVGGLGDVVTS (SEQ ID NO:39);

(B) GHTVEVILPKY (SEQ ID NO:40);

(C) HDWSSAPVAWLYKEHY (SEQ ID NO:41);

(D) GILNGIDPDIWDPYTD (SEQ ID NO:42);

(E) DVPIVGIITRLTAQKG (SEQ ID NO:43);

(F) NGQVVLLGSA (SEQ ID NO:44);

(G) AGSDFIIVPSIFEPCGLTQLVAMRYGS (SEQ ID NO:45); and (H) TGGLVDTV (SEQ ID NO:46)

wherein said wheat starch synthase polypeptide further comprises an amino acid sequence having at least about 85% identity overall to an amino acid sequence set forth in any one of SEQ ID NOS:2, 4, 6, 8 or 10; and (iv) a wheat starch synthase polypeptide, protein or enzyme or functional subunit thereof which comprises a conserved amino acid sequence having at least 25% identity to an amino acid sequence selected from the group consisting of:

(A) KTGGLGDVAGA (SEQ ID NO:47);

(B) GHRVMVVVPRY (SEQ ID NO:48);

(C) NDWHTALLPVYLKAYY (SEQ ID NO:49);

(D) GIVNGIDNMEWNPEVD (SEQ ID NO:50);

(E) DVPLLGFIGRLDGQKG (SEQ ID NO:51);

(F) DVQLVMLGTG (SEQ ID NO:52);

(G) AGADALLMPSRF(E/V) PCGLNQLYAMAYGT (SEQ ID NO:53); and (H) VGG(V/L)RDTV (SEQ ID NO:54).

wherein said wheat starch synthase polypeptide further comprises an amino acid sequence having at least about 85% identity overall to an amino acid sequence set forth in any one of SEQ ID NOS: 2, 4, 6, 8 or 10.

The present invention clearly encompasses the mature protein region of a wheat starch synthase polypeptide which is obtained by removal of the N-terminal transit peptide sequence.

A further aspect of the invention provides a method of assaying for the presence or absence of a starch synthase isoenzyme or the copy number of a gene encoding same in a plant, comprising contacting a biological sample derived from said plant with an isolated nucleic acid molecule derived from any one of SEQ ID NOS 1, 3, 5, 7, 9, 11–16, 37 or 38, or any one of SEQ ID NOS: 25 to 34, or a complementary nucleotide sequence thereto for a time and under conditions sufficient for hybridisation to occur and then detecting said hybridisation using a detection means.

The detection means according to this aspect of the invention is any nucleic acid based hybridisation or amplification reaction.

A further aspect of the present invention utilises the above-mentioned assay method in the breeding and/or selection of plants which express or do not express particular starch synthase isoenzymes or alternatively, which express a particular starch synthase isoenzyme at a particular level in one or more plant tissues. This aspect clearly extends to the selection of transformed plant material which contains one or more of the isolated nucleic acid molecules of the present invention.

A further aspect of the present invention provides a method of modifying the starch content and/or starch composition of one or more tissues or organs of a plant, comprising expressing therein a sense molecule, antisense molecule, ribozyme molecule, co-suppression molecule, or gene-targeting molecule having at least about 85% nucleotide sequence identity to any one of any one of SEQ ID NOS: 1, 3, 5, 7, 9, 11–16, 37 or 38, or a complementary nucleotide sequence thereto for a time and under conditions sufficient for the enzyme activity of one or more starch synthase isoenzymes to be modified. This aspect of the invention clearly extends to the introduction of the sense molecule, antisense molecule, ribozyme molecule, co-suppression molecule, or gene-targeting molecule to isolated plant cells, tissues or organs or organelles by cell fusion or transgenic means and the regeneration of intact plants therefrom.

A further aspect of the present invention provides an isolated promoter that is operable in the endosperm of a monocotyledonous plant cell, tissue or organ, and preferably in the endosperm of a monocotyledonous plant cell, tissue or organ. For example, the HMG promoter from wheat, or the maize zein gene promoter are particularly preferred, as is the promoter derived from a starch synthase gene of the present invention, such as a promoter that is linked in vivo to any one of SEQ ID NOS 1, 3, 5, 7, 9, 11–16, 37 or 38, or a complementary nucleotide sequence thereto.

A still further aspect of the present invention contemplates a transgenic plant comprising an introduced sense molecule, antisense molecule, ribozyme molecule, co-suppression molecule, or gene-targeting molecule having at least about 85% nucleotide sequence identity to any one of any one of SEQ ID NOS: 1, 3, 5, 7, 9, 11–16, 37 or 38, or a complementary nucleotide sequence thereto or a genetic construct comprising same, and to plant propagules, cells, tissues, organs or plant parts derived from said transgenic plant that also carry the introduced molecule(s).

BRIEF DESCRIPTION OF THE DRAWINGS

FIG. 2 (Figure panel 2A–2O) is a copy of a schematic representation comparing the nucleotide sequences of cDNA clones designated wSSIIA (SEQ ID NO:3), wSSIIB (SEQ ID NO:1) and wSSIID (SEQ ID NO:5), encoding the starch synthase II polypeptides from wheat, using the PILEUP programme of Devereaux et al. (1984).

DETAILED DESCRIPTION OF THE PREFERRED EMBODIMENTS

Figure 1:
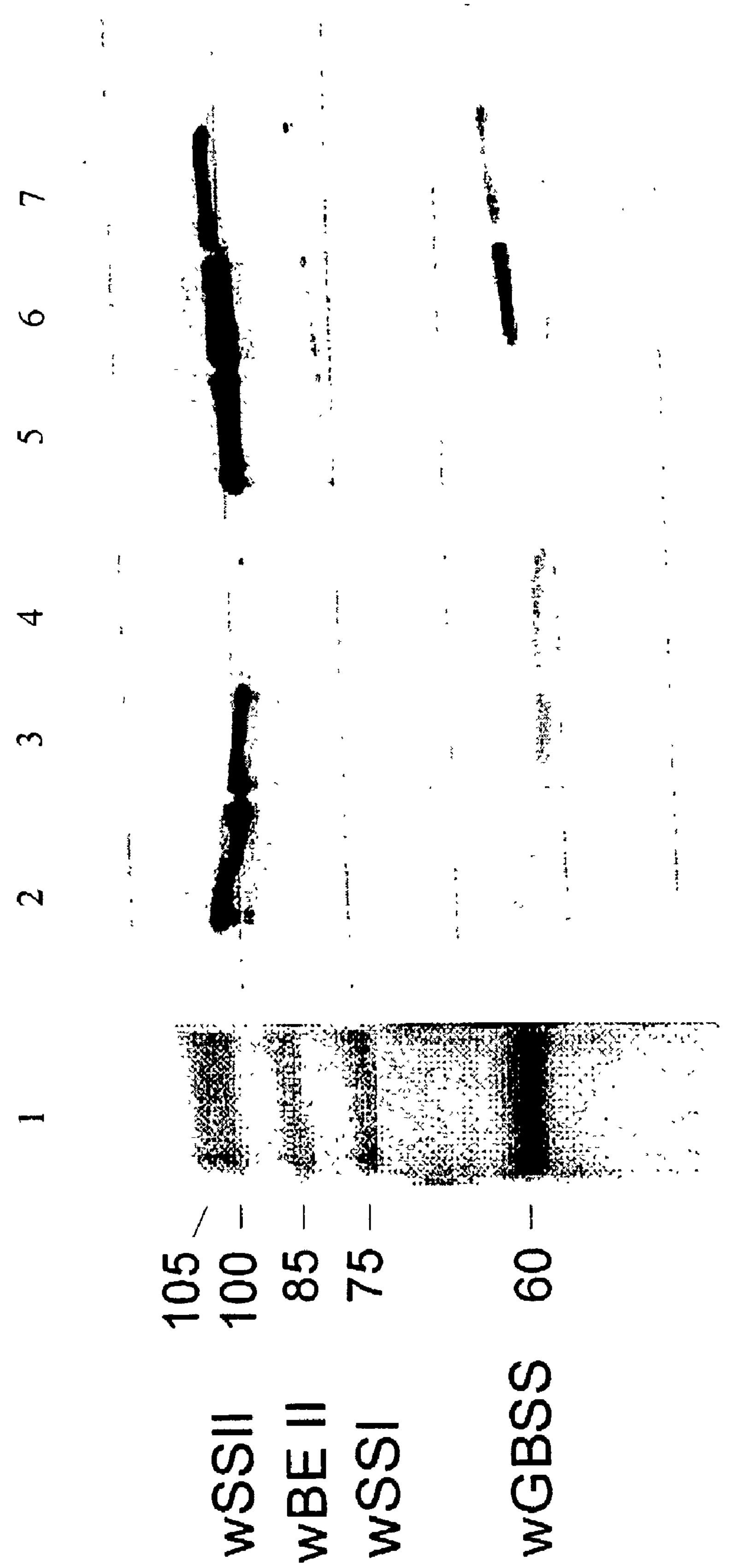
FIG. 1 is a copy of a photographic representation showing the distribution of wheat endosperm starch synthases between the starch granule and soluble fractions. Lane 1, SDS-PAGE of wheat endosperm starch granule proteins revealed by silver staining; lanes 2–7, immunoblot of wheat endosperm soluble phase and starch granule proteins separated by SDS-PAGE from various developmental stages and probed with an anti-(wheat wSSII peptide) monoclonal antibody. Lanes 2–4 contain proteins from the soluble fraction of wheat endosperm at 15 days post anthesis (Lane 2); 20 days post anthesis (Lane 3); and at 25 days post anthesis (Lane 4). Lanes 5–7 contain proteins from the starch granule of wheat endosperm at 15 days post anthesis (Lane 5); 20 days post anthesis (Lane 6); and at 25 days post anthesis (Lane 7).

One aspect of the present invention provides an isolated nucleic acid molecule which comprises a sequence of nucleotides which encodes, or is complementary to a nucleic acid molecule which encodes a wheat starch synthase polypeptide, protein or enzyme molecule or a functional subunit thereof selected from the following:

(i) a wheat starch synthase II (wSSII) polypeptide, protein or enzyme or functional subunit thereof which comprises an amino acid sequence set forth in any one of SEQ ID NOS: 2, 4, or 6; and (ii) a wheat starch synthase III (wSSIII) polypeptide, protein or enzyme or functional subunit thereof which comprises an amino acid sequence set forth in any one of SEQ ID NOS: 8 or 10.

Alternatively or in addition, the isolated nucleic acid molecule of the present invention encodes a wheat starch synthase II (wSSII) polypeptide, protein or enzyme or functional subunit thereof and comprises a nucleotide sequence set forth in any one of SEQ ID NOS: 1, 3, 5, or 37.

Alternatively or in addition, the isolated nucleic acid molecule of the present invention encodes a wheat starch synthase III (wSSIII) polypeptide, protein or enzyme or functional subunit thereof and comprises a nucleotide sequence set forth in any one of SEQ ID NOS: 7, 9, or 38.

As used herein, the term "starch synthase" shall be taken to refer to any enzymatically-active peptide, polypeptide, oligopeptide, polypeptide, protein or enzyme molecule that is at least capable of transferring a glucosyl moiety from ADP-glucose to an α-1,4-glucan molecule, or a peptide, polypeptide, oligopeptide or polypeptide fragment of such an enzymatically-active molecule.

The term "wheat starch synthase" refers to a starch synthase derived from hexaploid wheat or barley or a progenitor species, or a relative thereto such as the diploid *Triticum tauschii* or other diploid, tetraploid, aneuploid, polyploid, nullisomic, or a wheat/barley addition line, amongst others, the only requirement that the genomic DNA is at least about 80% identical to the genome of a wheat plant as determined by standard DNA melting curve analyses.

The term "starch synthase II" or "wSSII" or similar term shall be taken to refer to a starch synthase as hereinbefore defined that is detectable in the starch granule of a plant seed endosperm and possesses one or more properties selected from the group consisting of:

(i) it is immunologically cross-reactive with the wheat starch granule proteins designated Sgp-B1 and/or Sgp-D1 and/or Sgp-A1, having estimated molecular weights of about 85 kDa to about 115 kDa;

(ii) it is encoded by one of a homeologous set of genes localised on wheat chromosomes 7B or 7A or 7D;

(iii) it is encoded by a nucleotide sequence that comprises at least about 15 nucleotides in length derived from any one or more of SEQ ID NOS: 1, 3, 5, or 37 or a complementary nucleotide sequence thereto;

(iv) it is encoded by a nucleotide sequence that is at least about 85% identical to one or more of the nucleotide sequences set forth in SEQ ID NOS: 1, 3, 5, or 37, or a complementary nucleotide sequence thereto;

(v) it comprises an amino acid sequence having at least about 85% identity to one or more of SEQ ID NOS: 2 or 4 or 6;

(vi) it comprises at least about 5 contiguous amino acids, preferably at least about 10 contiguous amino acids, more preferably at least about 15 contiguous amino acids, even more preferably at least about 20 contiguous amino acids and still even more preferably at least about 25–50 contiguous amino acids of the amino acid sequences set forth in SEQ ID NOS: 2 or 4 or 6;

(vii) it which comprises a conserved amino acid sequence having at least 25% identity to an amino acid sequence selected from a group consisting of:

(A) KVGGLGDVVTS (SEQ ID NO:39);
(B) GHTVEVILPKY (SEQ ID NO:40);
(C) HDWSSAPVAWLYKEHY (SEQ ID NO:41);
(D) GILNGIDPDIWDPYTD (SEQ ID NO:42);
(E) DVPIVGIITRLTAQKG (SEQ ID NO:43);
(F) NGQVVLLGSA (SEQ ID NO:44);
(G) AGSDFIIVPSIFEPCGLTQLVAMRYGS (SEQ ID NO:45); and
(H) TGGLVDTV (SEQ ID NO:46), in addition to any one or more of (i) to (vi); and (viii) it which comprises a conserved amino acid sequence having at least 25% identity to an amino acid sequence selected from the group consisting of:

(A) KTGGLGDVAGA (SEQ ID NO:47);
(B) GHRVMVVVPRY (SEQ ID NO:48);
(C) NDWHTALLPVYLKAYY (SEQ ID NO:49);
(D) GIVNGIDNMEWNPEVD (SEQ ID NO:50);
(E) DVPLLGFIGRLDGQKG (SEQ ID NO:51);
(F) DVQLVMLGTG (SEQ ID NO:52);
(G) AGADALLMPSRF (E/V) PCGLNQLYAMAYGT (SEQ ID NO:53); and
(H) VGG(V/L)RDTV (SEQ ID NO:54), The term "starch synthase III" or "wSSIII" or similar term shall be taken to refer to a starch synthase as hereinbefore defined that possesses one or more properties selected from the group consisting of:

(i) it is encoded by a nucleotide sequence that comprises at least about 15 nucleotides in length derived from any one or more of SEQ ID NOS: 7, 9, 11–16, or 38, or a complementary nucleotide sequence thereto;

(ii) it is encoded by a nucleotide sequence that is at least about 85% identical to one or more of the nucleotide sequences set forth in SEQ ID NOS: 7, 9, 11–16, or 38, or a complementary nucleotide sequence thereto; and (iii) it comprises an amino acid sequence having at least about 85% identity to one or more of SEQ ID NOS: 8 or 10;

(iv) it comprises at least about 5 contiguous amino acids, preferably at least about 10 contiguous amino acids, more preferably at least about 15 contiguous amino acids, even more preferably at least about 20 contiguous amino acids and still even more preferably at least about 25–50 contiguous amino acids of the amino acid sequences set forth in SEQ ID NOS: 8 or 10;

(v) which comprises a conserved amino acid sequence having at least 25% identity to an amino acid sequence selected from the group consisting of:

(A) KVGGLGDVVTS (SEQ ID NO:39);
(B) GHTVEVILPKY (SEQ ID NO:40);
(C) HDWSSAPVAWLYKEHY (SEQ ID NO:41);
(D) GILNGIDPDIWDPYTD (SEQ ID NO:42);
(E) DVPIVGIITRLTAQKG (SEQ ID NO:43);
(F) NGQVVLLGSA (SEQ ID NO:44);
(G) AGSDFIIVPSIFEPCGLTQLVAMRYGS (SEQ ID NO:45); and
(H) TGGLVDTV (SEQ ID NO:46) in addition to any one or more of (i) to (iv); and (vi) it which comprises a conserved amino acid sequence having at least 25% identity to an amino acid sequence selected from the group consisting of:

(A) KTGGLGDVAGA (SEQ ID NO:47);
(B) GHRVMVVVPRY (SEQ ID NO:48);
(C) NDWHTALLPVYLKAYY (SEQ ID NO:49);
(D) GIVNGIDNMEWNPEVD (SEQ ID NO:50);
(E) DVPLLGFIGRLDGQKG (SEQ ID NO:51);
(F) DVQLVMLGTG (SEQ ID NO:52);
(G) AGADALLMPSRF(E/V) PCGLNQLYAMAYGT (SEQ ID NO:53); and
(H) VGG(V/L)RDTV (SEQ ID NO:54), in addition to any one or more of (i) to (iv).

In a more preferred embodiment, the WSSII or WSSIII polypeptide encoded by the nucleic acid molecule of the present invention will comprise a substantial contiguous region of any one of SEQ ID NOS: 2, 4, 6, 8 or 10 or 17 sufficient to possess the biological activity of a starch synthase polypeptide.

For the purposes of nomenclature, the nucleotide sequence set forth in SEQ ID NO: 1 relates to the cDNA molecule encoding the WSSII (i.e. Sgp-B1) polypeptide of wheat. The amino acid sequence of the corresponding polypeptide is set forth herein as SEQ ID NO:2. The nucleotide sequence set forth in SEQ ID NO: 3 relates to the cDNA molecule encoding the WSSII (i.e. Sgp-A1) polypeptide of wheat. The amino acid sequence of the corresponding polypeptide is set forth herein as SEQ ID NO:4. The nucleotide sequence set forth in SEQ ID NO: 5 relates to the cDNA molecule encoding the WSSII (i.e. Sgp-D1) polypeptide of wheat. The amino acid sequence of the corresponding polypeptide is set forth herein as SEQ ID NO:6. The nucleotide sequences set forth in SEQ ID NOs: 7 and 9 relate, respectively, to full-length and partial cDNA molecules encoding the WSSIII polypeptide of wheat. The amino acid sequences of the corresponding polypeptides are set forth herein as SEQ ID NOS: 8 and 10, respectively. The nucleotide sequences set forth in SEQ ID NOs: 11 to 16 relates to fragments of the genomic gene encoding the WSSIII polypeptide of wheat, significant protein-encoding regions of which are described by reference to Table 4 and FIG. 11. The nucleotide sequence set forth in SEQ ID NO: 37 relates to the WSSII genomic gene of *Triticum tauschii*, corresponding to the WSSII gene of the D-genome of wheat, which encodes the WSSIII polypeptide. The nucleotide sequence set forth in SEQ ID NO: 38 relates to the wheat WSSIII genomic gene.

Preferably, the isolated nucleic acid molecule of the present invention comprises a sequence of nucleotides which encodes, or is complementary to a nucleic acid molecule which encodes a wheat starch synthase polypeptide, protein or enzyme molecule or a functional subunit thereof which comprises an amino acid sequence which is at least about 85% identical overall to an amino acid sequence set forth in any one of SEQ ID NOS: 2, 4, 6, 8 or 10 and more preferably, which additionally comprises which comprises one or more amino acid sequences selected from the group consisting of:

(A) KVGGLGDVVTS (SEQ ID NO:39);
(B) GHTVEVILPKY (SEQ ID NO:40);
(C) HDWSSAPVAWLYKEHY (SEQ ID NO:41);
(D) GILNGIDPDIWDPYTD (SEQ ID NO:42);
(E) DVPIVGIITRLTAQKG (SEQ ID NO:43);
(F) NGQVVLLGSA (SEQ ID NO:44);
(G) AGSDFIIVPSIFEPCGLTQLVAMRYGS (SEQ ID NO:45); and
(H) TGGLVDTV (SEQ ID NO:46);
(I) KTGGLGDVAGA (SEQ ID NO:47);
(J) GHRVMVVVPRY (SEQ ID NO:48);
(K) NDWHTALLPVYLKAYY (SEQ ID NO:49);
(L) GIVNGIDNMEWNPEVD (SEQ ID NO:50);
(M) DVPLLGFIGRLDGQKG (SEQ ID NO:51);
(N) DVQLVMLGTG (SEQ ID NO:52);
(O) AGADALLMPSRF(E/V) PCGLNQLYAMAYGT (SEQ ID NO: 53); and
(P) VGG(V/L)RDTV (SEQ ID NO:54).

The present invention clearly extends to homologues, analogues and derivatives of the wheat starch synthase II and III genes exemplified by the nucleotide sequences set forth herein as SEQ ID NOs: 1, 3, 5, 7, 9, 11–16, 37 or 38.

Preferred starch synthase genes may be derived from a naturally-occurring starch synthase gene by standard recombinant techniques. Generally, a starch synthase gene may be subjected to mutagenesis to produce single or multiple nucleotide substitutions, deletions and/or additions. Nucleotide insertional derivatives of the starch synthase gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

The present invention extends to the isolated nucleic acid molecule when integrated into the genome of a cell as an addition to the endogenous cellular complement of starch synthase genes, irrespective of whether or not the introduced nucleotide sequence is translatable or non-translatable to produce a polypeptide. The present invention clearly contemplates the introduction of additional copies of starch synthase genes into plants, particularly wheat plants, in the antisense orientation to reduce the expression of particular wheat starch synthase genes. As will be known to those skilled in the art, such antisense genes are non-translatable, notwithstanding that they can be expressed to produce antisense mRNA molecules.

The said integrated nucleic acid molecule may, or may not, contain promoter sequences to regulate expression of the subject genetic sequence.

Accordingly, the present invention clearly encompasses preferred homologues, analogues and derivatives that comprise a sequence of nucleotides which encodes, or is complementary to a nucleic acid molecule which encodes a wheat starch synthase polypeptide, protein or enzyme molecule or a functional subunit thereof selected from the following:

(i) a wheat starch synthase II (wSSII) polypeptide, protein or enzyme or functional subunit thereof which comprises an amino acid sequence which is at least about 85% identical overall to an amino acid sequence set forth in any one of SEQ ID NOS: 2, 4, or 6;

(ii) a wheat starch synthase III (wSSIII) polypeptide, protein or enzyme or functional subunit thereof which comprises an amino acid sequence which is at least about 85% identical overall to an amino acid sequence set forth in any one of SEQ ID NOS: 8 or 10;

(iii) a wheat starch synthase polypeptide, protein or enzyme or functional subunit thereof which comprises a conserved amino acid sequence having at least 25% identity to an amino acid sequence selected from the group consisting of:
(A) KVGGLGDVVTS (SEQ ID NO:39);
(B) GHTVEVILPKY (SEQ ID NO:40);
(C) HDWSSAPVAWLYKEHY (SEQ ID NO:41);
(D) GILNGIDPDIWDPYTD (SEQ ID NO:42);
(E) DVPIVGIITRLTAQKG (SEQ ID NO:43);
(F) NGQVVLLGSA (SEQ ID NO:44);
(G) AGSDFIIVPSIFEPCGLTQLVAMRYGS (SEQ ID NO:45); and
(H) TGGLVDTV (SEQ ID NO:46)
and wherein said wheat starch synthase polypeptide further comprises an amino acid sequence having at least about 85% identity overall to an amino acid sequence set forth in any one of SEQ ID NOS:2, 4, 6, 8 or 10; and (iv) a wheat starch synthase polypeptide, protein or enzyme or functional subunit thereof which comprises a conserved amino acid sequence having at least 25% identity to an amino acid sequence selected from the group consisting of:
(A) KTGGLGDVAGA (SEQ ID NO:47);
(B) GHRVMVVVPRY (SEQ ID NO:48);
(C) NDWHTALLPVYLKAYY (SEQ ID NO:49);
(D) GIVNGIDNMEWNPEVD (SEQ ID NO:50);
(E) DVPLLGFIGRLDGQKG (SEQ ID NO:51);
(F) DVQLVMLGTG (SEQ ID NO:52);
(G) AGADALLMPSRF(E/V) PCGLNQLYAMAYGT (SEQ ID NO:53); and
(H) VGG(V/L)RDTV (SEQ ID NO:54),
and wherein said wheat starch synthase polypeptide further comprises an amino acid sequence having at least about 85% identity overall to an amino acid sequence set forth in any one of SEQ ID NOS:2, 4, 6, 8 or 10.

Preferably, the isolated nucleic acid molecule encodes a starch synthase polypeptide, protein or enzyme that comprises two, more preferably three, more preferably four, more preferably five, more preferably six, more preferably seven and even more preferably eight of the conserved amino acid motifs listed supra. Even more preferably, the said amino acid motifs are located in a relative configuration such as that shown for the wheat SSII or wheat SSIII polypeptides described herein.

In a preferred embodiment, the isolated nucleic acid molecule encodes a starch synthase polypeptide, protein or enzyme having at least about 90% amino acid sequence identity to any one of SEQ ID NOS: 2, 4, 6, 8 or 10, more preferably having at least about 95% or about 97% or about 99% identity to any one of said amino acid sequences.

In an alternative embodiment, the present invention provides an isolated nucleic acid molecule which encodes a wheat starch synthase polypeptide, protein or enzyme molecule or a functional subunit thereof, wherein said nucleic acid molecule comprises a nucleotide sequence having at least about 85% nucleotide sequence identity to any one of SEQ ID NOS: 1, 3, 5, 7, 9, 11–16, 37, or 38, or a degenerate nucleotide sequence thereto or a complementary nucleotide sequence thereto.

By "degenerate nucleotide sequence" is meant a nucleotide sequence that encodes a substantially identical amino acid sequence as a stated nucleotide sequence.

In a preferred embodiment, the isolated nucleic acid molecule comprises the nucleotide sequence set forth in any one of SEQ ID NOS: 1, 3, 5, 7, 9, 11–16, 37, or 38, or is at least about 90% identical, more preferably at least about 95% or 97% or 99% identical to all or a protein-encoding part thereof.

In an alternative embodiment, preferred homologues, analogues and derivatives of the nucleic acid molecule of the present invention encodes a wheat starch synthase polypeptide, protein or enzyme molecule or a functional subunit thereof and comprises a nucleotide sequence that is capable of hybridising under at least moderate stringency hybridisation conditions to at least about 30 contiguous nucleotides derived from any one of SEQ ID NOS: 1, 3, 5, 7, 9, 11–16, 37, or 38, or a complementary nucleotide sequence thereto.

For the purposes of defining the level of stringency, a low stringency is defined herein as being a hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. A moderate stringency comprises a hybridisation and/or a wash carried out in 0.2×SSC-2×SSC buffer, 0.1% (w/v) SDS at 42° C. to 65° C., while a high stringency comprises a hybridisation and/or a wash carried out in 0.1×SSC-0.2×SSC buffer, 0.1% (w/v) SDS at a temperature of at least 55° C. Conditions for hybridisations and washes are well understood by one normally skilled in the art. For the purposes of further clarification only, reference to the parameters affecting hybridisation between nucleic acid molecules is found in pages 2.10.8 to 2.10.16. of Ausubel et al. (1987), which is herein incorporated by reference.

Those skilled in the art will be aware of procedures for the isolation of further wheat starch synthase genes to those specifically described herein or homologues, analogues or derivatives of said genes, for example further cDNA sequences and genomic gene equivalents, when provided with one or more of the nucleotide sequences set forth in SEQ ID NOs: 1, 3, 5, 7, 9, 11–16, 37, or 38. In particular, amplifications and/or hybridisations may be performed using one or more nucleic acid primers or hybridisation probes comprising at least 10 contiguous nucleotides and preferably at least about 20 contiguous nucleotides or 50 contiguous nucleotides derived from the nucleotide sequences set forth herein, to isolate cDNA clones, mRNA molecules, genomic clones from a genomic library (in particular genomic clones containing the entire 5' upstream region of the gene including the promoter sequence, and the entire coding region and 3'-untranslated sequences), and/or synthetic oligonucleotide molecules, amongst others. The present invention clearly extends to such related sequences.

Accordingly, a second aspect of the present invention provides a method of isolating a nucleic acid molecule that encodes a starch synthase polypeptide, protein or enzyme said method comprising:

(i) hybridising a probe or primer comprising at least about 15 contiguous nucleotides in length derived from any one of SEQ ID NOS 1, 3, 5, 7, 9, 11–16, 37, or 38, or a complementary nucleotide sequence thereto to single-stranded or double-stranded mRNA, cDNA or genomic DNA; and (ii) detecting the hybridised mRNA, cDNA or genomic DNA using a detecting means.

Preferably, the detecting means is a reporter molecule covalently attached to the probe or primer molecule or alternatively, a polymerase chain reaction format.

An alternative method contemplated in the present invention involves hybridising two nucleic acid “primer molecules” to a nucleic acid “template molecule” which comprises a related starch synthase gene or related starch synthase genetic sequence or a functional part thereof, wherein the first of said primers comprises contiguous nucleotides derived from any one or more of SEQ ID NOS: 1, 3, 5, 7, 9, 11–16, 37, or 38, and the second of said primers comprises contiguous nucleotides complementary to any one or more of SEQ ID NOS: 1, 3, 5, 7, 9, 11–16, 37, or 38. Specific nucleic acid molecule copies of the template molecule are amplified enzymatically in a polymerase chain reaction, a technique that is well known to one skilled in the art.

In a preferred embodiment, each nucleic acid primer molecule is at least 10 nucleotides in length, more preferably at least 20 nucleotides in length, even more preferably at least 30 nucleotides in length, still more preferably at least 40 nucleotides in length and even still more preferably at least 50 nucleotides in length.

Furthermore, the nucleic acid primer molecules consists of a combination of any of the nucleotides adenine, cytidine, guanine, thymidine, or inosine, or functional analogues or derivatives thereof which are at least capable of being incorporated into a polynucleotide molecule without having an inhibitory effect on the hybridisation of said primer to the template molecule in the environment in which it is used.

Furthermore, one or both of the nucleic acid primer molecules may be contained in an aqueous mixture of other nucleic acid primer molecules, for example a mixture of degenerate primer sequences which vary from each other by one or more nucleotide substitutions or deletions. Alternatively, one or both of the nucleic acid primer molecules may be in a substantially pure form.

The nucleic acid template molecule may be in a recombinant form, in a virus particle, bacteriophage particle, yeast cell, animal cell, or a plant cell. Preferably, the nucleic acid template molecule is derived from a plant cell, tissue or organ, in particular a cell, tissue or organ derived from a wheat or barley plant or a progenitor species, or a relative thereto such as the diploid *Triticum tauschii* or other diploid, tetraploid, aneuploid, polyploid, nullisomic, or a wheat/barley addition line, amongst others.

Those skilled in the art will be aware that there are many known variations of the basic polymerase chain reaction procedure, which may be employed to isolate a related starch synthase gene or related starch synthase genetic sequence when provided with the nucleotide sequences set forth herein. Such variations are discussed, for example, in McPherson et al (1991). The present invention extends to the use of all such variations in the isolation of related starch synthase genes or related starch synthase genetic sequences using the nucleotide sequences embodied by the present invention.

As exemplified herein, the present inventors have isolated several wheat starch synthase genes using both hybridisation and polymerase chain reaction approaches, employing novel probes and primer sequences to do so.

Accordingly, a third aspect of the invention provides an isolated probe or primer comprising at least about 15 contiguous nucleotides in length derived from any one of SEQ ID NOS: 1, 3, 5, 7, 9, 11–16, 37, or 38, or a complementary nucleotide sequence thereto.

Preferably, the probe or primer comprises a nucleotide sequence set forth in any one of SEQ ID NOS: 25 to 34.

The isolated nucleic acid molecule of the present invention may be introduced into and expressed in any cell, for example a plant cell, fungal cell, insect cell, animal cell, yeast cell or bacterial cell. Those skilled in the art will be aware of any modifications which are required to the codon usage or promoter sequences or other regulatory sequences, in order for expression to occur in such cells.

A further aspect of the invention provides a method of assaying for the presence or absence of a starch synthase isoenzyme or the copy number of a gene encoding same in a plant, comprising contacting a biological sample derived from said plant with an isolated nucleic acid molecule derived from any one of SEQ ID NOS 1, 3, 5, 7, 9, 11–16, 37, or 38, or any one of SEQ ID NOS: 25 to 34, or a complementary nucleotide sequence thereto for a time and under conditions sufficient for hybridisation to occur and then detecting said hybridisation using a detection means.

The detection means according to this aspect of the invention is any nucleic acid based hybridisation or amplification reaction.

Figure 13:
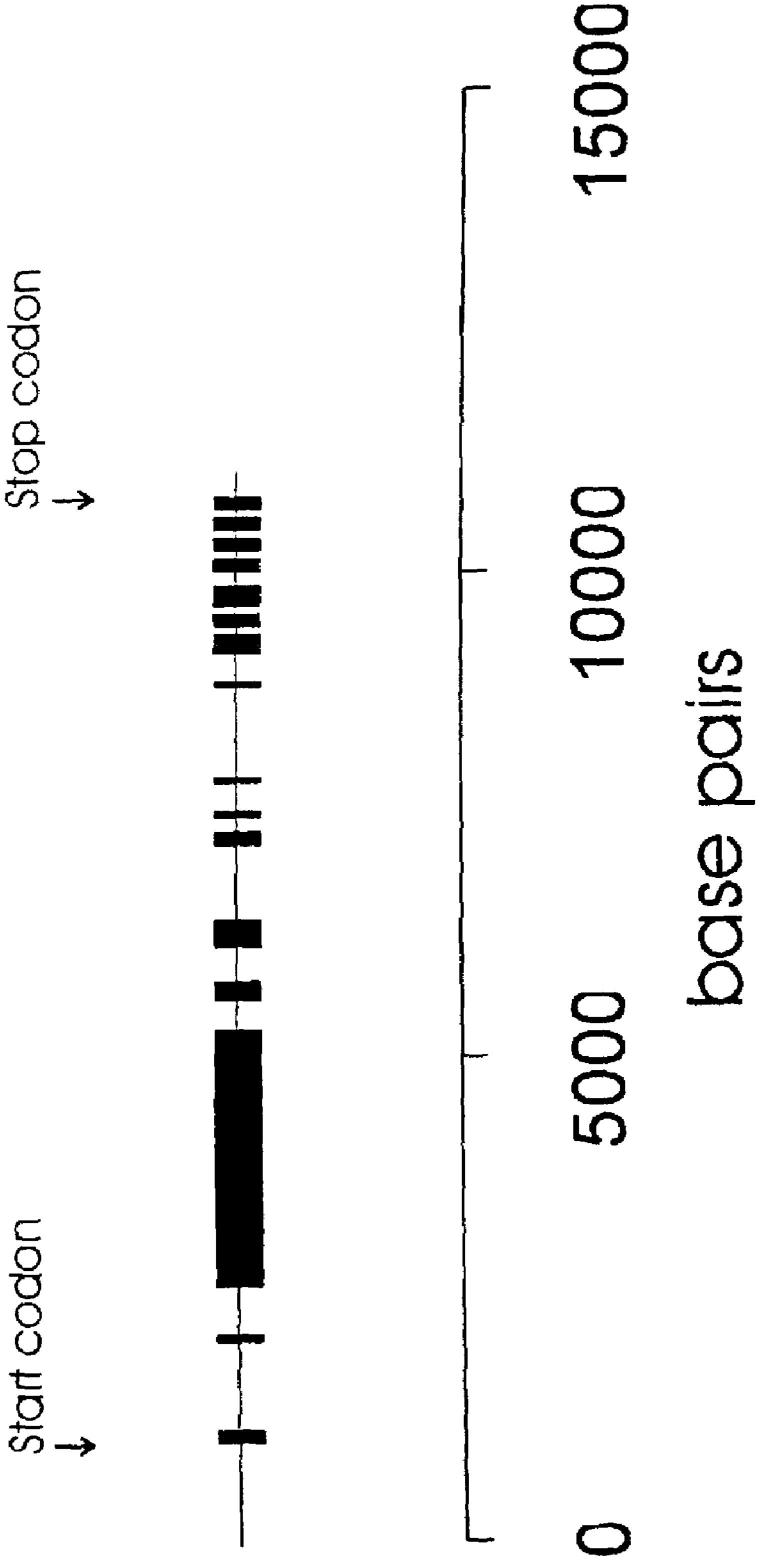
FIG. 13 is a schematic representation showing the organisation of introns (lines) and exons (boxes) in the wheat SSIII gene shown in SEQ ID NO: 38. The scale (bases), relative to the nucleotide sequence set forth in SEQ ID NO: 38, is provided at the bottom of the figure.

The hexaploid nature of wheat prevents the straightforward identification of starch synthase allelic variants by hybridisation using the complete starch synthase-encoding sequence, because the similarities between the various alleles generally results in significant cross-hybridisation. Accordingly, sequence-specific hybridisation probes are required to distinguish between the various alleles. Similarly, wherein PCR is used to amplify specific allelic variants of a starch synthase gene, one or more sequence-specific amplification primers are generally required. As will be apparent from the amino acid sequence comparisons provided herein, such as in FIGS. 3 and 13, non-conserved regions of particular wheat starch synthase polypeptides are particularly useful for the design of probes and primers that are capable of distinguishing between one or more starch synthase polypeptide isoenzyme or allelic variant. The present invention clearly contemplates the design of such probes and primers based upon the sequence comparisons provided herein.

In the performance of this embodiment of the present invention, the present inventors particularly contemplate the identification of wheat starch synthase null alleles or alternatively, mutations wherein specific amino acids are inserted or deleted or substituted, compared to one or more of the wheat SSII or SSIII alleles disclosed herein. Such null alleles and other allelic variants are readily identifiable using PCR screening which employs amplification primers based upon the nucleotide and amino acid sequences disclosed herein for SSII and/or SSIII. Once identified, the various mutations can be stacked or pyramided into one or more new wheat lines, such as by introgression and/or standard plant breeding and/or recombinant approaches (eg. transformation, transfection, etc) thereby producing a novel germplasm which exhibits altered starch properties compared to existing lines. DNA markers based upon the nucleotide and amino acid sequences disclosed herein for SSII and/or SSIII can be employed to monitor the stacking of genes into the new lines and to correlate the presence of particular genes with starch phenotypes of said lines.

In this regard, a significant advantage conferred by the present invention is the design of new DNA markers that reveal polymorphisms such as, for example, length polymorphisms, restriction site polymorphisms, and single nucleotide polymorphisms, amongst others, between wheat starch synthases and, in particular, between wheat GBSS and/or SSI and/or SSII and/or SSIII, or between allelic variants of one or more of said starch synthases, that can be used to identify the three genomes of hexaploid wheats (i.e., the A, B and D genomes).

Preferably, such DNA markers are derived from the intron region of a starch synthase gene disclosed herein, more preferably the wheat SSII and/or the wheat SSIII gene. Those skilled in the art will be aware that such regions generally have a higher degree of variation than in the protein-encoding regions and, as a consequence, are particularly useful in identifying specific allelic variants of a particular gene, such as allelic variants contained in any one of the three wheat genomes, or alternatively or in addition, for the purpose of distinguishing between wheat GBSS, SSI, SSII or SSIII genes.

A further approach contemplated by the present inventors is the design of unique isoenzyme-specific and/or allele-specific peptides based upon the amino acid sequence disclosed herein as SEQ ID NOS: 25 and/or SEQ ID NO: 4 and/or SEQ ID NO: 6 and/or SEQ ID NO: 8 and/or SEQ ID NO: 10, which peptides are then used to produce polyclonal or monoclonal antibodies by conventional means. Alternatively, the genes encoding these polypeptides or unique peptide regions thereof can be introduced in an expressible format into an appropriate prokaryotic or eukaryotic expression system, where they can be expressed to produce the isoenzyme-specific and/or allele-specific peptides for antibody production. Such antibodies may also be used as markers for the purpose of both identifying parental lines and germplasms and monitoring the stacking of genes in new lines, using conventional immunoassays such as, for example, ELISA and western blotting.

A further aspect of the present invention utilises the above-mentioned nucleic acid based assay method in the breeding and/or selection of plants which express or do not express particular starch synthase isoenzymes or alternatively, which express a particular starch synthase isoenzyme at a particular level in one or more plant tissues. This aspect clearly extends to the selection of transformed plant material which contains one or more of the isolated nucleic acid molecules of the present invention.

Yet another aspect of the present invention provides for the expression of the nucleic acid molecule of the present invention in a suitable host (e.g. a prokaryote or eukaryote) to produce full length or non-full length recombinant starch synthase gene products.

Hereinafter the term "starch synthase gene product" shall be taken to refer to a recombinant product of a starch synthase gene of the present invention.

Preferably, the recombinant starch synthase gene product comprises an amino acid sequence having the catalytic activity of a starch synthase polypeptide or a functional mutant, derivative part, fragment, or analogue thereof.

In a particularly preferred embodiment of the invention, the recombinant starch synthase gene product is selected from the following:

(i) a wheat starch synthase II (WSSII) polypeptide, protein or enzyme or functional subunit thereof which comprises an amino acid sequence which is at least about 85% identical overall to an amino acid sequence set forth in any one of SEQ ID NOS: 2,4, or 6;

(ii) a wheat starch synthase III (wSSIII) polypeptide, protein or enzyme or functional subunit thereof which comprises an amino acid sequence which is at least about 85% identical overall to an amino acid sequence set forth in any one of SEQ ID NOS: 8 or 10; and (iii) a wheat starch synthase polypeptide, protein or enzyme or functional subunit thereof which comprises a conserved amino acid sequence having at least 25% identity to an amino acid sequence selected from the group consisting of:
- (A) KVGGLGDVVTS (SEQ ID NO:39);
- (B) GHTVEVILPKY (SEQ ID NO:40);
- (C) HDWSSAPVAWLYKEHY (SEQ ID NO:41);
- (D) GILNGIDPDIWDPYTD (SEQ ID NO:42);
- (E) DVPIVGIITRLTAQKG (SEQ ID NO:43);
- (F) NGQVVLLGSA (SEQ ID NO:44);
- (G) AGSDFIIVPSIFEPCGLTQLVAMRYGS (SEQ ID NO:45);
- (H) TGGLVDTV (SEQ ID NO:46);

(i) a wheat starch synthase ii (wSSII) polypeptide, protein or enzyme or functional subunit thereof which comprises an amino acid sequence which is at least about 85% identical overall to an amino acid sequence set forth in any one of SEQ ID NOS:2, 4 or 6;

(ii) a wheat starch synthase III (wSSIII) polypeptide, protein or enzyme or functional subunit thereof which comprises an amino acid sequence which is at least about 85% identical overall to an amino acid sequence set forth in any one of SEQ ID NOS: 8 or 10;

(iii) a wheat starch synthase polypeptide, protein or enzyme or functional subunit thereof which comprises a conserved amino acid sequence having at least 25% identity to an amino acid sequence selected from the group consisting of:
- (A) KVGGLGDVVTS (SEQ ID NO:39);
- (B) GHTVEVILPKY (SEQ ID NO:40);
- (C) HDWSSAPVAWLYKEHY (SEQ ID NO:41);
- (D) GILNGIDPDIWDPYTD (SEQ ID NO:42);
- (E) DVPIVGIITRLTAQKG (SEQ ID NO:43);
- (F) NGQVVLLGSA (SEQ ID NO:44);
- (G) AGSDFIIVPSIFEPCGLTQLVAMRYGS (SEQ ID NO:45); and
- (H) TGGLVDTV (SEQ ID NO:46);
- (I) KTGGLGDVAGA (SEQ ID NO:47);
- (J) GHRVMVVVPRY (SEQ ID NO:48);
- (K) NDWHTALLPVYLKAYY (SEQ ID NO:49);
- (L) GIVNGIDNMEWNPEVD (SEQ ID NO:50);
- (M) DVPLLGFIGRLDGQKG (SEQ ID NO:51);
- (N) DVQLVMLGTG (SEQ ID NO:52);
- (O) AGADALLMPSRF(E/V) PCGLNQLYAMAYGT (SEQ ID NO: 53); and
- (P) VGG(V/L)RDTV (SEQ ID NO:54).

Accordingly, the present invention clearly extends to homologues, analogues and derivatives of the amino acid sequences set forth herein as SEQ ID NOS: 2, 4, 6, 8 and 10.

In the present context, "homologues" of an amino acid sequence refer to those polypeptides, enzymes or proteins which have a similar catalytic activity to the amino acid sequences described herein, notwithstanding any amino acid substitutions, additions or deletions thereto. A homologue may be isolated or derived from the same or another plant species as the species from which the polypeptides of the invention are derived.

"Analogues" encompass polypeptides of the invention notwithstanding the occurrence of any non-naturally occurring amino acid analogues therein.

"Derivatives" include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are particularly contemplated by the present invention. Additionally, derivatives of an amino acid sequence described herein which comprises fragments or parts of the subject amino acid sequences are within the scope of the invention, as are homopolymers or heteropolymers comprising two or more copies of the subject polypeptides. Procedures for derivatizing peptides are well-known in the art.

Substitutions encompass amino acid alterations in which an amino acid is replaced with a different naturally-occurring or a non-conventional amino acid residue. Such substitutions may be classified as "conservative", in which an amino acid residue contained in a starch synthase gene product is replaced with another naturally-occurring amino acid of similar character, for example Gly↔Ala, Val↔Ile ↔Leu, Asp↔Glu, Lys↔Arg, Asn↔Gln or Phe↔Trp↔Tyr.

Substitutions encompassed by the present invention may also be "non-conservative", in which an amino acid residue which is present in a starch synthase gene product described herein is substituted with an amino acid with different properties, such as a naturally-occurring amino acid from a different group (eg. substituted a charged or hydrophobic amino acid with alanine), or alternatively, in which a naturally-occurring amino acid is substituted with a non-conventional amino acid.

Non-conventional amino acids encompassed by the invention include, but are not limited to those listed in Table 2.

Amino acid substitutions are typically of single residues, but may be of multiple residues, either clustered or dispersed.

Amino acid deletions will usually be of the order of about 1–10 amino acid residues, while insertions may be of any length. Deletions and insertions may be made to the N-terminus, the C-terminus or be internal deletions or insertions. Generally, insertions within the amino acid sequence will be smaller than amino- or carboxy-terminal fusions and of the order of 1–4 amino acid residues.

A homologue, analogue or derivative of a starch synthase gene product as referred to herein may readily be made using peptide synthetic techniques well-known in the art, such as solid phase peptide synthesis and the like, or by recombinant DNA manipulations. Techniques for making substituent mutations at pre-determined sites using recombinant DNA technology, for example by M13 mutagenesis, are also well-known. The manipulation of nucleic acid molecules to produce variant peptides, polypeptides or proteins which manifest as substitutions, insertions or deletions are ell-known in the art.

The starch synthase gene products described herein may be derivatized further by the inclusion or attachment thereto of a protective group which prevents, inhibits or slows proteolytic or cellular degradative processes. Such derivatization may be useful where the half-life of the subject polypeptide is required to be extended, for example to increase the amount of starch produced in the endosperm or alternatively, to increase the amount of protein produced in a bacterial or eukaryotic expression system. Examples of chemical groups suitable for this purpose include, but are not limited to, any of the non-conventional amino acid residues listed in Table 2, in particular a D-stereoisomer or a methylated form of a naturally-occurring amino acid listed in Table 1. Additional chemical groups which are useful for this purpose are selected from the list comprising aryl or heterocyclic N-acyl substituents, polyalkylene oxide moieties, desulphatohirudin muteins, alpha-muteins, alpha-aminophosphonic acids, water-soluble polymer groups such as polyethylene glycol attached to sugar residues using hydrazone or oxime groups, benzodiazepine dione derivatives, glycosyl groups such as beta-glycosylamine or a derivative thereof, isocyanate conjugated to a polyol functional group or polyoxyethylene polyol capped with diisocyanate, amongst others. Similarly, a starch synthase gene product or a homologue, analogue or derivative thereof may be cross-linked or fused to itself or to a protease inhibitor peptide, to reduce susceptibility of said molecule to proteolysis.

In a particularly preferred embodiment, the percentage similarity to in any one of SEQ ID NOS: 2, 4, 6, 8 or 10 is at least about 90%, more preferably at least about 95%, even more preferably at least about 97% and even more preferably at least about 98%, or about 99% or 100%.

In a related embodiment, the present invention provides a "sequencably pure" form of the amino acid sequence described herein. "Sequencably pure" is hereinbefore described as substantially homogeneous to facilitate amino acid determination.

In a further related embodiment, the present invention provides a "substantially homogeneous" form of the subject amino acid sequence, wherein the term "substantially homogeneous" is hereinbefore defined as being in a form suitable for interaction with an immunologically interactive molecule. Preferably, the polypeptide is at least 20% homogeneous, more preferably at least 50% homogeneous, still more preferably at least 75% homogeneous and yet still more preferably at least about 95–100% homogenous, in terms of activity per microgram of total protein in the protein preparation.

To produce the recombinant polypeptide of the present invention, the coding region of a starch synthase gene described herein or a functional homologue, analogue or derivative thereof is placed operably in connection with a promoter sequence in the sense orientation, such that a starch synthase gene product is capable of being expressed under the control of said promoter sequence.

In the present context, the term "in operable connection with" means that expression of the isolated nucleotide sequence is under the control of the promoter sequence with which it is connected, regardless of the relative physical distance of the sequences from each other or their relative orientation with respect to each other.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a structural gene or other nucleic acid molecule, particularly in a plant cell and more preferably in a wheat plant or other monocotyledonous plant cell, tissue or organ. Preferred promoters may contain additional copies of one or more specific regulatory elements, to further enhance expression and/or to alter the spatial expression and/or temporal expression. For example, regulatory elements which confer copper inducibility may be placed adjacent to a heterologous promoter sequence, thereby conferring copper inducibility on the expression of said molecule.

Those skilled in the art will be aware that in order to obtain optimum expression of the starch synthase gene of the present invention, it is necessary to position said gene in an appropriate configuration such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for expressing the starch synthase gene of the present invention include viral, fungal, bacterial, animal and plant derived promoters capable of functioning in prokaryotic or eukaryotic cells. Preferred promoters are those capable of regulating the expression of the subject starch synthase genes in plants cells, fungal cells, insect cells, yeast cells, animal cells or bacterial cells, amongst others. Particularly preferred promoters are capable of regulating expression of the subject nucleic acid molecules in monocotyledonous plant cells. The promoter may regulate the expression of the said molecule constitutively, or differentially with respect to the tissue in which expression occurs or, with respect to the developmental stage at which expression occurs, or in response to external stimuli such as physiological stresses, or plant pathogens, or metal ions, amongst others.

Accordingly, strong constitutive promoters are particularly preferred for the purposes of the present invention.

Examples of preferred promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter, SCSV promoter, SCBV promoter and the like.

Particularly preferred promoters operable in plant cells include, for example the CaMV 35S promoter, and the SCBV promoter. Those skilled in the art will readily be aware of additional promoter sequences other than those specifically described.

In a particularly preferred embodiment, the promoter may be derived from a genomic starch synthase gene. Preferably, the promoter sequence comprises nucleotide sequences that are linked in vivo to nucleotide sequences set forth in any one of SEQ ID NOs: 1, 3, 5, 7, 9, 11–16, 37, or 38. By "linked in vivo" means that the promoter is present in its native state in the genome of a wheat plant where it controls expression of the starch synthase gene of the present invention.

Conveniently, genetic constructs are employed to facilitate expression of a starch synthase genetic sequence of the present invention or a functional derivative, part, homologue, or analogue thereof. To produce a genetic construct, the starch synthase gene of the invention is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced. The said genetic construct comprises the subject nucleic acid molecule placed operably under the control of a promoter sequence and optionally, a terminator sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in bacteria, yeasts, animal cells and plant cells are known and described in the literature. They may be isolated from bacteria, fungi, viruses, animals and/or plants.

Examples of terminators particularly suitable for use in expressing the nucleic acid molecule of the present invention in plant cells include the nopaline synthase (NOS) gene terminator of *Agrobacterium tumefaciens*, the terminator of the Cauliflower mosaic virus (CaMV) 35S gene, and the zein gene terminator from *Zea mays*.

Genetic constructs will generally further comprise one or more origins of replication and/or selectable marker gene sequences.

The origin of replication can be functional in a bacterial cell and comprise, for example, the pUC or the ColE1 origin. Alternatively, the origin of replication is operable in a eukaryotic cell, tissue and more preferably comprises the 2 micron (2 μm) origin of replication or the SV40 origin of replication.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin-resistance gene ($Amp^r$), tetracycline-resistance gene ($Tc^r$), bacterial kanamycin-resistance gene ($Kan^r$), is the zeocin resistance gene (Zeocin is a drug of bleomycin family which is trademark of InVitrogen Corporation), the AURI-C gene which confers resistance to the antibiotic aureobasidin A, phosphinothricin-resistance gene, neomycin phosphotransferase gene (nptII), hygromycin-resistance gene, β-glucuronidase (GUS) gene, chloramphenicol acetyltransferase (CAT) gene, green fluorescent protein-encoding gene or the luciferase gene, amongst others. Those skilled in the art will be aware of other selectable marker genes useful in the performance of the present invention and the subject invention is not limited by the nature of the selectable marker gene.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

Standard methods can be used to introduce genetic constructs into a cell, tissue or organ for the purposes of modulating gene expression. Particularly preferred methods suited to the introduction of synthetic genes and genetic constructs comprising same to eukaryotic cells include liposome-mediated transfection or transformation, transformation of cells with attenuated virus particles or bacterial cells and standard procedures for the transformation of plant and animal cells, tissues, organs or organisms. Any standard means may be used for their introduction including cell mating, transformation or transfection procedures known to those skilled in the art or described by Ausubel et al. (1992).

In a further embodiment of the present invention, the starch synthase genes of the present invention and genetic constructs comprising same are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the *Agrobacterium tumefaciens* Ti plasmid will generally be required.

The invention further contemplates increased starch and/or modified starch composition in transgenic plants expressing the nucleic acid molecule of the invention in the sense orientation such that the activity of one or more starch synthase isoenzymes is increased therein. By increasing the level of one or more starch synthase isoenzymes, the deposition of starch in the amyloplast or chloroplast is increased and/or a modified starch granule structure is produced and/or starch composition is modified and/or the amylose/amylopectin ratio is altered in the plant.

Wherein it is desired to increase the synthesis of a particular starch synthase isoenzyme in a plant cell, the coding region of a starch synthase gene is placed operably behind a promoter, in the sense orientation, such that said starch synthase is expressed under the control of said promoter sequence. In a preferred embodiment, the starch synthase genetic sequence is a starch synthase genomic sequence, cDNA molecule or protein-coding sequence.

Wherein it is desirable to reduce the level of a particular starch synthase isoenzyme in a plant cell, the nucleic acid molecule of the present invention can be expressed in the antisense orientation, as an antisense molecule or a ribozyme molecule, under the control of a suitable promoter.

Alternatively, the nucleic acid molecule of the present invention may also be expressed in the sense orientation, in the form of a co-suppression molecule, to reduce the level of a particular starch synthase isoenzyme in a plant cell. As will be known to those skilled in the art, co-suppression molecules that comprise inverted repeat sequences of a target nucleic acid molecule provide optimum efficiency at reducing expression of said target nucleic acid molecule and, as a consequence, the present invention clearly contemplates the use of inverted repeat sequences of any one or more of the starch synthase genetic sequences exemplified herein, or inverted repeat sequences of a homologue, analogue or derivative of said starch synthase genetic sequences, to reduce the level of a starch synthase isoenzyme in a plant.

The expression of an antisense, ribozyme or co-suppression molecule comprising a starch synthase gene in a cell such as a plant cell, fungal cell, insect cell. animal cell, yeast cell or bacterial cell, may also increase the availability of carbon as a precursor for a secondary metabolite other than starch (e.g. sucrose or cellulose). By targeting the endogenous starch synthase gene, expression is diminished, reduced or otherwise lowered to a level that results in reduced deposition of starch in the amyloplast or chloroplast and/or leads to modified starch granule structure and/or composition and/or altered amylose/amylopectin ratio.

Accordingly, a further aspect of the present invention provides a method of modifying the starch content and/or starch composition of one or more tissues or organs of a plant, comprising expressing therein a sense molecule, antisense molecule, ribozyme molecule, co-suppression molecule, or gene-targeting molecule having at least about 85% nucleotide sequence identity to any one of any one of SEQ ID NOS: 1, 3, 5, 7, 9, 11–16, 37, or 38, or a complementary nucleotide sequence thereto for a time and under conditions sufficient for the enzyme activity of one or more starch synthase isoenzymes to be modified. This aspect of the invention clearly extends to the introduction of the sense molecule, antisense molecule, ribozyme molecule, co-suppression molecule, or gene-targeting molecule to isolated plant cells, tissues or organs or organelles by cell fusion or transgenic means and the regeneration of intact plants therefrom.

Co-suppression is the reduction in expression of an endogenous gene that occurs when one or more copies of said gene, or one or more copies of a substantially similar gene are introduced into the cell, preferably in the form of an inverted repeat structure.

The present inventors have discovered that the genetic sequences disclosed herein are capable of being used to modify the level of starch when expressed, particularly when expressed in plants cells. Accordingly, the present invention clearly extends to the modification of starch biosynthesis in plants, in particular wheat or barley plants or a progenitor plant species, or a relative thereto such as the diploid *Triticum* tauschii or other diploid, tetraploid, aneuploid, polyploid, nullisomic, or a wheat/barley addition line, amongst others.

In particular, the present invention contemplates decreased starch production and/or modified starch composition in transgenic plants expressing the nucleic acid molecule of the invention in the antisense orientation or alternatively, expressing a ribozyme or co-suppression molecule comprising the nucleic acid sequence of the invention such that the activity of one or more starch synthase isoenzymes is decreased therein.

In the context of the present invention, an antisense molecule is an RNA molecule which is transcribed from the complementary strand of a nuclear gene to that which is normally transcribed to produce a "sense" mRNA molecule capable of being translated into a starch synthase polypeptide. The antisense molecule is therefore complementary to the mRNA transcribed from a sense starch synthase gene or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a polypeptide gene product.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852.

The present invention extends to ribozyme which target a sense mRNA encoding a native starch synthase gene product, thereby hybridising to said sense mRNA and cleaving it, such that it is no longer capable of being translated to synthesise a functional polypeptide product.

According to this embodiment, the present invention provides a ribozyme or antisense molecule comprising at least 5 contiguous nucleotide bases derived from any one of SEQ ID NOS: 1, 3, 5, 7, 9, 11–16, 37, or 38, or a complementary nucleotide sequence thereto or a homologue, analogue or derivative thereof, wherein said antisense or ribozyme molecule is able to form a hydrogen-bonded complex with a sense mRNA encoding a starch synthase gene product to reduce translation thereof.

In a preferred embodiment, the antisense or ribozyme molecule comprises at least 10 to 20 contiguous nucleotides derived from any one of SEQ ID NOS: 1, 3, 5, 7, 9, 11–16, 37, or 38, or a complementary nucleotide sequence thereto or a homologue, analogue or derivative thereof. Although the preferred antisense and/or ribozyme molecules hybridise to at least about 10 to 20 nucleotides of the target molecule, the present invention extends to molecules capable of hybridising to at least about 50–100 nucleotide bases in length, or a molecule capable of hybridising to a full-length or substantially full-length mRNA encoded by a starch synthase gene.

Those skilled in the art will be aware of the necessary conditions, if any, for selecting or preparing the antisense or ribozyme molecules of the invention.

It is understood in the art that certain modifications, including nucleotide substitutions amongst others, may be made to the antisense and/or ribozyme molecules of the present invention, without destroying the efficacy of said molecules in inhibiting the expression of a starch synthase gene. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridising to a sense mRNA molecule which encodes a starch synthase gene product.

Gene targeting is the replacement of an endogenous gene sequence within a cell by a related DNA sequence to which it hybridises, thereby altering the form and/or function of the endogenous gene and the subsequent phenotype of the cell. According to this embodiment, at least a part of the DNA sequence defined by any one of SEQ ID NOS: 1, 3, 5, 7, 9, 11–16, 37, or 38 may be introduced into target cells containing an endogenous gene that encodes a particular starch synthase isoenzyme, thereby replacing said endogenous gene. According to this embodiment, the polypeptide product of the gene targetting molecule generally encodes a starch synthase isoenzyme that possesses different catalytic activity to the polypeptide product of the endogenous gene, producing in turn modified starch content and/or composition in the target cell.

The present invention extends to genetic constructs designed to facilitate expression of a sense molecule, an antisense molecule, ribozyme molecule, co-suppression molecule, or gene targeting molecule of the present invention. The requirements for expressing such molecules are similar to those for expressing a recombinant polypeptide as described supra.

The present invention further extends to the production and use of starches and proteins produced using the novel genes described herein. Modified starches produced by plants which have been selected using marker-assisted selection, or alternatively, produced by transgenic plants carrying the introduced starch synthase genes, are particularly suitable for use in food products, such as, for example, flour and flour-based products, in particular those products selected from the group consisting of: flour-based sauce; leavened bread; unleavened bread; pasta, noodle; cereal; snack food; cake; and pastry. Modified proteins are also suitable for use in non-food products, such as, for example, those non-food products selected from the group consisting of: films; coatings; adhesives; building materials; and packaging materials.

Additionally, starch hydrolysates or undegraded starches are both useful in industry and, as a consequence, the present invention is useful in applications relating to the use of both starch hydrolysates and undegraded starches. By “starch hydrolysates” is meant the glucose and glucan components that are obtainable by the enzymatic or chemical degradation of starch in chemical modifications and processes, such as fermentation.

Starch produced by plants expressing the sense, antisense, co-suppression, gene-targetting or ribozyme molecules of the present invention may exhibit modified viscosities and/or gelling properties of its glues when compared to starch derived from wild-type plants. Native starches produced by the performance of the inventive method are useful as an additive in the following: (i) foodstuffs, for the purpose of increasing the viscosity or gelling properties of food; (ii) in non-foodstuffs, such as an adjuvant or additive in the paper and cardboard industries, for retention or as a size filler, or as a solidifying substance or for dehydration, or film coating, amongst others; (iii) in the adhesive industry as pure starch glue, as an additive to synthetic resins and polymer dispersions, or as an extenders for synthetic adhesives; (iv) in the textile and textile care industries to strengthen woven products and reduce burring or to thicken dye pastes; (v) in the building industry, such as a binding agent in the production of gypsum plaster boards, or for the deceleration of the sizing process; (vi) in ground stabilization or for the temporary protection of ground particles against water in artificial earth shifting; (vii) as a wetting agent in plant protectants and fertilizers; (viii) as a binding agent in drugs, pharmaceuticals and medicated foodstuff such as vitamins, etc; (ix) as an additive in coal and briquettes; (xi) as a flocculent in the processing of coal ore and slurries; (xii) as a binding agent in casting processes to increase flow resistance and improve binding strength; and (xiii) to improve the technical and optical quality of rubber and plastic products. Additional applications are not excluded.

A further aspect of the present invention provides an isolated promoter that is operable in the endosperm of a monocotyledonous plant cell, tissue or organ, and preferably in the endosperm of a monocotyledonous plant cell, tissue or organ. According to this embodiment, it is preferred that the promoter is derived from a starch synthase gene of the present invention, such as a promoter that is linked in vivo to any one of SEQ ID NOS: 1, 3, 5, 7, 9, 11–16, 37, or 38, or a complementary nucleotide sequence thereto.

In a particularly preferred embodiment, the promoter comprises a nucleotide sequence derivable from the 5'-upstream region of SEQ ID NO: 11 or SEQ ID NO: 37 or SEQ ID NO: 38, or a complementary nucleotide sequence thereto, an more preferably comprises nucleotides 1 to about 287 of SEQ ID NO: 11, or nucleotides 1 to about 1416 of SEQ ID NO: 37, or nucleotides 1 to about 973 of SEQ ID NO: 38, or a complementary nucleotide sequence thereto. The present invention clearly extends to promoter sequences that comprise further nucleotide sequences in the region upstream of the stated nucleotide sequence that are linked in vivo to said nucleotide sequence in the wheat genome.

In a related embodiment, the promoter sequence of the present invention will further comprise an exon sequence derived from a starch synthase gene, such as, for example, an intron I sequence described herein, or a complementary nucleotide sequence thereto. Those skilled in the art will be aware that the inclusion of such nucleotide sequences may increase the expression of a heterologous structural gene, the expression of which is controlled thereby. Preferred intron I sequences include, for example, nucleotide sequences in the region of about position 1744 to about 1847 of SEQ ID NO: 37, and/or about position 1100 to about position 2056 of SEQ ID NO: 38. Additional sequences comprising intron/exon junction boundary sequences which are readily determined by those skilled in the art are not excluded.

The present invention further extends to the expression of any structural gene operably under the control of the starch synthase promoter sequence exemplified herein or a functional homologue, analogue or derivative of said promoter sequence.

As with other embodiments described herein for expression in cells, a genetic construct may be employed to effect said expression and the present invention clearly extends to said genetic constructs.

The polypeptide encoded by the structural gene component may be a reporter molecule which is encoded by a gene such as the bacterial β-glucuronidase gene or chloramphenicol acetyltransferase gene or alternatively, the firefly luciferase gene. Alternatively, wherein it is desirable to alter carbon partitioning within the endosperm, the polypeptide may be an enzyme of the starch sucrose biosynthetic pathways. Preferably, the promoter sequence is used to regulate the expression of one or more of the starch synthase genes of the present invention or a sense, antisense, ribozyme, co-suppression or gene-targetting molecule comprising or derived from same.

Recombinant DNA molecules carrying the aforesaid nucleic acid molecule of the present invention or a sense, antisense, ribozyme, gene-targetting or co-suppression molecule and/or genetic construct comprising same, may be introduced into plant tissue, thereby producing a "transgenic plant", by various techniques known to those skilled in the art. The technique used for a given plant species or specific type of plant tissue depends on the known successful techniques. Means for introducing recombinant DNA into plant tissue include, but are not limited to, transformation (Paszkowski et al., 1984), electroporation (Fromm et al., 1985), or microinjection of the DNA (Crossway et al., 1986), or T-DNA-mediated transfer from *Agrobacterium* to the plant tissue. Representative T-DNA vector systems are described in the following references: An et al./(1985); Herrera-Estrella et al. (1983a, b); Herrera-Estrella et al. (1985). Once introduced into the plant tissue, the expression of the introduced gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

In general, plants are regenerated from transformed plant cells or tissues or organs on hormone-containing media and the regenerated plants may take a variety of forms, such as chimeras of transformed cells and non-transformed cells; clonal transformants (e.g., all cells transformed to contain the expression cassette); grafts of transformed and untransformed tissues (e.g., a transformed root stock grafted to an untransformed scion in citrus species). Transformed plants may be propagated by a variety of means, such as by clonal propagation or classical breeding techniques. For example, a first generation (or T1) transformed plants may be selfed to give homozygous second generation (or T2) transformed plants, and the T2 plants further propagated through classical breeding techniques.

Accordingly, a still further aspect of the present invention contemplates a transgenic plant comprising an introduced sense molecule, antisense molecule, ribozyme molecule, co-suppression molecule, or gene-targeting molecule having at least about 85% nucleotide sequence identity to any one of any one of SEQ ID NOS: 1, 3, 5, 7, 9, 11–16, 37, or 38, or a complementary nucleotide sequence thereto or a genetic construct comprising same. The present invention further extends to those plant parts, propagules and progeny of said transgenic plant or derived therefrom, the only requirement being that said propagules and progeny also carry the introduced nucleic acid molecule(s).

The present invention is further described by reference to the following non-limiting examples.

EXAMPLE 1

Plant Material

Genetic stocks of hexaploid bread wheat *Triticum aestivum* cv. Chinese Spring with various chromosome additions and deletions were kindly supplied by Dr E. Lagudah (CSIRO Plant Industry, Canberra) and derived from stocks described in Sears and Miller (1985). The hexaploid (*Triticum aestivum*) wheats cv Gabo and cv Wyuna were grown in controlled growth cabinet conditions (18° C. day and 13° C. night, with a photoperiod of 16 h). Wheat leaves and florets prior to anthesis, and endosperm were collected over the grain filling period, immediately frozen in liquid nitrogen and stored at −80° C. until required.

EXAMPLE 2

Gel Electrophoresis, Antibodies and Immunoblotting

Monoclonal antibodies against the Sgp-1 proteins, and their use in the immunoblotting of SDS-PAGE gels have been described previously (Rahman et al., 1995).

EXAMPLE 3

Preparation of Total RNA from Wheat

Total RNA was isolated from the leaf, floret and endosperm tissues of wheat essentially as described by Higgins et al. (1976) or Rahman et al. (1998). RNA was quantified by UV absorption and by separation in 1.4% (w/v) agarose-formaldehyde gels which were then visualised under UV light after staining with ethidium bromide.

EXAMPLE 4

Construction and Screening of cDNA Libraries

A first cDNA library, an expression cDNA library of wheat endosperm, was constructed from mRNA isolated from wheat cv Chinese Spring. RNA from 5, 7, 9, 11 and 13 days after anthesis was pooled and random primers were used for the first strand of cDNA synthesis. Monoclonal antibodies against 100–105 kDa proteins in wheat starch granules (Rahman et al., 1995) were used for immunoscreening of the expression cDNA library.

A second cDNA library was constructed from the endosperm mRNA of the hexaploid *Triticum aestivum* cultivar Wyuna, 8–12 days after anthesis, as described by Rahman et al. (1997). This library was screened with a 85-bp cDNA fragment, wSSIIp1, which as obtained by immunoscreening of the expression cDNA library as described above. The wSSIIp1 probe corresponded to nucleotide positions 988 to 1072 of wSSIIB (SEQ ID NO:1) at the hybridisation conditions as described earlier (Rahman et al., 1998).

A third cDNA library was constructed from RNA from the endosperm of the hexaploid *Triticum aestivum* cultivar Rosella as described by Rahman et al., (1997). This library was screened with a 347-bp cDNA fragment, wSSIIIp1 for the first screening, and a 478-bp cDNA fragment wSSIIIp3 for the second screening using the hybridisation conditions described herein.

EXAMPLE 5

Construction and Screening of *Triticum tauschii* Genomic Library

The genomic library used in this study, prepared from *Triticum tauschii*, var strangulata, (Accession Number CPI 110799), has been described in Rahman et al., (1997). Of all the accessions of *T. tauschii* surveyed, DNA marker analysis suggests that the genome of CPI 110799 is the most closely related to the D genome of hexaploid wheat (Lagudah et al., 1991).

Hybridisations were carried out in 25% formamide, 6×SSC, 0.1% SDS at 42° C. for 16 hours, then filters were washed 3 times using 2×SSC containing 0.1% SDS at 65° C. for 1 hour per wash.

For the isolation of a genomic wSSII clone, the probe comprised the PCR-derived DNA fragment wSSIIp2 and positive-hybridising plaques were digested using the restriction enzyme BamHI, separated on a 1% agarose gel, transferred to nitrocellulose membrane and hybridised to probe wSSIIp4 comprising nucleotides 1 to 367 of the wSSIIA cDNA clone, using the conditions described by Rahman et al. (1997).

For the isolation of a genomic wSSIII clone, plaques hybridising to the PCR-derived DNA fragment wSSIIIp1 from clone wSSIII.B3 (i.e. nucleotides 3620 to 3966 of SEQ ID NO:7) were selected and re-screened until plaque-purified.

EXAMPLE 6

DNA Sequencing and Analysis

DNA sequencing was performed using the automated ABI system with dye terminators as described by the manufacturers. DNA sequences were analysed using the GCG suite of programs (Devereaux et al., 1984).

EXAMPLE 7

DNA and RNA Analysis

DNA was isolated and analysed as previously described (Maniatis et al., 1982; Rahman et al., 1998). Approximately 20 μg of DNA was digested with restriction enzymes BamHI, DraI and EcoRI, separated on a 1% agarose gel and transferred to reinforced nitrocellulose membranes (BioRad) and hybridised with $^{32}$P-labelled DNA probe, either wSSIIIp1, corresponding to nucleotides 3620 to 3966 of the wheat SSIII gene, or alternatively, with the entire wSSII cDNA clone. DNA fragment probes were labelled with the Rapid Multiprime DNA Probe Labelling Kit (Promega).

The hybridisation and wash conditions were performed as described in Rahman et al. (1997). For RNA analysis, 10 μg of total RNA was separated in a 1.4% agarose-formaldehyde gel and transferred to a Hybond N+ membrane (Amersham), and hybridised with cDNA probe at 42° C. as previously described by Khandjian et al., (1987) or Rahman et al., (1998). After washing for 30 minutes at 65° C. with 2×SSC, 0.1% SDS; followed by three washes of 40 minutes at 65° C. with 0.2×SSC, 1% SDS, the membranes were visualised by overnight exposure at −80° C. with Kodak MR X-ray film.

EXAMPLE 8

Expression of Wheat Sgp-1 Polypeptides in the Wheat Endosperm

The development and use of monoclonal antibodies to the Sgp-1 proteins has been described previously (Rahman et al., 1995). These antibodies were used by the present inventors to characterise the expression and localisation of the Sgp-1 proteins.

The proteins found in the matrix of the wheat starch granule are shown in FIG. 1, lane 1. The remaining lanes show an immunoblot of proteins from the soluble phase (FIG. 1; lanes 2–4) and the starch granule (FIG. 1; lanes 5–7), respectively, following SDS-PAGE. In addition to cross-reactivity with the 100–105 kDa proteins, a weak cross-reaction with a 50 kDa protein in both the granule and the soluble fractions were observed (FIG. 1). The Sgp-1 polypeptides are present in the starch granule throughout endosperm development (FIG. 1; lanes 5–7, also see Rahman et al., 1995). However, as the endosperms matures, there is a reduction in the amount of Sgp-1 protein found in the soluble fraction. Lane 4 shows that by 25 days after anthesis, the level of these proteins in the soluble fraction is substantially reduced. This observation is consistent with previous results from Rahman et al., (1995), who suggested that the Sgp-1 proteins were exclusively granule bound based on studies of granules from endosperm in mid-late stages endosperm development, however, these results suggest that the partitioning of these proteins between the granule and the soluble phase changes during development.

EXAMPLE 9

Isolation of cDNA Clones Encoding Wheat Starch Synthase II (WSSII) Proteins

Monoclonal antibodies against Sgp-1 polypeptides (Rahman et al., 1995) were used to probe the expression library described in Example 4 (i.e. the first cDNA library). Three immunoreactive plaques were identified and sequenced. One clone, designated wSSIIp1, contained an 85-bp cDNA insert with homology to maize SSIIa (Harn et al., 1998).

DNA from the wSSIIp1 clone was used as a probe in the hybridisation screening of the second cDNA library, prepared from *Triticum aestivum* cultivar Wyuna endosperm RNA as described in Example 4. Ten hybridising cDNA clones were selected and sequenced. On the basis of the DNA sequences obtained, the 10 cDNA clones can be classified into three groups. Group 1 contains 7 cDNA clones, group 2 contains 2 cDNA clones and group 3 contains 1 cDNA clone.

The longest clone from group 1 (designated wSSIIB) is 2939 bp in length (SEQ ID NO:1) and encodes a 798-amino acid polypeptide in the region from nucleotide position 176 to nucleotide position 2569 (SEQ ID NO:2).

The longest clone from group 2 (designated wSSIIA) is 2842 bp in length (SEQ ID NO:3) and encodes a 799-amino acid polypeptide in the region from nucleotide position 89 to nucleotide position 2485 (SEQ ID NO:4).

The cDNA from group 3 is a partial cDNA clone (designated wSSIID), which is 2107 bp in length (SEQ ID NO:5) and encodes a 597-amino acid polypeptide in the region from nucleotide position 1 to nucleotide position 1791 (SEQ ID NO:6). The encoded polypeptide is approximately a 200 amino acid residues shorter than that of polypeptides encoded by longest clones of group 1 or 2 clones, respectively (FIG. 2).

Figure 3:
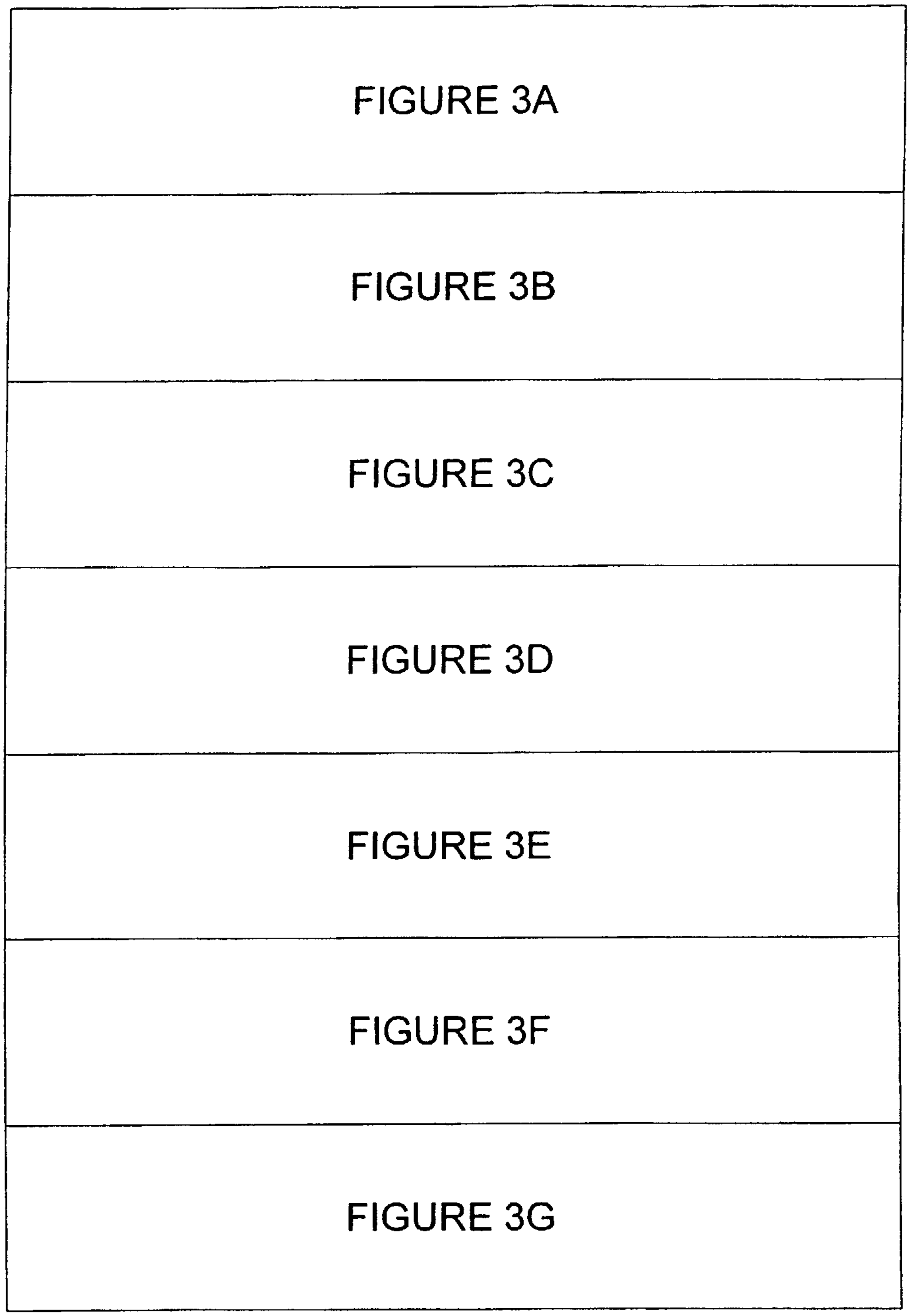
FIG. 3 (Figure panels 3A–3G) is a copy of a schematic representation comparing the deduced amino acid sequences of starch synthase II from wheat (wSSIIA (SEQ ID NO:3), wSSIIB (SEQ ID NO:1) and wSSIID (SEQ ID NO:5), maize (maize SSIIa and maize SSIIb; Harn et al., 1998), pea (pea SSII; Dry et al., 1992) and potato (potato SSII; van der Leij et al., 1991). Identical amino acid residues among each of these sequences are indicated below the sequences with "*". The alignments of maize SSIIa with maize SSIIb, and pea SSII and potato SSII are essentially as described in Harn et al. (1998) and Edwards et al. (1995). All sequences are aligned to position the transit peptide cleavage site below the arrow (⇓) between residues 59 and 60 of the wSSIIA sequence. The wSSIIp1 sequence, the sequence of SGP-B1 (peptide3), and of eight conserved regions are annotated and underlined.

Comparison of the three cDNA clones, wSSIIB, wSSIIA and WSSIID shows that they share 95.7% to 96.6% identity at the amino acid level, with variation at 44 amino acid positions between the three sequences (FIG. 3). Of the 44 amino acid changes between these sequences, 31 changes occur in the N-terminal region (residues 1 to 300), 10 changes occur in the central region (residues 301 to 729) and 3 changes occur in the C-terminal region (residues 730 to 799). The wSSIIA polypeptide (799 amino acid residues) and wSSIIB polypeptide (798 amino acid residues) sequences differ in length by a single amino acid residue, due to the deletion of Asp-69 from the wSSIIB polypeptide sequence.

A comparison of the nucleotide sequences of the wSSIA, wSSIIB and wSSIID cDNA clones with the nucleotide sequence of the wSSIIp1 cDNA obtained by immunoscreening confirms that the wSSIIp1 sequence is found in each cDNA (FIG. 3). The peptide encoded by the wSSIIp1 cDNA clone corresponds to amino acid residues in the region from residue 272 to residue 298 of the wSSIIA polypeptide, and to amino acid residues in the region from residue 271 to residue 297 of the wSSIIB polypeptide (see FIG. 3). Thus, the peptide epitope encoded by wSSIIp1 that reacts with the anti-Sgp-1 monoclonal antibodies can therefore be localised to this region of the wSSIIA and wSSIIB polypeptides and to the corresponding region of the wSSIID polypeptide.

Notwithstanding that a region having about 63% amino acid sequence identity to the peptide epitope encoded by clone wSSIIp1 is found in the maize SSIIa polypeptide (FIG. 3), the degree of amino acid conservation between maize and wheat sequences in this region of the polypeptide is insufficient for immunological cross-reactivity to occur between these species using the monoclonal antibodies to the wheat Sgp-1 proteins described by Rahman et al. (1995). Additionally, this peptide epitope is not found in granule-bound starch synthases, SSI, or SSIII (data not shown).

The wSSIIB cDNA (SEQ ID NO:1) encodes an amino acid sequence comprising the peptide motif AAGKKDAGID (SEQ ID NO: 18) between residues 60 and 69 of SEQ ID NO:2 (FIG. 3) which, with the exception of the second residue, is identical to the N-terminal of the 100 kDa ($A^T/_L$GKKDAGID: SEQ ID NOS:19 and 20) protein (Sgp-B1) from the wheat starch granule (note that the sequence given in Rahman et al., 1995 ($A^T/_L$GKKDAL: SEQ ID NOS: 21 and 22) has been revised following further amino acid sequence analysis).

The wSSIIA cDNA clone (SEQ ID NO:3) encodes an amino acid sequence comprising the peptide motif AAGKKDARVDDDAA (SEQ ID NO: 23) at residues 60 to 73 of SEQ ID NO:4, which is about 66% identical to the N-terminal amino acid sequence (i.e. ALGKKDAGIVDGA: SEQ ID NO: 24) of the 104 kDa and 105 kDa starch granule proteins, Sgp-D1 and Sgp-A1 respectively, as determined by sequence analysis of isolated protein (Rahman et al., 1995).

Furthermore, Takaoka et al. (1997) reported the amino acid sequences of 3 polypeptides obtained from sequencing starch granule proteins derived from the Sgp-1 proteins. Peptide 3 described by Takaoka et al. (1997) corresponds to amino acid residues 378 to 387 of the amino acid sequence of the wSSIIA cDNA (SEQ ID NO:4; FIG. 3). Peptides 1 and 2 described by Takaoka et al. (1997) could not be detected in the amino acid sequences of the wSSII cDNA clones of the present invention, however peptide 1 of Takaoka et al. (1997) can be found in the amino acid sequences of SSI from maize, rice, wheat and potato (data not shown).

Denyer et al. (1995) demonstrated that the Sgp-1 proteins possess starch synthase activity and, as a consequence, the wSSIIB, wSSIA and wSSIID cDNA clones encode starch synthase enzymes that are differentially expressed in a developmentally-regulated manner in both the soluble and granule-bound fractions of the endosperm (FIG. 1). Based on the nomenclature suggested by Harn et al. (1998), it is appropriate to describe the Sgp-1 proteins as "starch synthases" rather than "granule-bound starch synthases".

EXAMPLE 10

Analysis of Wheat Starch Synthase II mRNA Expression

Figure 4:
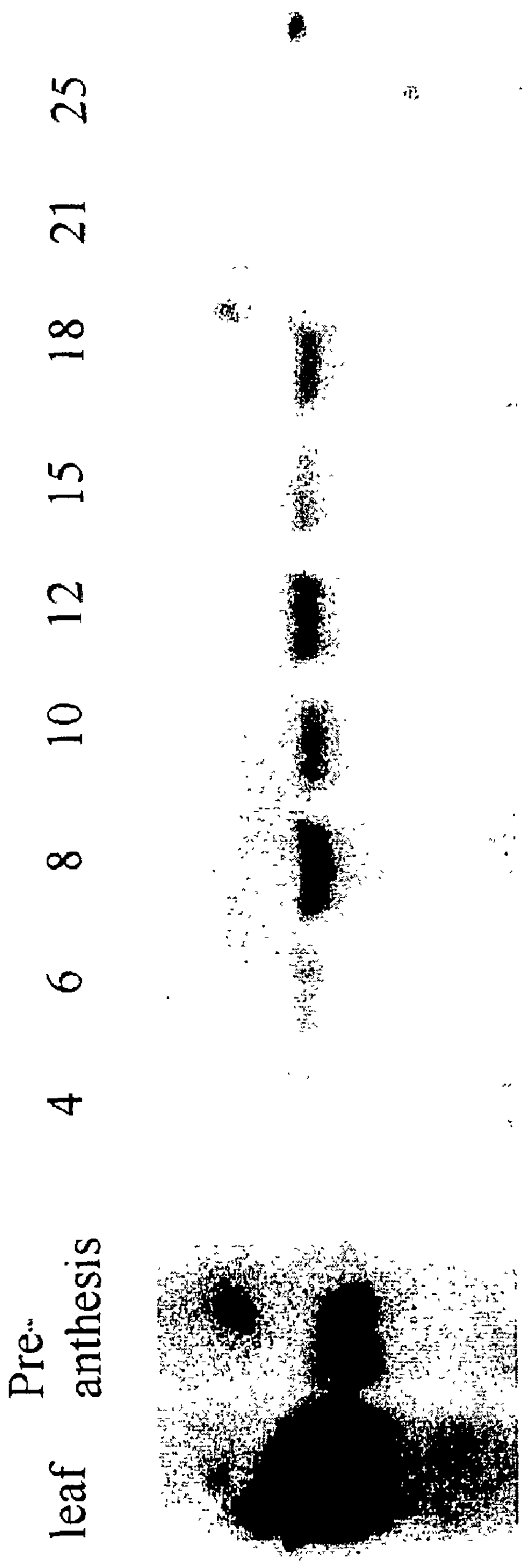
FIG. 4 is a copy of a photographic representation of a northern blot showing the expression of wheat wSSII mRNA in wheat plants. Total RNAs were isolated from leaves pre-anthesis florets and endosperm of the wheat cultivar "Gabo", grown under a photoperiod comprising 16 hours daylength, and at 18° C. during the day, and at 13° C. during the night cycle, and probed with the wSSIIp2 DNA fragment. The source of each RNA is indicated at the top of the Figure as follows: Lane 1, leaf; Lane 2, pre-anthesis florets; Lanes 3–11, endosperm at: 4 days post-anthesis (Lane 3); 6 days post-anthesis (Lane 4); 8 days post-anthesis (Lane 5); 10 days post-anthesis (Lane 6); 12 days post-anthesis (Lane 7); 15 days post-anthesis (Lane 8); 18 days post-anthesis (Lane 9); 21 days post-anthesis (Lane 10); and 25 days post-anthesis (Lane 11).

The mRNA for wheat starch synthase II could be detected in leaves, pre-anthesis florets and endosperm of wheat when total RNAs isolated from these tissue were probed with a PCR probe, wSSIIp2, corresponding to nucleotide positions 1435 to 1835 bp of wSSIIB-cDNA (SEQ ID NO:1; FIG. 4). Unlike WSSI, which could not be detected in wheat leaves derived from plants grown under the same conditions, wSSII genes are highly-expressed in the leaves (FIG. 4, lane 1), and expressed at an intermediate level in pre-anthesis florets (FIG. 4, lane 2), and at much lower levels in developing wheat endosperm cells (FIG. 4, lanes 3–11). In contrast, the maize SSIIa is expressed predominantly in the endosperm, whilst the maize SSIIb is detected mainly in the leaf, albeit at low levels (Harn et al., 1998).

The wSSII mRNA was detectable in the endosperm 6 days after anthesis and mRNA levels increase between 8 and 18 days post-anthesis, after which time levels of mRNA decline.

Southern blotting experiments in wheat demonstrated that the wSSIIp2 probe used detected only a single copy of the SSII gene in each genome (data not shown). Thus, it is unlikely that this probe cross-hybridised with mRNAs encoded by genes other than wSSII.

EXAMPLE 11

Chromosomal Localization of the Wheat wSSII Genes

I. Amplification of Specific cDNA Regions of Wheat Starch Synthase II Using PCR

Two PCR products, wSSIIp2 and wSSIIp3 were amplified from the cDNA clone wSSIIB and used for the northern hybridisation and Southern hybridisation, respectively.

The primers ssIIa (5' TGTTGAGGTTCCATGGCACGTTC 3': SEQ ID NO: 25) and ssIIb (5' AGTCGTTCTGCCGTATGATGTCG 3': SEQ ID NO: 26) were used to amplify the cDNA fragment wSSIIp2 (i.e. nucleotide positions 1435 to 1835 of SEQ ID NO:1).

The primers ssIIc (5' CCAAGTACCAGTGGTGMCGC 3': SEQ ID NO: 27) and ssIId (5' CGGTGGGATCCMCGGCCC 3': SEQ ID NO: 28) were used to amplify the cDNA fragment wSSIIp3 (i.e. nucleotide positions 2556 to 2921 of SEQ ID NO:1).

The amplification reactions were performed using a FTS-1 thermal sequencer (Corbett, Australia) for 1 cycle of 95° C. for 2 minutes; 35 cycles of 95° C. for 30 seconds, 60° C. for 1 minutes, 72° C. for 2 minutes and 1 cycle of 25° C. for 1 minute.

II. PCR and Nucleotide Sequence Analysis of 3' Sequences of Wheat SSII Genes

Genomic DNA was extracted from wild-type Chinese Spring wheat, and from three nullisomic-tetrasomic lines of chromosome 7 of Chinese Spring wheat, and from *Triticum tauschii* (var *strangulate*, accession number CPI 100799), and used as a template for the amplification and nucleotide sequence analysis of wheat SSII genes.

RFLP analysis of BamHI and EcoRI restricted DNA from each wheat or *T. Tauschii* line was carried out using the wSSIIp3 fragment as a probe. Three hybridising bands were obtained which could be assigned to chromosomes 7A, 7B and 7D, respectively (data not shown). This analysis indicates that there is a single copy of the wSSII gene in each genome in hexaploid wheat, consistent with the findings of Yamamori and Endo (1996) who located the SGP-A1, B1 and D1 proteins to the short arm of chromosome 7.

Figure 5:
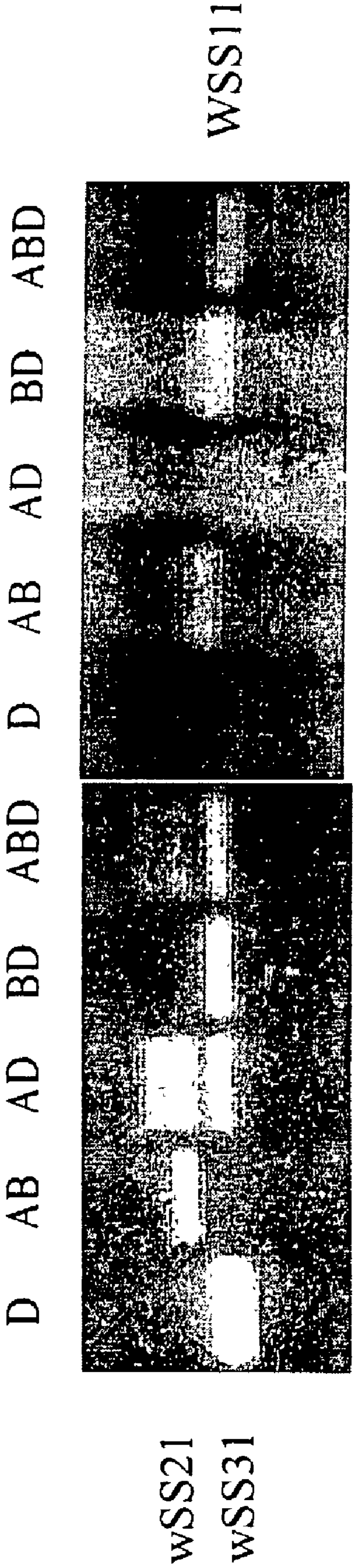
FIG. 5 is a copy of a photographic representation showing the localization of wheat starch synthase II genes on the wheat genome by PCR, using the primers ssIIc, ssIId and ssIIe in the amplification reaction. The nullisomic-tetrasomic genomic DNA of wheat cv. Chinese Spring was used as template DNA. Lane D, *Triticum tauschii*; Lane AB, Accession line N7DT7B having no 7D chromosome and four copies of the 7B chromosome; Lane AD, Accession line N7BT7A having no 7B chromosome and four copies of the 7A chromosome; Lane BD, Accession line N7AT7B having no 7A chromosome and four copies of the 7B chromosome; Lane ABD, wheat cv. Chinese Spring. PCR products derived from each cDNA clone are labelled. The results indicate that the cDNA clones, wSSIIB, wSSIIA and wSSIID are derived from the B-, A- and D-genomes of wheat, respectively.

PCR analysis was used to assign each of the cDNA clones to the individual wheat genomes. A single 365 bp PCR fragment was obtained from nullisomic-tetrasomic genomic DNA of Chinese Spring when primers ssIIc and ssIId were used for the PCR amplification (FIG. 5, right panel). This PCR product is obtained only from lines bearing the B genome. The fragment was cloned and sequenced and shown to be identical to a 365 bp region of the wSSIIB cDNA. An identical fragment is obtained by PCR amplification of the wSSIIB cDNA clone, but not by amplification of the wSSIIA or wSSIID clones, supporting the conclusion that the wSSIIB cDNA is the product of a gene located on chromosome 7 of the B genome of hexaploid wheat.

Two PCR products were also amplified from nullisomic-tetrasomic genomic DNA of Chinese Spring using the primers ssIIc and ssIIe (FIG. 5, left panel). One PCR fragment, approximately 350 bp is only amplified when the A genome is present, and a second 322 bp product is only amplified when the D-genome is present. The 350 and 322 bp PCR products were also cloned and sequenced and shown to be identical to the wSSIIA and wSSIID cDNAs, respectively, supporting the conclusion that the wSSIIA and wSSIID cDNAs are the products of genes located on chromosomes 7A and 7D, respectively.

EXAMPLE 12

Isolation of Genomic wSSII Clones

Screening of a genomic library from the D-genome donor of wheat, *T. tauschii*, was performed as described in Example 5, using the PCR-derived DNA fragment wSSIIp2 as a hybridisation probe. A positive-hybridising clone, designated wSSII-8, and comprising a putative *T. tauschii* homologue of the wSSII gene, was isolated.

Positive-hybridising plaques were digested using the restriction enzyme BamHI, separated on a 1% agarose gel, transferred to nitrocellulose membrane and hybridised to probe wSSIIp4 comprising nucleotides 1 to 367 of the wSSIIA cDNA clone, using the conditions described by Rahman et al. (1997). Clone wSSII-8 also hybridises strongly to the wSSIIp4 probe, confirming its identity as a genomic wSSII gene.

Figure 6:
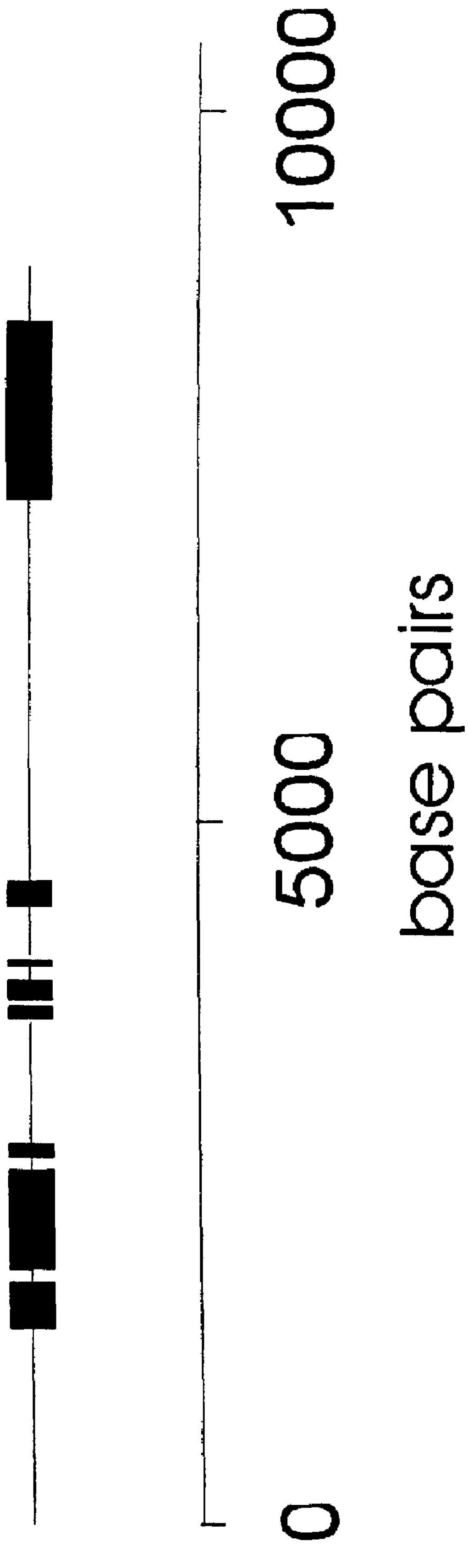
FIG. 6 is a schematic representation showing the organisation of introns (lines) and exons (boxes) in the wheat SSII gene shown in SEQ ID NO: 37. The scale (bases), relative to the nucleotide sequence set forth in SEQ ID NO: 37, is provided at the bottom of the figure.

The complete nucleotide sequence of the wSSII gene was determined and is presented herein as SEQ ID NO: 37. The structural features of this gene are present in Table 3. A schematic representation of the intron/exon organisation of this gene is also presented in FIG. 6.

TABLE 3

Structural features of the wheat starch synthase II genomic gene

| Nucleotide Position in SEQ ID NO: 37 | Feature | Length (bases) |
|---|---|---|
| 1–1416 | 5'-untranscribed region and promoter sequence | 1416 |
| 1417–1743 | exon 1 | 327 |
| 1480–1482 | translation start codon (ATG) | 3 |
| 1744–1847 | intron 1 | 104 |
| 1848–2553 | exon 2 | 706 |
| 2554–2641 | intron 2 | 88 |
| 2642–2706 | exon 3 | 65 |
| 2707–3606 | intron 3 | 900 |
| 3607–3684 | exon 4 | 78 |
| 3685–3773 | intron 4 | 89 |
| 3774–3884 | exon 5 | 111 |
| 3885–3981 | intron 5 | 97 |
| 3982–4026 | exon 6 | 45 |
| 4027–4406 | intron 6 | 380 |
| 4407–4580 | exon 7 | 174 |
| 4581–7296 | intron 7 | 2716 |
| 7297–8547 | exon 8 | 1251 |
| 8251–8253 | translation stop codon (TGA) | 3 |
| 8548–9024 | 3'-untranscribed region | 477 |

EXAMPLE 13

Cloning of Specific cDNA Regions of Wheat Starch Synthase III Using RT-PCR

PCR primers were used to amplify sequences of starch synthase III from wheat endosperm cDNA. The design of PCR primers was based on the sequences of starch synthase III from potato and the du1 starch synthase III gene of maize.

First-strand cDNAs were synthesised from 1 μg of total RNA (derived from endosperm of the cultivar Rosella, 12 days after anthesis) as described by Maniatis et al. (1982), and then used as templates to amplify two specific cDNA regions, wSSIIIp1 and wSSIIIp2, of wheat starch synthase III by PCR.

The primers used to obtain the cDNA clone wSSIIIp1 were as follows: Primer wSS3pa (5' GGAGGTCTTGGTGATGTTGT 3': SEQ ID NO: 29); and Primer wSS3pb (5'CTTGACCAATCATGGCMTG 3': SEQ ID NO: 30).

The primers used to obtain the cDNA clone wSSIIIp2 were as follows: Primer wSS3 pc (5'CATTGCCATGATTGGTCAAG 3': SEQ ID NO: 31); and Primer wSS3pd (5' ACCACCTGTCCGTTCCGTTGC 3': SEQ ID NO: 32).

The amplified clones wSSIIIp1 and wSSIIIp2 were used as probes to screen the third cDNA library and *T. tauschii* genomic DNA library as described in Example 4.

A further probe designated wSSIIIp3 was used for screening the third cDNA library, as described in Example 4. Probe wSSIIIp3 was amplified by PCR from a cDNA clone produced from the first screening using the following amplification primers: Primer wSS3pe (5' GCACGGTCTATGAGMCMTGGC 3': SEQ ID NO: 33); and Primer wSS3pf (5' TCTGCATACCACCMTCGCCG 3': SEQ ID NO: 34).

The amplification reactions were performed using a FTS-1 or FTS4000 thermal sequencer (Corbett, Australia) for 1 cycle of 95° C. for 2 minutes; 35 cycles of 95° C. for seconds, 60° C. for 1 minutes, 72° C. for 2 minutes and 1 cycle of 25° C. for 1 minute.

Amplified sequences of the expected length were obtained, cloned and sequenced, and shown to contain DNA sequences highly homologous to the maize and potato SSIII genes. PCR fragments were subsequently used to probe a wheat cDNA library by DNA hybridisation and 8 positive clones were obtained, including one 3 kb cDNA. A region from the 5' end of this cDNA was amplified by PCR and used a probe for a second round of screening the cDNA library, obtaining 8 cDNA clones. Of these, one cDNA was demonstrated to be full length (wSSIII.B3, 5.36 kb insert). The sequence of the 5,346 bp wSSIII.B3 cDNA clone is given in SEQ ID NO:7.

Sequencing of the 8 cDNA clones obtained from the second round screening of the wheat cDNA library revealed that there were at least 2 classes of cDNA encoding SSIII present, possibly being encoded by homeologous genes on different wheat genomes. The sequence of a representative of this second class of cDNA clones, wSSIII.B1, is shown in SEQ ID NO:9. The 3261 bp clone wSSIII.B1 is not full length, however it is similar to nucleotides 1739 to 5346 of the homeologous clone wSSIII.B3 (SEQ ID NO: 7). Clone wSSIII.B1 has an open reading frame between nucleotide positions 1 and 3177.

An open reading frame is found in the cDNA clone wSSIII.B3 (SEQ ID NO:7), in the region between position 29, commencing the ATG start codon, and nucleotide position 4912. The amino acid sequence deduced from this open reading frame is shown in SEQ ID NO:8.

Figure 7:
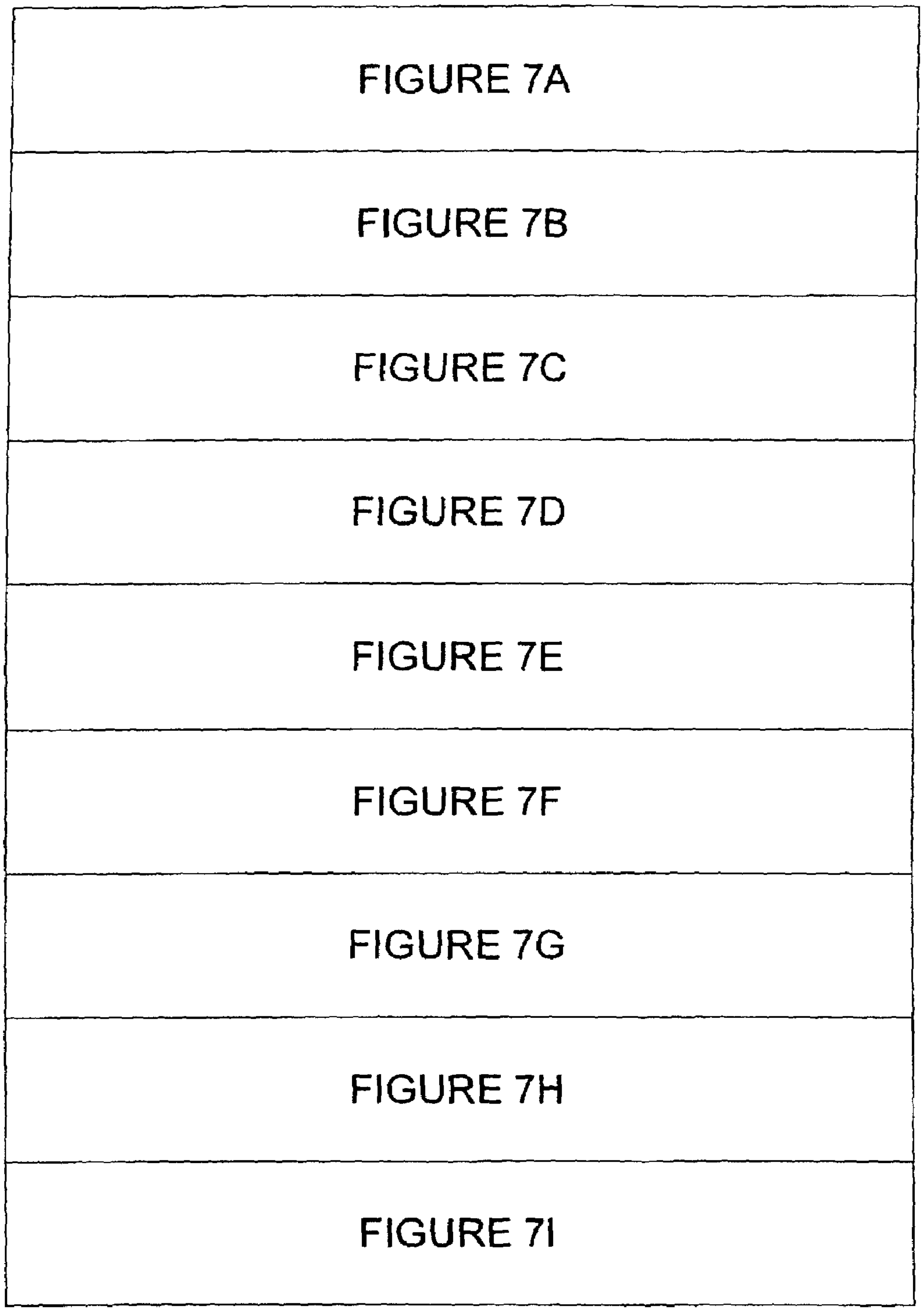
FIG. 7 (Figure panels 7A–7I) is a schematic representation comparing the deduced amino acid Sequences of the maize (SEQ ID NO:55), potato (SEQ ID NO:56) and wheat SSIII (SEQ ID NO:8) polypeptides.

An alignment of the deduced amino acid sequences of SSIII from maize, potato and wheat is shown in FIG. 7. There is about 56.6% identity between the maize SSIII and wheat wSSIII.B3 sequence at the amino acid level.

The C-terminal domain of starch synthases comprise the catalytic domain, and a characteristic amino acid sequence motif KVGGLGDVVTSLSRAVQDLGHNVEV (SEQ ID NO: 35) in maize, or alternatively KVGGLGDVVTSLSRAIQDLGHTVEV (SEQ ID NO: 36) in wheat, marking the first conserved region in the C-terminal domain. This amino acid sequence is present at amino acid residues 1194 to 1218 of SEQ ID NO: 8.

The amino acid identity between maize dull1 and wSSIII.B3 in the N-terminal region (i.e. amino acids 1 to 600 in FIG. 7) is only 32.2%; whilst the amino acid identity in the central region (i.e. amino acids 601 to 1248 in FIG. 7) is 68.4%; and in the C-terminal region (i.e. amino acids 1249 to 1631 in FIG. 7) is 84.6%. Accordingly, the SSIII starch synthases are much more highly conserved between maize and wheat in the region comprising the catalytic domain of the proteins.

EXAMPLE 14

Analysis of Wheat Starch Synthase III mRNA Expression

Figure 8:
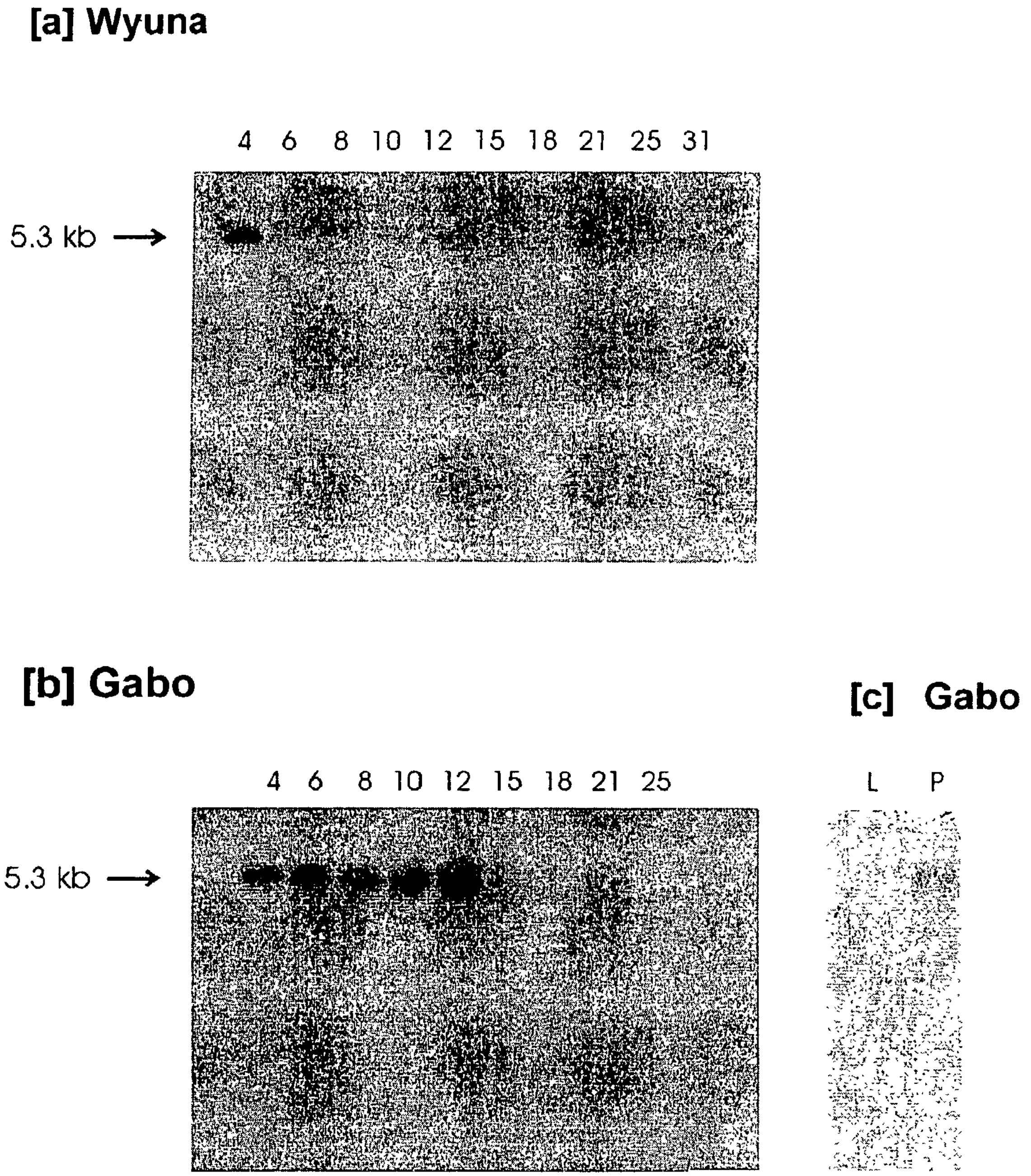
FIG. 8 is a copy of a photographic representation showing the expression of wheat wSSIII mRNA in wheat. Total RNAs were isolated from the endosperm of the wheat cultivars Wyuna (Panel a) and Gabo (Panel b) leaves pre-anthesis florets and endosperm of the wheat cultivar "Gabo", grown under a photoperiod comprising 16 hours daylength, and at 18° C. during the day cycle, and at 13° C. during the night cycle, and probed with the wSSIIIp1 DNA fragment derived from wSSIII.B3 cDNA. The source of each RNA is indicated at the top of the Figure as follows: Lane 1, endosperm at: 4 days post-anthesis; Lane 2, endosperm at 6 days post-anthesis; Lane 4, endosperm at 8 days post-anthesis; Lane 4, endosperm at 10 days post-anthesis; Lane 5, endosperm at 12 days post-anthesis; Lane 6, endosperm at 15 days post-anthesis; Lane 7, endosperm at 18 days post-anthesis; Lane 8, endosperm at 21 days post-anthesis; Lane 9, endosperm at 25 days post-anthesis; and Lane 10, endosperm at 31 days post-anthesis (Panel a only). In panel (c), L refers to leaf RNA, and P refers to RNA from pre-anthesis florets derived from the cultivar Gabo.

FIG. 8 shows the expression of wSSIII mRNA during endosperm development in two wheat varieties grown under defined environmental conditions. The expression of the gene is seen very early in endosperm development in both cultivars, 4 days after anthesis (FIG. 8, panels a and b). Expression in the leaf of the variety Gabo is very weak (FIG. 8, panel c, Lane L) whereas strong expression is seen in pre-anthesis florets (FIG. 8, panel c, Lane P).

EXAMPLE 15

Amino Acid Sequence Comparisons Between Wheat SSII and SSIII Polypeptides

Figure 9:
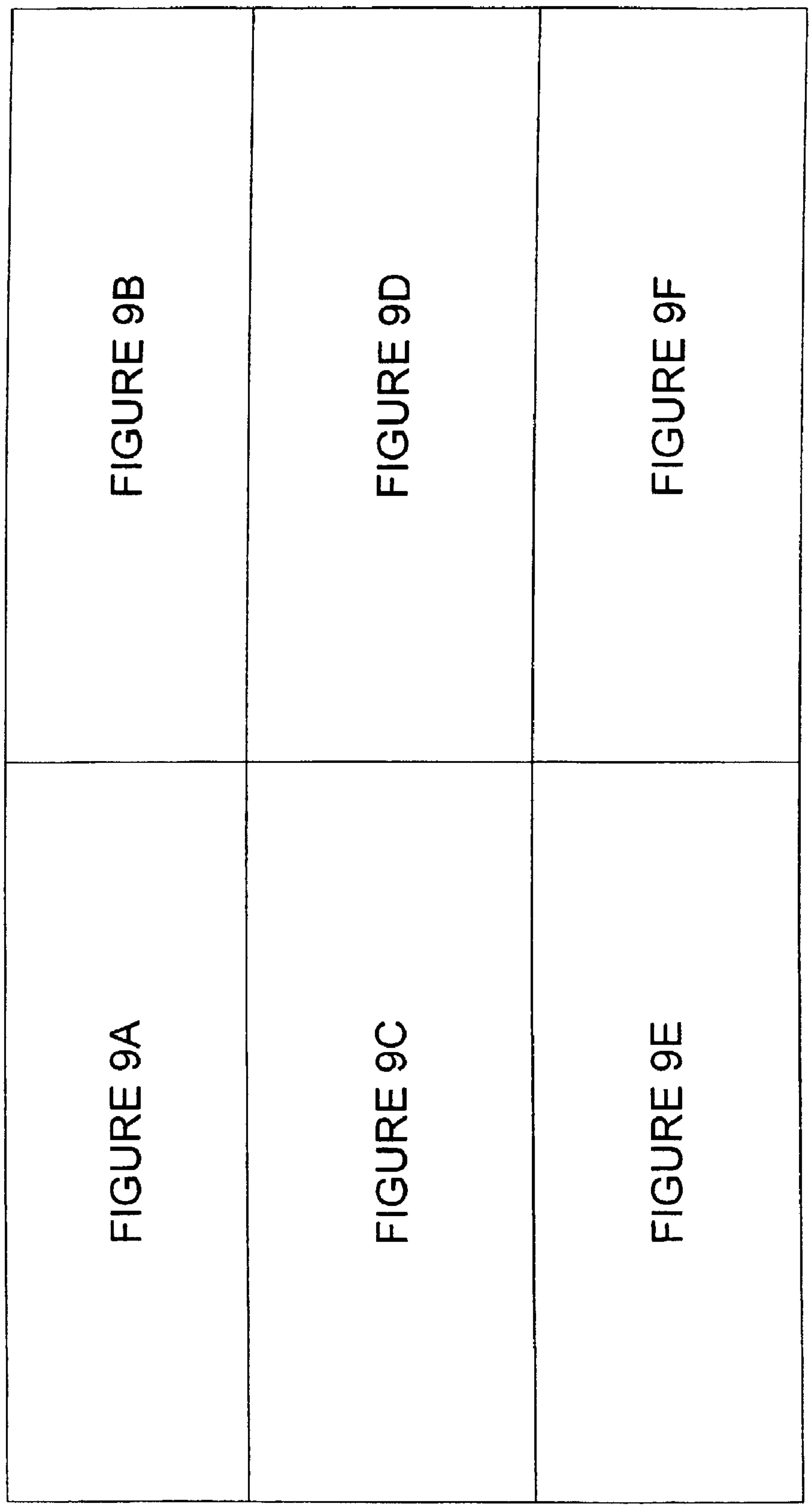
FIG. 9 (Figure panels 9A–9F) is a schematic representation showing the position of conserved amino acid sequences within four wheat starch synthase proteins. The eight highly-conserved regions between the wheat starch synthase polypeptides are underlined and annotated at the top of each group of amino acid sequences. The sequences included in the alignment are the wheat SSII-A1 and wheat SSIII polypeptides of the present invention; wheat GBSS (wGBSS; SEQ ID NO:57 Yan et al., 1999); wheat SSI (wSS1; SEQ ID NO:58 Li et al., 1999); wheat SSII (wSS2; SEQ ID NO:4); ans wheat SSIII (wSS3; SEQ ID NO:8).

Amino acid sequence comparisons between wheat BSSS, SSI, SSII and SSIII polypeptides reveals eight highly-conserved domains (FIG. 9). The amino acid sequences of these domains ar represented in the wheat SSIII amino acid sequence by the following sequence motifs:

(A) Region 1: KVGGLGDVVTS (SEQ ID NO:39);
(B) Region 2: GHTVEVILPKY (SEQ ID NO:40);
(C) Region 3: HDWSSAPVAWLYKEHY (SEQ ID NO:41);
(D) Region 4: GILNGIDPDIWDPYTD (SEQ ID NO:42);
(E) Region 5: DVPIVGIITRLTAQKG (SEQ ID NO:43);
(F) Region 5a: NGQVVLLGSA (SEQ ID NO:44);
(G) Region 6: AGSDFIIVPSIFEPCGLTQLVAMRYGS (SEQ ID NO:45); and
(H) Region 7: TGGLVDTV (SEQ ID NO:46).

These conserved amino acid sequences are summarised in Table 4. As shown in Table 4 below, there is at least about 25% amino acid sequence identity, preferably at least about 30% amino acid sequence identity, more preferably at least about 35% amino acid sequence identity, more preferably at least about 40% amino acid sequence identity, more preferably at least about 45% amino acid sequence identity, more preferably at least about 50% amino acid sequence identity, more preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity and even more preferably at least about 95% amino acid sequence identity between the amino acid sequences of plant starch synthase enzymes, in particular wheat starch synthases.

From the data presented in Table 4, the most conserved regions of the wheat SSII and SSIII polypeptides are a region of 6 or 7 identical amino acids in Region 1 and a region of 8 or 9 identical amino acids in Region 6. The lowest regions of identity are found in regions 3 and 5a.

For each of the amino acid sequences presented in the first column of Table 4, which are specific for wSSIII polypeptides, corresponding signature motifs which are specific for wSSII-A, wSSII-B, and wSSII-D polypeptides can be derived from the alignment, as follows:

Region 1: KTGGLGDVAGA (SEQ ID NO:47);
Region 2: GHRVMVVVPRY (SEQ ID NO:48);
Region 3: NDWHTALLPVYLKAYY (SEQ ID NO:49);
Region 4: GIVNGIDNMEWNPEVD (SEQ ID NO:50);
Region 5: DVPLLGFIGRLDGQKG (SEQ ID NO:51);
Region 5a: DVQLVMLGTG (SEQ ID NO:52);
Region 6: AGADALLMPSRF(E/V)PCGLNQLYAMAYGT (SEQ ID NO:53); and
Region 7: VGG(V/L)RDTV (SEQ ID NO:54).

Figure 10:
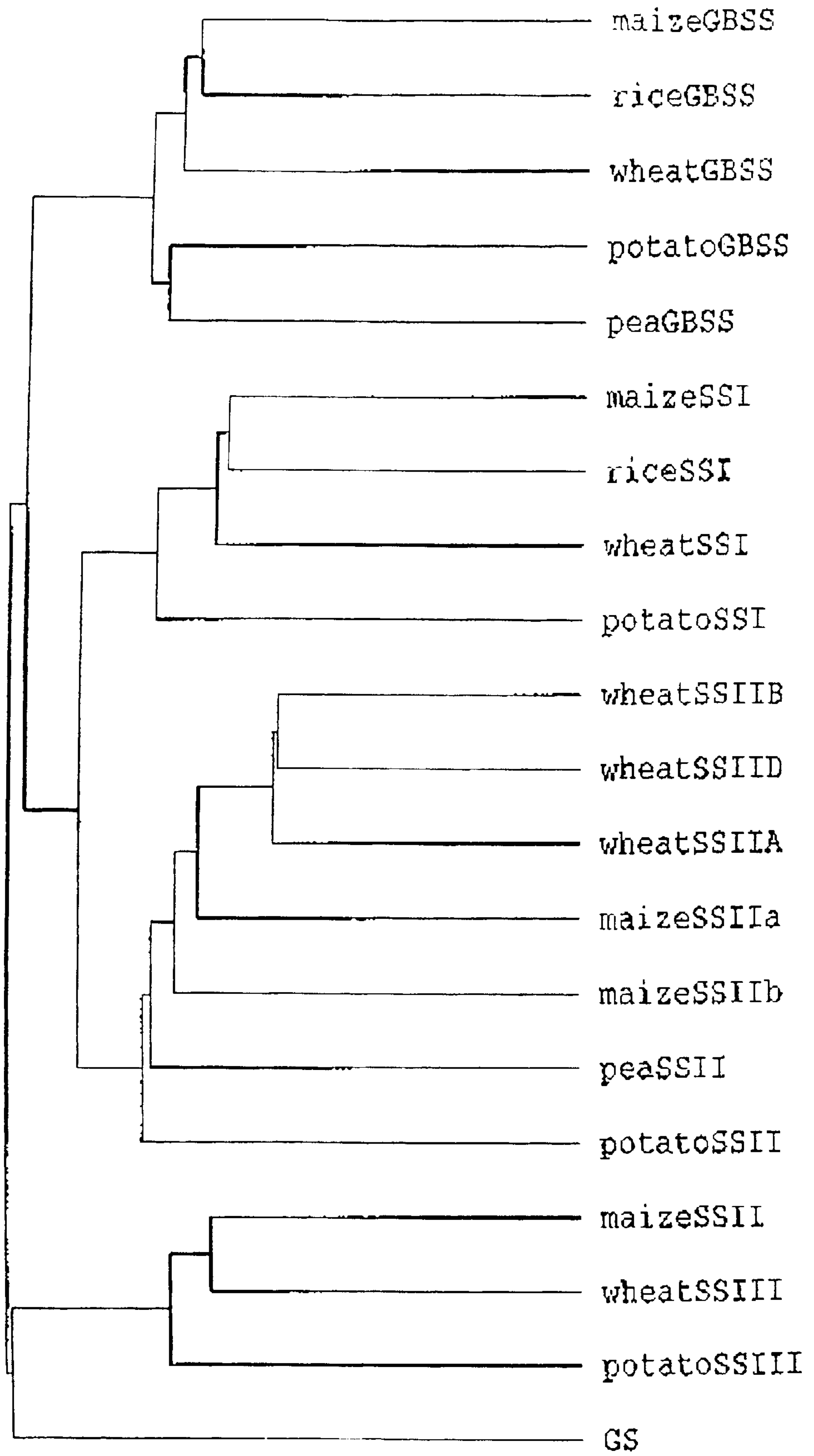
FIG. 10 is a schematic representation showing the relationships between the primary amino acid sequences of starch synthases (SS) and glycogen synthase of *E. coli* (GS). The dendrogram was generated by the program PILEUP (Devereaux et al., 1984). The amino acid sequences used for the analysis are those of the wheat SSIIA, wheat SSIIB, wheat SSIID, and wheat SSIII polypeptides of the present invention compared to the deduced amino acid sequences of wheat GBSS (Clark et al., 1991), wheat SSI (Li et al., 1999), rice GBSS (Okagaki, 1992), rice SSI (Baba et al., 1993), maize GBSS (Kloesgen et al., 1986), maize SSI (Knight et al., 1998), maize SSIIa and maize SSIIb (Harn et al., 1998), maize SSIII (Gao et al., 1998), pea GBSS (Dry et al., 1992), pea SSII (Dry et al., 1992), potato GBSS (van der Leij et al., 1991), potato SSI (Genbank accession number: STSTA-SYNT), potato SSII (Edwards et al., 1995), potato SSIII (Abel et al., 1996), and *E. coli* glycogen synthase (GS) (Kumar et al., 1986). Five groups of enzymes included in the alignment are granule-bound starch synthase (GBSS), starch synthase-I (SSI), starch synthase-II (SSII), starch synthase-III (SSIII) and glycogen synthase (GS).

Comparison of the amino acid sequences of all available starch synthases with the deduced amino acid sequences of the three wSSII cDNA clones of the present invention (i.e. WSSIIB, wSSIIA and WSSIID) was conducted using PILEUP analysis (Devereaux et al., 1984) and data are presented herein as a dendrogram (FIG. 10). The sequence of the glycogen synthase of *E. coli* was also included. Based upon their amino acid similarities, four classes of plant starch synthases can be defined: GBSS, SSI, SSII and SSIII.

Table 5 shows that levels of identity at the amino acid level between the WSSII sequences, as determined using the BESTFIT programme in GCG (Devereaux et al., 1984), and other class II starch synthases range from 70% identity with potato SSII to 85% identity with maize SSIIa. Both wSSIIB and wSSIID showed significantly higher homology to maize SSIIa than wSSIIA. Based upon sequence identities and the function of the Sgp-1 proteins in wheat, the wSSIIB, wSSIIA and WSSID cDNA clones are members of the starch synthase II (SSII) group and are more similar in sequence to maize SSIIa than maize SSIIb.

between the classes of genes are found in the length of the N-terminal region between the transit peptide and the first conserved region. At one extreme, the GBSS genes have a very short N-terminal arm, whereas the du1 starch synthase contains a very long N-terminal extension containing several distinct regions. The wSSII genes contain an N-terminal extension which is longer than either GBSS, SSI, or SSIIb, and slightly longer than the maize SSIIa gene.

EXAMPLE 16

Isolation of Genomic Clones for SSIII

Screening of a genomic library from the D-genome donor of wheat, *T. tauschii*, identified a number of clones which hybridised to the wSSIII PCR fragment. Positive plaques in the genomic library were selected as those hybridising with a probe that had been generated by PCR (amplifying between nucleotide positions 3620 to 3966) from the SSIII cDNA as template. The primer sequences used were as follows: wSS3pa (5' GGAGGTCTTGGTGATGTTGT 3': SEQ ID NO: 29); and wSS3pb (5'CTTGACCMTCATGGCMTG 3': SEQ ID NO: 30).

Hybridisation was carried out in 25% formamide, 6×SSC, 0.1% SDS at 42° C. for 16 hour, then washed three times with 2×SSC containing 0.1% SDS at 65° C., for 1 hour per wash. shows an example of a plaque lift showing positive and negative hybridisations for plaques containing the *T. tauschii* homologue of the wSSIII.B3 gene.

DNA was isolated from positive-hybridising λ clones using methods described by Maniatis et al. Briefly, DNA

TABLE 4

Identities between conserved motifs of plant starch synthases

| Sequence in wSSIII polypeptide | Number of conserved residues between wheat starch synthases | Number of conserved residues between wheat SSII and SSIII polypeptides |
|---|---|---|
| Region 1: KVGGLGDVVTS | 6/11 residues | 6/11 residues |
| Region 2: GHTVEVILPKY | 6/11 residues | 6/11 residues |
| Region 3: HDWSSAPVAWLYKEHY | 4/16 residues | 5/16 residues |
| Region 4: GILNGIDPDIWDPYTD | 7/16 residues | 8/16 residues |
| Region 5: DVPIVGIITRLTAQKG | 8/16 residues | 10/16 residues |
| Region 5a: NGQVVLLGSA | 4/10 residues | 4/10 residues |
| Region 6: AGSDFIIVPSIFEPCGLTQLVAMRYGS | 15/27 residues | 17/27 residues |
| Region 7: TGGLVDTV | 5/9 residues | 5/9 residues |

TABLE 5

| | wSSII-A | wSSII-B | wSSII-D |
|---|---|---|---|
| wSSI-A | 100% | | |
| wSSII-B | 95.9% | 100% | |
| wSSII-D | 96.3% | 96.7% | 100% |
| maize SSIIa | 76.1% | 85.2% | 84.7% |
| maize SSIIb | 76.3% | 76.7% | 75.9% |
| pea SSII | 72.0% | 72.2% | 71.8% |
| potato SSII | 70.9% | 71.1% | 70.3% |

Figure 11:
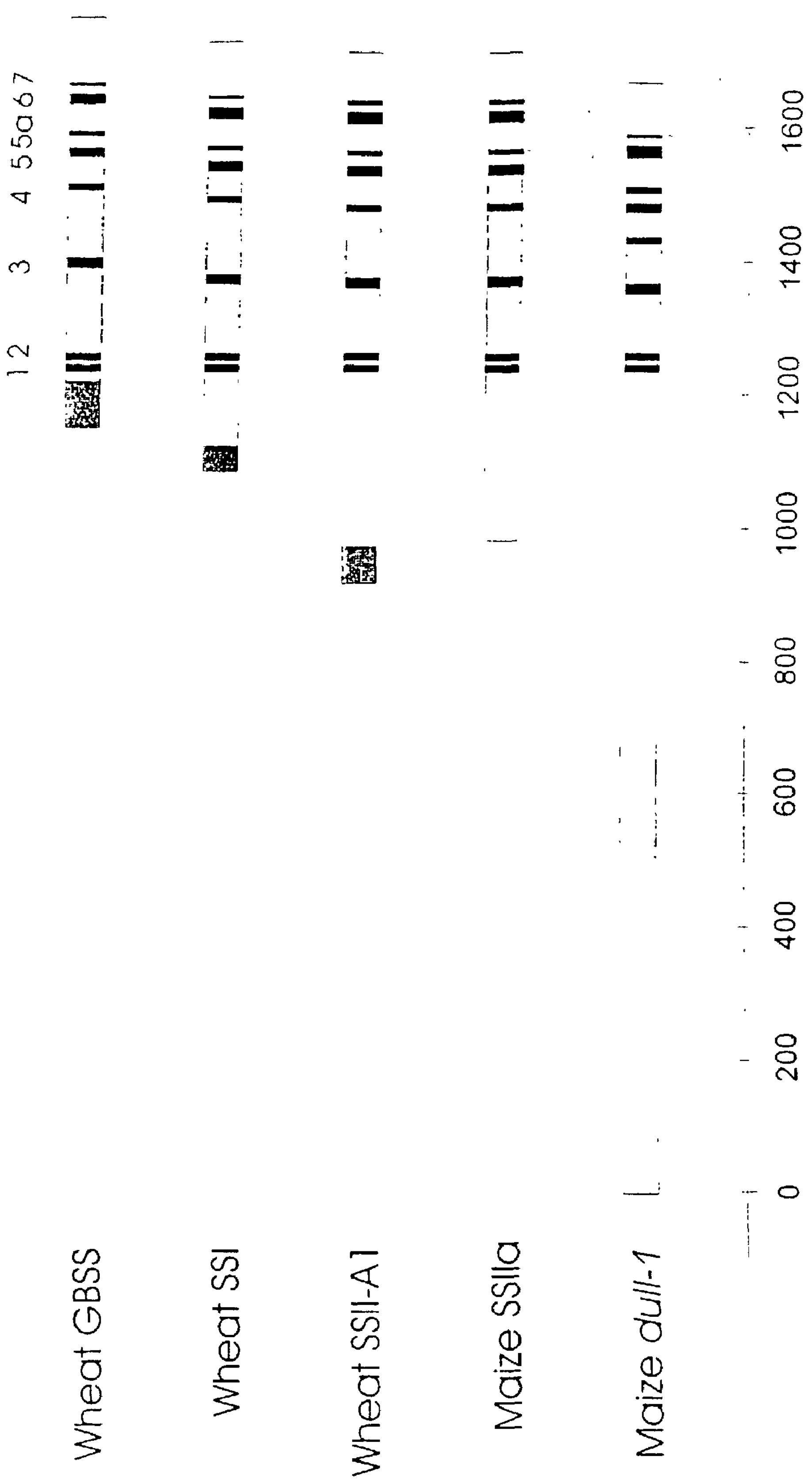
FIG. 11 is a schematic representation showing the position of conserved regions within cereal starch synthase genes. Comparisons of cereal starch synthases were made based on their deduced amino acid sequences and 8 conserved regions identified. Conserved regions are shown in bold and transit peptides (where defined) in grey. The sequences included in the alignment are the wheat SSII-A1 and wheat SSIII polypeptides of the present invention; wheat GBSS (Ainsworth et al., 1993); wheat SSI (Li et al., 1999); maize SSIIa (Harn et al., 1998); and maize dull-1 (Gao et al., 1998).

FIG. 11 shows a schematic representation of an alignment of plant starch synthase sequences, including wheat GBSS, wheat SSI, wheat SSII-A1, maize SSIIa, and maize dull-1 polypeptides, in which the position of the first homologous region, comprising the consensus motif KXGG, is used as the basis of the alignment. The major differences in structure was digested using BamHI or BglI and sub-cloned in to the vector pJKKmfm. DNA sequencing was performed using the automated ABI system with dye terminators as described by the manufacturers. DNA sequences were analysed using the GCG suite of programs (Devereaux et al., 1984).

Nucleotide sequences of the genomic SSIII clone from *T. tauschii* are provided herein as 6 contiguous sequences designated fragments 1 to 6 (SEQ ID NOs: 11 to 16, respectively). Table 6 defines the relative positions of these fragments with respect to the SSIII cDNA and describes the positions of exons. FIG. 11 shows this information schematically.

Figure 12:
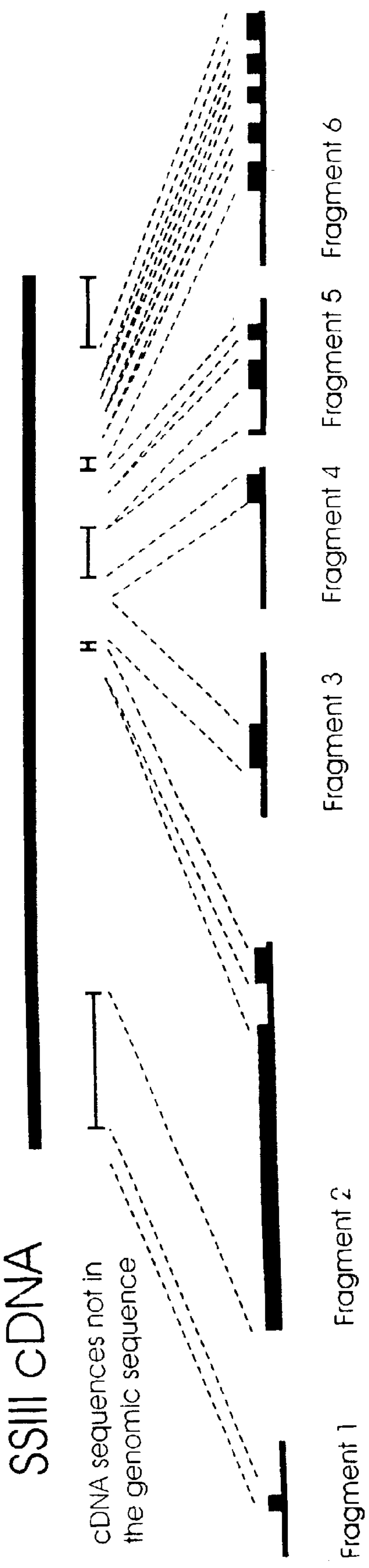
FIG. 12 is a copy of a schematic representation of a gene map showing the alignment of fragments 1 to 6 of the genomic SSIII gene (lower line) with the corresponding SSIII cDNA clone (upper line). Raised regions in the genomic clone fragments (lower line) represent protein-encoding regions of the gene.

The complete nucleotide sequence of a wheat SSIII genomic gene is presented herein as SEQ ID NO: 38. The structural features of this gene are presented in Table 7. A schematic representation of the intron/exon organisation of this gene is also presented in FIG. 12.

EXAMPLE 17

Discussion

Early work on the Sgp-1 starch synthase proteins (Denyer et al., 1995; Rahman et al., 1995) was based on the localisation of these proteins in the wheat starch granule, and no definitive conclusion concerning their presence or absence in soluble extracts of the wheat endosperm was presented.

We have now demonstrated that a monoclonal antibody against the Sgp-1 proteins cross reacts strongly with those starch synthase proteins having apparent molecular weights of 100–105 kDa in soluble extracts, however, the appearance of these proteins in soluble extracts is dependant on the developmental stage of the endosperm material. Whilst the proteins can be detected in the soluble phase in early to mid endosperm development, little or no soluble protein remains in late endosperm development (FIG. 1). This observation accounts for the failure of Rahman et al. (1995) to detect the protein in soluble extracts in a previous report.

Based upon the localisation of the Sgp-1 starch synthase proteins in the wheat endosperm, the following nomenclature is suggested for wheat starch synthase enzymes: wGBSS for the 60 kDa granule bound starch synthase (Wx); wSSI for the 75 kDa starch synthase I (Sgp-3); wSSII for the 100–105 kDa proteins (Sgp-1); and wSSIII for a soluble high molecular starch synthase.

The present invention provides cDNA and genomic clones encoding the wSSII and wSSIII polypeptides and the corresponding genomic clones. Whilst the evidence is compelling that the wSSIIA, wSSIIB and WSSIID cDNAs encode the Sgp-A1, Sgp-B1 and Sgp-D1 proteins of the wheat starch granule, molecular weights calculated from the deduced amino acid sequences of the clones are considerably lower than estimates obtained from SDS-PAGE. The molecular weight of the precursor wSSIIA protein is 87,229 Da, and the mature protein 81,164 Da, yet the estimated molecular weight in our experience is 105 kDa. The assignment of the wSSIIA cDNA to the A-genome of wheat is demonstrated in FIG. 5, and the assignment of the 105 kDa protein to the A-genome in Denyer et al. (1995) and Yamamori and Endo (1996). Similarly, the molecular weight of the wSSIIB protein is 86,790 Da and the mature protein 80,759 Da, yet the molecular weight of the Sgp-B1 protein is estimated to be 100 kDa. No comparison can be made of the wSSIID sequences as a full length cDNA clone was not obtained. The wSSIIA and wSSIIB amino acid sequences differ by just a single amino acid residue, yet there is an apparent difference of 5 kDa in molecular weight when estimated by SDS-PAGE. Several possibilities can be advanced to account for this apparent discrepancy in molecular weights. Firstly, the wSSII proteins may not migrate in SDS-PAGE in accordance with their molecular weight because they retain some conformation under the denaturing conditions used. Secondly, the proteins may be glycosylated. It is also possible that the proteins may be non-covalently linked to starch through a high affinity starch binding site which survives denaturation and SDS-PAGE. Differences between the apparent molecular weights and those calculated from the deduced amino acid sequences will have to be defined in establishing the relationship between the wSSII proteins and proteins encoded by the analogous SSII genes of other species.

The catalytic domain of the starch synthases is found at the C-terminal end of the protein (Gao et al., 1998; Harn et al., 1998). Harn et al. (1998) identified 7 conserved regions among SSIIa, SSIIb, SSI and GBSS sequences. We have identified an additional conserved region (designated region 5a in Table 4 and FIG. 10) comprising the amino acid sequence motif DVQLVMLGTG (SEQ ID NO:52), by a comparison of the wSSII and wSSIII sequences of the present invention with differing isoforms of other plant starch synthase (GBSS, SS1, SSII and SSIII). The conservation of eight peptide regions among the 4 classes of starch synthases is striking, in terms of their sequence homologies and their alignment.

Analysis of the wheat SSII genes shows that there is a motif, PVNGENK (SEQ ID NO:59) which is repeated. The area surrounding the repeated PVNGENK (SEQ ID NO:59) motif is not homologous to maize SSIIa and the insertion of this region is responsible for the difference in length between the wheat SSII and maize SSIIa genes. In pea and potato SSII polypeptides, a PPP motif (FIG. 3; residues 251–253 and 287–289 respectively) has been suggested to mark the end of the N-terminal region and to facilitate the flexibility of an "N-terminal arm". This motif is not found in either the maize or wheat SSII sequences.

The generation of a wheat line combining null alleles at each of the three wSSII loci, wSSIIA, wSSIIB and wSSIID, has been reported recently by Yamamori (1998). In this triple null line, the large starch granules were reported to be mostly deformed and a novel starch with high blue value was observed when stained with iodine, indicating that wSSII is a key enzyme for the synthesis of starch in wheat. Further analysis of the starch derived from this triple null mutant is in progress.

Mutations in starch synthases are known in three other species. In pea, mutation in SSII gives rise to starch with altered granule morphology and an amylopectin which yields an oligosaccharide distribution with reduced chain length on debranching, compared to the wild type (Craig et al., 1998). A similar mutation in a gene designated SSII is known in *Chlamydomonas* (the sta-3 mutation) and similar effects on granule morphology and amylopectin structure are observed (Fontaine et al., 1993). In maize, two mutations affecting starch synthases are known. First, the dull1 mutation has been shown to be caused by a lesion within the du1 SSIII-type starch synthase gene (Gao et al., 1998). A second mutation, the sugary-2 mutation yields a starch with reduced amylopectin chain lengths on debranching (this mutation co-segregates with the SSIIa locus (Harn et al., 1998) although direct evidence that the sugary-2 mutation is caused by a lesion in the SSIIa gene is lacking). In the SSII mutants of each of these species, amylose biosynthesis capacity is retained, suggesting different roles in amylose and amylopectin synthesis for the GBSS and SSII genes. Given the conservation in overall organisation of the GBSS and SSII genes (see FIGS. 12 and 13), when an alignment is made based on the KTGGL motif of the first conserved region, this focuses attention on the role(s) of the N-terminal region in defining substrate specificity and the localisation of the proteins as the N-terminal region is the major area of divergence between the 4 classes of starch synthases. However, it is premature to exclude the influence of more subtle mutations in central and C-terminal regions of the gene.

The cloning of the wSSII and wSSIII cDNAs and genomic clones described herein provides useful tools for the further study of the roles of the starch synthases in wheat. Firstly, they provide a source of markers which can be used to recover and combine null or divergent alleles. Secondly, genetic manipulation of wheat by gene suppression or over-expression can be carried out, and the genes may be used for over expression in other species. The promoter regions of these genes are also useful in regulating the expression of starch synthase genes and other heterologous genes in the developing wheat endosperm and in pre-anthesis florets of wheat.

TABLE 6

Summary of the Wheat Starch Synthase III Genomic Sequence

| Fragment in genomic DNA clone | Length (bp) | Features in SEQ ID NOS: 11 to 16 | Corresponding region in cDNA sequence |
|---|---|---|---|
| Fragment 1 (SEQ ID NO: 11) | 728 | Translation start codon (nucleotides 287 to 289); Exon 1.1 (nucleotides 260 to 385). | Exon 1.1: nucleotides 1 to 126 |
| Fragment 2 (SEQ ID NO: 12) | 2446 | Exon 2.1 (nucleotides 1 to 1938); Exon 2.2 (nucleotides 2197 to 2418). | Exon 2.1: nucleotides 1008 to 2948; Exon 2.2: nucleotides 2949 to 3171 |
| Fragment 3 (SEQ ID NO: 13) | 1032 | Exon 3.1 (nucleotides 310 to 580) | Exon 3.1: nucleotides 3172 to 3440 |
| Fragment 4 (SEQ ID NO: 14) | 892 | Exon 4.1 (nucleotides 678 to 853) | Exon 4.1: nucleotides 3441 to 3616 |
| Fragment 5 (SEQ ID NO: 15) | 871 | Partial Exon 5.1 (nucleotides 1 to 29) Exon 5.2 (nucleotides 293 to 463) Exon 5.3 (nucleotides 589 to 695) | Exon 5.1: nucleotides 3908 to 3937 (partial) Exon 5.2: nucleotides 3938 to 4108 Exon 5.3: nucleotides 4109 to 4215 |
| Fragment 6 (SEQ ID NO: 16) | 1583 | Exon 6.1 (nucleotides 471 to 653); Exon 6.2 (nucleotides 770 to 902); Exon 6.3 (nucleotides 999 to 1110); Exon 6.4 (nucleotides 1201 to 1328); Partial Exon 6.5 (nucleotides 1408 to 1583); Translation stop codon (nucleotides 1536 to 1538) | Exon 6.1: nucleotides 4238 to 4420 Exon 6.2: nucleotides 4421 to 4552 Exon 6.3: nucleotides 4553 to 4664 Exon 6.4: nucleotides 4665 to 4793 Exon 6.5: nucleotides 4794 to 4966 (partial) |

TABLE 7

Structural features of the wheat starch synthase III genomic gene

| Nucleotide Position in SEQ ID NO: 38 | Feature | Length (bases) |
|---|---|---|
| 1–973 | 5'-untranscribed region and promoter sequence | 973 |
| 974–1099 | exon 1 | 126 |
| 1001–1003 | translation start codon (ATG) | 3 |
| 1100–2056 | intron 1 | 957 |
| 2057–2120 | exon 2 | 64 |
| 2121–2588 | intron 2 | 468 |
| 2589–5291 | exon 3 | 2703 |
| 5292–5549 | intron 3 | 258 |
| 5550–5767 | exon 4 | 218 |
| 5768–6103 | intron 4 | 336 |
| 6104–6374 | exon 5 | 271 |
| 6375–7148 | intron 5 | 774 |
| 7149–7324 | exon 6 | 176 |
| 7325–7438 | intron 6 | 114 |
| 7439–7546 | exon 7 | 108 |
| 7547–7792 | intron 7 | 246 |
| 7793–7902 | exon 8 | 110 |
| 7903–8797 | intron 8 | 895 |
| 8798–8900 | exon 9 | 103 |
| 8901–9164 | intron 9 | 264 |
| 9165–9335 | exon 10 | 171 |
| 9336–9460 | intron 10 | 125 |
| 9461–9589 | exon 11 | 129 |
| 9590–9677 | intron 11 | 88 |
| 9678–9860 | exon 12 | 183 |
| 9861–9977 | intron 12 | 117 |
| 9978–10109 | exon 13 | 132 |
| 10110–10205 | intron 13 | 96 |
| 10206–10317 | exon 14 | 112 |
| 10318–10407 | intron 14 | 90 |
| 10408–10536 | exon 15 | 129 |
| 10537–10618 | intron 15 | 82 |
| 10619–11146 | exon 16 | 128 |
| 10744–10746 | translation stop codon (TGA) | 3 |
| 11147–11611 | 3'-untranscribed region | 465 |

REFERENCES

1. Ausubel, F. M., Brent, R., Kingston, RE, Moore, D. D., Seidman, J. G., Smith, J. A., and Struhl, K. (1987). In: Current Protocols in Molecular Biology. Wiley Interscience (ISBN 047150338).
2. Abel G J W, Springer F, Willmitzer L, Kossmann J (1996) Cloning and functional analysis of a cDNA encoding a novel 139 kDa starch synthase from potato (*Solanum tuberosum* L.). Plant J 10: 981–991.
3. Ainsworth C, Clark J, Balsdon J (1993) Expression, organisation and structure of the genes encoding the waxy protein (granule-bound starch synthase) in wheat. Plant Mol Biol 22: 67–82.
4. Baba T, Nishihara M, Mizuno K, Kawasaki T, Shimada H, Kobayabashi E, Ohnishi S, Tanaka K, Arai Y (1993) Identification, cDNA cloning, and Gene Expression of Soluble Starch Synthase in Rice (*Oryza sativa* L.) Immature Seeds. Plant Physiol 103: 565–573.
5. Craig J, Lloyd J R, Tomlinson K, Barber L, Edwards A, Wang T L, Martin C, Hedley C L, Smith A M (1998) Mutations in the gene encoding starch synthase II profoundly alter amylopectin structure in pea embryos. Plant Cell 10: 413–426.
6. Denyer K, Hylton C M, Jenner C F, Smith A M (1995) Identification of multiple isoforms of soluble and granule-bound starch synthase in developing wheat endosperm. Planta 196: 256–265.
7. Devereaux, J, Haeberli P, Smithies O (1984) A comprehensive set of sequence analysis programs for the VAX. Nucleic Acids Res 12: 387–395.
8. Dry I, Smith A, Edwards A, Bhattacharyya M, Dunn P, Martin C (1992) Characterisation of cDNAs encoding two isoforms of granule-bound starch synthase which show differential expression in developing storage organ of pea and potato. Plant J 2: 193–202.
9. Edwards A, Marshall J, Sidebottom C, Visser RGF, Smith A M, Martin C (1995) Biochemical and molecular characterization of a novel starch synthase from potato tubers. Plant J 8: 283–294.
10. Fontaine T, D'Hulst C, Maddelein M-L, Routier F, Pépin T M, Decq A, Wieruszeski J-M, Delrue B, Van den Koornhuyse N, Bossu J-P, Fournet B, Ball S (1993) Toward an understanding of the biogenesis of the starch granule. Evidence that *Chlamydomonas* soluble starch synthase II controls the synthesis of intermediate size glucans of amylopectin. J Biol Chem 22: 16223–16230.
11. Furukawa K, Tagaya M, Inouye M, Preiss J, Fukui T (1990) Identification of lysine 15 at the active site in *Escherichia coli* glycogen synthase. J Biol Chem 265: 2086–2090.

12. Gao M, Wanat J, Stinard P S, James M G, Myers A M (1998) Characterization of dull1, a maize gene coding for a novel starch synthase. Plant Cell 10: 399–412.
13. Harn C, Knight M, Ramakrishnan A, Guan H, Keeling P L, Wasserman B P (1998) Isolation and characterization of the zSSIIa and zSSIIb starch synthase cDNA clones from maize endosperm. Plant Mol Biol 37: 639–649.
14. Kloesgen RB, Gierl A, Schwarz-Sommer Z S, Saedler H (1986) Molecular analysis of the waxy locus of *Zea mays*. Mol Gen Genet 203: 237–244.
15. Knight ME, Ham C, Lilley CER, Guan H, Singletary G W, MuForster C, Wasserman B P, Keeling P L (1998) Molecular cloning of starch synthase I from maize (W64) endosperm and expression in *Escherichia*. Plant J 14: 613–622.
16. Kumar A, Larsen C E, Preiss J (1986) Biosynthesis of bacterial glycogen: Primary structure of *Escherichia coli* ADP-glucose:alpha-1,4-glucan, 4-glucosyltransferase as deduced from the nucleotide sequence of the g/gA gene. J Biol Chem 261: 16256–16259.
17. Li Z, Rahman S, Kosar-Hashemi B, Mouille G, Appels R Morell, M K (1999) Cloning and characterisation of a gene encoding wheat starch synthase 1. Theor Appl Genet: In press.
18. Mouille G, Maddelein M-L, Libessart N, Talaga P, Decq A, Delrue B Ball, S (1996). Preamylopectin processing: A mandatory step for starch biosynthesis in plants. Plant Cell 8: 1353–1366.
19. Nakamura T, Yamamori M, Hirano H, Hidaka S, Nagamine T (1995) Production of waxy (amylose-free) wheats. Mol Gen Genet 248: 253–259.
20. Okagaki, RJ (1992) Nucleotide sequence of a long cDNA from the rice waxy gene. Plant Mol Biol 19: 513–516.
21. Ozbun, J. L., Hawker, J. S. and Preiss, J. (1971) Adensine diphosphoglucose-starch glucosyltransferases from developing kernels of waxy maize. Plant Physiology 48: 765–769
22. Ozbun, J. L., Hawker, J. S., Greenberg, E., Lammel, C., Preiss, J. and Lee, E. Y. C.(11973) Starch synthetase, phosphorylase, ADPglucose pyrophosphorylase, and UDPglucose pyrophosphorylase in developing maize kernels. Plant Physiology 51: 1–5.
23. Pollock, C. and Preiss, J.(1980) The citrate-stimulated starch synthase of starchy maize kernels: purification and properties. Arch Biochem Biophys 204: 578–588.
24. Rahman S, Abrahams S, Abbott D, Mukai Y, Samuel M, Morell M, Appels R (1997) A complex arrangement of genes at a starch branching enzyme I locus in D-genome donor of wheat. Genome 40: 465–474.
25. Rahman S, Kosar-Hashemi B, Samuel M, Hill A, Abbott D C, Skerritt J H, Preiss J, Appels R, Morell M (1995) The major proteins of wheat endosperm starch granules. Aust J Plant Physiol 22: 793–803.
26. Rahman S, Li Z, Abrahams S, Abbott D, Appels R, Morell M (1998) Characterisation of a gene encoding wheat endosperm starch branching enzyme-1. Theor Appl Genet 98: In press.
27. Sears E R, Miller T G (1985) The history of Chinese spring wheat. Cereal Res Comm 13: 261–263.
28. Takaoka M, Watanabe S, Sassa H, Yamamori M, Nakamura T, Sasakuma T, Hirano H (1997) Structural characterisation of high molecular weight starch granule-bound proteins in wheat (*Triticum aestivum* L). J Agric Food Chem 45: 2929–2934.
29. van der Leij F R, Visser R G F, Ponstein A S, Jacobsen E, Feenstra W J (1991) Sequence of the structural gene for granule bound starch synthase of potato (*Solanum tuberosum* L.) and evidence for a single point deletion in the amf allele. Mol Gen Genet 228: 240–248.
30. Yamamori M, Endo T R (1996) Variation of starch granule proteins and chromosome mapping of their coding genes in common wheat. Theor Appl Genet 93: 275–281.
31. Yamamori M (1998) Selection of a wheat lacking a putative enzyme for starch synthesis, SGP-1 *Proc 9th In Wheat Gen Symp* 4, 300–302.

What is claimed is:

1. An isolated nucleic acid molecule comprising a nucleotide sequence encoding a polypeptide having starch synthase II activity or a nucleotide sequence complementary thereto, said nucleotide sequence selected from the group consisting of:

(i) a nucleotide sequence having at least 97% identity to the nucleotide sequence of the protein-encoding region of the nucleotide sequence set forth in SEQ ID NO: 3;

(ii) a nucleotide sequence encoding a polypeptide having at least 97% identity to the amino acid sequence set forth in SEQ ID NO: 4; and (iii) a nucleotide sequence which is complementary to (i) or (ii).

2. The isolated nucleic acid molecule according to claim 1 wherein the starch synthase II polypeptide comprises one or more amino acid sequences selected from the group consisting of:

(a) KTGGLGDVAGA (SEQ ID NO: 47);

(b) GHRVMVVVPRY (SEQ ID NO: 48);

(c) NDWHTALLPVYLKAYY (SEQ ID NO: 49);

(d) GIVNGIDNMEWNPEVD (SEQ ID NO: 50);

(e) DVPLLGFIGRLDGQKG (SEQ ID NO: 51);

(f) DVQLVMLGTG (SEQ ID NO: 52);

(g) AGADALLMPSRF(E/V)PCGLNQLYAMAYGT (SEQ ID NO: 53); and (h) VGG(V/L)RDTV (SEQ ID NO: 54).

3. The isolated nucleic acid molecule of claim 2 wherein the starch synthase II polypeptide comprises at least three of said amino acid sequences selected from the group of (a) to (h).

4. The isolated nucleic acid molecule of claim 1 wherein the starch synthase polypeptide comprises at least six of said amino acid sequences selected from the group consisting of (a) to (h).

5. The isolated nucleic acid molecule of claim 1 wherein the polypeptide is a wheat starch synthase II polypeptide.

6. The isolated nucleic acid molecule of claim 2 wherein the starch synthase II polypeptide further comprises one or more amino acid sequences selected from the group consisting of:

(a) GIVNGIDNMEWNPEVD (SEQ ID NO:50); and (b) AGADALLMPSRF(E/V)PCGLNQLYAMAYGT (SEQ ID NO: 53).

7. The isolated nucleic acid molecule of claim 5 wherein the polypeptide has the amino acid sequence set forth in SEQ ID NO: 4.

8. A method of modifying the starch content and/or starch composition of one or more tissues or organs of a plant, said method comprising the step of expressing in said plant a nucleic acid molecule for a time and under conditions sufficient for the expression of a gene encoding one or more starch synthase II isoenzymes to be modified, wherein said nucleic acid molecule is selected from the group consisting of:

(i) the isolated nucleic acid molecule of claim 1; and (ii) an antisense molecule or a co-suppression molecule which comprises a fragment of (i) which is expressed to down-regulate the expression of an endogenous starch synthase II isoenzyme of said plant.

9. The method of claim 8 comprising introducing the nucleic acid molecule to an isolated plant cell, tissue, or organ, and regenerating the plant from the cell, tissue or organ.

10. The method claim 9 wherein the nucleic acid molecule is introduced to the plant cell, tissue, or organ by transformation.

11. A plant comprising a transgenic nucleic acid molecule comprising a nucleotide sequence, said nucleotide sequence selected from the group consisting of:

(i) a nucleotide sequence encoding a polypeptide having starch synthase II activity having at least 97% identity to the nucleotide sequence of the protein-encoding region of the nucleotide sequence set forth in SEQ ID NO: 3;

(ii) a nucleotide sequence encoding a polypeptide having starch synthase II activity the polypeptide having at least 97% identity to the amino acid sequence set forth in SEQ ID NO: 4;

(iii) a nucleotide sequence which is complementary to (i) or (ii); and (iv) an antisense molecule or co-supression molecule which comprises a fragment of (i), (ii) or (iii) which is expressed to down-regulate the expression of an endogenous starch synthase isoenzyme of the plant.

12. A progeny plant of the plant of claim 11 wherein said progeny plant comprises the transgenic nucleic acid molecule.

13. A propagule of the plant of claim 11 wherein said propagule comprises the transgenic nucleic acid molecule.

14. A gene construct or vector which comprises the isolated nucleic acid molecule of claim 1 and one or more origins of replication.

15. The gene construct of claim 14 further comprising a promoter sequence in operable connection with said isolated nucleic acid molecule.

* * * * *

SEQUENCE LISTING

```
<160> NUMBER OF SEQ ID NOS: 59

<210> SEQ ID NO 1
<211> LENGTH: 2939
<212> TYPE: DNA
<213> ORGANISM: Triticum aestivum
<220> FEATURE:
<221> NAME/KEY: CDS
<222> LOCATION: (176)..(2569)
<223> OTHER INFORMATION:

<400> SEQUENCE: 1

atttcctcgg cctgaccccg tgcgtttacc ccacacagag cacactccag tccagtccag      60

cccactgccg cgctactccc cactcccact gccaccacct ccgcctgcgc cgcgctctgg     120

gcggaccaac ccgcgcatcg tatcacgatc acccaccccg atcccggccg ccgcc atg      178
                                                             Met
                                                             1

tcg tcg gcg gtc gcg tcc gcc gcg tcc ttc ctc gcg ctc gcg tcc gcc       226
Ser Ser Ala Val Ala Ser Ala Ala Ser Phe Leu Ala Leu Ala Ser Ala
        5                   10                  15
```

-continued

```
tcc ccc ggg aga tca cgg agg agg acg agg gtg agc gcg tcg cca ccc      274
Ser Pro Gly Arg Ser Arg Arg Arg Thr Arg Val Ser Ala Ser Pro Pro
        20                  25                  30

cac acc ggg gct ggc agg ttg cac tgg ccg ccg tcg ccg ccg cag cgc      322
His Thr Gly Ala Gly Arg Leu His Trp Pro Pro Ser Pro Pro Gln Arg
    35                  40                  45

acg gct cgc gac gga gcg gtg gcc gcg cgc gcc gcc ggg aag aag gac      370
Thr Ala Arg Asp Gly Ala Val Ala Ala Arg Ala Ala Gly Lys Lys Asp
50                  55                  60                  65

gcg ggg atc gac gac gcc gcg ccc gcg agg cag ccc cgc gca ctc cgc      418
Ala Gly Ile Asp Asp Ala Ala Pro Ala Arg Gln Pro Arg Ala Leu Arg
                70                  75                  80

ggt ggc gcc gcc acc aag gtt gcg gag cgg agg gat ccc gtc aag acg      466
Gly Gly Ala Ala Thr Lys Val Ala Glu Arg Arg Asp Pro Val Lys Thr
            85                  90                  95

ctc gat cgc gac gcc gcg gaa ggt ggc gcg ccg tcc ccg ccg gca ccg      514
Leu Asp Arg Asp Ala Ala Glu Gly Gly Ala Pro Ser Pro Pro Ala Pro
        100                 105                 110

agg cag gag gac gcc cgt ctg ccg agc atg aac ggc atg ccg gtg aac      562
Arg Gln Glu Asp Ala Arg Leu Pro Ser Met Asn Gly Met Pro Val Asn
    115                 120                 125

ggt gaa aac aaa tct acc ggc ggc ggc ggc gcg act aaa gac agc ggg      610
Gly Glu Asn Lys Ser Thr Gly Gly Gly Gly Ala Thr Lys Asp Ser Gly
130                 135                 140                 145

ctg ccc gca ccc gca cgc gcg ccc cag ccg tcg agc cag aac aga gta      658
Leu Pro Ala Pro Ala Arg Ala Pro Gln Pro Ser Ser Gln Asn Arg Val
                150                 155                 160

ccg gtg aat ggt gaa aac aaa gct aac gtc gcc tcg ccg ccg acg agc      706
Pro Val Asn Gly Glu Asn Lys Ala Asn Val Ala Ser Pro Pro Thr Ser
            165                 170                 175

ata gcc gag gtc gcg gct ccg gat ccc gca gct acc att tcc atc agt      754
Ile Ala Glu Val Ala Ala Pro Asp Pro Ala Ala Thr Ile Ser Ile Ser
        180                 185                 190

gac aag gcg cca gag tcc gtt gtc cca gcc gag aag gcg ccg ccg tcg      802
Asp Lys Ala Pro Glu Ser Val Val Pro Ala Glu Lys Ala Pro Pro Ser
    195                 200                 205

tcc ggc tca aat ttc gtg ccc tcg gct tct gct ccc ggg tct gac act      850
Ser Gly Ser Asn Phe Val Pro Ser Ala Ser Ala Pro Gly Ser Asp Thr
210                 215                 220                 225

gtc agc gac gtg gaa ctt gaa ctg aag aag ggt gcg gtc att gtc aaa      898
Val Ser Asp Val Glu Leu Glu Leu Lys Lys Gly Ala Val Ile Val Lys
                230                 235                 240

gaa gct cca aac cca aag gct ctt tcg ccg ccc gca gca ccc gct gta      946
Glu Ala Pro Asn Pro Lys Ala Leu Ser Pro Pro Ala Ala Pro Ala Val
            245                 250                 255

caa caa gac ctt tgg gac ttc aag aaa tac att ggt ttc gag gag ccc      994
Gln Gln Asp Leu Trp Asp Phe Lys Lys Tyr Ile Gly Phe Glu Glu Pro
        260                 265                 270

gtg gag gcc aag gat gat ggc cgg gct gtt gca gat gat gcg ggc tcc     1042
Val Glu Ala Lys Asp Asp Gly Arg Ala Val Ala Asp Asp Ala Gly Ser
    275                 280                 285

ttc gaa cac cac cag aat cac gat tcc ggg cct ttg gca ggg gag aac     1090
Phe Glu His His Gln Asn His Asp Ser Gly Pro Leu Ala Gly Glu Asn
290                 295                 300                 305

gtc atg aac gtg gtc gtc gtg gct gct gaa tgt tct ccc tgg tgc aaa     1138
Val Met Asn Val Val Val Val Ala Ala Glu Cys Ser Pro Trp Cys Lys
                310                 315                 320

aca ggt ggt ctt gga gat gtt gcc ggt gct ttg ccc aag gct ttg gcg     1186
Thr Gly Gly Leu Gly Asp Val Ala Gly Ala Leu Pro Lys Ala Leu Ala
            325                 330                 335
```

-continued

```
aag aga gga cat cgt gtt atg gtt gtg gta cca agg tat ggg gac tat      1234
Lys Arg Gly His Arg Val Met Val Val Val Pro Arg Tyr Gly Asp Tyr
        340                 345                 350

gag gaa gcc tac gat gtc gga gtc cga aaa tac tac aag gct gct gga      1282
Glu Glu Ala Tyr Asp Val Gly Val Arg Lys Tyr Tyr Lys Ala Ala Gly
    355                 360                 365

cag gat atg gaa gtg aat tat ttc cat gct tat atc gat gga gtt gat      1330
Gln Asp Met Glu Val Asn Tyr Phe His Ala Tyr Ile Asp Gly Val Asp
370                 375                 380                 385

ttt gtg ttc att gac gct cct ctc ttc cga cac cgc cag gaa gac att      1378
Phe Val Phe Ile Asp Ala Pro Leu Phe Arg His Arg Gln Glu Asp Ile
                390                 395                 400

tat ggg ggc agc aga cag gaa att atg aag cgc atg att ttg ttc tgc      1426
Tyr Gly Gly Ser Arg Gln Glu Ile Met Lys Arg Met Ile Leu Phe Cys
            405                 410                 415

aag gcc gct gtc gag gtt cca tgg cac gtt cca tgc ggc ggt gtc cct      1474
Lys Ala Ala Val Glu Val Pro Trp His Val Pro Cys Gly Gly Val Pro
        420                 425                 430

tat ggg gat gga aat ctg gtg ttt att gca aat gat tgg cac acg gca      1522
Tyr Gly Asp Gly Asn Leu Val Phe Ile Ala Asn Asp Trp His Thr Ala
    435                 440                 445

ctc ctg cct gtc tat ctg aaa gca tat tac agg gac cat ggt ttg atg      1570
Leu Leu Pro Val Tyr Leu Lys Ala Tyr Tyr Arg Asp His Gly Leu Met
450                 455                 460                 465

cag tac act cgg tcc att atg gtg ata cat aac atc gct cac cag ggc      1618
Gln Tyr Thr Arg Ser Ile Met Val Ile His Asn Ile Ala His Gln Gly
                470                 475                 480

cgt ggc cca gta gat gag ttc ccg ttc acc gag ttg cct gag cac tac      1666
Arg Gly Pro Val Asp Glu Phe Pro Phe Thr Glu Leu Pro Glu His Tyr
            485                 490                 495

ctg gaa cac ttc aga ctg tac gac ccc gtg ggt ggt gaa cac gcc aac      1714
Leu Glu His Phe Arg Leu Tyr Asp Pro Val Gly Gly Glu His Ala Asn
        500                 505                 510

tac ttc gcc gcc ggc ctg aag atg gcg gac cag gtt gtc gtc gtg agc      1762
Tyr Phe Ala Ala Gly Leu Lys Met Ala Asp Gln Val Val Val Val Ser
    515                 520                 525

ccg ggg tac ctg tgg gag ctg aag acg gtg gag ggc ggc tgg ggg ctt      1810
Pro Gly Tyr Leu Trp Glu Leu Lys Thr Val Glu Gly Gly Trp Gly Leu
530                 535                 540                 545

cac gac atc ata cgg cag aac gac tgg aag acc cgc ggc atc gtg aac      1858
His Asp Ile Ile Arg Gln Asn Asp Trp Lys Thr Arg Gly Ile Val Asn
                550                 555                 560

ggc atc gac aac atg gag tgg aac ccc gag gtg gac gtc cac ctc aag      1906
Gly Ile Asp Asn Met Glu Trp Asn Pro Glu Val Asp Val His Leu Lys
            565                 570                 575

tcg gac ggc tac acc aac ttc tcc ctg ggg acg ctg gac tcc ggc aag      1954
Ser Asp Gly Tyr Thr Asn Phe Ser Leu Gly Thr Leu Asp Ser Gly Lys
        580                 585                 590

cgg cag tgc aag gag gcc ctg cag cgg gag ctg ggc ctg cag gtc cgc      2002
Arg Gln Cys Lys Glu Ala Leu Gln Arg Glu Leu Gly Leu Gln Val Arg
    595                 600                 605

ggc gac gtg ccg ctg ctc ggc ttc atc ggg cgc ctg gac ggg cag aag      2050
Gly Asp Val Pro Leu Leu Gly Phe Ile Gly Arg Leu Asp Gly Gln Lys
610                 615                 620                 625

ggc gtg gag atc atc gcg gac gcg atg ccc tgg atc gtg agc cag gac      2098
Gly Val Glu Ile Ile Ala Asp Ala Met Pro Trp Ile Val Ser Gln Asp
                630                 635                 640

gtg cag ctg gtc atg ctg ggc acc ggg cgc cac gac ctg gag ggc atg      2146
Val Gln Leu Val Met Leu Gly Thr Gly Arg His Asp Leu Glu Gly Met
```

-continued

```
            645                 650                 655

ctg cgg cac ttc gag cgg gag cac cac gac aag gtg cgc ggg tgg gtg     2194
Leu Arg His Phe Glu Arg Glu His His Asp Lys Val Arg Gly Trp Val
        660                 665                 670

ggg ttc tcc gtg cgg ctg gcg cac cgg atc acg gcc ggc gcc gac gcg     2242
Gly Phe Ser Val Arg Leu Ala His Arg Ile Thr Ala Gly Ala Asp Ala
    675                 680                 685

ctc ctc atg ccc tcc cgg ttc gag ccg tgc gga ctg aac cag ctc tac     2290
Leu Leu Met Pro Ser Arg Phe Glu Pro Cys Gly Leu Asn Gln Leu Tyr
690                 695                 700                 705

gcc atg gcc tac ggc acc gtc ccc gtc gtg cat gcc gtc ggt ggc ctg     2338
Ala Met Ala Tyr Gly Thr Val Pro Val Val His Ala Val Gly Gly Leu
                710                 715                 720

agg gac acc gtg ccg ccg ttc gac ccc ttc aac cac tcc ggg ctc ggg     2386
Arg Asp Thr Val Pro Pro Phe Asp Pro Phe Asn His Ser Gly Leu Gly
            725                 730                 735

tgg acg ttc gac cgc gca gag gcg cag aag ctg atc gag gcg ctc ggg     2434
Trp Thr Phe Asp Arg Ala Glu Ala Gln Lys Leu Ile Glu Ala Leu Gly
        740                 745                 750

cac tgc ctc cgc acc tac cgg gac tac aag gag agc tgg agg ggg ctc     2482
His Cys Leu Arg Thr Tyr Arg Asp Tyr Lys Glu Ser Trp Arg Gly Leu
    755                 760                 765

cag gag cgc ggc atg tcg cag gac ttc agc tgg gag cat gcc gcc aag     2530
Gln Glu Arg Gly Met Ser Gln Asp Phe Ser Trp Glu His Ala Ala Lys
770                 775                 780                 785

ctc tac gag gac gtc ctc gtc aag gcc aag tac cag tgg tgaacgctag      2579
Leu Tyr Glu Asp Val Leu Val Lys Ala Lys Tyr Gln Trp
                790                 795

ctgctagccg gtccagcccc gcatgcgtgc atgacaggat ggaattgcgc attgcgcacg   2639

caggaaggtg ccatggagcg ccggcatccg cgaagtacag tgacatgagg tgtgtgtggt   2699

tgagacgctg attccgatct ggtccgtagc agagtagagc ggaggtaggg aagcgctcct   2759

tgttacaggt atatgggaat gttgttaact tggtattgta atttgttatg ttgtgtgcat   2819

tattacagag ggcaacgatc tgcgccggcg caccggccca actgttgggc cggtcgcaca   2879

gcagccgttg gatccgaccg cctgggccgt tggatcccac cgaaaaaaaa aaaaaaaaaa   2939


<210> SEQ ID NO 2
<211> LENGTH: 798
<212> TYPE: PRT
<213> ORGANISM: Triticum aestivum

<400> SEQUENCE: 2

Met Ser Ser Ala Val Ala Ser Ala Ala Ser Phe Leu Ala Leu Ala Ser
1               5                   10                  15

Ala Ser Pro Gly Arg Ser Arg Arg Arg Thr Arg Val Ser Ala Ser Pro
            20                  25                  30

Pro His Thr Gly Ala Gly Arg Leu His Trp Pro Pro Ser Pro Pro Gln
        35                  40                  45

Arg Thr Ala Arg Asp Gly Ala Val Ala Ala Arg Ala Ala Gly Lys Lys
    50                  55                  60

Asp Ala Gly Ile Asp Asp Ala Ala Pro Ala Arg Gln Pro Arg Ala Leu
65                  70                  75                  80

Arg Gly Gly Ala Ala Thr Lys Val Ala Glu Arg Arg Asp Pro Val Lys
                85                  90                  95

Thr Leu Asp Arg Asp Ala Ala Glu Gly Gly Ala Pro Ser Pro Pro Ala
            100                 105                 110
```

-continued

```
Pro Arg Gln Glu Asp Ala Arg Leu Pro Ser Met Asn Gly Met Pro Val
        115                 120                 125

Asn Gly Glu Asn Lys Ser Thr Gly Gly Gly Gly Ala Thr Lys Asp Ser
    130                 135                 140

Gly Leu Pro Ala Pro Ala Arg Ala Pro Gln Pro Ser Ser Gln Asn Arg
145                 150                 155                 160

Val Pro Val Asn Gly Glu Asn Lys Ala Asn Val Ala Ser Pro Pro Thr
                165                 170                 175

Ser Ile Ala Glu Val Ala Ala Pro Asp Pro Ala Ala Thr Ile Ser Ile
            180                 185                 190

Ser Asp Lys Ala Pro Glu Ser Val Val Pro Ala Glu Lys Ala Pro Pro
        195                 200                 205

Ser Ser Gly Ser Asn Phe Val Pro Ser Ala Ser Ala Pro Gly Ser Asp
    210                 215                 220

Thr Val Ser Asp Val Glu Leu Glu Leu Lys Lys Gly Ala Val Ile Val
225                 230                 235                 240

Lys Glu Ala Pro Asn Pro Lys Ala Leu Ser Pro Pro Ala Ala Pro Ala
                245                 250                 255

Val Gln Gln Asp Leu Trp Asp Phe Lys Lys Tyr Ile Gly Phe Glu Glu
            260                 265                 270

Pro Val Glu Ala Lys Asp Asp Gly Arg Ala Val Ala Asp Asp Ala Gly
        275                 280                 285

Ser Phe Glu His His Gln Asn His Asp Ser Gly Pro Leu Ala Gly Glu
    290                 295                 300

Asn Val Met Asn Val Val Val Val Ala Ala Glu Cys Ser Pro Trp Cys
305                 310                 315                 320

Lys Thr Gly Gly Leu Gly Asp Val Ala Gly Ala Leu Pro Lys Ala Leu
                325                 330                 335

Ala Lys Arg Gly His Arg Val Met Val Val Val Pro Arg Tyr Gly Asp
            340                 345                 350

Tyr Glu Glu Ala Tyr Asp Val Gly Val Arg Lys Tyr Tyr Lys Ala Ala
        355                 360                 365

Gly Gln Asp Met Glu Val Asn Tyr Phe His Ala Tyr Ile Asp Gly Val
    370                 375                 380

Asp Phe Val Phe Ile Asp Ala Pro Leu Phe Arg His Arg Gln Glu Asp
385                 390                 395                 400

Ile Tyr Gly Gly Ser Arg Gln Glu Ile Met Lys Arg Met Ile Leu Phe
                405                 410                 415

Cys Lys Ala Ala Val Glu Val Pro Trp His Val Pro Cys Gly Gly Val
            420                 425                 430

Pro Tyr Gly Asp Gly Asn Leu Val Phe Ile Ala Asn Asp Trp His Thr
        435                 440                 445

Ala Leu Leu Pro Val Tyr Leu Lys Ala Tyr Tyr Arg Asp His Gly Leu
    450                 455                 460

Met Gln Tyr Thr Arg Ser Ile Met Val Ile His Asn Ile Ala His Gln
465                 470                 475                 480

Gly Arg Gly Pro Val Asp Glu Phe Pro Phe Thr Glu Leu Pro Glu His
                485                 490                 495

Tyr Leu Glu His Phe Arg Leu Tyr Asp Pro Val Gly Gly Glu His Ala
            500                 505                 510

Asn Tyr Phe Ala Ala Gly Leu Lys Met Ala Asp Gln Val Val Val Val
        515                 520                 525

Ser Pro Gly Tyr Leu Trp Glu Leu Lys Thr Val Glu Gly Gly Trp Gly
```

-continued

```
    530                 535                 540

Leu His Asp Ile Ile Arg Gln Asn Asp Trp Lys Thr Arg Gly Ile Val
545                 550                 555                 560

Asn Gly Ile Asp Asn Met Glu Trp Asn Pro Glu Val Asp Val His Leu
                565                 570                 575

Lys Ser Asp Gly Tyr Thr Asn Phe Ser Leu Gly Thr Leu Asp Ser Gly
            580                 585                 590

Lys Arg Gln Cys Lys Glu Ala Leu Gln Arg Glu Leu Gly Leu Gln Val
        595                 600                 605

Arg Gly Asp Val Pro Leu Leu Gly Phe Ile Gly Arg Leu Asp Gly Gln
    610                 615                 620

Lys Gly Val Glu Ile Ile Ala Asp Ala Met Pro Trp Ile Val Ser Gln
625                 630                 635                 640

Asp Val Gln Leu Val Met Leu Gly Thr Gly Arg His Asp Leu Glu Gly
                645                 650                 655

Met Leu Arg His Phe Glu Arg Glu His His Asp Lys Val Arg Gly Trp
            660                 665                 670

Val Gly Phe Ser Val Arg Leu Ala His Arg Ile Thr Ala Gly Ala Asp
        675                 680                 685

Ala Leu Leu Met Pro Ser Arg Phe Glu Pro Cys Gly Leu Asn Gln Leu
    690                 695                 700

Tyr Ala Met Ala Tyr Gly Thr Val Pro Val Val His Ala Val Gly Gly
705                 710                 715                 720

Leu Arg Asp Thr Val Pro Pro Phe Asp Pro Phe Asn His Ser Gly Leu
                725                 730                 735

Gly Trp Thr Phe Asp Arg Ala Glu Ala Gln Lys Leu Ile Glu Ala Leu
            740                 745                 750

Gly His Cys Leu Arg Thr Tyr Arg Asp Tyr Lys Glu Ser Trp Arg Gly
        755                 760                 765

Leu Gln Glu Arg Gly Met Ser Gln Asp Phe Ser Trp Glu His Ala Ala
    770                 775                 780

Lys Leu Tyr Glu Asp Val Leu Val Lys Ala Lys Tyr Gln Trp
785                 790                 795


<210> SEQ ID NO 3
<211> LENGTH: 2842
<212> TYPE: DNA
<213> ORGANISM: Triticum aestivum
<220> FEATURE:
<221> NAME/KEY: CDS
<222> LOCATION: (89)..(2485)
<223> OTHER INFORMATION:

<400> SEQUENCE: 3

gctgccacca cctccgcctg cgccgcgctc tgggcggagg accaacccgc gcatcgtacc      60

atcgcccgcc ccgatcccgg ccgccgcc atg tcg tcg gcg gtc gcg tcc gcc       112
                               Met Ser Ser Ala Val Ala Ser Ala
                               1               5

gcg tcc ttc ctc gcg ctc gcc tcc gcc tcc ccc ggg aga tca cgc agg      160
Ala Ser Phe Leu Ala Leu Ala Ser Ala Ser Pro Gly Arg Ser Arg Arg
    10                  15                  20

cgg gcg agg gtg agc gcg ccg cca ccc cac gcc ggg gcc ggc agg ctg      208
Arg Ala Arg Val Ser Ala Pro Pro Pro His Ala Gly Ala Gly Arg Leu
25                  30                  35                  40

cac tgg ccg ccg tgg ccg ccg cag cgc acg gct cgc gac gga ggt gtg      256
His Trp Pro Pro Trp Pro Pro Gln Arg Thr Ala Arg Asp Gly Gly Val
                45                  50                  55
```

-continued

```
gcc gcg cgc gcc gcc ggg aag aag gac gcg agg gtc gac gac gac gcc      304
Ala Ala Arg Ala Ala Gly Lys Lys Asp Ala Arg Val Asp Asp Asp Ala
            60                  65                  70

gcg tcc gcg agg cag ccc cgc gca cgc cgc ggt ggc gcc gcc acc aag      352
Ala Ser Ala Arg Gln Pro Arg Ala Arg Arg Gly Gly Ala Ala Thr Lys
        75                  80                  85

gtc gcg gag cgg agg gat ccc gtc aag acg ctc gat cgc gac gcc gcg      400
Val Ala Glu Arg Arg Asp Pro Val Lys Thr Leu Asp Arg Asp Ala Ala
    90                  95                  100

gaa ggt ggc gcg ccg gca ccg ccg gca ccg agg cag gac gcc gcc cgt      448
Glu Gly Gly Ala Pro Ala Pro Pro Ala Pro Arg Gln Asp Ala Ala Arg
105                 110                 115                 120

cca ccg agt atg aac ggc acg ccg gtg aac ggt gag aac aaa tct acc      496
Pro Pro Ser Met Asn Gly Thr Pro Val Asn Gly Glu Asn Lys Ser Thr
                125                 130                 135

ggc ggc ggc ggc gcg acc aaa gac agc ggg ctg ccc gca ccc gca cgc      544
Gly Gly Gly Gly Ala Thr Lys Asp Ser Gly Leu Pro Ala Pro Ala Arg
            140                 145                 150

gcg ccc cat ccg tcg acc cag aac aga gta cca gtg aac ggt gaa aac      592
Ala Pro His Pro Ser Thr Gln Asn Arg Val Pro Val Asn Gly Glu Asn
        155                 160                 165

aaa gct aac gtc gcc tcg ccg ccg acg agc ata gcc gag gtc gtg gct      640
Lys Ala Asn Val Ala Ser Pro Pro Thr Ser Ile Ala Glu Val Val Ala
    170                 175                 180

ccg gat tcc gca gct acc att tcc atc agt gac aag gcg ccg gag tcc      688
Pro Asp Ser Ala Ala Thr Ile Ser Ile Ser Asp Lys Ala Pro Glu Ser
185                 190                 195                 200

gtt gtc cca gcc gag aag ccg ccg ccg tcg tcc ggc tca aat ttc gtg      736
Val Val Pro Ala Glu Lys Pro Pro Pro Ser Ser Gly Ser Asn Phe Val
                205                 210                 215

gtc tcg gct tct gct ccc agg ctg gac att gac agc gat gtt gaa cct      784
Val Ser Ala Ser Ala Pro Arg Leu Asp Ile Asp Ser Asp Val Glu Pro
            220                 225                 230

gaa ctg aag aag ggt gcg gtc atc gtc gaa gaa gct cca aac cca aag      832
Glu Leu Lys Lys Gly Ala Val Ile Val Glu Glu Ala Pro Asn Pro Lys
        235                 240                 245

gct ctt tcg ccg cct gca gcc ccc gct gta caa gaa gac ctt tgg gac      880
Ala Leu Ser Pro Pro Ala Ala Pro Ala Val Gln Glu Asp Leu Trp Asp
    250                 255                 260

ttc aag aaa tac att ggc ttc gag gag ccc gtg gag gcc aag gat gat      928
Phe Lys Lys Tyr Ile Gly Phe Glu Glu Pro Val Glu Ala Lys Asp Asp
265                 270                 275                 280

ggc tgg gct gtt gca gat gat gcg ggc tcc ttt gaa cat cac cag aac      976
Gly Trp Ala Val Ala Asp Asp Ala Gly Ser Phe Glu His His Gln Asn
            285                 290                 295

cat gat tcc gga cct ttg gca ggg gag aac gtc atg aac gtg gtc gtc     1024
His Asp Ser Gly Pro Leu Ala Gly Glu Asn Val Met Asn Val Val Val
            300                 305                 310

gtg gct gct gaa tgt tct ccc tgg tgc aaa aca ggt ggt ctt gga gat     1072
Val Ala Ala Glu Cys Ser Pro Trp Cys Lys Thr Gly Gly Leu Gly Asp
        315                 320                 325

gtt gcc ggt gct ttg ccc aag gct ttg gcg aag aga gga cat cgt gtt     1120
Val Ala Gly Ala Leu Pro Lys Ala Leu Ala Lys Arg Gly His Arg Val
    330                 335                 340

atg gtt gtg gta cca agg tat ggg gac tat gag gaa gcc tac gat gtc     1168
Met Val Val Val Pro Arg Tyr Gly Asp Tyr Glu Glu Ala Tyr Asp Val
345                 350                 355                 360

gga gtc cga aaa tac tac aag gct gct gga cag gat atg gaa gtg aat     1216
Gly Val Arg Lys Tyr Tyr Lys Ala Ala Gly Gln Asp Met Glu Val Asn
```

-continued

```
                365                 370                 375

tat ttc cat gct tat atc gat gga gtt gat ttt gtg ttc att gac gct      1264
Tyr Phe His Ala Tyr Ile Asp Gly Val Asp Phe Val Phe Ile Asp Ala
            380                 385                 390

cct ctc ttc cga cac cgc cag gaa gac att tat ggg ggc agc aga cag      1312
Pro Leu Phe Arg His Arg Gln Glu Asp Ile Tyr Gly Gly Ser Arg Gln
        395                 400                 405

gaa att atg aag cgc atg att ttg ttc tgc aag gcc gct gtc gag gtt      1360
Glu Ile Met Lys Arg Met Ile Leu Phe Cys Lys Ala Ala Val Glu Val
    410                 415                 420

cct tgg cac gtt cca tgc ggc ggt gtc cct tat ggg gat gga aat ctg      1408
Pro Trp His Val Pro Cys Gly Gly Val Pro Tyr Gly Asp Gly Asn Leu
425                 430                 435                 440

gtg ttt att gca aat gat tgg cac acg gca ctc ctg cct gtc tat ctg      1456
Val Phe Ile Ala Asn Asp Trp His Thr Ala Leu Leu Pro Val Tyr Leu
                445                 450                 455

aaa gca tat tac agg gac cat ggt ttg atg cag tac act cgg tcc att      1504
Lys Ala Tyr Tyr Arg Asp His Gly Leu Met Gln Tyr Thr Arg Ser Ile
            460                 465                 470

atg gtg ata cat aac atc gcg cac cag ggc cgt ggc cca gta gat gaa      1552
Met Val Ile His Asn Ile Ala His Gln Gly Arg Gly Pro Val Asp Glu
        475                 480                 485

ttc ccg ttc acc gag ttg cct gag cac tac ctg gaa cac ttc aga ctg      1600
Phe Pro Phe Thr Glu Leu Pro Glu His Tyr Leu Glu His Phe Arg Leu
    490                 495                 500

tac gac ccc gtg ggt ggt gag cac gcc aac tac ttc gcc gcc ggc ctg      1648
Tyr Asp Pro Val Gly Gly Glu His Ala Asn Tyr Phe Ala Ala Gly Leu
505                 510                 515                 520

aag atg gcg gac cag gtt gtc gtg gtg agc ccc ggg tac ctg tgg gag      1696
Lys Met Ala Asp Gln Val Val Val Val Ser Pro Gly Tyr Leu Trp Glu
                525                 530                 535

ctc aag acg gtg gag ggc ggc tgg ggg ctt cac gac atc ata cgg cag      1744
Leu Lys Thr Val Glu Gly Gly Trp Gly Leu His Asp Ile Ile Arg Gln
            540                 545                 550

aac gac tgg aag acc cgc ggc atc gtc aac ggc atc gac aac atg gag      1792
Asn Asp Trp Lys Thr Arg Gly Ile Val Asn Gly Ile Asp Asn Met Glu
        555                 560                 565

tgg aac ccc gag gtg gac gtc cac ctc aag tcg gac ggc tac acc aac      1840
Trp Asn Pro Glu Val Asp Val His Leu Lys Ser Asp Gly Tyr Thr Asn
    570                 575                 580

ttc tcc ctg ggg acg ctg gac tcc ggc aag cgg cag tgc aag gag gcc      1888
Phe Ser Leu Gly Thr Leu Asp Ser Gly Lys Arg Gln Cys Lys Glu Ala
585                 590                 595                 600

ctg cag cgc gag ctg ggc ctg cag gtc cgc gcc gac gtg ccg ctg ctc      1936
Leu Gln Arg Glu Leu Gly Leu Gln Val Arg Ala Asp Val Pro Leu Leu
                605                 610                 615

ggc ttc atc ggc cgc ctg gac ggg cag aag ggc gtg gag atc atc gcg      1984
Gly Phe Ile Gly Arg Leu Asp Gly Gln Lys Gly Val Glu Ile Ile Ala
            620                 625                 630

gac gcc atg ccc tgg atc gtg agc cag gac gtg cag ctg gtc atg ctg      2032
Asp Ala Met Pro Trp Ile Val Ser Gln Asp Val Gln Leu Val Met Leu
        635                 640                 645

ggc acc ggc cgc cac gac ctg gag agc atg ctg cgg cac ttc gag cgg      2080
Gly Thr Gly Arg His Asp Leu Glu Ser Met Leu Arg His Phe Glu Arg
    650                 655                 660

gag cac cac gac aag gtg cgc ggg tgg gtg ggg ttc tcc gtg cgc ctg      2128
Glu His His Asp Lys Val Arg Gly Trp Val Gly Phe Ser Val Arg Leu
665                 670                 675                 680

gcg cac cgg atc acg gcg ggc gcc gac gcg ctc ctc atg ccc tcc cgg      2176
```

-continued

```
Ala His Arg Ile Thr Ala Gly Ala Asp Ala Leu Leu Met Pro Ser Arg
            685                 690                 695

ttc gag ccg tgc ggg ttg aac cag ctt tac gcc atg gcc tac ggc acc      2224
Phe Glu Pro Cys Gly Leu Asn Gln Leu Tyr Ala Met Ala Tyr Gly Thr
        700                 705                 710

gtc ccc gtc gtg cac gcc gtc ggc ggg gtg agg gac acc gtg ccg ccg      2272
Val Pro Val Val His Ala Val Gly Gly Val Arg Asp Thr Val Pro Pro
    715                 720                 725

ttc gac ccc ttc aac cac tcc ggc ctc ggg tgg acg ttc gac cgc gcc      2320
Phe Asp Pro Phe Asn His Ser Gly Leu Gly Trp Thr Phe Asp Arg Ala
730                 735                 740

gag gcg cac aag ctg atc gag gcg ctc ggg cac tgc ctc cgc acc tac      2368
Glu Ala His Lys Leu Ile Glu Ala Leu Gly His Cys Leu Arg Thr Tyr
745                 750                 755                 760

cgg gac tac aag gag agc tgg agg ggc ctc cag gag cgc ggc atg tcg      2416
Arg Asp Tyr Lys Glu Ser Trp Arg Gly Leu Gln Glu Arg Gly Met Ser
            765                 770                 775

cag gac ttc agc tgg gag cat gcc gcc aag ctc tac gag gac gtc ctc      2464
Gln Asp Phe Ser Trp Glu His Ala Ala Lys Leu Tyr Glu Asp Val Leu
        780                 785                 790

ctc aag gcc aag tac cag tgg tgaacgctag ctgctagccg ctccagcccc         2515
Leu Lys Ala Lys Tyr Gln Trp
    795

gcatgcgtgc atgcatgaga gggtggaact gcgcattgcg cccgcaggaa cgtgccatcc   2575

ttctcgatgg gagcgccggc atccgcgagg tgcagtgaca tgagaggtgt gtgtggttga   2635

gacgctgatt ccgatctcga tctggtccgt agcagagtag agcggacgta gggaagcgct   2695

ccttgttgca ggtatatggg aatgttgtca acttggtatt gtagtttgct atgttgtatg   2755

cgttattaca atgttgttac ttattcttgt taagtcggag gcaaagggcg aaagctagct   2815

cacatgaaaa aaaaaaaaaa aaaaaaa                                        2842


<210> SEQ ID NO 4
<211> LENGTH: 799
<212> TYPE: PRT
<213> ORGANISM: Triticum aestivum

<400> SEQUENCE: 4

Met Ser Ser Ala Val Ala Ser Ala Ala Ser Phe Leu Ala Leu Ala Ser
1               5                   10                  15

Ala Ser Pro Gly Arg Ser Arg Arg Arg Ala Arg Val Ser Ala Pro Pro
            20                  25                  30

Pro His Ala Gly Ala Gly Arg Leu His Trp Pro Pro Trp Pro Pro Gln
        35                  40                  45

Arg Thr Ala Arg Asp Gly Gly Val Ala Ala Arg Ala Ala Gly Lys Lys
    50                  55                  60

Asp Ala Arg Val Asp Asp Asp Ala Ala Ser Ala Arg Gln Pro Arg Ala
65                  70                  75                  80

Arg Arg Gly Gly Ala Ala Thr Lys Val Ala Glu Arg Arg Asp Pro Val
                85                  90                  95

Lys Thr Leu Asp Arg Asp Ala Ala Glu Gly Gly Ala Pro Ala Pro Pro
            100                 105                 110

Ala Pro Arg Gln Asp Ala Ala Arg Pro Pro Ser Met Asn Gly Thr Pro
        115                 120                 125

Val Asn Gly Glu Asn Lys Ser Thr Gly Gly Gly Gly Ala Thr Lys Asp
    130                 135                 140

Ser Gly Leu Pro Ala Pro Ala Arg Ala Pro His Pro Ser Thr Gln Asn
```

-continued

```
145                 150                 155                 160

Arg Val Pro Val Asn Gly Glu Asn Lys Ala Asn Val Ala Ser Pro Pro
                165                 170                 175

Thr Ser Ile Ala Glu Val Val Ala Pro Asp Ser Ala Ala Thr Ile Ser
            180                 185                 190

Ile Ser Asp Lys Ala Pro Glu Ser Val Val Pro Ala Glu Lys Pro Pro
        195                 200                 205

Pro Ser Ser Gly Ser Asn Phe Val Val Ser Ala Ser Ala Pro Arg Leu
    210                 215                 220

Asp Ile Asp Ser Asp Val Glu Pro Glu Leu Lys Lys Gly Ala Val Ile
225                 230                 235                 240

Val Glu Glu Ala Pro Asn Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Trp Ala Val Ala Asp Asp Ala
        275                 280                 285

Gly Ser Phe Glu His His Gln Asn His Asp Ser Gly Pro Leu Ala Gly
    290                 295                 300

Glu Asn Val Met Asn Val Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Val Pro Arg Tyr Gly
            340                 345                 350

Asp Tyr Glu Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
    370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
            420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
    450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Val His
                565                 570                 575
```

-continued

```
Leu Lys Ser Asp Gly Tyr Thr Asn Phe Ser Leu Gly Thr Leu Asp Ser
            580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Arg His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
    690                 695                 700

Leu Tyr Ala Met Ala Tyr Gly Thr Val Pro Val Val His Ala Val Gly
705                 710                 715                 720

Gly Val Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Tyr Lys Glu Ser Trp Arg
        755                 760                 765

Gly Leu Gln Glu Arg Gly Met Ser Gln Asp Phe Ser Trp Glu His Ala
    770                 775                 780

Ala Lys Leu Tyr Glu Asp Val Leu Leu Lys Ala Lys Tyr Gln Trp
785                 790                 795


<210> SEQ ID NO 5
<211> LENGTH: 2107
<212> TYPE: DNA
<213> ORGANISM: Triticum aestivum
<220> FEATURE:
<221> NAME/KEY: CDS
<222> LOCATION: (1)..(1791)
<223> OTHER INFORMATION:

<400> SEQUENCE: 5

cca gct gag aag acg ccg ccg tcg tcc ggc tca aat ttc gag tcc tcg       48
Pro Ala Glu Lys Thr Pro Pro Ser Ser Gly Ser Asn Phe Glu Ser Ser
1               5                   10                  15

gcc tct gct ccc ggg tct gac act gtc agc gac gtg gaa caa gaa ctg       96
Ala Ser Ala Pro Gly Ser Asp Thr Val Ser Asp Val Glu Gln Glu Leu
            20                  25                  30

aag aag ggt gcg gtc gtt gtc gaa gaa gct cca aag cca aag gct ctt      144
Lys Lys Gly Ala Val Val Val Glu Glu Ala Pro Lys Pro Lys Ala Leu
        35                  40                  45

tcg ccg cct gca gcc ccc gct gta caa gaa gac ctt tgg gat ttc aag      192
Ser Pro Pro Ala Ala Pro Ala Val Gln Glu Asp Leu Trp Asp Phe Lys
    50                  55                  60

aaa tac att ggt ttc gag gag ccc gtg gag gcc aag gat gat ggc cgg      240
Lys Tyr Ile Gly Phe Glu Glu Pro Val Glu Ala Lys Asp Asp Gly Arg
65                  70                  75                  80

gct gtc gca gat gat gcg ggc tcc ttt gaa cac cac cag aat cac gac      288
Ala Val Ala Asp Asp Ala Gly Ser Phe Glu His His Gln Asn His Asp
                85                  90                  95
```

-continued

```
tcc gga cct ttg gca ggg gag aat gtc atg aac gtg gtc gtc gtg gct      336
Ser Gly Pro Leu Ala Gly Glu Asn Val Met Asn Val Val Val Val Ala
            100                 105                 110

gct gag tgt tct ccc tgg tgc aaa aca ggt ggt ctg gga gat gtt gcg      384
Ala Glu Cys Ser Pro Trp Cys Lys Thr Gly Gly Leu Gly Asp Val Ala
        115                 120                 125

ggt gct ctg ccc aag gct ttg gca aag aga gga cat cgt gtt atg gtt      432
Gly Ala Leu Pro Lys Ala Leu Ala Lys Arg Gly His Arg Val Met Val
    130                 135                 140

gtg gta cca agg tat ggg gac tat gaa gaa cct acg gat gtc gga gtc      480
Val Val Pro Arg Tyr Gly Asp Tyr Glu Glu Pro Thr Asp Val Gly Val
145                 150                 155                 160

cga aaa tac tac aag gct gct gga cag gat atg gaa gtg aat tat ttc      528
Arg Lys Tyr Tyr Lys Ala Ala Gly Gln Asp Met Glu Val Asn Tyr Phe
                165                 170                 175

cat gct tat atc gat gga gtt gat ttt gtg ttc att gac gct cct ctc      576
His Ala Tyr Ile Asp Gly Val Asp Phe Val Phe Ile Asp Ala Pro Leu
            180                 185                 190

ttc cga cac cga gag gaa gac att tat ggg ggc agc aga cag gaa att      624
Phe Arg His Arg Glu Glu Asp Ile Tyr Gly Gly Ser Arg Gln Glu Ile
        195                 200                 205

atg aag cgc atg att ttg ttc tgc aag gcc gct gtt gag gtt cca tgg      672
Met Lys Arg Met Ile Leu Phe Cys Lys Ala Ala Val Glu Val Pro Trp
    210                 215                 220

cac gtt cca tgc ggc ggt gtc cct tat ggg gat gga aat ctg gtg ttt      720
His Val Pro Cys Gly Gly Val Pro Tyr Gly Asp Gly Asn Leu Val Phe
225                 230                 235                 240

att gca aat gat tgg cac acg gca ctc ctg cct gtc tat ctg aaa gca      768
Ile Ala Asn Asp Trp His Thr Ala Leu Leu Pro Val Tyr Leu Lys Ala
                245                 250                 255

tat tac agg gac cat ggt ttg atg cag tac act cgg tcc att atg gtg      816
Tyr Tyr Arg Asp His Gly Leu Met Gln Tyr Thr Arg Ser Ile Met Val
            260                 265                 270

ata cat aac atc gct cac cag ggc cgt ggc cct gta gat gaa ttc ccg      864
Ile His Asn Ile Ala His Gln Gly Arg Gly Pro Val Asp Glu Phe Pro
        275                 280                 285

ttc acc gag ttg cct gag cac tac ctg gaa cac ttc aga ctg tac gac      912
Phe Thr Glu Leu Pro Glu His Tyr Leu Glu His Phe Arg Leu Tyr Asp
    290                 295                 300

ccc gtg ggt ggt gaa cac gcc aac tac ttc gcc gcc ggc ctg aag atg      960
Pro Val Gly Gly Glu His Ala Asn Tyr Phe Ala Ala Gly Leu Lys Met
305                 310                 315                 320

gcg gac cag gtt gtc gtg gtg agc ccc ggg tac ctg tgg gag ctg aag     1008
Ala Asp Gln Val Val Val Val Ser Pro Gly Tyr Leu Trp Glu Leu Lys
                325                 330                 335

acg gtg gag ggc ggc tgg ggg ctt cac gac atc ata cgg cag aac gac     1056
Thr Val Glu Gly Gly Trp Gly Leu His Asp Ile Ile Arg Gln Asn Asp
            340                 345                 350

tgg aag acc cgc ggc atc gtc aac ggc atc gac aac atg gag tgg aac     1104
Trp Lys Thr Arg Gly Ile Val Asn Gly Ile Asp Asn Met Glu Trp Asn
        355                 360                 365

ccc gag gtg gac gcc cac ctc aag tcg gac ggc tac acc aac ttc tcc     1152
Pro Glu Val Asp Ala His Leu Lys Ser Asp Gly Tyr Thr Asn Phe Ser
    370                 375                 380

ctg agg acg ctg gac tcc ggc aag cgg cag tgc aag gag gcc ctg cag     1200
Leu Arg Thr Leu Asp Ser Gly Lys Arg Gln Cys Lys Glu Ala Leu Gln
385                 390                 395                 400

cgc gag ctg ggc ctg cag gtc cgc gcc gac gtg ccg ctg ctc ggc ttc     1248
Arg Glu Leu Gly Leu Gln Val Arg Ala Asp Val Pro Leu Leu Gly Phe
                405                 410                 415
```

-continued

```
atc ggc cgc ctg gac ggg cag aag ggc gtg gag atc atc gcg gac gcc      1296
Ile Gly Arg Leu Asp Gly Gln Lys Gly Val Glu Ile Ile Ala Asp Ala
            420                 425                 430

atg ccc tgg atc gtg agc cag gac gtg cag ctg gtg atg ctg ggc acc      1344
Met Pro Trp Ile Val Ser Gln Asp Val Gln Leu Val Met Leu Gly Thr
        435                 440                 445

ggg cgc cac gac ctg gag agc atg ctg cag cac ttc gag cgg gag cac      1392
Gly Arg His Asp Leu Glu Ser Met Leu Gln His Phe Glu Arg Glu His
    450                 455                 460

cac gac aag gtg cgc ggg tgg gtg ggg ttc tcc gtg cgc ctg gcg cac      1440
His Asp Lys Val Arg Gly Trp Val Gly Phe Ser Val Arg Leu Ala His
465                 470                 475                 480

cgg atc acg gcg ggg gcg gac gcg ctc ctc atg ccc tcc cgg ttc gtg      1488
Arg Ile Thr Ala Gly Ala Asp Ala Leu Leu Met Pro Ser Arg Phe Val
                485                 490                 495

ccg tgc ggg ctg aac cag ctc tac gcc atg gcc tac ggc acc gtc ccc      1536
Pro Cys Gly Leu Asn Gln Leu Tyr Ala Met Ala Tyr Gly Thr Val Pro
            500                 505                 510

gtc gtg cac gcc gtc ggc ggc ctc agg gac acc gtg ccg ccg ttc gac      1584
Val Val His Ala Val Gly Gly Leu Arg Asp Thr Val Pro Pro Phe Asp
        515                 520                 525

ccc ttc aac cac tcc ggg ctc ggg tgg acg ttc gac cgc gcc gag gcg      1632
Pro Phe Asn His Ser Gly Leu Gly Trp Thr Phe Asp Arg Ala Glu Ala
    530                 535                 540

cac aag ctg atc gag gcg ctc ggg cac tgc ctc cgc acc tac cga gac      1680
His Lys Leu Ile Glu Ala Leu Gly His Cys Leu Arg Thr Tyr Arg Asp
545                 550                 555                 560

ttc aag gag agc tgg agg gcc ctc cag gag cgc ggc atg tcg cag gac      1728
Phe Lys Glu Ser Trp Arg Ala Leu Gln Glu Arg Gly Met Ser Gln Asp
                565                 570                 575

ttc agc tgg gag cac gcc gcc aag ctc tac gag gac gtc ctc gtc aag      1776
Phe Ser Trp Glu His Ala Ala Lys Leu Tyr Glu Asp Val Leu Val Lys
            580                 585                 590

gcc aag tac cag tgg tgaacgctag ctgctagccg ctccagcccc gcatgcgtgc      1831
Ala Lys Tyr Gln Trp
        595

atgacaggat ggaactgcat tgcgcacgca ggaaagtgcc atggagcgcc ggcatccgcg   1891

aagtacagtg acatgaggtg tgtgtggttg agacgctgat tccaatccgg cccgtagcag   1951

agtagagcgg aggtatatgg gaatcttaac ttggtattgt aatttgttat gttgtgtgca   2011

ttattacaat gttgttactt attcttgtta agtcggaggc caagggcgaa agctagctca   2071

catgtctgat ggatgcaaaa aaaaaaaaaa aaaaaa                              2107


<210> SEQ ID NO 6
<211> LENGTH: 597
<212> TYPE: PRT
<213> ORGANISM: Triticum aestivum

<400> SEQUENCE: 6

Pro Ala Glu Lys Thr Pro Pro Ser Ser Gly Ser Asn Phe Glu Ser Ser
1               5                   10                  15

Ala Ser Ala Pro Gly Ser Asp Thr Val Ser Asp Val Glu Gln Glu Leu
            20                  25                  30

Lys Lys Gly Ala Val Val Val Glu Glu Ala Pro Lys Pro Lys Ala Leu
        35                  40                  45

Ser Pro Pro Ala Ala Pro Ala Val Gln Glu Asp Leu Trp Asp Phe Lys
    50                  55                  60
```

-continued

```
Lys Tyr Ile Gly Phe Glu Glu Pro Val Glu Ala Lys Asp Asp Gly Arg
65                  70                  75                  80

Ala Val Ala Asp Asp Ala Gly Ser Phe Glu His His Gln Asn His Asp
                85                  90                  95

Ser Gly Pro Leu Ala Gly Glu Asn Val Met Asn Val Val Val Val Ala
            100                 105                 110

Ala Glu Cys Ser Pro Trp Cys Lys Thr Gly Gly Leu Gly Asp Val Ala
        115                 120                 125

Gly Ala Leu Pro Lys Ala Leu Ala Lys Arg Gly His Arg Val Met Val
    130                 135                 140

Val Val Pro Arg Tyr Gly Asp Tyr Glu Glu Pro Thr Asp Val Gly Val
145                 150                 155                 160

Arg Lys Tyr Tyr Lys Ala Ala Gly Gln Asp Met Glu Val Asn Tyr Phe
                165                 170                 175

His Ala Tyr Ile Asp Gly Val Asp Phe Val Phe Ile Asp Ala Pro Leu
            180                 185                 190

Phe Arg His Arg Glu Glu Asp Ile Tyr Gly Gly Ser Arg Gln Glu Ile
        195                 200                 205

Met Lys Arg Met Ile Leu Phe Cys Lys Ala Ala Val Glu Val Pro Trp
    210                 215                 220

His Val Pro Cys Gly Gly Val Pro Tyr Gly Asp Gly Asn Leu Val Phe
225                 230                 235                 240

Ile Ala Asn Asp Trp His Thr Ala Leu Leu Pro Val Tyr Leu Lys Ala
                245                 250                 255

Tyr Tyr Arg Asp His Gly Leu Met Gln Tyr Thr Arg Ser Ile Met Val
            260                 265                 270

Ile His Asn Ile Ala His Gln Gly Arg Gly Pro Val Asp Glu Phe Pro
        275                 280                 285

Phe Thr Glu Leu Pro Glu His Tyr Leu Glu His Phe Arg Leu Tyr Asp
    290                 295                 300

Pro Val Gly Gly Glu His Ala Asn Tyr Phe Ala Ala Gly Leu Lys Met
305                 310                 315                 320

Ala Asp Gln Val Val Val Val Ser Pro Gly Tyr Leu Trp Glu Leu Lys
                325                 330                 335

Thr Val Glu Gly Gly Trp Gly Leu His Asp Ile Ile Arg Gln Asn Asp
            340                 345                 350

Trp Lys Thr Arg Gly Ile Val Asn Gly Ile Asp Asn Met Glu Trp Asn
        355                 360                 365

Pro Glu Val Asp Ala His Leu Lys Ser Asp Gly Tyr Thr Asn Phe Ser
    370                 375                 380

Leu Arg Thr Leu Asp Ser Gly Lys Arg Gln Cys Lys Glu Ala Leu Gln
385                 390                 395                 400

Arg Glu Leu Gly Leu Gln Val Arg Ala Asp Val Pro Leu Leu Gly Phe
                405                 410                 415

Ile Gly Arg Leu Asp Gly Gln Lys Gly Val Glu Ile Ile Ala Asp Ala
            420                 425                 430

Met Pro Trp Ile Val Ser Gln Asp Val Gln Leu Val Met Leu Gly Thr
        435                 440                 445

Gly Arg His Asp Leu Glu Ser Met Leu Gln His Phe Glu Arg Glu His
    450                 455                 460

His Asp Lys Val Arg Gly Trp Val Gly Phe Ser Val Arg Leu Ala His
465                 470                 475                 480

Arg Ile Thr Ala Gly Ala Asp Ala Leu Leu Met Pro Ser Arg Phe Val
```

-continued

```
                485                 490                 495

Pro Cys Gly Leu Asn Gln Leu Tyr Ala Met Ala Tyr Gly Thr Val Pro
            500                 505                 510

Val Val His Ala Val Gly Gly Leu Arg Asp Thr Val Pro Pro Phe Asp
        515                 520                 525

Pro Phe Asn His Ser Gly Leu Gly Trp Thr Phe Asp Arg Ala Glu Ala
    530                 535                 540

His Lys Leu Ile Glu Ala Leu Gly His Cys Leu Arg Thr Tyr Arg Asp
545                 550                 555                 560

Phe Lys Glu Ser Trp Arg Ala Leu Gln Glu Arg Gly Met Ser Gln Asp
                565                 570                 575

Phe Ser Trp Glu His Ala Ala Lys Leu Tyr Glu Asp Val Leu Val Lys
            580                 585                 590

Ala Lys Tyr Gln Trp
        595


<210> SEQ ID NO 7
<211> LENGTH: 5346
<212> TYPE: DNA
<213> ORGANISM: Triticum aestivum
<220> FEATURE:
<221> NAME/KEY: CDS
<222> LOCATION: (29)..(4912)
<223> OTHER INFORMATION:

<400> SEQUENCE: 7

cggcacgagg tttagtaggt tccgggaa atg gag atg tct ctc tgg cca cgg        52
                               Met Glu Met Ser Leu Trp Pro Arg
                               1               5

agc ccc ctg tgc cct cgg agc agg cag ccg ctc gtc gtc gtc cgg ccg       100
Ser Pro Leu Cys Pro Arg Ser Arg Gln Pro Leu Val Val Val Arg Pro
    10                  15                  20

gcc ggc cgc ggc ggc ctc acg cag cct ttt ttg atg aat ggc aga ttt       148
Ala Gly Arg Gly Gly Leu Thr Gln Pro Phe Leu Met Asn Gly Arg Phe
25                  30                  35                  40

act cga agc agg acc ctt cga tgc atg gta gca agt tca gat cct cct       196
Thr Arg Ser Arg Thr Leu Arg Cys Met Val Ala Ser Ser Asp Pro Pro
                45                  50                  55

aat agg aaa tca aga agg atg gta cca cct cag gtt aaa gtc att tct       244
Asn Arg Lys Ser Arg Arg Met Val Pro Pro Gln Val Lys Val Ile Ser
            60                  65                  70

tct aga gga tat acg aca aga ctc att gtt gaa cca agc aac gag aat       292
Ser Arg Gly Tyr Thr Thr Arg Leu Ile Val Glu Pro Ser Asn Glu Asn
        75                  80                  85

aca gaa cac aat aat cgg gat gaa gaa act ctt gat aca tac aat gcg       340
Thr Glu His Asn Asn Arg Asp Glu Glu Thr Leu Asp Thr Tyr Asn Ala
    90                  95                  100

cta tta agt acc gag aca gca gaa tgg aca gat aat aga gaa gcc gag       388
Leu Leu Ser Thr Glu Thr Ala Glu Trp Thr Asp Asn Arg Glu Ala Glu
105                 110                 115                 120

act gct aaa gcg gac tcg tcg caa aat gct tta agc agt tct ata att       436
Thr Ala Lys Ala Asp Ser Ser Gln Asn Ala Leu Ser Ser Ser Ile Ile
                125                 130                 135

ggg gaa gtg gat gtg gcg gat gaa gat ata ctt gcg gct gat ctg aca       484
Gly Glu Val Asp Val Ala Asp Glu Asp Ile Leu Ala Ala Asp Leu Thr
            140                 145                 150

gtg tat tca ttg agc agt gta atg aag aag gaa gtg gat gca gcg gac       532
Val Tyr Ser Leu Ser Ser Val Met Lys Lys Glu Val Asp Ala Ala Asp
        155                 160                 165
```

-continued

```
aaa gct aga gtt aaa gaa gac gca ttt gag ctg gat ttg cca gca act      580
Lys Ala Arg Val Lys Glu Asp Ala Phe Glu Leu Asp Leu Pro Ala Thr
    170                 175                 180

aca ttg aga agt gtg ata gta gat gtg atg gat cat aat ggg act gta      628
Thr Leu Arg Ser Val Ile Val Asp Val Met Asp His Asn Gly Thr Val
185                 190                 195                 200

caa gag aca ttg aga agt gtg ata gta gat gtg atg gat cat aat ggg      676
Gln Glu Thr Leu Arg Ser Val Ile Val Asp Val Met Asp His Asn Gly
                205                 210                 215

act gta caa gag aca ttg aga agt gtg ata gta gat gtg atg gat gat      724
Thr Val Gln Glu Thr Leu Arg Ser Val Ile Val Asp Val Met Asp Asp
            220                 225                 230

gcg gcg gac aaa gct aga gtt gaa gaa gac gta ttt gag ctg gat ttg      772
Ala Ala Asp Lys Ala Arg Val Glu Glu Asp Val Phe Glu Leu Asp Leu
        235                 240                 245

tca gga aat att tca agc agt gcg acg acc gtg gaa cta gat gcg gtt      820
Ser Gly Asn Ile Ser Ser Ser Ala Thr Thr Val Glu Leu Asp Ala Val
    250                 255                 260

gac gaa gtc ggg cct gtt caa gac aaa ttt gag gcg acc tca tca gga      868
Asp Glu Val Gly Pro Val Gln Asp Lys Phe Glu Ala Thr Ser Ser Gly
265                 270                 275                 280

aat gtt tca aac agt gca acg gta cgg gaa gtg gat gca agt gat gaa      916
Asn Val Ser Asn Ser Ala Thr Val Arg Glu Val Asp Ala Ser Asp Glu
                285                 290                 295

gct ggg aat gat caa ggc ata ttt aga gca gat ttg tca gga aat gtt      964
Ala Gly Asn Asp Gln Gly Ile Phe Arg Ala Asp Leu Ser Gly Asn Val
            300                 305                 310

ttt tca agc agt aca aca gtg gaa gtg ggt gca gtg gat gaa gct ggg     1012
Phe Ser Ser Ser Thr Thr Val Glu Val Gly Ala Val Asp Glu Ala Gly
        315                 320                 325

tct ata aag gac agg ttt gag acg gat tcg tca gga aat gtt tca aca     1060
Ser Ile Lys Asp Arg Phe Glu Thr Asp Ser Ser Gly Asn Val Ser Thr
    330                 335                 340

agt gcg ccg atg tgg gat gca att gat gaa acc gtg gct gat caa gac     1108
Ser Ala Pro Met Trp Asp Ala Ile Asp Glu Thr Val Ala Asp Gln Asp
345                 350                 355                 360

aca ttt gag gcg gat ttg tcg gga aat gct tca agc tgc gca aca tac     1156
Thr Phe Glu Ala Asp Leu Ser Gly Asn Ala Ser Ser Cys Ala Thr Tyr
                365                 370                 375

aga gaa gtg gat gat gtg gtg gat gaa act aga tca gaa gag gaa aca     1204
Arg Glu Val Asp Asp Val Val Asp Glu Thr Arg Ser Glu Glu Glu Thr
            380                 385                 390

ttt gca atg gat ttg ttt gca agt gaa tca ggc cat gag aaa cat atg     1252
Phe Ala Met Asp Leu Phe Ala Ser Glu Ser Gly His Glu Lys His Met
        395                 400                 405

gca gtg gat tat gtg ggt gaa gct acc gat gaa gaa gag act tac caa     1300
Ala Val Asp Tyr Val Gly Glu Ala Thr Asp Glu Glu Glu Thr Tyr Gln
    410                 415                 420

cag caa tat cca gta ccg tct tca ttc tct atg tgg gac aag gct att     1348
Gln Gln Tyr Pro Val Pro Ser Ser Phe Ser Met Trp Asp Lys Ala Ile
425                 430                 435                 440

gct aaa aca ggt gta agt ttg aat cct gag ctg cga ctt gtc agg gtt     1396
Ala Lys Thr Gly Val Ser Leu Asn Pro Glu Leu Arg Leu Val Arg Val
                445                 450                 455

gaa gaa caa ggc aaa gta aat ttt agt gat aaa aaa gac ctg tca att     1444
Glu Glu Gln Gly Lys Val Asn Phe Ser Asp Lys Lys Asp Leu Ser Ile
            460                 465                 470

gat gat tta cca gga caa aac caa tcg atc att ggt tcc tat aaa caa     1492
Asp Asp Leu Pro Gly Gln Asn Gln Ser Ile Ile Gly Ser Tyr Lys Gln
        475                 480                 485
```

-continued

```
gat aaa tca att gct gat gtt gcg gga ccg acc caa tca att ttt ggt     1540
Asp Lys Ser Ile Ala Asp Val Ala Gly Pro Thr Gln Ser Ile Phe Gly
    490                 495                 500

tct agt aaa caa cac cgg tca att gtt gct ttc ccc aaa caa aac cag     1588
Ser Ser Lys Gln His Arg Ser Ile Val Ala Phe Pro Lys Gln Asn Gln
505                 510                 515                 520

tca att gtt agt gtc act gag caa aag cag tcc ata gtt gga ttc cgt     1636
Ser Ile Val Ser Val Thr Glu Gln Lys Gln Ser Ile Val Gly Phe Arg
                525                 530                 535

agt caa gat ctt tcg gct gtt agt ctc cct aaa caa aac gta cca att     1684
Ser Gln Asp Leu Ser Ala Val Ser Leu Pro Lys Gln Asn Val Pro Ile
            540                 545                 550

gtt ggt acg tcg aga gag ggt caa aca aag caa gtt cct gtt gtt gat     1732
Val Gly Thr Ser Arg Glu Gly Gln Thr Lys Gln Val Pro Val Val Asp
        555                 560                 565

aga cag gat gca ttg tat gtg aat gga ctg gaa gct aag gag gga gat     1780
Arg Gln Asp Ala Leu Tyr Val Asn Gly Leu Glu Ala Lys Glu Gly Asp
    570                 575                 580

cac aca tcc gag aaa act gat gag gat gcg ctt cat gta aag ttt aat     1828
His Thr Ser Glu Lys Thr Asp Glu Asp Ala Leu His Val Lys Phe Asn
585                 590                 595                 600

gtt gac aat gtg ttg cgg aag cat cag gca gat aga acc caa gca gtg     1876
Val Asp Asn Val Leu Arg Lys His Gln Ala Asp Arg Thr Gln Ala Val
                605                 610                 615

gaa aag aaa act tgg aag aaa gtt gat gag gaa cat ctt tac atg act     1924
Glu Lys Lys Thr Trp Lys Lys Val Asp Glu Glu His Leu Tyr Met Thr
            620                 625                 630

gaa cat cag aaa cgt gct gcc gaa gga cag atg gta gtt aac gag gat     1972
Glu His Gln Lys Arg Ala Ala Glu Gly Gln Met Val Val Asn Glu Asp
        635                 640                 645

gag ctt tct ata act gaa att gga atg ggg aga ggt gat aaa att cag     2020
Glu Leu Ser Ile Thr Glu Ile Gly Met Gly Arg Gly Asp Lys Ile Gln
    650                 655                 660

cat gtg ctt tct gag gaa gag ctt tca tgg tct gaa gat gaa gtg cag     2068
His Val Leu Ser Glu Glu Glu Leu Ser Trp Ser Glu Asp Glu Val Gln
665                 670                 675                 680

tta att gag gat gat gga caa tat gaa gtt gac gag acc tct gtg tcc     2116
Leu Ile Glu Asp Asp Gly Gln Tyr Glu Val Asp Glu Thr Ser Val Ser
                685                 690                 695

gtt aac gtt gaa caa gat atc cag ggg tca cca cag gat gtt gtg gat     2164
Val Asn Val Glu Gln Asp Ile Gln Gly Ser Pro Gln Asp Val Val Asp
            700                 705                 710

ccg caa gca cta aag gtg atg ctg caa gaa ctc gct gag aaa aat tat     2212
Pro Gln Ala Leu Lys Val Met Leu Gln Glu Leu Ala Glu Lys Asn Tyr
        715                 720                 725

tcg atg agg aac aag ctg ttt gtt ttt cca gag gta gtg aaa gct gat     2260
Ser Met Arg Asn Lys Leu Phe Val Phe Pro Glu Val Val Lys Ala Asp
    730                 735                 740

tca gtt att gat ctt tat tta aat cgt gac cta aca gct ttg gcg aat     2308
Ser Val Ile Asp Leu Tyr Leu Asn Arg Asp Leu Thr Ala Leu Ala Asn
745                 750                 755                 760

gaa ccc gat gtc gtc atc aaa gga gca ttc aat ggt tgg aaa tgg agg     2356
Glu Pro Asp Val Val Ile Lys Gly Ala Phe Asn Gly Trp Lys Trp Arg
                765                 770                 775

ctt ttc act gaa aga ttg cac aag agt gac ctt gga ggg gtt tgg tgg     2404
Leu Phe Thr Glu Arg Leu His Lys Ser Asp Leu Gly Gly Val Trp Trp
            780                 785                 790

tct tgc aaa ctg tac ata ccc aag gag gcc tac aga tta gac ttt gtg     2452
Ser Cys Lys Leu Tyr Ile Pro Lys Glu Ala Tyr Arg Leu Asp Phe Val
```

-continued

```
        795                 800                 805

ttc ttc aac ggt cgc acg gtc tat gag aac aat ggc aac aat gat ttc      2500
Phe Phe Asn Gly Arg Thr Val Tyr Glu Asn Asn Gly Asn Asn Asp Phe
    810                 815                 820

tgt ata gga ata gaa ggc act atg aat gaa gat ctg ttt gag gat ttc      2548
Cys Ile Gly Ile Glu Gly Thr Met Asn Glu Asp Leu Phe Glu Asp Phe
825                 830                 835                 840

ttg gtt aaa gaa aag caa agg gag ctt gag aaa ctt gcc atg gaa gaa      2596
Leu Val Lys Glu Lys Gln Arg Glu Leu Glu Lys Leu Ala Met Glu Glu
                845                 850                 855

gct gaa agg agg aca cag act gaa gaa cag cgg cga aga aag gaa gca      2644
Ala Glu Arg Arg Thr Gln Thr Glu Glu Gln Arg Arg Arg Lys Glu Ala
            860                 865                 870

agg gct gca gat gaa gct gtc agg gca caa gcg aag gcc gag ata gag      2692
Arg Ala Ala Asp Glu Ala Val Arg Ala Gln Ala Lys Ala Glu Ile Glu
        875                 880                 885

atc aag aag aaa aaa ttg caa agt atg ttg agt ttg gcc aga aca tgt      2740
Ile Lys Lys Lys Lys Leu Gln Ser Met Leu Ser Leu Ala Arg Thr Cys
    890                 895                 900

gtt gat aat ttg tgg tac ata gag gct agc aca gat aca aga gga gat      2788
Val Asp Asn Leu Trp Tyr Ile Glu Ala Ser Thr Asp Thr Arg Gly Asp
905                 910                 915                 920

act atc agg tta tat tat aac aga aac tcg agg cca ctt gcg cat agt      2836
Thr Ile Arg Leu Tyr Tyr Asn Arg Asn Ser Arg Pro Leu Ala His Ser
                925                 930                 935

act gag att tgg atg cat ggt ggt tac aac aat tgg aca gat gga ctc      2884
Thr Glu Ile Trp Met His Gly Gly Tyr Asn Asn Trp Thr Asp Gly Leu
            940                 945                 950

tct att gtt gaa agc ttt gtc aag tgc aat gac aaa gac ggc gat tgg      2932
Ser Ile Val Glu Ser Phe Val Lys Cys Asn Asp Lys Asp Gly Asp Trp
        955                 960                 965

tgg tat gca gat gtt att cca cct gaa aag gca ctt gtg ttg gac tgg      2980
Trp Tyr Ala Asp Val Ile Pro Pro Glu Lys Ala Leu Val Leu Asp Trp
    970                 975                 980

gtt ttt gct gat ggg cca gct ggg aat gca agg aac tat gac aac aat      3028
Val Phe Ala Asp Gly Pro Ala Gly Asn Ala Arg Asn Tyr Asp Asn Asn
985                 990                 995                 1000

gct cga caa gat ttc  cat gct att ctt ccg  aac aac aat gta acc      3073
Ala Arg Gln Asp Phe  His Ala Ile Leu Pro  Asn Asn Asn Val Thr
                1005                 1010                 1015

gag gaa ggc ttc tgg  gcg caa gag gag caa  aac atc tat aca agg      3118
Glu Glu Gly Phe Trp  Ala Gln Glu Glu Gln  Asn Ile Tyr Thr Arg
                1020                 1025                 1030

ctt ctg caa gaa agg  aga gaa aag gaa gaa  acc atg aaa aga aag      3163
Leu Leu Gln Glu Arg  Arg Glu Lys Glu Glu  Thr Met Lys Arg Lys
                1035                 1040                 1045

gct gag aga agt gca  aat atc aaa gct gag  atg aag gca aaa act      3208
Ala Glu Arg Ser Ala  Asn Ile Lys Ala Glu  Met Lys Ala Lys Thr
                1050                 1055                 1060

atg cga agg ttt ctg  ctt tcc cag aaa cac  att gtt tat acc gaa      3253
Met Arg Arg Phe Leu  Leu Ser Gln Lys His  Ile Val Tyr Thr Glu
                1065                 1070                 1075

ccg ctt gaa ata cgt  gcc gga acc aca gtg  gat gtg cta tac aat      3298
Pro Leu Glu Ile Arg  Ala Gly Thr Thr Val  Asp Val Leu Tyr Asn
                1080                 1085                 1090

ccc tct aac aca gtg  cta aat gga aag tcg  gag ggt tgg ttt aga      3343
Pro Ser Asn Thr Val  Leu Asn Gly Lys Ser  Glu Gly Trp Phe Arg
                1095                 1100                 1105

tgc tcc ttt aac ctt  tgg atg cat tca agt  ggg gca ttg cca ccc      3388
```

-continued

```
Cys Ser Phe Asn Leu  Trp Met His Ser Ser  Gly Ala Leu Pro Pro
                1110                1115                1120

cag aag atg gtg aaa  tca ggg gat ggg ccg  ctc tta aaa gca aca      3433
Gln Lys Met Val Lys  Ser Gly Asp Gly Pro  Leu Leu Lys Ala Thr
                1125                1130                1135

gtt gat gtt cca ccg  gat gcc tat atg atg  gac ttt gtt ttc tcc      3478
Val Asp Val Pro Pro  Asp Ala Tyr Met Met  Asp Phe Val Phe Ser
                1140                1145                1150

gag tgg gaa gaa gat  ggg atc tat gac aac  agg aat ggg atg gac      3523
Glu Trp Glu Glu Asp  Gly Ile Tyr Asp Asn  Arg Asn Gly Met Asp
                1155                1160                1165

tat cat att cct gtt  tct gat tca att gaa  aca gag aat tac atg      3568
Tyr His Ile Pro Val  Ser Asp Ser Ile Glu  Thr Glu Asn Tyr Met
                1170                1175                1180

cgt att atc cac att  gcc gtt gag atg gcc  ccc gtt gca aag gtt      3613
Arg Ile Ile His Ile  Ala Val Glu Met Ala  Pro Val Ala Lys Val
                1185                1190                1195

gga ggt ctt ggg gat  gtt gtt aca agt ctt  tca cgt gcc att caa      3658
Gly Gly Leu Gly Asp  Val Val Thr Ser Leu  Ser Arg Ala Ile Gln
                1200                1205                1210

gat cta gga cat act  gtc gag gtt att ctc  ccg aag tac gac tgt      3703
Asp Leu Gly His Thr  Val Glu Val Ile Leu  Pro Lys Tyr Asp Cys
                1215                1220                1225

ttg aac caa agc agt  gtc aag gat tta cat  tta tat caa agt ttt      3748
Leu Asn Gln Ser Ser  Val Lys Asp Leu His  Leu Tyr Gln Ser Phe
                1230                1235                1240

tct tgg ggt ggt aca  gaa ata aaa gta tgg  gtt gga cga gtc gaa      3793
Ser Trp Gly Gly Thr  Glu Ile Lys Val Trp  Val Gly Arg Val Glu
                1245                1250                1255

gac ctg acc gtt tac  ttc ctg gaa cct caa  aat ggg atg ttt ggc      3838
Asp Leu Thr Val Tyr  Phe Leu Glu Pro Gln  Asn Gly Met Phe Gly
                1260                1265                1270

gtt gga tgt gta tat  gga agg aat gat gac  cgc aga ttt ggg ttc      3883
Val Gly Cys Val Tyr  Gly Arg Asn Asp Asp  Arg Arg Phe Gly Phe
                1275                1280                1285

ttc tgt cat tct gct  cta gag ttt atc ctc  cag aat gaa ttt tct      3928
Phe Cys His Ser Ala  Leu Glu Phe Ile Leu  Gln Asn Glu Phe Ser
                1290                1295                1300

cca cat ata ata cat  tgc cat gat tgg tca  agt gct ccg gtc gcc      3973
Pro His Ile Ile His  Cys His Asp Trp Ser  Ser Ala Pro Val Ala
                1305                1310                1315

tgg cta tat aag gaa  cac tat tcc caa tcc  aga atg gca agc act      4018
Trp Leu Tyr Lys Glu  His Tyr Ser Gln Ser  Arg Met Ala Ser Thr
                1320                1325                1330

cgg gtt gta ttt acc  atc cac aat ctt gaa  ttt gga gca cat tat      4063
Arg Val Val Phe Thr  Ile His Asn Leu Glu  Phe Gly Ala His Tyr
                1335                1340                1345

att ggt aaa gca atg  aca tac tgt gat aaa  gcc aca act gtt tct      4108
Ile Gly Lys Ala Met  Thr Tyr Cys Asp Lys  Ala Thr Thr Val Ser
                1350                1355                1360

cct aca tat tca agg  gac gtg gca ggc cat  ggc gcc att gct cct      4153
Pro Thr Tyr Ser Arg  Asp Val Ala Gly His  Gly Ala Ile Ala Pro
                1365                1370                1375

cat cgt gag aaa ttc  tac ggc att ctc aat  gga att gat cca gat      4198
His Arg Glu Lys Phe  Tyr Gly Ile Leu Asn  Gly Ile Asp Pro Asp
                1380                1385                1390

atc tgg gat ccg tac  act gac aat ttt atc  ccg gtc cct tat act      4243
Ile Trp Asp Pro Tyr  Thr Asp Asn Phe Ile  Pro Val Pro Tyr Thr
                1395                1400                1405
```

-continued

```
tgt gag aat gtt gtc  gaa ggc aag aga gct  gca aaa agg gcc ttg       4288
Cys Glu Asn Val Val  Glu Gly Lys Arg Ala  Ala Lys Arg Ala Leu
                1410                 1415                 1420

cag cag aag ttt gga  tta cag caa act gat  gtc cct att gtc gga       4333
Gln Gln Lys Phe Gly  Leu Gln Gln Thr Asp  Val Pro Ile Val Gly
                1425                 1430                 1435

atc atc acc cgt ctg  aca gcc cag aag gga  atc cac ctc atc aag       4378
Ile Ile Thr Arg Leu  Thr Ala Gln Lys Gly  Ile His Leu Ile Lys
                1440                 1445                 1450

cac gca att cac cga  act ctc gaa agc aac  gga cat gtg gtt ttg       4423
His Ala Ile His Arg  Thr Leu Glu Ser Asn  Gly His Val Val Leu
                1455                 1460                 1465

ctt ggt tca gct cca  gat cat cga ata caa  ggc gat ttt tgc aga       4468
Leu Gly Ser Ala Pro  Asp His Arg Ile Gln  Gly Asp Phe Cys Arg
                1470                 1475                 1480

ttg gcc gat gct ctt  cat ggt gtt tac cat  ggt agg gtg aag ctt       4513
Leu Ala Asp Ala Leu  His Gly Val Tyr His  Gly Arg Val Lys Leu
                1485                 1490                 1495

gtt cta acc tat gat  gag cct ctt tct cac  ctg ata tac gct ggc       4558
Val Leu Thr Tyr Asp  Glu Pro Leu Ser His  Leu Ile Tyr Ala Gly
                1500                 1505                 1510

tcg gac ttc ata att  gtt cct tca atc ttc  gaa ccc tgt ggc tta       4603
Ser Asp Phe Ile Ile  Val Pro Ser Ile Phe  Glu Pro Cys Gly Leu
                1515                 1520                 1525

aca caa ctt gtt gcc  atg cgt tat gga tcg  atc cct ata gtt cgg       4648
Thr Gln Leu Val Ala  Met Arg Tyr Gly Ser  Ile Pro Ile Val Arg
                1530                 1535                 1540

aaa act gga gga ctt  cac gac aca gtc ttc  gac gta gac aat gat       4693
Lys Thr Gly Gly Leu  His Asp Thr Val Phe  Asp Val Asp Asn Asp
                1545                 1550                 1555

aag gac cgg gct cgg  tct ctt ggt ctt gaa  cca aat ggg ttc agt       4738
Lys Asp Arg Ala Arg  Ser Leu Gly Leu Glu  Pro Asn Gly Phe Ser
                1560                 1565                 1570

ttc gac gga gcc gac  agc aat ggc gtg gat  tat gcc ctc aac aga       4783
Phe Asp Gly Ala Asp  Ser Asn Gly Val Asp  Tyr Ala Leu Asn Arg
                1575                 1580                 1585

gca atc ggc gct tgg  ttc gat gcc cgt gat  tgg ttc cac tcc ctg       4828
Ala Ile Gly Ala Trp  Phe Asp Ala Arg Asp  Trp Phe His Ser Leu
                1590                 1595                 1600

tgt aag agg gtc atg  gag caa gac tgg tcg  tgg aac cgg ccc gca       4873
Cys Lys Arg Val Met  Glu Gln Asp Trp Ser  Trp Asn Arg Pro Ala
                1605                 1610                 1615

ctg gac tac att gaa  ttg tac cat gcc gct  cga aaa ttc tgacacccaa    4922
Leu Asp Tyr Ile Glu  Leu Tyr His Ala Ala  Arg Lys Phe
                1620                 1625

ctgaaccaat gacaagaaca agcgcattgt gggatcgact agtcatacag ggctgtgcag   4982

atcgtcttgc ttcagttagt gccctcttca gttagttcca agcgcactac agtcgtacat   5042

agctgaggat cctcttgcct cctaccaggg ggaacaaagc agaaatgcat gagtgcattg   5102

ggaagacttt tatgtatatt gttaaaaaaa tttccttttc ttttccttcc ctgcacctgg   5162

aaatggttaa gcgcatcgcc gagataagaa ccgcagtgac attctgtgag tagctttgta   5222

tattctctca tcttgtgaaa actaatgttc atgttaggct gtctgatcat gtggaagctt   5282

tgttatatgt tacttatggt atacatcaat gatatttaca tttgtggaaa aaaaaaaaaa   5342

aaaa                                                                5346

<210> SEQ ID NO 8
<211> LENGTH: 1628
```

-continued

<212> TYPE: PRT
<213> ORGANISM: Triticum aestivum

<400> SEQUENCE: 8

```
Met Glu Met Ser Leu Trp Pro Arg Ser Pro Leu Cys Pro Arg Ser Arg
1               5                   10                  15

Gln Pro Leu Val Val Val Arg Pro Ala Gly Arg Gly Gly Leu Thr Gln
            20                  25                  30

Pro Phe Leu Met Asn Gly Arg Phe Thr Arg Ser Arg Thr Leu Arg Cys
        35                  40                  45

Met Val Ala Ser Ser Asp Pro Pro Asn Arg Lys Ser Arg Arg Met Val
    50                  55                  60

Pro Pro Gln Val Lys Val Ile Ser Ser Arg Gly Tyr Thr Thr Arg Leu
65                  70                  75                  80

Ile Val Glu Pro Ser Asn Glu Asn Thr Glu His Asn Asn Arg Asp Glu
                85                  90                  95

Glu Thr Leu Asp Thr Tyr Asn Ala Leu Leu Ser Thr Glu Thr Ala Glu
            100                 105                 110

Trp Thr Asp Asn Arg Glu Ala Glu Thr Ala Lys Ala Asp Ser Ser Gln
        115                 120                 125

Asn Ala Leu Ser Ser Ser Ile Ile Gly Glu Val Asp Val Ala Asp Glu
    130                 135                 140

Asp Ile Leu Ala Ala Asp Leu Thr Val Tyr Ser Leu Ser Ser Val Met
145                 150                 155                 160

Lys Lys Glu Val Asp Ala Ala Asp Lys Ala Arg Val Lys Glu Asp Ala
                165                 170                 175

Phe Glu Leu Asp Leu Pro Ala Thr Thr Leu Arg Ser Val Ile Val Asp
            180                 185                 190

Val Met Asp His Asn Gly Thr Val Gln Glu Thr Leu Arg Ser Val Ile
        195                 200                 205

Val Asp Val Met Asp His Asn Gly Thr Val Gln Glu Thr Leu Arg Ser
    210                 215                 220

Val Ile Val Asp Val Met Asp Asp Ala Ala Asp Lys Ala Arg Val Glu
225                 230                 235                 240

Glu Asp Val Phe Glu Leu Asp Leu Ser Gly Asn Ile Ser Ser Ser Ala
                245                 250                 255

Thr Thr Val Glu Leu Asp Ala Val Asp Glu Val Gly Pro Val Gln Asp
            260                 265                 270

Lys Phe Glu Ala Thr Ser Ser Gly Asn Val Ser Asn Ser Ala Thr Val
        275                 280                 285

Arg Glu Val Asp Ala Ser Asp Glu Ala Gly Asn Asp Gln Gly Ile Phe
    290                 295                 300

Arg Ala Asp Leu Ser Gly Asn Val Phe Ser Ser Ser Thr Thr Val Glu
305                 310                 315                 320

Val Gly Ala Val Asp Glu Ala Gly Ser Ile Lys Asp Arg Phe Glu Thr
                325                 330                 335

Asp Ser Ser Gly Asn Val Ser Thr Ser Ala Pro Met Trp Asp Ala Ile
            340                 345                 350

Asp Glu Thr Val Ala Asp Gln Asp Thr Phe Glu Ala Asp Leu Ser Gly
        355                 360                 365

Asn Ala Ser Ser Cys Ala Thr Tyr Arg Glu Val Asp Asp Val Val Asp
    370                 375                 380

Glu Thr Arg Ser Glu Glu Glu Thr Phe Ala Met Asp Leu Phe Ala Ser
385                 390                 395                 400
```

-continued

```
Glu Ser Gly His Glu Lys His Met Ala Val Asp Tyr Val Gly Glu Ala
                405                 410                 415

Thr Asp Glu Glu Glu Thr Tyr Gln Gln Gln Tyr Pro Val Pro Ser Ser
            420                 425                 430

Phe Ser Met Trp Asp Lys Ala Ile Ala Lys Thr Gly Val Ser Leu Asn
        435                 440                 445

Pro Glu Leu Arg Leu Val Arg Val Glu Glu Gln Gly Lys Val Asn Phe
    450                 455                 460

Ser Asp Lys Lys Asp Leu Ser Ile Asp Asp Leu Pro Gly Gln Asn Gln
465                 470                 475                 480

Ser Ile Ile Gly Ser Tyr Lys Gln Asp Lys Ser Ile Ala Asp Val Ala
                485                 490                 495

Gly Pro Thr Gln Ser Ile Phe Gly Ser Ser Lys Gln His Arg Ser Ile
            500                 505                 510

Val Ala Phe Pro Lys Gln Asn Gln Ser Ile Val Ser Val Thr Glu Gln
        515                 520                 525

Lys Gln Ser Ile Val Gly Phe Arg Ser Gln Asp Leu Ser Ala Val Ser
    530                 535                 540

Leu Pro Lys Gln Asn Val Pro Ile Val Gly Thr Ser Arg Glu Gly Gln
545                 550                 555                 560

Thr Lys Gln Val Pro Val Val Asp Arg Gln Asp Ala Leu Tyr Val Asn
                565                 570                 575

Gly Leu Glu Ala Lys Glu Gly Asp His Thr Ser Glu Lys Thr Asp Glu
            580                 585                 590

Asp Ala Leu His Val Lys Phe Asn Val Asp Asn Val Leu Arg Lys His
        595                 600                 605

Gln Ala Asp Arg Thr Gln Ala Val Glu Lys Lys Thr Trp Lys Lys Val
    610                 615                 620

Asp Glu Glu His Leu Tyr Met Thr Glu His Gln Lys Arg Ala Ala Glu
625                 630                 635                 640

Gly Gln Met Val Val Asn Glu Asp Glu Leu Ser Ile Thr Glu Ile Gly
                645                 650                 655

Met Gly Arg Gly Asp Lys Ile Gln His Val Leu Ser Glu Glu Glu Leu
            660                 665                 670

Ser Trp Ser Glu Asp Glu Val Gln Leu Ile Glu Asp Asp Gly Gln Tyr
        675                 680                 685

Glu Val Asp Glu Thr Ser Val Ser Val Asn Val Glu Gln Asp Ile Gln
    690                 695                 700

Gly Ser Pro Gln Asp Val Val Asp Pro Gln Ala Leu Lys Val Met Leu
705                 710                 715                 720

Gln Glu Leu Ala Glu Lys Asn Tyr Ser Met Arg Asn Lys Leu Phe Val
                725                 730                 735

Phe Pro Glu Val Val Lys Ala Asp Ser Val Ile Asp Leu Tyr Leu Asn
            740                 745                 750

Arg Asp Leu Thr Ala Leu Ala Asn Glu Pro Asp Val Val Ile Lys Gly
        755                 760                 765

Ala Phe Asn Gly Trp Lys Trp Arg Leu Phe Thr Glu Arg Leu His Lys
    770                 775                 780

Ser Asp Leu Gly Gly Val Trp Trp Ser Cys Lys Leu Tyr Ile Pro Lys
785                 790                 795                 800

Glu Ala Tyr Arg Leu Asp Phe Val Phe Phe Asn Gly Arg Thr Val Tyr
                805                 810                 815
```

-continued

```
Glu Asn Asn Gly Asn Asn Asp Phe Cys Ile Gly Ile Glu Gly Thr Met
            820                 825                 830

Asn Glu Asp Leu Phe Glu Asp Phe Leu Val Lys Glu Lys Gln Arg Glu
        835                 840                 845

Leu Glu Lys Leu Ala Met Glu Glu Ala Glu Arg Arg Thr Gln Thr Glu
    850                 855                 860

Glu Gln Arg Arg Arg Lys Glu Ala Arg Ala Ala Asp Glu Ala Val Arg
865                 870                 875                 880

Ala Gln Ala Lys Ala Glu Ile Glu Ile Lys Lys Lys Lys Leu Gln Ser
                885                 890                 895

Met Leu Ser Leu Ala Arg Thr Cys Val Asp Asn Leu Trp Tyr Ile Glu
            900                 905                 910

Ala Ser Thr Asp Thr Arg Gly Asp Thr Ile Arg Leu Tyr Tyr Asn Arg
        915                 920                 925

Asn Ser Arg Pro Leu Ala His Ser Thr Glu Ile Trp Met His Gly Gly
    930                 935                 940

Tyr Asn Asn Trp Thr Asp Gly Leu Ser Ile Val Glu Ser Phe Val Lys
945                 950                 955                 960

Cys Asn Asp Lys Asp Gly Asp Trp Trp Tyr Ala Asp Val Ile Pro Pro
                965                 970                 975

Glu Lys Ala Leu Val Leu Asp Trp Val Phe Ala Asp Gly Pro Ala Gly
            980                 985                 990

Asn Ala Arg Asn Tyr Asp Asn Asn  Ala Arg Gln Asp Phe  His Ala Ile
        995                 1000                 1005

Leu Pro  Asn Asn Asn Val Thr  Glu Glu Gly Phe Trp  Ala Gln Glu
    1010                 1015                 1020

Glu Gln  Asn Ile Tyr Thr Arg  Leu Leu Gln Glu Arg  Arg Glu Lys
    1025                 1030                 1035

Glu Glu  Thr Met Lys Arg Lys  Ala Glu Arg Ser Ala  Asn Ile Lys
    1040                 1045                 1050

Ala Glu  Met Lys Ala Lys Thr  Met Arg Arg Phe Leu  Leu Ser Gln
    1055                 1060                 1065

Lys His  Ile Val Tyr Thr Glu  Pro Leu Glu Ile Arg  Ala Gly Thr
    1070                 1075                 1080

Thr Val  Asp Val Leu Tyr Asn  Pro Ser Asn Thr Val  Leu Asn Gly
    1085                 1090                 1095

Lys Ser  Glu Gly Trp Phe Arg  Cys Ser Phe Asn Leu  Trp Met His
    1100                 1105                 1110

Ser Ser  Gly Ala Leu Pro Pro  Gln Lys Met Val Lys  Ser Gly Asp
    1115                 1120                 1125

Gly Pro  Leu Leu Lys Ala Thr  Val Asp Val Pro Pro  Asp Ala Tyr
    1130                 1135                 1140

Met Met  Asp Phe Val Phe Ser  Glu Trp Glu Glu Asp  Gly Ile Tyr
    1145                 1150                 1155

Asp Asn  Arg Asn Gly Met Asp  Tyr His Ile Pro Val  Ser Asp Ser
    1160                 1165                 1170

Ile Glu  Thr Glu Asn Tyr Met  Arg Ile Ile His Ile  Ala Val Glu
    1175                 1180                 1185

Met Ala  Pro Val Ala Lys Val  Gly Gly Leu Gly Asp  Val Val Thr
    1190                 1195                 1200

Ser Leu  Ser Arg Ala Ile Gln  Asp Leu Gly His Thr  Val Glu Val
    1205                 1210                 1215

Ile Leu  Pro Lys Tyr Asp Cys  Leu Asn Gln Ser Ser  Val Lys Asp
```

-continued

```
    1220                1225                1230

Leu His  Leu Tyr Gln Ser Phe  Ser Trp Gly Gly Thr  Glu Ile Lys
    1235                1240                1245

Val Trp  Val Gly Arg Val Glu  Asp Leu Thr Val Tyr  Phe Leu Glu
    1250                1255                1260

Pro Gln  Asn Gly Met Phe Gly  Val Gly Cys Val Tyr  Gly Arg Asn
    1265                1270                1275

Asp Asp  Arg Arg Phe Gly Phe  Phe Cys His Ser Ala  Leu Glu Phe
    1280                1285                1290

Ile Leu  Gln Asn Glu Phe Ser  Pro His Ile Ile His  Cys His Asp
    1295                1300                1305

Trp Ser  Ser Ala Pro Val Ala  Trp Leu Tyr Lys Glu  His Tyr Ser
    1310                1315                1320

Gln Ser  Arg Met Ala Ser Thr  Arg Val Val Phe Thr  Ile His Asn
    1325                1330                1335

Leu Glu  Phe Gly Ala His Tyr  Ile Gly Lys Ala Met  Thr Tyr Cys
    1340                1345                1350

Asp Lys  Ala Thr Thr Val Ser  Pro Thr Tyr Ser Arg  Asp Val Ala
    1355                1360                1365

Gly His  Gly Ala Ile Ala Pro  His Arg Glu Lys Phe  Tyr Gly Ile
    1370                1375                1380

Leu Asn  Gly Ile Asp Pro Asp  Ile Trp Asp Pro Tyr  Thr Asp Asn
    1385                1390                1395

Phe Ile  Pro Val Pro Tyr Thr  Cys Glu Asn Val Val  Glu Gly Lys
    1400                1405                1410

Arg Ala  Ala Lys Arg Ala Leu  Gln Gln Lys Phe Gly  Leu Gln Gln
    1415                1420                1425

Thr Asp  Val Pro Ile Val Gly  Ile Ile Thr Arg Leu  Thr Ala Gln
    1430                1435                1440

Lys Gly  Ile His Leu Ile Lys  His Ala Ile His Arg  Thr Leu Glu
    1445                1450                1455

Ser Asn  Gly His Val Val Leu  Leu Gly Ser Ala Pro  Asp His Arg
    1460                1465                1470

Ile Gln  Gly Asp Phe Cys Arg  Leu Ala Asp Ala Leu  His Gly Val
    1475                1480                1485

Tyr His  Gly Arg Val Lys Leu  Val Leu Thr Tyr Asp  Glu Pro Leu
    1490                1495                1500

Ser His  Leu Ile Tyr Ala Gly  Ser Asp Phe Ile Ile  Val Pro Ser
    1505                1510                1515

Ile Phe  Glu Pro Cys Gly Leu  Thr Gln Leu Val Ala  Met Arg Tyr
    1520                1525                1530

Gly Ser  Ile Pro Ile Val Arg  Lys Thr Gly Gly Leu  His Asp Thr
    1535                1540                1545

Val Phe  Asp Val Asp Asn Asp  Lys Asp Arg Ala Arg  Ser Leu Gly
    1550                1555                1560

Leu Glu  Pro Asn Gly Phe Ser  Phe Asp Gly Ala Asp  Ser Asn Gly
    1565                1570                1575

Val Asp  Tyr Ala Leu Asn Arg  Ala Ile Gly Ala Trp  Phe Asp Ala
    1580                1585                1590

Arg Asp  Trp Phe His Ser Leu  Cys Lys Arg Val Met  Glu Gln Asp
    1595                1600                1605

Trp Ser  Trp Asn Arg Pro Ala  Leu Asp Tyr Ile Glu  Leu Tyr His
    1610                1615                1620
```

-continued

```
Ala Ala  Arg Lys Phe
    1625


<210> SEQ ID NO 9
<211> LENGTH: 3621
<212> TYPE: DNA
<213> ORGANISM: Triticum aestivum
<220> FEATURE:
<221> NAME/KEY: CDS
<222> LOCATION: (1)..(3177)
<223> OTHER INFORMATION:
<220> FEATURE:
<221> NAME/KEY: misc_feature
<222> LOCATION: (1520)..(1520)
<223> OTHER INFORMATION: n can be a or g or c or t, and the encoded
      amino acid cannot be assigned with certainty.

<400> SEQUENCE: 9

gat gca ttg tat gtg aat gga ctg gaa gct aag gag gga gat cac aca       48
Asp Ala Leu Tyr Val Asn Gly Leu Glu Ala Lys Glu Gly Asp His Thr
1               5                   10                  15

tcc gag aaa act gat gag gat gcg ctt cat gta aag ttt aat gtt gac       96
Ser Glu Lys Thr Asp Glu Asp Ala Leu His Val Lys Phe Asn Val Asp
            20                  25                  30

aat gtg ttg cgg aag cat cag gca gat aga acc caa gca gtg gaa aag      144
Asn Val Leu Arg Lys His Gln Ala Asp Arg Thr Gln Ala Val Glu Lys
        35                  40                  45

aaa act tgg aag aaa gtt gat gag gaa cat ctt tac atg act gaa cat      192
Lys Thr Trp Lys Lys Val Asp Glu Glu His Leu Tyr Met Thr Glu His
    50                  55                  60

cag aaa cgt gct gcc gaa gga cag atg gta gtt aac gag gat gag ctt      240
Gln Lys Arg Ala Ala Glu Gly Gln Met Val Val Asn Glu Asp Glu Leu
65                  70                  75                  80

tct ata act gaa att gga atg ggg aga ggt gat aaa att cag cat gtg      288
Ser Ile Thr Glu Ile Gly Met Gly Arg Gly Asp Lys Ile Gln His Val
                85                  90                  95

ctt tct gag gaa gag ctt tca tgg tct gaa gat gaa gtg cag tta att      336
Leu Ser Glu Glu Glu Leu Ser Trp Ser Glu Asp Glu Val Gln Leu Ile
            100                 105                 110

gag gat gat gga caa tat gaa gtt gac gag acc tct gtg tcc gtt aac      384
Glu Asp Asp Gly Gln Tyr Glu Val Asp Glu Thr Ser Val Ser Val Asn
        115                 120                 125

gtt gaa caa gat atc cag ggg tca cca cag gat gtt gtg gat ccg caa      432
Val Glu Gln Asp Ile Gln Gly Ser Pro Gln Asp Val Val Asp Pro Gln
    130                 135                 140

gca cta aag gtg atg ctg caa gaa ctc gct gag aaa aat tat tcg atg      480
Ala Leu Lys Val Met Leu Gln Glu Leu Ala Glu Lys Asn Tyr Ser Met
145                 150                 155                 160

agg aac aag ctg ttt gtt ttt cca gag gta gtg aaa gct gat tca gtt      528
Arg Asn Lys Leu Phe Val Phe Pro Glu Val Val Lys Ala Asp Ser Val
                165                 170                 175

att gat ctt tat tta aat cgt gac cta aca gct ttg gcg aat gaa ccc      576
Ile Asp Leu Tyr Leu Asn Arg Asp Leu Thr Ala Leu Ala Asn Glu Pro
            180                 185                 190

gat gtc gtc atc aaa gga gca ttc aat ggt tgg aaa tgg agg ctt ttc      624
Asp Val Val Ile Lys Gly Ala Phe Asn Gly Trp Lys Trp Arg Leu Phe
        195                 200                 205

act gaa aga ttg cac aag agt gac ctt gga ggg gtt tgg tgg tct tgc      672
Thr Glu Arg Leu His Lys Ser Asp Leu Gly Gly Val Trp Trp Ser Cys
    210                 215                 220

aaa ctg tac ata ccc aag gag gcc tac aga tta gac ttt gtg ttc ttc      720
Lys Leu Tyr Ile Pro Lys Glu Ala Tyr Arg Leu Asp Phe Val Phe Phe
```

-continued

```
225                 230                 235                 240

aac ggt cgc acg gtc tat gag aac aat ggc aac aat gat ttc tgt ata      768
Asn Gly Arg Thr Val Tyr Glu Asn Asn Gly Asn Asn Asp Phe Cys Ile
                245                 250                 255

gga ata gaa ggc act atg aat gaa gat ctg ttt gag gat ttc ttg gtt      816
Gly Ile Glu Gly Thr Met Asn Glu Asp Leu Phe Glu Asp Phe Leu Val
            260                 265                 270

aaa gaa aag caa agg gag ctt gag aaa ctt gcc atg gaa gaa gct gaa      864
Lys Glu Lys Gln Arg Glu Leu Glu Lys Leu Ala Met Glu Glu Ala Glu
        275                 280                 285

agg agg aca cag act gaa gaa cag cgg cga aga aag gaa gca agg gct      912
Arg Arg Thr Gln Thr Glu Glu Gln Arg Arg Arg Lys Glu Ala Arg Ala
    290                 295                 300

gca gat gaa gct gtc agg gca caa gcg aag gcc gag ata gag atc aag      960
Ala Asp Glu Ala Val Arg Ala Gln Ala Lys Ala Glu Ile Glu Ile Lys
305                 310                 315                 320

aag aaa aaa ttg caa agt atg ttg agt ttg gcc aga aca tgt gtt gat     1008
Lys Lys Lys Leu Gln Ser Met Leu Ser Leu Ala Arg Thr Cys Val Asp
                325                 330                 335

aat ttg tgg tac ata gag gct agc aca gat aca aga gga gat act atc     1056
Asn Leu Trp Tyr Ile Glu Ala Ser Thr Asp Thr Arg Gly Asp Thr Ile
            340                 345                 350

agg tta tat tat aac aga aac tcg agg cca ctt gcg cat agt act gag     1104
Arg Leu Tyr Tyr Asn Arg Asn Ser Arg Pro Leu Ala His Ser Thr Glu
        355                 360                 365

att tgg atg cat ggt ggt tac aac aat tgg tca gat gga ctc tct att     1152
Ile Trp Met His Gly Gly Tyr Asn Asn Trp Ser Asp Gly Leu Ser Ile
    370                 375                 380

gtt gaa agc ttt gtc aag tgc aat gac aaa gac ggc gat tgg tgg tat     1200
Val Glu Ser Phe Val Lys Cys Asn Asp Lys Asp Gly Asp Trp Trp Tyr
385                 390                 395                 400

gca gat gtt att cca cct gaa aag gca ctt gtg ttg gac tgg gtt ttt     1248
Ala Asp Val Ile Pro Pro Glu Lys Ala Leu Val Leu Asp Trp Val Phe
                405                 410                 415

gct gat ggg cca gct ggg aat gca agg aac tat gac aac aat gct cga     1296
Ala Asp Gly Pro Ala Gly Asn Ala Arg Asn Tyr Asp Asn Asn Ala Arg
            420                 425                 430

caa gat ttc cat gct att ctt ccg aac aac aat gta acc gag gaa ggc     1344
Gln Asp Phe His Ala Ile Leu Pro Asn Asn Asn Val Thr Glu Glu Gly
        435                 440                 445

ttc tgg gcg caa gag gag caa aac atc tat aca agg ctt ctg caa gaa     1392
Phe Trp Ala Gln Glu Glu Gln Asn Ile Tyr Thr Arg Leu Leu Gln Glu
    450                 455                 460

agg aga gaa aag gaa gaa acc atg aaa aga aag gct gag aga agt gca     1440
Arg Arg Glu Lys Glu Glu Thr Met Lys Arg Lys Ala Glu Arg Ser Ala
465                 470                 475                 480

aat atc aaa gct gag atg aag gca aaa act atg cga agg ttt ctg ctt     1488
Asn Ile Lys Ala Glu Met Lys Ala Lys Thr Met Arg Arg Phe Leu Leu
                485                 490                 495

tcc cag aaa cac att gtt tat acc cga acc gnc ttg aaa tac gtg ccc     1536
Ser Gln Lys His Ile Val Tyr Thr Arg Thr Xaa Leu Lys Tyr Val Pro
            500                 505                 510

gga acc aca gtg gat gtg cta tac aat ccc tct aac aca gtg cta aat     1584
Gly Thr Thr Val Asp Val Leu Tyr Asn Pro Ser Asn Thr Val Leu Asn
        515                 520                 525

gga aag tcg gag ggt tgg ttt aga tgc tcc ttt aac ctt tgg atg cat     1632
Gly Lys Ser Glu Gly Trp Phe Arg Cys Ser Phe Asn Leu Trp Met His
    530                 535                 540

tca agt ggg gca ttg cca ccc cag aag atg gtg aaa tca ggg gat ggg     1680
```

-continued

```
Ser Ser Gly Ala Leu Pro Pro Gln Lys Met Val Lys Ser Gly Asp Gly
545                 550                 555                 560

ccg ctc tta aaa gca aca gtt gat gtt cca ccg gat gcc tat atg atg     1728
Pro Leu Leu Lys Ala Thr Val Asp Val Pro Pro Asp Ala Tyr Met Met
                565                 570                 575

gac ttt gtt ttc tcc gag tgg gaa gaa gat ggg atc tat gac aac agg     1776
Asp Phe Val Phe Ser Glu Trp Glu Glu Asp Gly Ile Tyr Asp Asn Arg
            580                 585                 590

aat ggg atg gac tat cat att cct gtt tct gat tca att gaa aca gag     1824
Asn Gly Met Asp Tyr His Ile Pro Val Ser Asp Ser Ile Glu Thr Glu
        595                 600                 605

aat tac atg cgt att atc cac att gcc gtt gag atg gcc ccc gtt gca     1872
Asn Tyr Met Arg Ile Ile His Ile Ala Val Glu Met Ala Pro Val Ala
    610                 615                 620

aag gtt gga ggt ctt ggg gat gtt gtt aca agt ctt tca cgt gcc att     1920
Lys Val Gly Gly Leu Gly Asp Val Val Thr Ser Leu Ser Arg Ala Ile
625                 630                 635                 640

caa gat cta gga cat act gtc gag gtt att ctc ccg aag tac gac tgt     1968
Gln Asp Leu Gly His Thr Val Glu Val Ile Leu Pro Lys Tyr Asp Cys
                645                 650                 655

ttg aac caa agc agt gtc aag gat tta cat tta tat caa agt ttt tct     2016
Leu Asn Gln Ser Ser Val Lys Asp Leu His Leu Tyr Gln Ser Phe Ser
            660                 665                 670

tgg ggt ggt aca gaa ata aaa gta tgg gtt gga cga gtc gaa gac ctg     2064
Trp Gly Gly Thr Glu Ile Lys Val Trp Val Gly Arg Val Glu Asp Leu
        675                 680                 685

acc gtt tac ttc ctg gaa cct caa aat ggg atg ttt ggc gtt gga tgt     2112
Thr Val Tyr Phe Leu Glu Pro Gln Asn Gly Met Phe Gly Val Gly Cys
    690                 695                 700

gta tat gga agg aat gat gac cgc aga ttt ggg ttc ttc tgt cat tct     2160
Val Tyr Gly Arg Asn Asp Asp Arg Arg Phe Gly Phe Phe Cys His Ser
705                 710                 715                 720

gct cta gag ttt atc ctc cag aat gaa ttt tct cca cat ata ata cat     2208
Ala Leu Glu Phe Ile Leu Gln Asn Glu Phe Ser Pro His Ile Ile His
                725                 730                 735

tgc cat gat tgg tca agt gct ccg gtc gcc tgg cta tat aag gaa cac     2256
Cys His Asp Trp Ser Ser Ala Pro Val Ala Trp Leu Tyr Lys Glu His
            740                 745                 750

tat tcc caa tcc aga atg gca agc act cgg gtt gta ttt acc atc cac     2304
Tyr Ser Gln Ser Arg Met Ala Ser Thr Arg Val Val Phe Thr Ile His
        755                 760                 765

aat ctt gaa ttt gga gca cat tat att ggt aaa gca atg aca tac tgt     2352
Asn Leu Glu Phe Gly Ala His Tyr Ile Gly Lys Ala Met Thr Tyr Cys
    770                 775                 780

gat aaa gcc aca act gtt tct cct aca tat tca agg gac gtg gca ggc     2400
Asp Lys Ala Thr Thr Val Ser Pro Thr Tyr Ser Arg Asp Val Ala Gly
785                 790                 795                 800

cat ggc gcc att gct cct cat cgt gag aaa ttc tac ggc att ctc aat     2448
His Gly Ala Ile Ala Pro His Arg Glu Lys Phe Tyr Gly Ile Leu Asn
                805                 810                 815

gga att gat cca gat atc tgg gat ccg tac act gac aat ttt atc ccg     2496
Gly Ile Asp Pro Asp Ile Trp Asp Pro Tyr Thr Asp Asn Phe Ile Pro
            820                 825                 830

gtc cct tat act tgt gag aat gtt gtc gaa ggc aag agg gct gca aaa     2544
Val Pro Tyr Thr Cys Glu Asn Val Val Glu Gly Lys Arg Ala Ala Lys
        835                 840                 845

agg gcc ttg cag cag aag ttt gga tta cag caa act gat gtc cct att     2592
Arg Ala Leu Gln Gln Lys Phe Gly Leu Gln Gln Thr Asp Val Pro Ile
    850                 855                 860
```

-continued

```
gtc gga atc atc acc cgt ctg aca gca cag aag gga atc cac ctc atc     2640
Val Gly Ile Ile Thr Arg Leu Thr Ala Gln Lys Gly Ile His Leu Ile
865                 870                 875                 880

aag cac gca att cac cga acc ctc gag agc aat gga caa gtg gtt ttg     2688
Lys His Ala Ile His Arg Thr Leu Glu Ser Asn Gly Gln Val Val Leu
                885                 890                 895

ctt ggt tca gct cca gat cat cga ata caa ggc gat ttt tgc aga ttg     2736
Leu Gly Ser Ala Pro Asp His Arg Ile Gln Gly Asp Phe Cys Arg Leu
            900                 905                 910

gcc gat gct ctt cac ggt gtt tac cat ggt agg gtg aag ctt gtt cta     2784
Ala Asp Ala Leu His Gly Val Tyr His Gly Arg Val Lys Leu Val Leu
        915                 920                 925

acc tac gat gag cct ctt tct cac ctg ata tac gct ggc tcc gac ttc     2832
Thr Tyr Asp Glu Pro Leu Ser His Leu Ile Tyr Ala Gly Ser Asp Phe
    930                 935                 940

att att gtc cct tca atc ttt gaa ccc tgt ggc tta aca caa ctt gtt     2880
Ile Ile Val Pro Ser Ile Phe Glu Pro Cys Gly Leu Thr Gln Leu Val
945                 950                 955                 960

gcc atg cgt tat gga tcg atc cct ata gtt cgg aaa acc gga gga ctt     2928
Ala Met Arg Tyr Gly Ser Ile Pro Ile Val Arg Lys Thr Gly Gly Leu
                965                 970                 975

tac gac act gtc ttc gac gta gac aat gat aag gac cgg gct cgg tct     2976
Tyr Asp Thr Val Phe Asp Val Asp Asn Asp Lys Asp Arg Ala Arg Ser
            980                 985                 990

ctt ggt ctt gaa cca aat ggg ttc  agt ttc gac gga gcc  gac agc aat   3024
Leu Gly Leu Glu Pro Asn Gly Phe  Ser Phe Asp Gly Ala  Asp Ser Asn
        995                 1000                1005

ggc gtg  gat tat gcc ctc aac  aga gca atc ggc gct  tgg ttc gat      3069
Gly Val  Asp Tyr Ala Leu Asn  Arg Ala Ile Gly Ala  Trp Phe Asp
    1010                1015                1020

gcc cgt  gat tgg ttc cac tcc  ctg tgt aag agg gtc  atg gag caa      3114
Ala Arg  Asp Trp Phe His Ser  Leu Cys Lys Arg Val  Met Glu Gln
    1025                1030                1035

gac tgg  tcg tgg aac cgg cct  gca ctg gac tac att  gaa ttg tac      3159
Asp Trp  Ser Trp Asn Arg Pro  Ala Leu Asp Tyr Ile  Glu Leu Tyr
    1040                1045                1050

cat gcc  gct cga aaa ttc tgacacccaa ctgaaccaat ggcaagaaca          3207
His Ala  Ala Arg Lys Phe
    1055

agcgcattgt gggatcgact acagtcatac agggctgtgc agatcgtctt gcttcagtta   3267

gtgccctctt cagttagttc caagcgcact acagtcgtac atagctgagg atcctcttgc   3327

ctcctccacc aggggaaaca aagcagaaat gcataagtgc attgggaaga cttttatgta   3387

tattgttaaa tttttccttt tcttttcctt ccctgcacct ggaaatggtt aagcgcatcg   3447

ccgagataag aaccacagta acattctgtg agtagctttg tatattctct catcttgtga   3507

aaactaatgt gcatgttagg ctctctgatc atgtggaagc tttgttatat gttacttatg   3567

gttatatggt atacatcaat gatatttaca tttgtggaaa aaaaaaaaaa aaaa         3621


<210> SEQ ID NO 10
<211> LENGTH: 1059
<212> TYPE: PRT
<213> ORGANISM: Triticum aestivum
<220> FEATURE:
<221> NAME/KEY: misc_feature
<222> LOCATION: (507)..(507)
<223> OTHER INFORMATION: The 'Xaa' at location 507 stands for Asp, Gly,
      Ala, or Val.
<220> FEATURE:
<221> NAME/KEY: misc_feature
<222> LOCATION: (1520)..(1520)
```

-continued

<223> OTHER INFORMATION: n can be a or g or c or t, and the encoded amino acid cannot be assigned with certainty.

<400> SEQUENCE: 10

```
Asp Ala Leu Tyr Val Asn Gly Leu Glu Ala Lys Glu Gly Asp His Thr
1               5                   10                  15

Ser Glu Lys Thr Asp Glu Asp Ala Leu His Val Lys Phe Asn Val Asp
            20                  25                  30

Asn Val Leu Arg Lys His Gln Ala Asp Arg Thr Gln Ala Val Glu Lys
        35                  40                  45

Lys Thr Trp Lys Lys Val Asp Glu Glu His Leu Tyr Met Thr Glu His
    50                  55                  60

Gln Lys Arg Ala Ala Glu Gly Gln Met Val Val Asn Glu Asp Glu Leu
65                  70                  75                  80

Ser Ile Thr Glu Ile Gly Met Gly Arg Gly Asp Lys Ile Gln His Val
                85                  90                  95

Leu Ser Glu Glu Glu Leu Ser Trp Ser Glu Asp Glu Val Gln Leu Ile
            100                 105                 110

Glu Asp Asp Gly Gln Tyr Glu Val Asp Glu Thr Ser Val Ser Val Asn
        115                 120                 125

Val Glu Gln Asp Ile Gln Gly Ser Pro Gln Asp Val Val Asp Pro Gln
    130                 135                 140

Ala Leu Lys Val Met Leu Gln Glu Leu Ala Glu Lys Asn Tyr Ser Met
145                 150                 155                 160

Arg Asn Lys Leu Phe Val Phe Pro Glu Val Val Lys Ala Asp Ser Val
                165                 170                 175

Ile Asp Leu Tyr Leu Asn Arg Asp Leu Thr Ala Leu Ala Asn Glu Pro
            180                 185                 190

Asp Val Val Ile Lys Gly Ala Phe Asn Gly Trp Lys Trp Arg Leu Phe
        195                 200                 205

Thr Glu Arg Leu His Lys Ser Asp Leu Gly Gly Val Trp Trp Ser Cys
    210                 215                 220

Lys Leu Tyr Ile Pro Lys Glu Ala Tyr Arg Leu Asp Phe Val Phe Phe
225                 230                 235                 240

Asn Gly Arg Thr Val Tyr Glu Asn Asn Gly Asn Asn Asp Phe Cys Ile
                245                 250                 255

Gly Ile Glu Gly Thr Met Asn Glu Asp Leu Phe Glu Asp Phe Leu Val
            260                 265                 270

Lys Glu Lys Gln Arg Glu Leu Glu Lys Leu Ala Met Glu Glu Ala Glu
        275                 280                 285

Arg Arg Thr Gln Thr Glu Glu Gln Arg Arg Arg Lys Glu Ala Arg Ala
    290                 295                 300

Ala Asp Glu Ala Val Arg Ala Gln Ala Lys Ala Glu Ile Glu Ile Lys
305                 310                 315                 320

Lys Lys Lys Leu Gln Ser Met Leu Ser Leu Ala Arg Thr Cys Val Asp
                325                 330                 335

Asn Leu Trp Tyr Ile Glu Ala Ser Thr Asp Thr Arg Gly Asp Thr Ile
            340                 345                 350

Arg Leu Tyr Tyr Asn Arg Asn Ser Arg Pro Leu Ala His Ser Thr Glu
        355                 360                 365

Ile Trp Met His Gly Gly Tyr Asn Asn Trp Ser Asp Gly Leu Ser Ile
    370                 375                 380

Val Glu Ser Phe Val Lys Cys Asn Asp Lys Asp Gly Asp Trp Trp Tyr
385                 390                 395                 400
```

-continued

```
Ala Asp Val Ile Pro Pro Glu Lys Ala Leu Val Leu Asp Trp Val Phe
                405                 410                 415

Ala Asp Gly Pro Ala Gly Asn Ala Arg Asn Tyr Asp Asn Asn Ala Arg
            420                 425                 430

Gln Asp Phe His Ala Ile Leu Pro Asn Asn Asn Val Thr Glu Glu Gly
        435                 440                 445

Phe Trp Ala Gln Glu Glu Gln Asn Ile Tyr Thr Arg Leu Leu Gln Glu
    450                 455                 460

Arg Arg Glu Lys Glu Glu Thr Met Lys Arg Lys Ala Glu Arg Ser Ala
465                 470                 475                 480

Asn Ile Lys Ala Glu Met Lys Ala Lys Thr Met Arg Arg Phe Leu Leu
                485                 490                 495

Ser Gln Lys His Ile Val Tyr Thr Arg Thr Xaa Leu Lys Tyr Val Pro
            500                 505                 510

Gly Thr Thr Val Asp Val Leu Tyr Asn Pro Ser Asn Thr Val Leu Asn
        515                 520                 525

Gly Lys Ser Glu Gly Trp Phe Arg Cys Ser Phe Asn Leu Trp Met His
    530                 535                 540

Ser Ser Gly Ala Leu Pro Pro Gln Lys Met Val Lys Ser Gly Asp Gly
545                 550                 555                 560

Pro Leu Leu Lys Ala Thr Val Asp Val Pro Pro Asp Ala Tyr Met Met
                565                 570                 575

Asp Phe Val Phe Ser Glu Trp Glu Glu Asp Gly Ile Tyr Asp Asn Arg
            580                 585                 590

Asn Gly Met Asp Tyr His Ile Pro Val Ser Asp Ser Ile Glu Thr Glu
        595                 600                 605

Asn Tyr Met Arg Ile Ile His Ile Ala Val Glu Met Ala Pro Val Ala
    610                 615                 620

Lys Val Gly Gly Leu Gly Asp Val Val Thr Ser Leu Ser Arg Ala Ile
625                 630                 635                 640

Gln Asp Leu Gly His Thr Val Glu Val Ile Leu Pro Lys Tyr Asp Cys
                645                 650                 655

Leu Asn Gln Ser Ser Val Lys Asp Leu His Leu Tyr Gln Ser Phe Ser
            660                 665                 670

Trp Gly Gly Thr Glu Ile Lys Val Trp Val Gly Arg Val Glu Asp Leu
        675                 680                 685

Thr Val Tyr Phe Leu Glu Pro Gln Asn Gly Met Phe Gly Val Gly Cys
    690                 695                 700

Val Tyr Gly Arg Asn Asp Asp Arg Arg Phe Gly Phe Phe Cys His Ser
705                 710                 715                 720

Ala Leu Glu Phe Ile Leu Gln Asn Glu Phe Ser Pro His Ile Ile His
                725                 730                 735

Cys His Asp Trp Ser Ser Ala Pro Val Ala Trp Leu Tyr Lys Glu His
            740                 745                 750

Tyr Ser Gln Ser Arg Met Ala Ser Thr Arg Val Val Phe Thr Ile His
        755                 760                 765

Asn Leu Glu Phe Gly Ala His Tyr Ile Gly Lys Ala Met Thr Tyr Cys
    770                 775                 780

Asp Lys Ala Thr Thr Val Ser Pro Thr Tyr Ser Arg Asp Val Ala Gly
785                 790                 795                 800

His Gly Ala Ile Ala Pro His Arg Glu Lys Phe Tyr Gly Ile Leu Asn
                805                 810                 815
```

-continued

```
Gly Ile Asp Pro Asp Ile Trp Asp Pro Tyr Thr Asp Asn Phe Ile Pro
            820                 825                 830

Val Pro Tyr Thr Cys Glu Asn Val Val Glu Gly Lys Arg Ala Ala Lys
        835                 840                 845

Arg Ala Leu Gln Gln Lys Phe Gly Leu Gln Gln Thr Asp Val Pro Ile
    850                 855                 860

Val Gly Ile Ile Thr Arg Leu Thr Ala Gln Lys Gly Ile His Leu Ile
865                 870                 875                 880

Lys His Ala Ile His Arg Thr Leu Glu Ser Asn Gly Gln Val Val Leu
                885                 890                 895

Leu Gly Ser Ala Pro Asp His Arg Ile Gln Gly Asp Phe Cys Arg Leu
            900                 905                 910

Ala Asp Ala Leu His Gly Val Tyr His Gly Arg Val Lys Leu Val Leu
        915                 920                 925

Thr Tyr Asp Glu Pro Leu Ser His Leu Ile Tyr Ala Gly Ser Asp Phe
    930                 935                 940

Ile Ile Val Pro Ser Ile Phe Glu Pro Cys Gly Leu Thr Gln Leu Val
945                 950                 955                 960

Ala Met Arg Tyr Gly Ser Ile Pro Ile Val Arg Lys Thr Gly Gly Leu
                965                 970                 975

Tyr Asp Thr Val Phe Asp Val Asp Asn Asp Lys Asp Arg Ala Arg Ser
            980                 985                 990

Leu Gly Leu Glu Pro Asn Gly Phe  Ser Phe Asp Gly Ala  Asp Ser Asn
        995                 1000                1005

Gly Val  Asp Tyr Ala Leu Asn  Arg Ala Ile Gly Ala  Trp Phe Asp
    1010                1015                1020

Ala Arg  Asp Trp Phe His Ser  Leu Cys Lys Arg Val  Met Glu Gln
    1025                1030                1035

Asp Trp  Ser Trp Asn Arg Pro  Ala Leu Asp Tyr Ile  Glu Leu Tyr
    1040                1045                1050

His Ala  Ala Arg Lys Phe
    1055
```

```
<210> SEQ ID NO 11
<211> LENGTH: 728
<212> TYPE: DNA
<213> ORGANISM: Triticum sp.

<400> SEQUENCE: 11

gatcttgaac ggcacgtgaa agacttgtaa caacatcccc gagacctcca acctatgaga     60

tcatcgatca tgacagagca tagtattatg gcatagaatg aaaaaaaggc ataaggtgat    120

gagatctcca cgccagagcg ttgtattcca attttagttc tttccccgtg aggaggggag    180

gctaggcggg cgaggcagag gggatagggc agtcgccgct gcgtggtgga ctgactggtg    240

tggtgggtgg tgggttttgc gggcggggtt tagtaggttc ccggaaatgg agatggctct    300

ccggccacgg agccctctgt gccctcggag cagtcagccg ctcgtcgtcg tccggccggc    360

cggccgcggc ggcggcctcg cgcaggtacg ggtgattatg gttcttgatt cggtcggttc    420

acggaatgtt gtttgatttg gttctgtccc gggtcaggtt catagtgatt ttattccgca    480

aaaaaaaaag gtttatagtg attttgattt ctttcatctc gggaacattt ttatatctgg    540

gagtcaaagg gcattggttt tgatttgcat gcggaacata ttggttattt attaatgtgg    600

tgagctggaa ttcatactgc ttaaaacgac gtgattttaa ttgctggaag aggtaaagaa    660

catgaattct tgttatattt gttaaaaaaa atcccctgtt ctagcgtttc aatctgcatg    720
```

-continued atcatgga 728

<210> SEQ ID NO 12
<211> LENGTH: 2446
<212> TYPE: DNA
<213> ORGANISM: Triticum sp.

<400> SEQUENCE: 12
gtgggtctat aaaagacagg tttgagcgga ttcgtcagga aatgtttcaa caagtgcgac 60
gatgtgggat gcaattgatg aaaccgtggc ttgatcaaga cgcagttgag gcggatttgt 120
cgggaaatgc ttcaagctgc gcgacataca gagaagtgga tgatgtggtg gatgaaacta 180
gatcagaaga ggaaacattt gcgatggatt tgtttgcaag tgaatcaggc catgagaaac 240
atatggcagt ggatcatgtg ggtgaagcta ccgatgaaga agagacttac caacagcaat 300
atccagtacc gtcttcattc tctatgtggg acaaggctat tgctaaaaca ggtgtaagtt 360
tgaatcctga gctgcgactt gtcagggttg aagaacaagg caaagtaaat tttagtgata 420
aaaaagacct gtcaattgat gatttaccag gacaaaacca atcgatcatt ggttcctata 480
aacaagataa atcaattgct gatgttgcgg gaccgaccca atcaattttt ggttctagta 540
aacaacaccg gtcaattgtt gctttcccca aacaaaacca gtcaattgtt agtgtcactg 600
agcaaaagca gtccatagtt ggattccgta gtcaagatct ttcggctgtt agtctcccta 660
aacaaaacgt accaattgtt ggtacgtcga gagagggtca aacaaagcaa gttcctgttg 720
ttgatagaca ggatgcgttg tatgtgaatg gactggaagc taaggaggga gatcacacat 780
ccgagaaaac cgatgaggat gtgcttcatg taaaatttaa tgttgacaat gtgttgcgga 840
agcatcaggc agatagaacc caagcagtgg aaacgataac ttggaagaaa gttgatgagg 900
aacatcttta catgactgaa catcagatag gtgctgccga aggacagatg gtagttaacg 960
aggatgagct ttctataact gaaattggaa tggggagagg tgataaaatt cagcatgtgc 1020
tttctgagga agagctttca tggtctgaag atgaagtgca gttaattgag gatgatggac 1080
aatatgaagt tgatgagacc tctgtgtccg ttaacgttga acaagatatc caggggtcac 1140
cacaggatgt tgtggatccg caagcactaa aggtgatgct gcaagaactc gctgagaaaa 1200
attattcgat gaggaacaag ctgtttgttt ttccagaggt agtgaaagct gattcagtta 1260
ttgatcttta tttcaatcgt gacctaacag ctttggcgaa tgaacccgat gttgtcatca 1320
aaggagcatt caatggttgg aaatggaggc ttttcactga aagattgcat aagagtgacc 1380
ttggaggggt ttggtggtct tgcaaactgt acatacccaa ggaggcctac agattagact 1440
ttgtgttctt caacggtcgc acggtctatg agaacaatgg caacaatgat ttctgtatag 1500
gaatagaagg cactatgaat gaagatctgt ttgaggattt cttggttaaa gaaaagcaaa 1560
gggagcttga gaaacttgcc atggaagaag ctgaaaggag gacacagact gaagaacagc 1620
ggcgaagtaa ggaagcaagg gctgcagatg aagctgtcag ggcacaagcg aaggccgaga 1680
tagagatcaa gaacaaaaaa ttgcagagta tgttgagttt ggccagaaca tgtgttgata 1740
atttgtggta catagaggct agcacagata caagcggaga tactatcagg ttatactata 1800
acagaaactc gaggccactt gcgcatagta ctgagatttg gatgcatggt ggttacaaca 1860
attggtcaga tggactctct attgttgaaa gctttgtcaa gtgcaatgac agagacggcg 1920
attggtggta tgcagatggt acgacacctc aacctttgta cataaggcaa cattgttttg 1980 atttttttttg ttgaggaaac atttgttttg attctagcat aatgctccta caaatatggc 2040

-continued

```
atgaatttcc ttgttttatt gatgtcatga gaaagtattt tattaactcg aaggccatgg   2100

aagctcaaca tttaccatag acagacgctt aaagatcatt tgtattccgt ggatcatata   2160

tgtaatgtaa tacctgtctt ttctctatat gtacagttat tccacctgaa aaagcacttg   2220

tgttggactg ggtttttgct gatgggccag ctgggaatgc aaggaactat gacaacaatg   2280

ctcgacaaga tttccatgct attcttccaa acaacaatgt aaccgaggaa ggcttctggg   2340

tgcaagagga gcaaaacatc tatacaaggc ttctgcaaga aaggagagaa aaggaagaaa   2400

ccatgaaaag aaaggtgagt tgcaacaaaa tctttgcata tagatc                  2446
```

```
<210> SEQ ID NO 13
<211> LENGTH: 1032
<212> TYPE: DNA
<213> ORGANISM: Triticum sp.

<400> SEQUENCE: 13

gatctctata attttggcag ttaacccctg agtgatggca aatatattcc ctttcgtcta     60

ttttccaaat tcaaaatgca tggttccatg caagcttatc caaaatcact tgataatata    120

ccaatcacaa cataactttg tttaccataa gaacattcct acttaaaatt tgcaaggtaa    180

ctccctttcg aggctggttg gcttgatgag taactggcaa ttaacaaaga aaagatatat    240

ctgatgtttg gaacaaaaca tatgatcagg gttgtttggg ttgactcatg ttccttttta    300

cctacacagg ctgagagaag tgcaaatatc aaagctgaga tgaaggcaaa aactatgcga    360

aggtttctgc tttcccagaa acacattgtt tataccgaac cgcttgaaat acgtgccgga    420

accacagtgg atgtgctata caatccctct aacacagtgc taaatggaaa gccggaggtt    480

tggtttagat gctcttttaa cctttggatg catccaagtg gagcattgcc accccagaag    540

atggtgaaat caggggatgg gccgctctta aaagccacag gtttattgcg ttattacatc    600

actgttatta gtatatatat aaccattttt atgcaatcaa tagagtcaag tgcaactaat    660

gatgcacaga taggatcaca tcattaggag aatgatgtga tggacaagac ccaatcctaa    720

gcatagcaca agatcgtgta gttcgttcgc tagagctttt ctaatgtcaa gtatcatttc    780

cttagaccat gagattgtgc aactcccgga tatcgtagga gtgctttggg tgtatcaaat    840

gtcacaacgt aactgggtga ctataaaggt gcactacagg tatctccgaa agtttctgtt    900

gggttggcac gaatcgagac tgggatttgt cactccgtat gacggagagg tatctttggg    960

cccactcggt aatgcatcat cataatgagc tcaatgtgac taaggagtta gccacgggat   1020

cgagaattcc cg                                                       1032
```

```
<210> SEQ ID NO 14
<211> LENGTH: 892
<212> TYPE: DNA
<213> ORGANISM: Triticum sp.

<400> SEQUENCE: 14

aatatttctt gttctattat tggtaataat tagctagttt aatgccataa gcccataaca     60

gatatgcaac tactccctcc aatccatatt acttgtcgca actttggtac aactttagta    120

caaagttata ctaaagctgt gacaagtaat atggaccgga gggagtacta tataagcttg    180

tagctgtttt gagaccgagt gtctgctcgg gtggctagct ggagcgggct gaagtgcttg    240

caggcacctc ttctctaaaa aaaagtgctt gcagcccccc cgccccctcc atagggtgag    300

tggtcacctt tcttcttaaa aattatggca ccaagggaaa ttctcggctg gtcgagcttg    360

tagctatttt ttcggagcgt gaatgggagc gtctttctgt ataaggccta taggcttact    420
```

-continued

```
ttgatatata ttgtgaagtc acttaagcct tgttaaaacg tagaaactta gttccgcaac    480

ttggccaaat ccctgttaaa ttggtttact gtgtactaga tgcatcgatg gcgcagagtc    540

ccggggggta ataaagcttc cattttctac aatgaagtta attatcctac ttgccttgta    600

attactgagt acaatacaga gcaccgaaaa gctgtatcct tcctacttcc ttatgtttat    660

ctgtgttcct tgtctagtta atgttccacc ggatgcctat atgatggact ttgttttctc    720

cgagtgggaa gaagatggga tctatgacaa caggaatggg atggactatc atattcctgt    780

ttctgattca attgaaacag agaattacat gcgtattatc cacattgccg ttgagatggc    840

ccccgttgca aaggtaatat aattctaagg ctagtttctt tgatgcgagg cg            892
```

<210> SEQ ID NO 15
<211> LENGTH: 871
<212> TYPE: DNA
<213> ORGANISM: Triticum sp.

<400> SEQUENCE: 15

```
aggttatcct ccagaatgaa ttttttccag tacgtattat ttagaatact agcggtatat     60

tgactttttc tttgtgagac tacactttct tgtttaccat tccagtgcac catgttcaaa    120

atcttgtatt cagcgcgtta ctttcagttt ctttactact agcttatttg gtgcattggt    180

gtttcctttc ctactctact atctgaatgc tacttgtgtt ttcgcaacag ttgcttcttt    240

atccccttcc atttctcagt taaaaaaact tgcatctgta ttcacgtgac agcatataat    300

acattgccat gattggtcaa gtgctccggt cgcctggcta tataaggaac actattccca    360

atccagaatg gcaagcactc gggttgtatt taccatccac aatcttgaat ttggagcaca    420

ttatattggt aaagcaatga catactgtga taaagccaca actgtgagtg ccttactgtc    480

ttgtaatttt taatctttct gtttggcgca cagaaaatct tccacatttt acagaatcat    540

gttcttgtgt tttgtacgta ttcaactatt tccacccaaa cttttcaggt ttctcctaca    600

tattcaaggg acgtggcagg ccatggtgcc attgctcctc atcgtgagaa attctacggc    660

attctcaatg gaattgatcc agatatctgg gatcctgatt gccaacatgc tgtttggtcg    720

tctcgaggtc tttacattgc tggtgctctt taccccgact ttctggcgtg aatgatggag    780

taatacgtga aaacattaat tcttttctca acaagggacg gacaaacgcg cgagattgcc    840

tcctacctgg cttcggaact gaaagaactg g                                   871
```

<210> SEQ ID NO 16
<211> LENGTH: 1592
<212> TYPE: DNA
<213> ORGANISM: Triticum sp.

<400> SEQUENCE: 16

```
cgggaattct cgatcccgtg gctaactcct tagtcacatt gagctcatta tgatgatgca     60

ttaccgagtg ggcccaaaga tacctctccg tcatacggag tgacaaatcc cagtctcgat    120

tcgtgccaac ccaacagaaa ctttcggaga tacctgtagt gcacctttat agtcacccag    180

ttacgttgtg acatttgata cacccaaagc actcctacga tatccgggag ttgcacaatc    240

tcatggtcta aggaaatgat acttgacatt agaaaagctc tagcgaacga actacacgat    300

cttgtgctat gcttaggatt gggtcttgtc catcacatca ttctcctaat gatgtgatcc    360

atacactgac aattttatcc cggtaccaga tttttcccca gagtgcaagt agatatatac    420

caaggccaca gatagtttta tgcttaacta tgtgtttcat actacttcag gtcccttata    480
```

-continued

```
cttgtgagaa tgttgtcgaa ggcaagagag ctgcaaaaag ggccttgcag cagaagtttg    540

gattacagca aactgatgtc cctattgtcg gaatcatcac ccgtctgaca gcccagaagg    600

gaatccacct catcaagcac gcaattcacc gaaccctcga aagcaacgga caggttcatc    660

atcccttgtg aacgaataaa catcaaacgt tttgtttata aaaagttgct tactatttgt    720

ttttgtttac ttcaaaacaa aagtctgaaa atgaagtgtt tggttcctag gtggttttgc    780

ttggttcagc tccagatcat cgaatacaag gcgatttttg cagattggcc gatgctcttc    840

acggtgttta ccacggtagg gtgaagcttg ttctaaccta cgatgagcct ctttctcacc    900

tggtgagctc caatatccta cacaccatct agccagccct tcattatggg agctggagac    960

tactttataa tttaggttga tgatcgatca tgctgcagat atacgctggc tccgacttca   1020

ttattgtccc ttcaatcttc gaaccctgtg gcttaacaca acttgttgcc atgcgttatg   1080

gatcgatccc tatagttcgg aaaaccggag gtgtgtgact atttctctcc attatgctgc   1140

actgatttgc atatgtcgag ctgttggaca tgaaatggaa actatccttt ggtatcgcag   1200

gactttacga cactgtcttc gacgtagaca atgataagga ccgggctcgg tctcttggtc   1260

ttgaaccaaa tgggttcagt ttcgacggag ccgacagcaa cggcgtggat tatgccctca   1320

acaggcaagt atcgttcctc aattagccct gaattcagca gtagtgctag gttatttacc   1380

ttgcatgttc catacctcat ttcagagcaa tcggcgcttg gttcgatgcc cgtgattggt   1440

tccactccct gtgtaagagg gtcatggaac aagactggtc atggaaccgg cccgcactgg   1500

actacattga attgtaccat gccgctcgaa aattctgaca cccaactgaa ccaatggcaa   1560

gaacaagcgc attgtgggat cgagaattcc cg                                 1592
```

```
<210> SEQ ID NO 17
<211> LENGTH: 10
<212> TYPE: PRT
<213> ORGANISM: Artificial Sequence
<220> FEATURE:
<223> OTHER INFORMATION: Peptide Motif

<400> SEQUENCE: 17

Asp Val Gln Leu Val Met Leu Gly Thr Gly
1               5                   10


<210> SEQ ID NO 18
<211> LENGTH: 10
<212> TYPE: PRT
<213> ORGANISM: Artificial Sequence
<220> FEATURE:
<223> OTHER INFORMATION: Peptide Motif

<400> SEQUENCE: 18

Ala Ala Gly Lys Lys Asp Ala Gly Ile Asp
1               5                   10


<210> SEQ ID NO 19
<211> LENGTH: 10
<212> TYPE: PRT
<213> ORGANISM: Artificial Sequence
<220> FEATURE:
<223> OTHER INFORMATION: Peptide Motif

<400> SEQUENCE: 19

Ala Thr Gly Lys Lys Asp Ala Gly Ile Asp
1               5                   10


<210> SEQ ID NO 20
```

-continued

<211> LENGTH: 10
<212> TYPE: PRT
<213> ORGANISM: Artificial Sequence
<220> FEATURE:
<223> OTHER INFORMATION: Peptide Motif

<400> SEQUENCE: 20

Ala Leu Gly Lys Lys Asp Ala Gly Ile Asp
1 5 10

<210> SEQ ID NO 21
<211> LENGTH: 8
<212> TYPE: PRT
<213> ORGANISM: Artificial Sequence
<220> FEATURE:
<223> OTHER INFORMATION: Peptide Motif

<400> SEQUENCE: 21

Ala Thr Gly Lys Lys Asp Ala Leu
1 5

<210> SEQ ID NO 22
<211> LENGTH: 8
<212> TYPE: PRT
<213> ORGANISM: Artificial Sequence
<220> FEATURE:
<223> OTHER INFORMATION: Peptide Motif

<400> SEQUENCE: 22

Ala Leu Gly Lys Lys Asp Ala Leu
1 5

<210> SEQ ID NO 23
<211> LENGTH: 14
<212> TYPE: PRT
<213> ORGANISM: Artificial Sequence
<220> FEATURE:
<223> OTHER INFORMATION: Peptide Motif

<400> SEQUENCE: 23

Ala Ala Gly Lys Lys Asp Ala Arg Val Asp Asp Asp Ala Ala
1 5 10

<210> SEQ ID NO 24
<211> LENGTH: 13
<212> TYPE: PRT
<213> ORGANISM: Artificial Sequence
<220> FEATURE:
<223> OTHER INFORMATION: Peptide Motif

<400> SEQUENCE: 24

Ala Leu Gly Lys Lys Asp Ala Gly Ile Val Asp Gly Ala
1 5 10

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
tgttgaggtt ccatggcacg ttc 23

<210> SEQ ID NO 26
<211> LENGTH: 23
<212> TYPE: DNA

-continued

<213> ORGANISM: Artificial Sequence
<220> FEATURE:
<223> OTHER INFORMATION: Primer

<400> SEQUENCE: 26
agtcgttctg ccgtatgatg tcg 23

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ccaagtacca gtggtgaacg c 21

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
cggtgggatc caacggccc 19

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ggaggtcttg gtgatgttgt 20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cttgaccaat catggcaatg 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cattgccatg attggtcaag 20

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
accacctgtc cgttccgttg c 21

-continued

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gcacggtcta tgagaacaat ggc 23

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
tctgcatacc accaatcgcc g 21

<210> SEQ ID NO 35
<211> LENGTH: 25
<212> TYPE: PRT
<213> ORGANISM: Artificial Sequence
<220> FEATURE:
<223> OTHER INFORMATION: Peptide Motif

<400> SEQUENCE: 35

Lys Val Gly Gly Leu Gly Asp Val Val Thr Ser Leu Ser Arg Ala Val
1 5 10 15

Gln Asp Leu Gly His Asn Val Glu Val
20 25

<210> SEQ ID NO 36
<211> LENGTH: 25
<212> TYPE: PRT
<213> ORGANISM: Artificial Sequence
<220> FEATURE:
<223> OTHER INFORMATION: Peptide Motif

<400> SEQUENCE: 36

Lys Val Gly Gly Leu Gly Asp Val Val Thr Ser Leu Ser Arg Ala Ile
1 5 10 15

Gln Asp Leu Gly His Thr Val Glu Val
20 25

<210> SEQ ID NO 37
<211> LENGTH: 9024
<212> TYPE: DNA
<213> ORGANISM: Triticum sp.

<400> SEQUENCE: 37
aaatatgaaa ccaaaaaaaa aatagaaaaa ggaaaggtaa aatagaaagt taaataggaa 60
taatggataa aaaataaaac atcaaagaaa aacgaaatgc agaagaaaaa aacgtcactt 120
gttcccttat tatctcccgt gcaccccggt agcgtaggac aaaaagaaaa aatagaacgg 180
acccaacgtc acaagctcac acatgcccag cgagagaaaa gaaaaatggt gcgacaaaaa 240
aaaggaaacg ggctgagagc cgaaacacat gggctgcgct ttgttcgcta cgaagctctc 300
ccctcgacaa aatatgaatc gcgacgtgat tggatcctat ggtggaaaaa gtgaatgaga 360
ccaaaagaat tctcagctga atgagtttta gcaagactga tcattatatc caacataaat 420

-continued

```
agattttttt tttgcaaaaa taatccaaat ctattagcaa agttcagtag aagtacaaag    480
catctcgaac attataaaca ttacactgag attccaggac caccaaacaa cccactactg    540
ccgcgaaaag aaaaggattc ggaagacaga aattatccaa accacgttcg tccttggttg    600
ttggtctcat tgcgcgctaa acaacctgga cagcagaaga agcaaagcag tgtgcttccg    660
ctccgcagca agaagacaag tcgtcacatg tcagacgccg tcactcaagc aagcaaactg    720
caatgcttct cgttcggttt atcccctagc acgcacgaac gcatgtgccg caccgcgtca    780
cgcaacgcat gcatgcacaa accaacaaac gaaacagtgc agttgcagtg ctctatctac    840
atatacgcaa tcaacgcggg cctcctcctt cgccgcgagc cccgttccgt cctcggtctt    900
cacgtggatt ttgcaacttc cttccagcag cttgtcacca cggacgcttc ctctctgaca    960
actggccccg tgggcggaac ggggcctccg ctcgcccctt gcgaaaccca cggctcgtcc   1020
gttcgcttct ctagcgggca ccgacagaag gggccggcgc agggtaggac caggctgtca   1080
gctggtgagg agcctgccgc tcgttgtgcc gcagctggag accgagcggg gcaacggaac   1140
ggctgccgcc ctcgtgtgct gctcgcgtgg cacgccgcaa cggcaccggg cccgctttcc   1200
agcgtgctcg cccgcaaacc gcagacccaa cacgccagcc gccagggggc cgttcgtacg   1260
tacccgcccc tcgtgtaaag ccgccgccgt cgtcgccgtc ccccgctcgc ggccatttct   1320
tcggcctgac cccgttcgtt tacccccaca cagagcacac tccagtccag tccagcccac   1380
tgccaccgcg ctactctcca ctcccactgc caccacctcc gcctgcgccg cgctctgggc   1440
ggaccaaccc gcgaaccgta ccatctcccg ccccgatcca tgtcgtcggc ggtcgcgtcc   1500
gccgcatcct tcctcgcgct cgcgtcagcc tcccccggga gatcacgcag gcgggcgagg   1560
gtgagcgcgc agccacccca cgccggggcc ggcaggttgc actggccgcc gtggccgccg   1620
cagcgcacgg ctcgcgacgg agctgtggcg gcgctcgccg ccgggaagaa ggacgcgggg   1680
atcgacgacg ccgccgcgtc cgtgaggcag ccccgcgcac tccgcggtgg cgccgccacc   1740
aaggtagtta gttatgacca agttatgacg cgtgcgcgcg cctcgagatc atcgtcgtct   1800
cgctcacgaa ttgtttattt atacaaaacg cacgcccgcg tgtgcaggtc gcggagcgaa   1860
gggatcccgt caagacgctc gaccgcgacg ccgcggaagg cggcgggccg tccccgccgg   1920
cagcgaggca ggacgccgcc cgtccgccga gtatgaacgg catgccggtg aacggcgaga   1980
acaaatctac cggcggcggc ggcgcgacta aagacagcgg gctgcccacg cccgcacgcg   2040
cgccccatcc gtcgacccag aacagagcac cggtgaacgg tgaaaacaaa gctaacgtcg   2100
cctcgccgcc gacgagcata gccgaggccg cggcttcgga ttccgcagct accatttcca   2160
tcagcgacaa ggcgccggag tccgttgtcc cagctgagaa gacgccgccg tcgtccggct   2220
caaatttcga gtcctcggcc tctgctcccg ggtctgacac tgtcagcgac gtggaacaag   2280
aactgaagaa gggtgcggtc gttgtcgaag aagctccaaa gccaaaggct ctttcgccgc   2340
ctgcagcccc cgctgtacaa gaagaccttt gggatttcaa gaaatacatt ggtttcgagg   2400
agcccgtgga ggccaaggat gatggccggg ctgtcgcaga tgatgcgggc tcctttgaac   2460
accaccagaa tcacgactcc ggacctttgg caggggagaa tgtcatgaac gtggtcgtcg   2520
tggctgctga gtgttctccc tggtgcaaaa caggcatgga cattacctct tcagtctctc   2580
ttcctgttgt tcataaaact ttgctcgaat tactcataag aacaaacatt gtgttgcata   2640
ggtggtctgg gagatgttgc gggtgctctg cccaaggctt tggcaaagag aggacatcgt   2700
gttatggtac tacaagcttt catttaactc tgttgggtcc atatgttcga ataatatcag   2760
tgagtagtat aatgttatta agtgcaagac atgaaagtgt tcttctgtca tactccctcc   2820
```

-continued

```
gtaaattaat ataagagcgt ttagattact actttagtga tctaaacgct cttatagtag   2880
tttacagacg gagtagagta tttcatagcc aaccctggag gttaggttgc tgaggcctac   2940
tgggtggggg agggggtttg aaacaagtgg tggttagcag ccagatttca caaagaagga   3000
ggctgataac cacaccatca gtgaaggaat gaatgtcggg tacccgatcg accgttttgc   3060
ccaacgtcgg gtttacccgc cctatagatc cgaataagta gttcctatct tcaattaggt   3120
accaaatatc gccagcgccc gtgtgtgtat ttatactact ggatgatcaa tttatcaaca   3180
tttccggtta atggtttcta tcatattcac tgtaattgtt agtaaacagt agatgtttgt   3240
aatgtagatg atggataaat gtatgttgtc gagctttcat ttcaatgcaa ttttgattgg   3300
gagctagttt cgcggttcgg ttagagccat caaaacccca gaatttttgg gagttggctt   3360
gtgagagagg gttttgggga gttaactttc gggattcagt tagagacgct cttactagtt   3420
ccagtaaaga gtaaactatt ttctgcaggc atcccaatta ttctgtagaa attagaagtg   3480
gaaaatagtt atggtatcat ataaaccata tattattcaa aatctagaat catggacttg   3540
gctagacttt gataatctga aattttaaat ttgatgataa ttgagaaatg atcctttcta   3600
tcttaggttg tggtaccaag gtatggggac tatgaagaag cctacgatgt cggagtccga   3660
aaatactaca aggctgctgg acaggtaagc aaaaatgcaa tcgaagggga gctgaaattt   3720
tattgcttat tgtcataata aatcaatttt taagtgtttt ttttgtcctg caggatatgg   3780
aagtgaatta tttccatgct tatatcgatg gagttgattt tgtgttcatt gacgctcctc   3840
tcttccgaca ccgtcaggaa gacatttatg gggcagcag acaggttaat cttctatatg   3900
ttggtgtttg attgcactga taaactgaga acaagccaag gcctactgac tggcatatga   3960
ttacacattt tatttttca ggaaattatg aagcgcatga ttttgttctg caaggccgct   4020
gttgaggtat ctctccaact caattgacaa cctattacca ctatacaatt atgtgtatgc   4080
atgtatttca acagatacat aatctcttgt gaagtgcata tatactaata acatttcaat   4140
accttacatg cacatttggt caagcgttat gatttaactt ctgataatct attgcactga   4200
tgaacaatta tcttgatgat ccttgttact tcatcgttat gtttccatgt tctcttcacc   4260
gcgaattgat ttggaaatag catttccacc tgccacaaac aataatatac actcctactt   4320
tcatccaatt tagatatttt cgtacttggc atatcatccc attaaatatt attggtccat   4380
catttttatt cctctataat ttgcaggttc catggcacgt tccatgcggc ggtgtccctt   4440
atggggatgg aaatctggtg tttattgcaa atgattggca cacggcactc ctgcctgtct   4500
atctgaaagc atattacagg gaccatggtt tgatgcagta cactcggtcc attatggtga   4560
tacataacat cgctcaccag gttccttttc tcctaatctt gatttttctc tagtctctac   4620
tatttactcc acattgtttg aggaaactaa acgggttgca aaattatgat ggcttatgaa   4680
agttatagtc ttatagaggt aaatgcacca gtggtgcttg aacttgtcac gcgtgttcac   4740
tttggtgctt acagttgtag actatgaaaa acgggtgcaa aaacttgctg ttgtgtgcca   4800
tacggtgcat tttccgtatg taggagtcaa acgttgccta tgtgggcatt gtattcccgt   4860
ctatagctgt tagaccgtgc ctacgtcgcc attgggccca cacactctct atttacatgt   4920
gggccccact tgtcaaccta tgacataaat aaatggaaat ttataataaa aatgatggcc   4980
tggggtcttg aaaatgggac ctcgcaggta tgctggtagc cagcacgccc taaacattaa   5040
tcccctatgc acttcatgtc ttgtgtatgt gtgtgtctgt gtggggaggg gggggtatgc   5100
atgctgtttt tctttggttc aaggctacca tgctcaacaa gcccacctcc gcttcaacac   5160
```

-continued

```
ggccagcgcc ttcatgatgg cccaagtgct ccgcaccatc gctcaaagcg gcaacgtcgt   5220
tgtcatgacc atccaccaac ccaacacaca aaatcctcaa catccgcaaa tagtgagcat   5280
gcccctcttg tcctttcccc tcgtacccaa acatgtcttg ataacccttg gagctgcaca   5340
agttgtgacc atcgcctgcg tcgcctcata gagcccgacc tagccggacc gttatagaag   5400
cctacttggg agcccatacc tccctgcaca tcctcctctt tccccataga tcgtgccgcc   5460
atcgcaaacc aacttctcct ctccttctcc cactctggcc gtttccccccg ccgcgaagct   5520
gcaatacatg ccgagttggc catggcccta ttccccaatt gctcgcacta ggaggtcctc   5580
ctctaagcct agcacctttt cccctcacca attgcaagtt ggggagcccc tcgcgagctc   5640
cctacgtcgg ctgcagttgc ctgccgcctc aactctgatc cagacctcgt tcccgtggcc   5700
tcggcgacat ctcctcgacc tcccattcca cacgtggcct ggcgaggatc accgcatgtt   5760
catccatgtg aaccgaatca tcatagaact aacaccggag aggtcatccc gacggcgtcg   5820
cactgttcct ctattccccc caagccgtgt cgcgtcataa tataagacgg acttatttgt   5880
atcccttggg tcatcggttc aatggctatt tctttctcct gtctactgat aagtgggacc   5940
cacacgccac actaagccct ttctttctcc tacccgttga taagtgggac ccacacacag   6000
tacttagcca gagagagaac atgagcttgt tggtgccacg tcggcaagcc atgtcagcag   6060
tcttaacggc tacaaacaac ggatatggtg tcacgtgagc gtttacgaat ggaaagtgca   6120
tcatactgca tgcgagagcc agagccaggt ttttgcacca gtttctgta ttttacaact   6180
gcgagcatca aagtgtacat atgccgaacc aaagtgaaca tggtgagtcc attcttttct   6240
ggtgcggtgg gtggctcaaa gacaccccaa tagaagctat tgcctccgac attgccaatt   6300
cggtgccgaa ccatattgaa gtggtgaggt cagttgcttg tgctatgact actaggtatt   6360
ggatgaggga cataaaggat ctcataaata ttgcaatgtt cattcaaatt cttaacattt   6420
gcgaagcgct tcatgatttc catctcccct agatcagaga cacttggtcg tgtacactga   6480
atttctcagg tcgcttctcg tctaaatccg catatgtagc tcacttcaat gacttgcctt   6540
tggtccagct aacgccattt gcgtagcaaa tttttcatat ggctcgctct gcgcaagagg   6600
atttggatca cgggcagacg cgctagacaa ggtcttccgc acaatgaaca ttgagttttt   6660
tgatccgctc ttcccgaaga cacttgtgat cttattacga gttgtgccat ttcaaacatc   6720
tgtctctcca tggtcgcccc agccatagat gccttgttct ctgaatggtg ggtttcagct   6780
aggaacaggg tgccaccttc ggacaagaag ttgcgtagtt tggtcgtctt aactgcttgg   6840
ttgatttgga aggaacacaa caacagtctt tgaaggcaaa gctaattcct tcgatcaagt   6900
tattagacgg atcaagtgtg atgaatccta ctggtacaat gccgttgcta gttgcttgga   6960
gtcactattt ggctaggtcg cttgccatcc cgctctgtgc taagcgcttg ggtcgcttt   7020
tgctcaattt gtattttgtt gttatgtgtt tttagtaatg taacctgaac tttctggact   7080
aagtagaaaa aaattctcct ccataatgat cacatacagt tctcctgcat ggttcgaaaa   7140
aaaaatgaga acatccgtgg caagtttaag caccaccggt gcatttttac ctcaaagtta   7200
tatacaacac tgacatgccg aattacatgc tttggtcagt tattccattc ttcggtactc   7260
cgttgggcta attctttctc ttcatgttgc atgcagggcc gtggccctgt agatgaattc   7320
ccgttcaccg agttgcctga gcactacctg gaacacttca gactgtacga ccccgtgggt   7380
ggtgaacacg ccaactactt cgccgccggc ctgaagatgg cggaccaggt tgtcgtggtg   7440
agccccgggt acctgtggga gctgaagacg gtggagggcg gctgggggct tcacgacatc   7500
atacggcaga acgactggaa gacccgcggc atcgtcaacg gcatcgacaa catggagtgg   7560
```

-continued

```
aaccccgagg tggacgccca cctcaagtcg gacggctaca ccaacttctc cctgaggacg   7620
ctggactccg gcaagcggca gtgcaaggag gccctgcagc gcgagctggg cctgcaggtc   7680
cgcgccgacg tgccgctgct cggcttcatc ggccgcctgg acgggcagaa gggcgtggag   7740
atcatcgcgg acgccatgcc ctggatcgtg agccaggacg tgcagctggt gatgctgggc   7800
accgggcgcc acgacctgga gagcatgctg cggcacttcg agcgggagca ccacgacaag   7860
gtgcgcgggt gggtggggtt ctccgtgcgc ctggcgcacc ggatcacggc gggggcggac   7920
gcgctcctca tgccctcccg gttcgagccg tgcgggctga accagctcta cgccatggcc   7980
tacggcaccg tccccgtcgt gcacgccgtt ggcggcctca gggacaccgt gccgccgttc   8040
gaccccttca accactccgg gctcgggtgg acgttcgacc gcgccgaggc gcacaagctg   8100
atcgaggcgc tcgggcactg cctccgcacc taccgagact tcaaggagag ctggagggcc   8160
ctccaggagc gcggcatgtc gcaggacttc agctgggagc acgccgccaa gctctacgag   8220
gacgtcctcg tcaaggccaa gtaccagtgg tgaacgctag ctgctagccg ctccagcccc   8280
gcatgcgtgc atgacaggat ggaactgcat tgcgcacgca ggaaagtgcc atggagcgcc   8340
ggcatccgcg aagtacagtg acatgaggtg tgtgtggttg agacgctgat tccaatccgg   8400
cccgtagcag agtagagcgg aggtatatgg gaatcttaac ttggtattgt aatttgttat   8460
gttgtgtgca ttattacaat gttgttactt attcttgtta agtcggaggc caagggcgaa   8520
agctagctca catgtctgat ggatgcacgt gccatggttg gtttggtagc gcagtgcaaa   8580
cggcaagaat gggaagtgaa ttcctccctg cttgaattag cactttcagt aataatcagt   8640
cagttaaaac aatagcactt cgagtggaag tgaacaagaa aaccaacatc acacccggta   8700
tggactcata gcatgttacc aaaaaatgcc tttcgccccg ctgtatatat aaagcaacga   8760
ccatcaacat ttgaacctat acaaactaga acacaccact caaaacccac acactcaggg   8820
ccagatacat aggtgccaaa gggctacaac cacaacacac cgaaagactc acatagacta   8880
caagtgaagg caacaagcat cactacggag cctccggcgt ccttccgatg aagaaatcat   8940
gaagagttga agttgtgatt tgacgaaacc gtgcgctcca aaacggtgcc ttcaggaagg   9000
acacgtcacc gtccaatcca aaga                                          9024
```

<210> SEQ ID NO 38
<211> LENGTH: 11611
<212> TYPE: DNA
<213> ORGANISM: Triticum aestivum

<400> SEQUENCE: 38

```
taatccgttt gtctaatgaa atatatgtga tgggagagga tttggagcat tggggtgctc     60
cacccccccc ctatatgagt attaaattca aaaaacaaac cgaggatatt caaaaagtct    120
acaattttgg gatactaaac ctggatgctc agtctactcc catgtgaagt ttcatgaaaa    180
aaatatcagg aaacgtattc tcagtaaaaa cagacaaaaa attcttatgc acagaaaaaa    240
ctgtttgggt ggatcatagg tcagactata ttttcttcca tggatacatg tcatggtatt    300
ttttcacaaa acttcacatg agagtagatt tgggcatcca agtttgatat ccccatattc    360
caagttcttt cgaattttcc tagtattttt tgaaattaat attcgtatag gggtggagca    420
tccaggagct ctggtgtatt tttcaatata tgtatggtta tttaaaaaaa aactcgtaca    480
acaatctcag aaaaaactgg acggtttatt ctagctgatt ttgtgtgcag tttcccataa    540
tcagaagtgg ccctcagccc ctcactcttc ttcctcctac cttctgctct gtcttccgct    600
```

-continued

```
tcctgcacga acattcgcgt tgaagttttt tcaaaagaaa acaatatact tgctggaaaa    660
agaaagcaag tacaaaaaac accagccatc caccaccgtc cgttactggt ccacctgcat    720
ttccatgtgt gcgcacacgg agaagcagct cgaacaaaaa aaccaaacga aaataaagga    780
tcgaagctgc tctcggacaa aatggttgaa ggacgaagga gccttttttgg tgcgcagatc    840
tccacgccag agcgttgtat tccaatttta gttctttccc cgtgaggagg ggaggctagg    900
cgggcgaggc agaggggata gggcagtcgc cgctgcgtgg tggactgact ggtgtggtgg    960
gtggtgggtt ttgcgggcgg ggtttagtag gttcccggaa atggagatgg ctctccggcc   1020
acggagccct ctgtgccctc ggagcagtca gccgctcgtc gtcgtccggc cggccggccg   1080
cggcggcggc ctcgcgcagg tacgggtgat tatggttctt gattcggtcg gttcacggaa   1140
tgttgtttga tttggttctg tcccgggtca ggttcatagt gattttattc cgcaaaaaaa   1200
aaaggtttat agtgattttg atttctttca tctcgggaac atttttatat ctgggagtca   1260
aagggcattg gttttgattt gcatgcggaa catattggtt atttattaat gtggtgagct   1320
ggaattcata ctgcttaaaa cgacgtgatt ttaattgctg gaagaggtaa agaacatgaa   1380
ttctgttata tttgttaaaa aaaatcccct gttctagcgt ttcagtctgc atgatcatgg   1440
aaatgttaat gttaatgctg gttaatttgg agtgaagatt tccacggcaa gagtttcgaa   1500
caagaaacag aaattcattg cgaaaaaatg gtggagcgaa ttcggagagt atttacattg   1560
tctgcacctt gtatgtttgt gatgaagtta tttccatata ttttttgcga taaagttact   1620
tccgtatgta aggcgagcat tgccatcttt ctataagctg gtatttgtct gccagatagc   1680
gagtgtatca gtagttcgaa ttgcgctaat gttttttgac gaaacgaaac tatgaagacg   1740
atataaattg gattacatcc tttctgttga acggagaaat ttatccttgc ttagaagtga   1800
ggtcagaaaa tgagatacag tggggacctt ccctactgta ttatgctaaa aagaagaagt   1860
gaggtcagaa ggcgatttca gtagaattta tatgagaggc ataaataatt tggtaggatt   1920
aaatgacctt gataattctg ttccgattgt tcgcaaatac cttcggattt tctcaagcat   1980
tatctataag aaggtttcct ttttacgctc aaacatgttg agctgcacaa cttattttcc   2040
cttttgtgtt ttccagcctt ttttgatgaa tggcagattt actcgaagca ggacccttcg   2100
atgcatggta gcaagttcag gtttgaggaa taatctgtca aatggcctat cattctatct   2160
gtttggaagc aatgtcttat tcaaacctca gtattttgat actacggttt tctatagcga   2220
tgacaatgaa tactgtagtt tatgaaacca acagtctttc taagtatttc ggcaacagtg   2280
gtatgtttgg caatcaaaag tatacagcgt tgcaataggc caccagtaga caaggccttt   2340
gttgcgtttc tcagtttttt aaaaagaggt cccaactact ttttttaata ctgcaaaaac   2400
actacagttt tgtggatact gtagtttata atactacaat ttttattaca gccaaacacc   2460
tcaaagtatt taaaaccata gtttttagaa aaactgtagt atccttgaaa tactttgaga   2520
atactttgca acgaaacaca gcccagatgt tctgttaact tcatgtcttt ccaaattgca   2580
tcattcagat cctcctaata ggaaatcaag aaagatggta tcacctcagg ttaaagtcat   2640
ttcttctaga ggatatacga caagactcat tgttgaacca agcaccgaga atatagaaca   2700
caataatcgg gatgaagaaa ctcttgatac atacaatgcg ctattaagta ccgagacagc   2760
agaatggaca gatactagag aagccgagac tgctaaagcg gactcgtcgc aaaatgcttt   2820
aagcagttct ataatcgggg gagtggatgt ggcggatgaa gatatacttg cggctgatct   2880
gacagtgaat tcattaagca gtataacgaa gaaggaagtg gatgcagtgg acaaagctag   2940
agttaaagaa gacgtatttg agctggattt gccagcaact acattgagaa gtgtgatagt   3000
```

-continued

```
ggatgtgatg gatcataatg ggactgtaca agagacattg agaagtgtga tagtagatgt   3060
gatggatgat gcggcggaca aagctagagt tgaagaagac gtatttgagc tggatttgtc   3120
aggaaatatt tcaagcagtg cgacgaccgt ggaactagat gcggttgacg aagtcgggcc   3180
tgttcaagac acatttgagg cgaactcgtc aggaaatgtt tcaaacagtg caacggtacg   3240
ggaagtggat acgagtgctg aagctgggaa tgatcaaggc atatttagag cagatttgtc   3300
aggaaatgtt ttttcaagca gtacaacagt ggaagtgggt gcagtggatg aagctgggtc   3360
tataaaagac aggtttgaga cggattcgtc aggaaatgtt tcaacaagtg cgacgatgtg   3420
ggatgcaatt gatgaaaccg tggctgatca agacgcagtt gaggcggatt tgtcgggaaa   3480
tgcttcaagc tgcgcgacat acagagaagt ggatgatgtg gtggatgaaa ctagatcaga   3540
agaggaaaca tttgcgatgg atttgtttgc aagtgaatca ggccatgaga aacatatggc   3600
agtggatcat gtgggtgaag ctaccgatga agaagagact taccaacagc aatatccagt   3660
accgtcttca ttctctatgt gggacaaggc tattgctaaa acaggtgtaa gtttgaatcc   3720
tgagctgcga cttgtcaggg ttgaagaaca aggcaaagta aattttagtg ataaaaaaga   3780
cctgtcaatt gatgatttac caggacaaaa ccaatcgatc attggttcct ataaacaaga   3840
taaatcaatt gctgatgttg cgggaccgac ccaatcaatt tttggttcta gtaaacaaca   3900
ccggtcaatt gttgctttcc ccaaacaaaa ccagtcaatt gttagtgtca ctgagcaaaa   3960
gcagtccata gttggattcc gtagtcaaga tctttcggct gttagtctcc ctaaacaaaa   4020
cgtaccaatt gttggtacgt cgagagaggg tcaaacaaag caagttcctg ttgttgatag   4080
acaggatgcg ttgtatgtga atggactgga agctaaggag ggagatcaca catccgagaa   4140
aaccgatgag gatgtgcttc atgtaaaatt taatgttgac aatgtgttgc ggaagcatca   4200
ggcagataga acccaagcag tggaaacgat aacttggaag aaagttgatg aggaacatct   4260
ttacatgact gaacatcaga taggtgctgc cgaaggacag atggtagtta acgaggatga   4320
gctttctata actgaaattg gaatggggag aggtgataaa attcagcatg tgctttctga   4380
ggaagagctt tcatggtctg aagatgaagt gcagttaatt gaggatgatg gacaatatga   4440
agttgatgag acctctgtgt ccgttaacgt tgaacaagat atccaggggt caccacagga   4500
tgttgtggat ccgcaagcac taaaggtgat gctgcaagaa ctcgctgaga aaaattattc   4560
gatgaggaac aagctgtttg tttttccaga ggtagtgaaa gctgattcag ttattgatct   4620
ttatttcaat cgtgacctaa cagctttggc gaatgaaccc gatgttgtca tcaaaggagc   4680
attcaatggt tggaaatgga ggcttttcac tgaaagattg cataagagtg accttggagg   4740
ggtttggtgg tcttgcaaac tgtacatacc caaggaggcc tacagattag actttgtgtt   4800
cttcaacggt cgcacggtct atgagaacaa tggcaacaat gatttctgta taggaataga   4860
aggcactatg aatgaagatc tgtttgagga tttcttggtt aaagaaaagc aaagggagct   4920
tgagaaactt gccatggaag aagctgaaag gaggacacag actgaagaac agcggcgaag   4980
taaggaagca agggctgcag atgaagctgt cagggcacaa gcgaaggccg agatagagat   5040
caagaacaaa aaattgcaga gtatgttgag tttggccaga acatgtgttg ataatttgtg   5100
gtacatagag gctagcacag atacaagcgg agatactatc aggttatact ataacagaaa   5160
ctcgaggcca cttgcgcata gtactgagat ttggatgcat ggtggttaca acaattggtc   5220
agatggactc tctattgttg aaagctttgt caagtgcaat gacagagacg gcgattggtg   5280
gtatgcagat ggtacgacac ctcaaccttt gtacataagg caacattgtt ttgatttttt   5340
```

-continued

```
ttgttgagga aacatttgtt ttgattctag cataatgctc ctacaaatat ggcatgaatt   5400
tccttgtttt attgatgtca tgagaaagta ttttattaac tcgaaggcca tggaagctca   5460
acatttacca tagacagacg cttaaagatc atttgtattc cgtggatcat atatgtaatg   5520
taatacctgt cttttctcta tatgtacagt tattccacct gaaaaagcac ttgtgttgga   5580
ctgggttttt gctgatgggc cagctgggaa tgcaaggaac tatgacaaca atgctcgaca   5640
agatttccat gctattcttc caaacaacaa tgtaaccgag gaaggcttct gggtgcaaga   5700
ggagcaaaac atctatacaa ggcttctgca agaaaggaga gaaaaggaag aaaccatgaa   5760
aagaaaggtg agttgcaaca aaatctttgc atatgatctc tataattttg gcagttaacc   5820
cctgagtgat ggcaaatata ttccctttcg tctattttcc aaattcaaaa tgcatggttc   5880
catgcaagct tatccaaaat cacttgataa tataccaatc acaacataac tttgtttacc   5940
ataagaacat tcctacttaa aatttgcaag gtaactccct ttcgaggctg gttggcttga   6000
tgagtaactg gcaattaaca aagaaaagat atatctgatg tttggaacaa aacatatgat   6060
cagggttgtt tgggttgact catgttcctt tttacctaca caggctgaga gaagtgcaaa   6120
tatcaaagct gagatgaagg caaaaactat gcgaaggttt ctgctttccc agaaacacat   6180
tgtttatacc gaaccgcttg aaatacgtgc cggaaccaca gtggatgtgc tatacaatcc   6240
ctctaacaca gtgctaaatg gaaagccgga ggtttggttt agatgctctt ttaacctttg   6300
gatgcatcca agtggagcat tgccacccca gaagatggtg aaatcagggg atgggccgct   6360
cttaaaagcc acaggtttat tgcgttatta catcactgtt attagtatat atataaccat   6420
ttttatgcaa tcaatagagt caagtgcaac taatgatgca cagataggat ccaatatttc   6480
ttgttctatt attggtaata attagctagt ttaatgccat aagcccataa cagatatgca   6540
actactccct ccaatccata ttacttgtcg caactttggt acaactttag tacaaagtta   6600
tactaaagct gtgacaagta atatggaccg gagggagtac tatataagct tgtagctgtt   6660
ttgagaccga gtgtctgctc gggtggctag ctggagcggg ctgaagtgct tgcaggcacc   6720
tcttctctaa aaaaaagtgc ttgcagcccc cccgccccct ccatagggtg agtggtcacc   6780
tttcttctta aaaattatgg caccaaggga aattctcggc tggtcgagct tgtagctatt   6840
ttttcggagc gtgaatggga gcgtctttct gtataaggcc tataggctta ctttgatata   6900
tattgtgaag tcacttaagc cttgttaaaa cgtagaaact tagttccgca acttggccaa   6960
atccctgtta aattggttta ctgtgtacta gatgcatcga tggcgcagag tccgggggt    7020
aataaagctt ccattttcta caatgaagtt aattatccta cttgccttgt aattactgag   7080
tacaatacag agcaccgaaa agctgtatcc ttcctacttc cttatgttta tctgtgttcc   7140
ttgtctagtt aatgttccac cggatgccta tatgatggac tttgttttct ccgagtggga   7200
agaagatggg atctatgaca acaggaatgg gatggactat catattcctg tttctgattc   7260
aattgaaaca gagaattaca tgcgtattat ccacattgcc gttgagatgg cccccgttgc   7320
aaaggtaata taattctaag gctagtttct ttgatgcgag gcgagatctc atcaccttat   7380
gccttttttt cattctatgc cataatacta tgctctgtca tgatcgatga tctcataggt   7440
tggaggtctc ggggatgttg ttacaagtct ttcacgtgcc gttcaagatc tagggcatac   7500
tgtcgaggtt attctcccga agtacgactg tttgaaccaa agcagtgtaa gttgaagtac   7560
tgtactacat aatctattca cttagtcttt aaaatttcaa ctcaaaatgc cacgaagctt   7620
caactgaagc taaagaattc tgagctgcga tggagcgcag tagggtggca cagatcccaa   7680
taaaccaata tatgaccaat aaggggtgc  caagatcagt aggcactaat gaatttcctt   7740
```

-continued

```
tgttttatat ccattataca ttattaatca agttacatct atttcaatgc aggtcaagga   7800
tttacattta tatcaaagtt tttcttgggg tggtacagaa ataaaagtat gggttggacg   7860
agtcgaagac ctgaccgttt acttcctgga acctcaaaat gggtatgaat cagctaatgt   7920
atagtttttt ttgtgggaaa tgtatagttg agtgatataa aacatattac ttcttttcac   7980
aaaattatta ggctagagcc ttgtactggt taataatgtg taccttttc tcattcatat    8040
aactacttat cgtagactat agaagccaat tagtaacaca atacattggc cttggcattc   8100
caggctgaga gctagttata acaatgatat gtgagattag tggctctata accacttttg   8160
agctaaagga atttgctgct agatgagcca atcaatccaa ctaattttaa attccatgat   8220
caccctagga cacgcagcct gcacaaccaa gaacacagct aagatcatcg cgtgggcaca   8280
aaaggttgtg cattaaggct aggccctggt cagtggctgt caaggactcc atggggctcc   8340
ttacagtttt tattctgata tctcttgcgc ccatatgacg ctaccaaacg cttgtaacct   8400
gtagcaaact attgccatct gtcactcaat gataaggtag acaatctttc ctttcccttt   8460
aagatgttca acctttattt atgcttgagg atgcgtttga ttgtcaaatt tcagtttctc   8520
tagattgcag acacacttgc acgtgctgtg tacaccttcc attatctggc atgggatttg   8580
catttcaatt aagagaaata tgaaagaaag aaatgttatc acctgaatgt tagagcttaa   8640
aaggcacaag caatcagcac catttatcaa aaataaatga tttacttgtc tagttgtctc   8700
tttttggttc tcttcctgta agtggatgcc aatatctcaa gaactctcct gaggattttt   8760
cttcacaacc tattcatttt gacatttcct tttctaggat gtttggcgtc ggatgtgtat   8820
atggaaggaa tgatgaccgc agatttgggt tcttctgtca ttctgctctt gagtttatcc   8880
tccagaatga attttctcca gtacgtatta tttagaatac tagctgctat attgactttt   8940
tctttgtgag actacacttt cttgtttacc attccagtgc accatgttca aaatcttgta   9000
ttcagcgcgt tactttcagt ttctttacta ctagcttatt tggtgcattg gtgtttcctt   9060
tcctactcta ctatctgaat gctacttgtg ttttcgcaac agttgcttct ttatcccctt   9120
ccatttctca gttaaaaaaa cttgcatctg tattcacgtg acagcatata atacattgcc   9180
atgattggtc aagtgctccg gtcgcctggc tatataagga acactattcc caatccagaa   9240
tggcaagcac tcgggttgta tttaccatcc acaatcttga atttggagca cattatattg   9300
gtaaagcaat gacatactgt gataaagcca caactgtgag tgccttactg tcttgtaatt   9360
tttaatcttt ctgtttggcg cacagaaaat cttccacatt ttacagaatc atgttcttgt   9420
gttttgtacg tattcaacta tttccaccca aacttttcag gtttctccta catattcaag   9480
ggacgtggca ggccatggtg ccattgctcc tcatcgtgag aaattctacg gcattctcaa   9540
tggaattgat ccagatatct gggatccata cactgacaat tttatcccgg taccagattt   9600
tttcccagag tgcaagtaga tatataccaa ggccacagat agttttatgc ttaactatgt   9660
gtttcatact acttcaggtc ccttatactt gtgagaatgt tgtcgaaggc aagagagctg   9720
caaaaagggc cttgcagcag aagtttggat tacagcaaac tgatgtccct attgtcggaa   9780
tcatcacccg tctgacagcc cagaagggaa tccacctcat caagcacgca attcaccgaa   9840
ccctcgaaag caacggacag gttcatcatc ccttgtgaac gaataaacat caaacgtttt   9900
gtttataaaa agttgcttac tatttgtttt tgtttacttc aaaacaaaag tctgaaaatg   9960
aagtgtttgg ttcctaggtg gttttgcttg gttcagctcc agatcatcga atacaaggcg  10020
atttttgcag attggccgat gctcttcacg gtgtttacca cggtagggtg aagcttgttc  10080
```

-continued

```
taacctacga tgagcctctt tctcacctgg tgagctccaa tatcctacac accatctagc  10140

cagcccttca ttatgggagc tggagactac tttataattt aggttgatga tcgatcatgc  10200

tgcagatata cgctggctcc gacttcatta ttgtcccttc aatcttcgaa ccctgtggct  10260

taacacaact tgttgccatg cgttatggat cgatccctat agttcggaaa accggaggtg  10320

tgtgactatt tctctccatt atgctgcact gatttgcata tgtcgagctg ttggacatga  10380

aatggaaact atcctttggt atcgcaggac tttacgacac tgtcttcgac gtagacaatg  10440

ataaggaccg ggctcggtct cttggtcttg aaccaaatgg gttcagtttc gacggagccg  10500

acagcaacgg cgtggattat gccctcaaca gagcaagtat cgttcctcaa ttagccctga  10560

attcagcagt agtgctaggt tatttacctt gcatgttcca tacctcattt cagagcaatc  10620

ggcgcttggt tcgatgcccg tgattggttc cactccctgt gtaagagggt catggaacaa  10680

gactggtcat ggaaccggcc cgcactggac tacattgaat tgtaccatgc cgctcgaaaa  10740

ttctgacacc caactgaacc aatggcaaga acaagcgcat tgtgggatcg actacagtca  10800

tacagggctg tgcagatcgt cttgcttcag ttagttccaa gcgcactgca gtcgtacata  10860

gctgaggatc ctcttgcctc ctccaccagg gggaacaaag cagaaatgca tgagtgcatt  10920

gggaagactt ttatgtatat tgttaagatt ttccttttct tttccttccc tgcacctgga  10980

aatggttaag cgcatcggca atataagaac cgcagtgaca ttttgtgagt agctttgtat  11040

attctctcat cttgtgcaaa cttatgtgca tgctaggctc tctgatcatg tggaagcttt  11100

gttatatgtt acttatggta tacatcaatg atatttacat ttgtggatga gctactgcac  11160

ttggtttctg ctatctgttt tgtgaaatgg cagggccatg attatgcaga ttcactggtt  11220

ctgaaacaga cacgctcctc taagctgtga ctgtgagctc tgaaaacagc attgttaaca  11280

tctattagta taaactaagg tacatcaacg gtgaagattt acgagctaaa ctccgtttgg  11340

ttgtagacat tcactagaag tataagcgcg cttttctgcg ccgcctaggc tgcaatgatt  11400

ttttttttat gtgtgtgtgg atatttcact atgacctgtg ggcaaaaggc tggccgagat  11460

ttaggaagcg ctcaagcaat tggccaatgg gaaggtgccg gccctgatgg tttcacggcc  11520

cagttcttgc gctcctgctg ggatatcatc aagggagatc gagaattccc gggatccgcg  11580

gccgcgagct tccctatagt gagtcgtatt a                                  11611
```

```
<210> SEQ ID NO 39
<211> LENGTH: 11
<212> TYPE: PRT
<213> ORGANISM: Artificial Sequence
<220> FEATURE:
<223> OTHER INFORMATION: Peptide

<400> SEQUENCE: 39

Lys Val Gly Gly Leu Gly Asp Val Val Thr Ser
1               5                   10


<210> SEQ ID NO 40
<211> LENGTH: 11
<212> TYPE: PRT
<213> ORGANISM: Artificial Sequence
<220> FEATURE:
<223> OTHER INFORMATION: Peptide

<400> SEQUENCE: 40

Gly His Thr Val Glu Val Ile Leu Pro Lys Tyr
1               5                   10
```

```
<210> SEQ ID NO 41
<211> LENGTH: 16
<212> TYPE: PRT
<213> ORGANISM: Artificial Sequence
<220> FEATURE:
<223> OTHER INFORMATION: Peptide

<400> SEQUENCE: 41

His Asp Trp Ser Ser Ala Pro Val Ala Trp Leu Tyr Lys Glu His Tyr
1               5                   10                  15


<210> SEQ ID NO 42
<211> LENGTH: 16
<212> TYPE: PRT
<213> ORGANISM: Artificial Sequence
<220> FEATURE:
<223> OTHER INFORMATION: Peptide

<400> SEQUENCE: 42

Gly Ile Leu Asn Gly Ile Asp Pro Asp Ile Trp Asp Pro Tyr Thr Asp
1               5                   10                  15


<210> SEQ ID NO 43
<211> LENGTH: 16
<212> TYPE: PRT
<213> ORGANISM: Artificial Sequence
<220> FEATURE:
<223> OTHER INFORMATION: Peptide

<400> SEQUENCE: 43

Asp Val Pro Ile Val Gly Ile Ile Thr Arg Leu Thr Ala Gln Lys Gly
1               5                   10                  15


<210> SEQ ID NO 44
<211> LENGTH: 10
<212> TYPE: PRT
<213> ORGANISM: Artificial Sequence
<220> FEATURE:
<223> OTHER INFORMATION: Peptide

<400> SEQUENCE: 44

Asn Gly Gln Val Val Leu Leu Gly Ser Ala
1               5                   10


<210> SEQ ID NO 45
<211> LENGTH: 27
<212> TYPE: PRT
<213> ORGANISM: Artificial Sequence
<220> FEATURE:
<223> OTHER INFORMATION: Peptide

<400> SEQUENCE: 45

Ala Gly Ser Asp Phe Ile Ile Val Pro Ser Ile Phe Glu Pro Cys Gly
1               5                   10                  15

Leu Thr Gln Leu Val Ala Met Arg Tyr Gly Ser
            20                  25


<210> SEQ ID NO 46
<211> LENGTH: 8
<212> TYPE: PRT
<213> ORGANISM: Artificial Sequence
<220> FEATURE:
<223> OTHER INFORMATION: Peptide

<400> SEQUENCE: 46

Thr Gly Gly Leu Val Asp Thr Val
1               5
```

<210> SEQ ID NO 47
<211> LENGTH: 11
<212> TYPE: PRT
<213> ORGANISM: Artificial Sequence
<220> FEATURE:
<223> OTHER INFORMATION: Peptide

<400> SEQUENCE: 47

Lys Thr Gly Gly Leu Gly Asp Val Ala Gly Ala
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Peptide

<400> SEQUENCE: 48

Gly His Arg Val Met Val Val Val Pro Arg Tyr
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Peptide

<400> SEQUENCE: 49

Asn Asp Trp His Thr Ala Leu Leu Pro Val Tyr Leu Lys Ala Tyr Tyr
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Peptide

<400> SEQUENCE: 50

Gly Ile Val Asn Gly Ile Asp Asn Met Glu Trp Asn Pro Glu Val Asp
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Peptide

<400> SEQUENCE: 51

Asp Val Pro Leu Leu Gly Phe Ile Gly Arg Leu Asp Gly Gln Lys Gly
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: Peptide

<400> SEQUENCE: 52

Asp Val Gln Leu Val Met Leu Gly Thr Gly
1               5                   10

<210> SEQ ID NO 53
<211> LENGTH: 27
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa is an amino acid which is not specifically identified

<400> SEQUENCE: 53

```
Ala Gly Ala Asp Ala Leu Leu Met Pro Ser Arg Phe Xaa Pro Cys Gly
1               5                   10                  15

Leu Asn Gln Leu Tyr Ala Met Ala Tyr Gly Thr
            20                  25
```

<210> SEQ ID NO 54
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(4)
<223> OTHER INFORMATION: Xaa is an amino acid which is not specifically identified

<400> SEQUENCE: 54

```
Val Gly Gly Xaa Arg Asp Thr Val
1               5
```

<210> SEQ ID NO 55
<211> LENGTH: 1674
<212> TYPE: PRT
<213> ORGANISM: Maize SSIII

<400> SEQUENCE: 55

```
Met Glu Met Val Leu Arg Ser Gln Ser Pro Leu Cys Leu Arg Ser Gly
1               5                   10                  15

Pro Val Leu Ile Phe Arg Pro Thr Val Ala Gly Gly Gly Gly Gly Thr
            20                  25                  30

Gln Ser Leu Leu Arg Thr Thr Arg Phe Ala Arg Arg Arg Val Ile Arg
        35                  40                  45

Cys Val Val Ala Ser Pro Gly Cys Pro Asn Arg Lys Ser Arg Thr Ala
    50                  55                  60

Ser Pro Asn Val Lys Val Ala Ala Tyr Ser Asn Tyr Ala Pro Arg Leu
65                  70                  75                  80

Leu Val Glu Ser Ser Ser Lys Lys Ser Glu His His Asp Ser Ser Arg
                85                  90                  95

His Arg Glu Glu Thr Ile Asp Thr Tyr Asn Gly Leu Ser Gly Ser Asp
            100                 105                 110

Ala Ala Glu Leu Thr Ser Asn Arg Asp Val Glu Ile Glu Val Asp Leu
        115                 120                 125

Gln His Ile Ser Glu Glu Glu Leu Pro Gly Lys Val Ser Ile Asn Ala
    130                 135                 140

Ser Leu Gly Glu Met Glu Thr Val Asp Glu Ala Glu Val Glu Glu Asp
145                 150                 155                 160

Lys Phe Glu Val Asp Thr Ser Gly Ile Val Leu Arg Asn Val Ala Val
                165                 170                 175
```

-continued

```
Arg Glu Val Asp Pro Lys Asp Glu His Asn Ala Lys Asp Val Phe Val
            180                 185                 190

Val Asp Ser Ser Gly Thr Ala Pro Asp Asn Ala Ala Val Glu Glu Val
        195                 200                 205

Val Asp Glu Ala Glu Val Glu Glu Asp Met Val Asp Val Asp Ile Leu
    210                 215                 220

Gly Leu Asp Leu Asn Asn Ala Thr Ile Glu Glu Ile Asp Leu Met Glu
225                 230                 235                 240

Glu Ala Leu Leu Glu Asn Phe Asp Val Asp Ser Pro Gly Asn Ala Ser
                245                 250                 255

Ser Gly Arg Thr Tyr Gly Gly Val Asp Glu Leu Gly Glu Leu Pro Ser
            260                 265                 270

Thr Ser Val Asp Cys Ile Ala Ile Asn Gly Lys Arg Arg Ser Leu Lys
        275                 280                 285

Pro Lys Pro Leu Pro Ile Val Arg Phe Gln Glu Gln Glu Gln Ile Val
    290                 295                 300

Leu Ser Ile Val Asp Glu Glu Gly Leu Ile Ala Ser Ser Cys Glu Glu
305                 310                 315                 320

Gly Gln Pro Val Val Asp Tyr Asp Lys Gln Glu Glu Asn Ser Thr Ala
                325                 330                 335

Phe Asp Glu Gln Lys Gln Leu Thr Asp Asp Phe Pro Glu Glu Gly Ile
            340                 345                 350

Ser Ile Val His Phe Pro Glu Pro Asn Asn Asp Ile Val Gly Ser Ser
        355                 360                 365

Lys Phe Leu Glu Gln Lys Gln Glu Leu Asp Gly Ser Tyr Lys Gln Asp
    370                 375                 380

Arg Ser Thr Thr Gly Leu His Glu Gln Asp Gln Ser Val Val Ser Ser
385                 390                 395                 400

His Gly Gln Asp Lys Ser Ile Val Gly Val Pro Gln Gln Ile Gln Tyr
                405                 410                 415

Asn Asp Gln Ser Ile Ala Gly Ser His Arg Gln Asp Gln Ser Ile Ala
            420                 425                 430

Gly Ala Pro Glu Gln Ile Gln Ser Val Ala Gly Tyr Ile Lys Pro Asn
        435                 440                 445

Gln Ser Ile Val Gly Ser Cys Lys Gln His Glu Leu Ile Ile Pro Glu
    450                 455                 460

Pro Lys Lys Ile Glu Ser Ile Ile Ser Tyr Asn Glu Ile Asp Gln Ser
465                 470                 475                 480

Ile Val Gly Ser His Lys Gln Asp Lys Ser Val Val Ser Val Pro Glu
                485                 490                 495

Gln Ile Gln Ser Ile Val Ser His Ser Lys Pro Asn Gln Ser Thr Val
            500                 505                 510

Asp Ser Tyr Arg Gln Ala Glu Ser Ile Ile Gly Val Pro Glu Lys Val
        515                 520                 525

Gln Ser Ile Thr Ser Tyr Asp Lys Leu Asp Gln Ser Ile Val Gly Ser
    530                 535                 540

Leu Lys Gln Asp Glu Pro Ile Ile Ser Val Pro Glu Lys Ile Gln Ser
545                 550                 555                 560

Ile Val His Tyr Thr Lys Pro Asn Gln Ser Ile Val Gly Leu Pro Lys
                565                 570                 575

Gln Gln Gln Ser Ile Val His Ile Val Glu Pro Lys Gln Ser Ile Asp
            580                 585                 590
```

-continued

```
Gly Phe Pro Lys Gln Asp Leu Ser Ile Val Gly Ile Ser Asn Glu Phe
        595                 600                 605

Gln Thr Lys Gln Leu Ala Thr Val Gly Thr His Asp Gly Leu Leu Met
    610                 615                 620

Lys Gly Val Glu Ala Lys Glu Thr Ser Gln Lys Thr Glu Gly Asp Thr
625                 630                 635                 640

Leu Gln Ala Thr Phe Asn Val Asp Asn Leu Ser Gln Lys Gln Glu Gly
                645                 650                 655

Leu Thr Lys Glu Ala Asp Glu Ile Thr Ile Ile Glu Lys Ile Asn Asp
            660                 665                 670

Glu Asp Leu Val Met Ile Glu Glu Gln Lys Ser Ile Ala Met Asn Glu
        675                 680                 685

Glu Gln Thr Ile Val Thr Glu Glu Asp Ile Pro Met Ala Lys Val Glu
    690                 695                 700

Ile Gly Ile Asp Lys Ala Lys Phe Leu His Leu Leu Ser Glu Glu Glu
705                 710                 715                 720

Ser Ser Trp Asp Glu Asn Glu Val Gly Ile Ile Glu Ala Asp Glu Gln
                725                 730                 735

Tyr Glu Val Asp Glu Thr Ser Met Ser Thr Glu Gln Asp Ile Gln Glu
            740                 745                 750

Ser Pro Asn Asp Asp Leu Asp Pro Gln Ala Leu Trp Ser Met Leu Gln
        755                 760                 765

Glu Leu Ala Glu Lys Asn Tyr Ser Leu Gly Asn Lys Leu Phe Thr Tyr
    770                 775                 780

Pro Asp Val Leu Lys Ala Asp Ser Thr Ile Asp Leu Tyr Phe Asn Arg
785                 790                 795                 800

Asp Leu Ser Ala Val Ala Asn Glu Pro Asp Val Leu Ile Lys Gly Ala
                805                 810                 815

Phe Asn Gly Trp Lys Trp Arg Phe Phe Thr Glu Lys Leu His Lys Ser
            820                 825                 830

Glu Leu Ala Gly Asp Trp Trp Cys Cys Lys Leu Tyr Ile Pro Lys Gln
        835                 840                 845

Ala Tyr Arg Met Asp Phe Val Phe Phe Asn Gly His Thr Val Tyr Glu
    850                 855                 860

Asn Asn Asn Asn Asn Asp Phe Val Ile Gln Ile Glu Ser Thr Met Asp
865                 870                 875                 880

Glu Asn Leu Phe Glu Asp Phe Leu Ala Glu Glu Lys Gln Arg Glu Leu
                885                 890                 895

Glu Asn Leu Ala Asn Glu Glu Ala Glu Arg Arg Arg Gln Thr Asp Glu
            900                 905                 910

Gln Arg Arg Met Glu Glu Glu Arg Ala Ala Asp Lys Ala Asp Arg Val
        915                 920                 925

Gln Ala Lys Val Glu Val Glu Thr Lys Lys Asn Lys Leu Cys Asn Val
    930                 935                 940

Leu Gly Leu Ala Arg Ala Pro Val Asp Asn Leu Trp Tyr Ile Glu Pro
945                 950                 955                 960

Ile Thr Thr Gly Gln Glu Ala Thr Val Arg Leu Tyr Tyr Asn Ile Asn
                965                 970                 975

Ser Arg Pro Leu Val His Ser Thr Glu Ile Trp Met His Gly Gly Tyr
            980                 985                 990

Asn Asn Trp Ile Asp Gly Leu Ser  Phe Ala Glu Arg Leu  Val His His
        995                 1000                1005

His Asp  Lys Asp Cys Asp Trp  Trp Phe Ala Asp Val  Val Val Pro
```

-continued

```
    1010                1015                1020

Glu Arg  Thr Tyr Val Leu Asp  Trp Val Phe Ala Asp  Gly Pro Pro
    1025                1030                1035

Gly Ser  Ala Arg Asn Tyr Asp  Asn Asn Gly Gly His  Asp Phe His
    1040                1045                1050

Ala Thr  Leu Pro Asn Asn Met  Thr Glu Glu Glu Tyr  Trp Met Glu
    1055                1060                1065

Glu Glu  Gln Arg Ile Tyr Thr  Arg Leu Gln Gln Glu  Arg Arg Glu
    1070                1075                1080

Arg Glu  Glu Ala Ile Lys Arg  Lys Ala Glu Arg Asn  Ala Lys Met
    1085                1090                1095

Lys Ala  Glu Met Lys Glu Lys  Thr Met Arg Met Phe  Leu Val Ser
    1100                1105                1110

Gln Lys  His Ile Val Tyr Thr  Glu Pro Leu Glu Ile  His Ala Gly
    1115                1120                1125

Thr Thr  Ile Asp Val Leu Tyr  Asn Pro Ser Asn Thr  Val Leu Thr
    1130                1135                1140

Gly Lys  Pro Glu Val Trp Phe  Arg Cys Ser Phe Asn  Arg Trp Met
    1145                1150                1155

Tyr Pro  Gly Gly Val Leu Pro  Pro Gln Lys Met Val  Gln Ala Glu
    1160                1165                1170

Asn Gly  Ser His Leu Lys Ala  Thr Val Tyr Val Pro  Arg Asp Ala
    1175                1180                1185

Tyr Met  Met Asp Phe Val Phe  Ser Glu Ser Glu Glu  Gly Gly Ile
    1190                1195                1200

Tyr Asp  Asn Arg Asn Gly Leu  Asp Tyr His Ile Pro  Val Phe Gly
    1205                1210                1215

Ser Ile  Ala Lys Glu Pro Pro  Met His Ile Val His  Ile Ala Val
    1220                1225                1230

Glu Met  Ala Pro Ile Ala Lys  Val Gly Gly Leu Gly  Asp Val Val
    1235                1240                1245

Thr Ser  Leu Ser Arg Ala Val  Gln Asp Leu Gly His  Asn Val Glu
    1250                1255                1260

Val Ile  Leu Pro Lys Tyr Gly  Cys Leu Asn Leu Ser  Asn Val Lys
    1265                1270                1275

Asn Leu  Gln Ile His Gln Ser  Phe Ser Trp Gly Gly  Ser Glu Ile
    1280                1285                1290

Asn Val  Trp Arg Gly Leu Val  Glu Gly Leu Cys Val  Tyr Phe Leu
    1295                1300                1305

Glu Pro  Gln Asn Gly Met Phe  Gly Val Gly Tyr Val  Tyr Gly Arg
    1310                1315                1320

Asp Asp  Asp Arg Arg Phe Gly  Phe Phe Cys Arg Ser  Ala Leu Glu
    1325                1330                1335

Phe Leu  Leu Gln Ser Gly Ser  Ser Pro Asn Ile Ile  His Cys His
    1340                1345                1350

Asp Trp  Ser Ser Ala Pro Val  Ala Trp Leu His Lys  Glu Asn Tyr
    1355                1360                1365

Ala Lys  Ser Ser Leu Ala Asn  Ala Arg Val Val Phe  Thr Ile His
    1370                1375                1380

Asn Leu  Glu Phe Gly Ala His  His Ile Gly Lys Ala  Met Arg Tyr
    1385                1390                1395

Cys Asp  Lys Ala Thr Thr Val  Ser Asn Thr Tyr Ser  Lys Glu Val
    1400                1405                1410
```

-continued

```
Ser Gly  His Gly Ala Ile Val  Pro His Leu Gly Lys  Phe Tyr Gly
    1415                 1420                 1425

Ile Leu  Asn Gly Ile Asp Pro  Asp Ile Trp Asp Pro  Tyr Asn Asp
    1430                 1435                 1440

Asn Phe  Ile Pro Val His Tyr  Thr Cys Glu Asn Val  Val Glu Gly
    1445                 1450                 1455

Lys Arg  Ala Ala Lys Arg Ala  Leu Gln Gln Lys Phe  Gly Leu Gln
    1460                 1465                 1470

Gln Ile  Asp Val Pro Val Val  Gly Ile Val Thr Arg  Leu Thr Ala
    1475                 1480                 1485

Gln Lys  Gly Ile His Leu Ile  Lys His Ala Ile His  Arg Thr Leu
    1490                 1495                 1500

Glu Arg  Asn Gly Gln Val Val  Leu Leu Gly Ser Ala  Pro Asp Ser
    1505                 1510                 1515

Arg Ile  Gln Ala Asp Phe Val  Asn Leu Ala Asn Thr  Leu His Gly
    1520                 1525                 1530

Val Asn  His Gly Gln Val Arg  Leu Ser Leu Thr Tyr  Asp Glu Pro
    1535                 1540                 1545

Leu Ser  His Leu Ile Tyr Ala  Gly Ser Asp Phe Ile  Leu Val Pro
    1550                 1555                 1560

Ser Ile  Phe Glu Pro Cys Gly  Leu Thr Gln Leu Val  Ala Met Arg
    1565                 1570                 1575

Tyr Gly  Thr Ile Pro Ile Val  Arg Lys Thr Gly Gly  Leu Phe Asp
    1580                 1585                 1590

Thr Val  Phe Asp Val Asp Asn  Asp Lys Glu Arg Ala  Arg Asp Arg
    1595                 1600                 1605

Gly Leu  Glu Pro Asn Gly Phe  Ser Phe Asp Gly Ala  Asp Ser Asn
    1610                 1615                 1620

Gly Val  Asp Tyr Ala Leu Asn  Arg Ala Ile Ser Ala  Trp Phe Asp
    1625                 1630                 1635

Ala Arg  Ser Trp Phe His Ser  Leu Cys Lys Arg Val  Met Glu Gln
    1640                 1645                 1650

Asp Trp  Ser Trp Asn Arg Pro  Ala Leu Asp Tyr Ile  Glu Leu Tyr
    1655                 1660                 1665

Arg Ser  Ala Ser Lys Leu
    1670
```

<210> SEQ ID NO 56
<211> LENGTH: 1230
<212> TYPE: PRT
<213> ORGANISM: Potato SSIII

<400> SEQUENCE: 56

```
Met Asp Val Pro Phe Pro Leu His Arg Ser Leu Ser Cys Thr Ser Val
1               5                   10                  15

Ser Asn Ala Ile Thr His Leu Lys Ile Lys Pro Ile Leu Gly Phe Val
            20                  25                  30

Ser His Gly Thr Thr Ser Leu Ser Val Gln Ser Ser Ser Trp Arg Lys
        35                  40                  45

Asp Gly Met Val Thr Gly Val Ser Phe Ser Ile Cys Ala Asn Phe Ser
    50                  55                  60

Gly Arg Arg Arg Arg Lys Val Ser Thr Pro Arg Ser Gln Gly Ser Ser
65                  70                  75                  80

Pro Lys Gly Phe Val Pro Arg Lys Pro Ser Gly Met Ser Thr Gln Arg
```

-continued

```
                85                  90                  95

Lys Val Gln Lys Ser Asn Gly Asp Lys Glu Ser Lys Ser Thr Ser Thr
            100                 105                 110

Ser Lys Glu Ser Glu Ile Ser Asn Gln Lys Thr Val Glu Ala Arg Val
        115                 120                 125

Glu Thr Ser Asp Asp Asp Thr Lys Gly Val Val Arg Asp His Lys Phe
    130                 135                 140

Leu Glu Asp Glu Asp Glu Ile Asn Gly Ser Thr Lys Ser Ile Ser Met
145                 150                 155                 160

Ser Pro Val Arg Val Ser Ser Gln Phe Val Glu Ser Glu Glu Thr Gly
                165                 170                 175

Gly Asp Asp Lys Asp Ala Val Lys Leu Asn Lys Ser Lys Arg Ser Glu
            180                 185                 190

Glu Ser Gly Phe Ile Ile Asp Ser Val Ile Arg Glu Gln Ser Gly Ser
        195                 200                 205

Gln Gly Glu Thr Asn Ala Ser Ser Lys Gly Ser His Ala Val Gly Thr
    210                 215                 220

Lys Leu Tyr Glu Ile Leu Gln Val Asp Val Glu Pro Gln Gln Leu Lys
225                 230                 235                 240

Glu Asn Asn Ala Gly Asn Val Glu Tyr Lys Gly Pro Val Ala Ser Lys
                245                 250                 255

Leu Leu Glu Ile Thr Lys Ala Ser Asp Val Glu His Thr Glu Ser Asn
            260                 265                 270

Glu Ile Asp Asp Leu Asp Thr Asn Ser Phe Phe Lys Ser Asp Leu Ile
        275                 280                 285

Glu Glu Asp Glu Pro Leu Ala Ala Gly Thr Val Glu Thr Gly Asp Ser
    290                 295                 300

Ser Leu Asn Leu Arg Leu Glu Met Glu Ala Asn Leu Arg Arg Gln Ala
305                 310                 315                 320

Ile Glu Arg Leu Ala Glu Glu Asn Leu Leu Gln Gly Ile Arg Leu Phe
                325                 330                 335

Cys Phe Pro Glu Val Val Lys Pro Asp Glu Asp Val Glu Ile Phe Leu
            340                 345                 350

Asn Arg Gly Leu Ser Thr Leu Lys Asn Glu Ser Asp Val Leu Ile Met
        355                 360                 365

Gly Ala Phe Asn Glu Trp Arg Tyr Arg Ser Phe Thr Thr Arg Leu Thr
    370                 375                 380

Glu Thr His Leu Asn Gly Asp Trp Trp Ser Cys Lys Ile His Val Pro
385                 390                 395                 400

Lys Glu Ala Tyr Arg Ala Asp Phe Val Phe Phe Asn Gly Gln Asp Val
                405                 410                 415

Tyr Asp Asn Asn Asp Gly Asn Asp Phe Ser Ile Thr Val Lys Gly Gly
            420                 425                 430

Met Gln Ile Ile Asp Phe Glu Asn Phe Leu Leu Glu Glu Lys Trp Arg
        435                 440                 445

Glu Gln Glu Lys Leu Ala Lys Glu Gln Ala Glu Arg Glu Arg Leu Ala
    450                 455                 460

Glu Glu Gln Arg Arg Ile Glu Ala Glu Lys Ala Glu Ile Glu Ala Asp
465                 470                 475                 480

Arg Ala Gln Ala Lys Glu Glu Ala Ala Lys Lys Lys Lys Val Leu Arg
                485                 490                 495

Glu Leu Met Val Lys Ala Thr Lys Thr Arg Asp Ile Thr Trp Tyr Ile
            500                 505                 510
```

```
Glu Pro Ser Glu Phe Lys Cys Glu Asp Lys Val Arg Leu Tyr Tyr Asn
        515                 520                 525

Lys Ser Ser Gly Pro Leu Ser His Ala Lys Asp Leu Trp Ile His Gly
    530                 535                 540

Gly Tyr Asn Asn Trp Lys Asp Gly Leu Ser Ile Val Lys Lys Leu Val
545                 550                 555                 560

Lys Ser Glu Arg Ile Asp Gly Asp Trp Trp Tyr Thr Glu Val Val Ile
                565                 570                 575

Pro Asp Gln Ala Leu Phe Leu Asp Trp Val Phe Ala Asp Gly Pro Pro
            580                 585                 590

Lys His Ala Ile Ala Tyr Asp Asn Asn His Arg Gln Asp Phe His Ala
        595                 600                 605

Ile Val Pro Asn His Ile Pro Glu Glu Leu Tyr Trp Val Glu Glu Glu
    610                 615                 620

His Gln Ile Phe Lys Thr Leu Gln Glu Glu Arg Arg Leu Arg Glu Ala
625                 630                 635                 640

Ala Met Arg Ala Lys Val Glu Lys Thr Ala Leu Leu Lys Thr Glu Thr
                645                 650                 655

Lys Glu Arg Thr Met Lys Ser Phe Leu Leu Ser Gln Lys His Val Val
            660                 665                 670

Tyr Thr Glu Pro Leu Asp Ile Gln Ala Gly Ser Ser Val Thr Val Tyr
        675                 680                 685

Tyr Asn Pro Ala Asn Thr Val Leu Asn Gly Lys Pro Glu Ile Trp Phe
    690                 695                 700

Arg Cys Ser Phe Asn Arg Trp Thr His Arg Leu Gly Pro Leu Pro Pro
705                 710                 715                 720

Gln Lys Met Ser Pro Ala Glu Asn Gly Thr His Val Arg Ala Thr Val
                725                 730                 735

Lys Val Pro Leu Asp Ala Tyr Met Met Asp Phe Val Phe Ser Glu Arg
            740                 745                 750

Glu Asp Gly Gly Ile Phe Asp Asn Lys Ser Gly Met Asp Tyr His Ile
        755                 760                 765

Pro Val Phe Gly Gly Val Ala Lys Glu Pro Pro Met His Ile Val His
    770                 775                 780

Ile Ala Val Glu Met Ala Pro Ile Ala Lys Val Gly Gly Leu Gly Asp
785                 790                 795                 800

Val Val Thr Ser Leu Ser Arg Ala Val Gln Asp Leu Asn His Asn Val
                805                 810                 815

Asp Ile Ile Leu Pro Lys Tyr Asp Cys Leu Lys Met Asn Asn Val Lys
            820                 825                 830

Asp Phe Arg Phe His Lys Asn Tyr Phe Trp Gly Gly Thr Glu Ile Lys
        835                 840                 845

Val Trp Phe Gly Lys Val Glu Gly Leu Ser Val Tyr Phe Leu Glu Pro
    850                 855                 860

Gln Asn Gly Leu Phe Ser Lys Gly Cys Val Tyr Gly Cys Ser Asn Asp
865                 870                 875                 880

Gly Glu Arg Phe Gly Phe Phe Cys His Ala Ala Leu Glu Phe Leu Leu
                885                 890                 895

Gln Gly Gly Phe Ser Pro Asp Ile Ile His Cys His Asp Trp Ser Ser
            900                 905                 910

Ala Pro Val Ala Trp Leu Phe Lys Glu Gln Tyr Thr His Tyr Gly Leu
        915                 920                 925
```

-continued

```
Ser Lys Ser Arg Ile Val Phe Thr Ile His Asn Leu Glu Phe Gly Ala
    930                 935                 940

Asp Leu Ile Gly Arg Ala Met Thr Asn Ala Asp Lys Ala Thr Thr Val
945                 950                 955                 960

Ser Pro Thr Tyr Ser Gln Glu Val Ser Gly Asn Pro Val Ile Ala Pro
                965                 970                 975

His Leu His Lys Phe His Gly Ile Val Asn Gly Ile Asp Pro Asp Ile
            980                 985                 990

Trp Asp Pro Leu Asn Asp Lys Phe  Ile Pro Ile Pro Tyr  Thr Ser Glu
        995                 1000                 1005

Asn Val  Val Glu Gly Lys Thr  Ala Ala Lys Glu Ala  Leu Gln Arg
    1010                 1015                 1020

Lys Leu  Gly Leu Lys Gln Ala  Asp Leu Pro Leu Val  Gly Ile Ile
    1025                 1030                 1035

Thr Arg  Leu Thr His Gln Lys  Gly Ile His Leu Ile  Lys His Ala
    1040                 1045                 1050

Ile Trp  Arg Thr Leu Glu Arg  Asn Gly Gln Val Val  Leu Leu Gly
    1055                 1060                 1065

Ser Ala  Pro Asp Pro Arg Val  Gln Asn Asn Phe Val  Asn Leu Ala
    1070                 1075                 1080

Asn Gln  Leu His Ser Lys Tyr  Asn Asp Arg Ala Arg  Leu Cys Leu
    1085                 1090                 1095

Thr Tyr  Asp Glu Pro Leu Ser  His Leu Ile Tyr Ala  Gly Ala Asp
    1100                 1105                 1110

Phe Ile  Leu Val Pro Ser Ile  Phe Glu Pro Cys Gly  Leu Thr Gln
    1115                 1120                 1125

Leu Thr  Ala Met Arg Tyr Gly  Ser Ile Pro Val Val  Arg Lys Thr
    1130                 1135                 1140

Gly Gly  Leu Tyr Asp Thr Val  Phe Asp Val Asp His  Asp Lys Glu
    1145                 1150                 1155

Arg Ala  Gln Gln Cys Gly Leu  Glu Pro Asn Gly Phe  Ser Phe Asp
    1160                 1165                 1170

Gly Ala  Asp Ala Gly Gly Val  Asp Tyr Ala Leu Asn  Arg Ala Leu
    1175                 1180                 1185

Ser Ala  Trp Tyr Asp Gly Arg  Asp Trp Phe Asn Ser  Leu Cys Lys
    1190                 1195                 1200

Gln Val  Met Glu Gln Asp Trp  Ser Trp Asn Arg Pro  Ala Leu Asp
    1205                 1210                 1215

Tyr Leu  Glu Leu Tyr His Ala  Ala Arg Lys Leu Glu
    1220                 1225                 1230


<210> SEQ ID NO 57
<211> LENGTH: 615
<212> TYPE: PRT
<213> ORGANISM: Wheat wGBSS

<400> SEQUENCE: 57

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60
```

-continued

```
Leu Ser Met Val Val Arg Ala Thr Gly Ser Gly Gly Met Asn Leu Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Ala Ala Met Ala Ala Asn Gly His Arg
            100                 105                 110

Val Met Val Ile Ser Pro Arg Tyr Asp Gln Tyr Lys Asp Ala Trp Asp
        115                 120                 125

Thr Ser Val Ile Ser Glu Ile Lys Val Val Asp Arg Tyr Glu Arg Val
    130                 135                 140

Arg Tyr Phe His Cys Tyr Lys Arg Gly Val Asp Arg Val Phe Val Asp
145                 150                 155                 160

His Pro Cys Phe Leu Glu Lys Val Arg Gly Lys Thr Lys Glu Lys Ile
                165                 170                 175

Tyr Gly Pro Asp Ala Gly Thr Asp Tyr Glu Asp Asn Gln Gln Arg Phe
            180                 185                 190

Ser Leu Leu Cys Gln Ala Ala Leu Glu Val Pro Arg Ile Leu Asp Leu
        195                 200                 205

Asn Asn Asn Pro His Phe Ser Gly Pro Tyr Ala Met Leu Cys Arg Ala
    210                 215                 220

Val Pro Arg Arg Ala Gly Glu Asp Val Val Phe Val Cys Asn Asp Trp
225                 230                 235                 240

His Thr Gly Leu Leu Ala Cys Tyr Leu Lys Ser Asn Tyr Gln Ser Asn
                245                 250                 255

Gly Ile Tyr Arg Thr Ala Lys Val Ala Phe Cys Ile His Asn Ile Ser
            260                 265                 270

Tyr Gln Gly Arg Phe Ser Phe Asp Asp Phe Ala Gln Leu Asn Leu Pro
        275                 280                 285

Asp Arg Phe Lys Ser Ser Phe Asp Phe Ile Asp Gly Tyr Asp Lys Pro
    290                 295                 300

Val Glu Gly Arg Lys Ile Asn Trp Met Lys Ala Gly Ile Leu Gln Ala
305                 310                 315                 320

Asp Lys Val Leu Thr Val Ser Pro Tyr Tyr Ala Glu Glu Leu Ile Ser
                325                 330                 335

Gly Glu Ala Arg Gly Cys Glu Leu Asp Asn Ile Met Arg Leu Thr Gly
            340                 345                 350

Ile Thr Gly Ile Val Asn Gly Met Asp Val Ser Glu Trp Asp Pro Ile
        355                 360                 365

Lys Asp Lys Phe Leu Thr Val Asn Tyr Asp Val Thr Thr Ala Leu Glu
    370                 375                 380

Gly Lys Ala Leu Asn Lys Glu Ala Leu Gln Ala Glu Val Gly Leu Pro
385                 390                 395                 400

Val Asp Arg Lys Val Pro Leu Val Ala Phe Ile Gly Arg Leu Glu Glu
                405                 410                 415

Gln Lys Gly Pro Asp Val Met Ile Ala Ala Ile Pro Glu Ile Val Lys
            420                 425                 430

Glu Glu Asp Val Gln Ile Val Leu Leu Gly Thr Gly Lys Lys Lys Phe
        435                 440                 445

Glu Arg Leu Leu Lys Ser Val Glu Glu Lys Phe Pro Thr Lys Val Arg
    450                 455                 460

Ala Val Val Arg Phe Asn Ala Pro Leu Ala His Gln Met Met Ala Gly
465                 470                 475                 480
```

-continued

```
Ala Asp Val Leu Ala Val Thr Ser Arg Phe Glu Pro Cys Gly Leu Ile
                485                 490                 495

Gln Leu Gln Gly Met Arg Tyr Gly Thr Pro Cys Ala Cys Ala Ser Thr
            500                 505                 510

Gly Gly Leu Val Asp Thr Ile Val Glu Gly Lys Thr Gly Phe His Met
        515                 520                 525

Gly Arg Leu Ser Val Asp Cys Asn Val Val Glu Pro Ala Asp Val Lys
    530                 535                 540

Lys Val Val Thr Thr Leu Lys Arg Ala Val Lys Val Val Gly Thr Pro
545                 550                 555                 560

Ala Tyr His Glu Met Val Lys Asn Cys Met Ile Gln Asp Leu Ser Trp
                565                 570                 575

Lys Gly Pro Ala Lys Asn Trp Glu Asp Val Leu Leu Glu Leu Gly Val
            580                 585                 590

Glu Gly Ser Glu Pro Gly Ile Val Gly Glu Glu Ile Ala Pro Leu Ala
        595                 600                 605

Leu Glu Asn Val Ala Ala Pro
    610                 615


<210> SEQ ID NO 58
<211> LENGTH: 647
<212> TYPE: PRT
<213> ORGANISM: Wheat wSS1

<400> SEQUENCE: 58

Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
            20                  25                  30

Arg Ala Arg Leu Arg Arg Leu Ala Arg Gly Arg Tyr Val Ala Glu Leu
        35                  40                  45

Ser Arg Glu Gly Pro Ala Ala Arg Pro Ala Gln Gln Gln Gln Leu Ala
    50                  55                  60

Pro Pro Leu Val Pro Gly Phe Leu Ala Pro Pro Pro Pro Ala Pro Ala
65                  70                  75                  80

Gln Ser Pro Ala Pro Thr Gln Pro Pro Leu Pro Asp Ala Gly Val Gly
                85                  90                  95

Glu Leu Ala Pro Asp Leu Leu Leu Glu Gly Ile Ala Glu Asp Ser Ile
            100                 105                 110

Asp Ser Ile Ile Val Ala Ala Ser Glu Gln Asp Ser Glu Ile Met Asp
        115                 120                 125

Ala Asn Glu Gln Pro Gln Ala Lys Val Thr Arg Ser Ile Val Phe Val
    130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
            180                 185                 190

Lys Ala Leu Tyr Thr Gly Lys His Ile Lys Ile Pro Cys Phe Gly Gly
        195                 200                 205

Ser His Glu Val Thr Phe Phe His Glu Tyr Arg Asp Asn Val Asp Trp
    210                 215                 220

Val Phe Val Asp His Pro Ser Tyr His Arg Pro Gly Ser Leu Tyr Gly
225                 230                 235                 240
```

-continued

```
Asp Asn Phe Gly Ala Phe Gly Asp Asn Gln Phe Arg Tyr Thr Leu Leu
                245                 250                 255

Cys Tyr Ala Ala Cys Glu Ala Pro Leu Ile Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
    290                 295                 300

Arg Asp Ser Arg Ser Thr Leu Val Ile His Asn Leu Ala His Gln Gly
305                 310                 315                 320

Leu Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
            340                 345                 350

Leu Asp Lys Gly Glu Ala Val Asn Phe Leu Lys Gly Ala Val Val Thr
        355                 360                 365

Ala Asp Arg Ile Val Thr Val Ser Gln Gly Tyr Ser Trp Glu Val Thr
    370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
                405                 410                 415

Pro Thr Thr Asp Lys Cys Leu Pro His His Tyr Ser Val Asp Asp Leu
            420                 425                 430

Ser Gly Lys Ala Lys Cys Lys Ala Glu Leu Gln Lys Glu Leu Gly Leu
        435                 440                 445

Pro Val Arg Glu Asp Val Pro Leu Ile Gly Phe Ile Gly Arg Leu Asp
    450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
                485                 490                 495

Glu Gly Trp Met Arg Ser Thr Glu Ser Ser Tyr Lys Asp Lys Phe Arg
            500                 505                 510

Gly Trp Val Gly Phe Ser Val Pro Val Ser His Arg Ile Thr Ala Gly
        515                 520                 525

Cys Asp Ile Leu Leu Met Pro Ser Arg Phe Glu Pro Cys Gly Leu Asn
    530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
        595                 600                 605

Pro Ser Trp Glu Gly Leu Met Lys Arg Gly Met Thr Lys Asp His Thr
    610                 615                 620

Trp Asp His Ala Ala Glu Gln Tyr Glu Gln Ile Phe Glu Trp Ala Phe
625                 630                 635                 640

Val Asp Gln Pro Tyr Val Met
                645
```

-continued

```
<210> SEQ ID NO 59
<211> LENGTH: 7
<212> TYPE: PRT
<213> ORGANISM: Wheat SSII

<400> SEQUENCE: 59

Pro Val Asn Gly Glu Asn Lys
1               5
```